United States Patent
Jeanguenat et al.

(10) Patent No.: US 10,750,742 B2
(45) Date of Patent: Aug. 25, 2020

(54) PESTICIDALLY ACTIVE PYRAZOLE DERIVATIVES

(71) Applicant: SYNGENTA PARTICIPATIONS AG, Basel (CH)

(72) Inventors: André Jeanguenat, Stein (CH); Myriem El Qacemi, Stein (CH); Thomas Pitterna, Stein (CH); André Stoller, Stein (CH); Regis Jean Georges Mondiere, Stein (CH); Aurelien Bigot, Stein (CH); Andrew Edmunds, Stein (CH)

(73) Assignee: Syngenta Participations AG, Basel (CH)

( * ) Notice: Subject to any disclaimer, the term of this patent is extended or adjusted under 35 U.S.C. 154(b) by 83 days.

(21) Appl. No.: 16/064,916

(22) PCT Filed: Dec. 15, 2016

(86) PCT No.: PCT/EP2016/081167
§ 371 (c)(1),
(2) Date: Jun. 21, 2018

(87) PCT Pub. No.: WO2017/108569
PCT Pub. Date: Jun. 29, 2017

(65) Prior Publication Data
US 2019/0014783 A1 Jan. 17, 2019

(30) Foreign Application Priority Data

Dec. 22, 2015 (EP) .................................... 15202160
May 12, 2016 (EP) .................................... 16169454

(51) Int. Cl.
| A01N 43/56 | (2006.01) |
| A01N 53/00 | (2006.01) |
| A01N 25/00 | (2006.01) |
| A01N 25/26 | (2006.01) |
| A01N 43/50 | (2006.01) |
| A01N 43/713 | (2006.01) |
| A01N 43/80 | (2006.01) |

(52) U.S. Cl.
CPC ............. *A01N 43/56* (2013.01); *A01N 25/00* (2013.01); *A01N 25/26* (2013.01); *A01N 43/50* (2013.01); *A01N 43/713* (2013.01); *A01N 43/80* (2013.01); *A01N 53/00* (2013.01)

(58) Field of Classification Search
None
See application file for complete search history.

(56) References Cited

FOREIGN PATENT DOCUMENTS

| WO | 2010051926 A2 | 5/2010 | |
| WO | WO-2012107434 A1 * | 8/2012 | ........... A01N 43/647 |
| WO | 2014122083 A1 | 8/2014 | |
| WO | 2015150442 A1 | 10/2015 | |

* cited by examiner

*Primary Examiner* — Alton N Pryor
(74) *Attorney, Agent, or Firm* — Baker & Hostetler, LLP; Toni-Junell Herbert

(57) ABSTRACT

Compounds of formula (I), as defined herein, to processes for preparing them, to pesticidal, in particular insecticidal, acaricidal, molluscicidal and nematicidal compositions comprising them and to methods of using them to combat and control pests such as insect, acarine, mollusc and nematode pests.

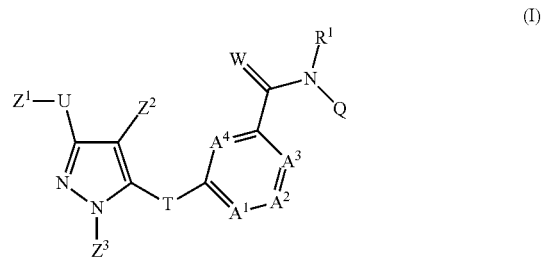

18 Claims, No Drawings

PESTICIDALLY ACTIVE PYRAZOLE DERIVATIVES

CROSS-REFERENCE TO RELATED APPLICATIONS

This application is a 371 National Stage application of International Application No. PCT/EP2016/081167, filed Dec. 15, 2016, which claims priority to European Patent Application No. 15202160.6, filed Dec. 22, 2015, and European Patent Application No. 16169454.2, filed May 12, 2016, the entire contents of which applications are hereby incorporated by reference.

The present invention relates to pyrazole derivatives, to processes for preparing them, to intermediates for preparing them, to pesticidal, in particular insecticidal, acaricidal, moluscicidal and nematicidal compositions comprising those derivatives and to methods of using them to combat and control pests such as insect, acarine, mollusc and nematode pests.

It has now surprisingly been found that certain pyrazole derivatives have highly potent insecticidal properties. Other compounds in this area are known from WO2014/122083, WO2012/107434, WO2015/067646, WO2015/067647, WO2015/067648, WO2015/150442 and WO2010/051926.

Thus, as embodiment 1, the present invention relates to a compound of formula (I),

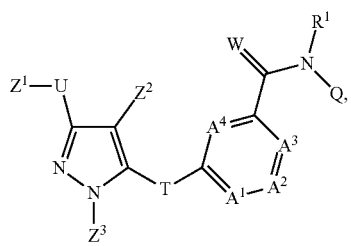

(I)

wherein $R^1$ is selected from H, $C_1$-$C_6$-alkyl, $C_2$-$C_6$ alkenyl, $C_2$-$C_6$ alkynyl, $C_3$-$C_7$ cycloalkyl, $C_3$-$C_7$ cycloalkyl-$C_1$-$C_3$-alkyl, $C_1$-$C_6$-alkylcarbonyl, $C_1$-$C_6$-alkoxycarbonyl, aryl($C_0$-$C_3$)-akyl and heteroaryl($C_0$-$C_3$)-alkyl, wherein each of $C_1$-$C_6$-alkyl, $C_2$-$C_6$ alkenyl, $C_2$-$C_6$ alkynyl, $C_3$-$C_7$ cycloalkyl, $C_3$-$C_7$ cycloalkyl-$C_1$-$C_3$-alkyl, $C_1$-$C_6$-akylcarbonyl, $C_1$-$C_6$-alkoxycarbonyl, aryl($C_0$-$C_3$)-alkyl and heteroaryl($C_0$-$C_3$)-alkyl is unsubstituted or substituted with 1 to 10 substituents independently selected from halogen, cyano, $C_1$-$C_6$-alkoxy and $C_1$-$C_6$-alkoxycarbonyl;

Q is selected from H, hydroxy, HC(=O)—, $C_1$-$C_6$-alkyl, $C_1$-$C_6$-alkoxy, $C_3$-$C_6$ alkenyl, $C_3$-$C_6$ alkynyl, $C_3$-$C_7$ cycloalkyl, $C_3$-$C_7$ heterocycloalkyl, $C_3$-$C_7$ cycloalkyl-$C_1$-$C_3$-alkyl, $C_1$-$C_3$-alkyl-$C_5$-$C_7$ cycloalkyl, aryl($C_0$-$C_3$)-alkyl, heteroaryl($C_0$-$C_3$)-alkyl, N—$C_1$-$C_6$-akylamino, N—$C_1$-$C_6$-alkylcarbonylamino and N,N-di($C_1$-$C_6$-akyl)amino, wherein each of $C_1$-$C_6$-alkyl, $C_1$-$C_6$-alkoxy, $C_3$-$C_6$ alkenyl, $C_3$-$C_6$ alkynyl, $C_3$-$C_7$ cycloalkyl, $C_3$-$C_7$ heterocycloalkyl, $C_3$-$C_7$ cycloalkyl-$C_1$-$C_3$-alkyl, $C_1$-$C_3$-akyl-$C_3$-$C_7$ cycloakyl, aryl($C_0$-$C_3$)-alkyl, heteroaryl($C_0$-$C_3$)-alkyl, N—$C_1$-$C_6$-alkylamino, N—$C_1$-$C_6$-alkylcarbonylamino and N,N-di ($C_1$-$C_6$-alkyl)amino is unsubstituted or substituted with 1 to 10 substituents independently selected from halogen, hydroxyl, nitro, amino, cyano, $C_1$-$C_6$-alkoxy, $C_1$-$C_6$-alkoxycarbonyl, hydroxycarbonyl, $C_1$-$C_6$-alkylcarbamoyl, $C_3$-$C_6$-cycloalkylcarbamoyl and phenyl;

W is O or S;
$A^1$ is $CR^2$ or N;
$A^2$ is $CR^3$ or N;
$A^3$ is $CR^1$ or N;
$A^4$ is $CR^5$ or N;
with the proviso that no more than 3 of $A^1$, $A^2$, $A^3$ and $A^4$ are N;
$R^2$, $R^3$, $R^4$ and $R^5$ are independently selected from H, halogen, cyano, nitro, $C_1$-$C_6$-alkyl, $C_1$-$C_6$-alkoxy, N—$C_1$-$C_6$-alkoxy-imino-$C_1$-$C_3$-alkyl, $C_1$-$C_6$-alkylsulfanyl, $C_1$-$C_6$-akylsulfinyl, $C_1$-$C_6$-alkylsulfonyl, N—$C_1$-$C_6$-akylamino and N,N-di-$C_1$-$C_6$-alkylamino, wherein each of $C_1$-$C_6$-alkyl, $C_1$-$C_6$-alkoxy, N—$C_1$-$C_6$-alkoxy-imino-$C_1$-$C_3$-akyl, $C_1$-$C_6$-akylsulfanyl, $C_1$-$C_6$-alkylsulfinyl, $C_1$-$C_6$-alkylsulfonyl, N—$C_1$-$C_6$-alkylamino and N,N-di-$C_1$-$C_6$-akylamino is unsubstituted or substituted with 1 to 5 substituents independently selected from halogen, hydroxy, nitro, amino, cyano, $C_1$-$C_6$-alkoxy, $C_1$-$C_6$-alkoxycarbonyl, hydroxycarbonyl, $C_1$-$C_6$-alkylcarbamoyl, $C_3$-$C_6$-cycloalkylcarbamoyl and phenyl;

T is a 5-membered heteroaryl of formula

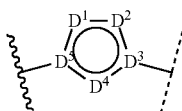

wherein

indicates the bond to the pyrazole group;
$D^1$ is selected from $CR^{6a}$, N, $NR^{6b}$, O and S;
$D^2$ is selected from $CR^{7a}$, N, $NR^{7b}$, O and S;
$D^3$ is C or N;
$D^4$ is selected from $CR^{8a}$, N, $NR^{8b}$, S and O;
$D^5$ is C or N;
with the proviso that at least one of $D^1$, $D^2$, $D^3$, $D^4$ and $D^5$ is selected from N, O and S, and that no more than one of $D^1$, $D^2$ and $D^4$ is O or S, and that at least one of $D^3$ and $D^5$ is C;
$R^{6a}$, $R^{7a}$ and $R^{8a}$ are independently selected from H, halogen, cyano, nitro, amino, $C_1$-$C_6$-alkyl, $C_1$-$C_6$-alkoxy, $C_1$-$C_6$-akylcarbonyl, $C_1$-$C_6$-alkylsulfanyl, $C_1$-$C_6$-alkylsulfinyl and $C_1$-$C_6$-alkylsulfonyl, wherein each of $C_1$-$C_6$-alkyl, $C_1$-$C_6$-alkoxy, $C_1$-$C_6$-alkylcarbonyl, $C_1$-$C_6$-alkylsulfanyl, $C_1$-$C_6$-alkylsulfinyl, $C_1$-$C_6$-alkylsulfonyl is unsubstituted or substituted with 1 to 5 halogen;
$R^{6b}$, $R^{7b}$ and $R^{8b}$ are independently selected from H and $C_1$-$C_6$-akyl, wherein each of $C_1$-$C_6$-alkyl is unsubstituted or substituted with 1 to 5 halogen;
U is selected from —O—, —S—, —SO—, —$SO_2$— and —$NR^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloakyl is unsubstituted or substituted with 1 to 13 substituents independently selected from halogen;

$Z^1$ is selected from $C_1$-$C_{10}$-alkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_2$-$C_{10}$-alkenyl, $C_2$-$C_{10}$-alkynyl, —($C_0$-$C_6$-alkyl)-$C_3$-$C_7$ heterocycloalkyl, —($C_0$-$C_6$-alkyl)-$C_3$-$C_6$-cycloalkyl and $C_1$-$C_{10}$-alkylsulfonyl, wherein each of $C_1$-$C_{10}$-alkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_2$-$C_{10}$-alkenyl, $C_2$-$C_{10}$-alkynyl, —($C_0$-$C_6$-alkyl)-$C_3$-$C_7$ heterocycloalkyl, —($C_0$-$C_6$-akyl)-$C_3$-$C_6$-cycloalkyl and $C_1$-$C_{10}$-alkylsulfonyl is unsubstituted or substituted with 1 to 20 substituents independently selected from halogen, hydroxy, nitro, amino, cyano, $C_1$-$C_6$-alkoxy, $C_1$-$C_6$-alkoxycarbonyl, hydroxycarbonyl, $C_1$-$C_6$-alkylcarbamoyl, $C_3$-$C_6$-cycloalkylcarbamoyl and phenyl;

$Z^2$ is selected from H, halogen, cyano, nitro, amino, $C_1$-$C_6$-alkyl, $C_1$-$C_6$-akylcarbonyl, $C_1$-$C_6$-akylsulfanyl, $C_1$-$C_6$-alkylsulfinyl and $C_1$-$C_6$-alkylsulfonyl, wherein each of $C_1$-$C_6$-alkyl, $C_1$-$C_6$-akylcarbonyl, $C_1$-$C_6$-akylsulfanyl, $C_1$-$C_6$-alkylsulfinyl and $C_1$-$C_6$-alkylsulfonyl is unsubstituted or substituted with 1 to 5 substituents independently selected from halogen, hydroxy, nitro, amino, cyano, $C_1$-$C_6$-alkoxy, $C_1$-$C_6$-alkoxycarbonyl, hydroxycarbonyl, $C_1$-$C_6$-alkylcarbamoyl, $C_3$-$C_6$-cycloalkylcarbamoyl and phenyl;

$Z^3$ is selected from H, $C_1$-$C_6$-alkyl, $C_1$-$C_6$-cycloalkyl, $C_1$-$C_6$-alkenyl, $C_1$-$C_6$-alkinyl, aryl and heteroaryl, wherein each of $C_1$-$C_6$-alkyl, $C_1$-$C_6$-cycloakyl, $C_1$-$C_6$-alkenyl, $C_1$-$C_6$-alkinyl, aryl and heteroaryl is unsubstituted or substituted with 1 to 5 substituents independently selected from halogen, hydroxy, nitro, amino, cyano, $C_1$-$C_6$-alkoxy, $C_1$-$C_6$-alkoxycarbonyl, hydroxycarbonyl, $C_1$-$C_6$-alkylcarbamoyl, $C_3$-$C_6$-cycloakylcarbamoyl and phenyl;

or an agrochemically acceptable salt or N-oxide thereof.

Preferred values of $A^1$, $A^2$, $A^3$, $A^4$, $D^1$, $D^2$, $D^3$, $D^4$, $D^5$, $R^1$, $R^2$, $R^3$, $R^4$, $R^5$, $R^{6a}$, $R^{6b}$, $R^{7a}$, $R^{7b}$, $R^{8a}$, $R^{8b}$, Q, U, $Z^1$, $Z^2$ and $Z^3$ in relation to each compound of the present invention, including the intermediate compounds, are as set out below in embodiments 2 to 78.

Embodiment 2

A compound or salt according to embodiment 1 of formula (I)

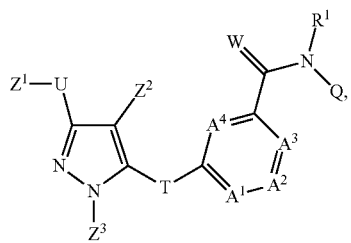

(I)

wherein $R^1$ is selected from H, $C_1$-$C_6$-alkyl, $C_3$-$C_6$ alkenyl, $C_3$-$C_6$ alkynyl, $C_3$-$C_7$ cycloalkyl, $C_3$-$C_7$ cycloalkyl-$C_1$-$C_3$-alkyl, $C_1$-$C_6$-alkylcarbonyl, $C_1$-$C_6$-alkoxycarbonyl, aryl($C_0$-$C_3$)-akyl and heteroaryl($C_0$-$C_3$)-alkyl, wherein each of $C_1$-$C_6$-alkyl, $C_3$-$C_6$ alkenyl, $C_3$-$C_6$ alkynyl, $C_3$-$C_7$ cycloalkyl, $C_3$-$C_7$ cycloalkyl-$C_1$-$C_3$-alkyl, $C_1$-$C_6$-akylcarbonyl, $C_1$-$C_6$-alkoxycarbonyl, aryl($C_0$-$C_3$)-alkyl and heteroaryl($C_0$-$C_3$)-alkyl is unsubstituted or substituted with 1 to 5 substituents independently selected from halogen, cyano, $C_1$-$C_6$-alkoxy and $C_1$-$C_6$-alkoxycarbonyl;

Q is selected from H, hydroxy, HC(=O)—, $C_1$-$C_6$-alkyl, $C_1$-$C_6$-alkoxy, $C_3$-$C_6$ alkenyl, $C_3$-$C_6$ alkynyl, $C_3$-$C_7$ cycloalkyl, $C_3$-$C_7$ heterocycloalkyl, $C_3$-$C_7$ cycloalkyl-$C_1$-$C_3$-alkyl, $C_1$-$C_3$-alkyl-$C_3$-$C_7$ cycloalkyl, aryl($C_0$-$C_3$)-akyl, heteroaryl($C_0$-$C_3$)-alkyl, N—$C_1$-$C_6$-alkylamino, N—$C_1$-$C_6$-alkylcarbonylamino and N,N-di ($C_1$-$C_6$-akyl)amino, wherein each of $C_1$-$C_6$-alkyl, $C_1$-$C_6$-alkoxy, $C_3$-$C_6$ alkenyl, $C_3$-$C_6$ alkynyl, $C_3$-$C_7$ cycloalkyl, $C_3$-$C_7$ heterocycloalkyl, $C_3$-$C_7$ cycloalkyl-$C_1$-$C_3$-alkyl, $C_1$-$C_3$-alkyl-$C_3$-$C_7$ cycloakyl, aryl($C_0$-$C_3$)-alkyl, heteroaryl($C_0$-$C_3$)-alkyl, N—$C_1$-$C_6$-alkylamino, N—$C_1$-$C_6$-alkylcarbonylamino and N,N-di ($C_1$-$C_6$-alkyl)amino is unsubstituted or substituted with 1 to 5 substituents independently selected from halogen, hydroxyl, nitro, amino, cyano, $C_1$-$C_6$-alkoxy, $C_1$-$C_6$-alkoxycarbonyl, hydroxycarbonyl, $C_1$-$C_6$-alkylcarbamoyl, $C_3$-$C_6$-cycloakylcarbamoyl and phenyl;

W is O or S;
$A^1$ is $CR^2$ or N;
$A^2$ is $CR^3$ or N;
$A^3$ is $CR^4$ or N;
$A^4$ is $CR^5$ or N;
with the proviso that no more than 3 of $A^1$, $A^2$, $A^3$ and $A^4$ are N;

$R^2$, $R^3$, $R^1$ and $R^5$ are independently selected from H, halogen, cyano, nitro, $C_1$-$C_6$-alkyl, $C_1$-$C_6$-alkoxy, N—$C_1$-$C_6$-alkoxy-imino-$C_1$-$C_3$-alkyl, $C_1$-$C_6$-alkylsulfanyl, $C_1$-$C_6$-akylsulfinyl, $C_1$-$C_6$-alkylsulfonyl, N—$C_1$-$C_6$-akylamino and N,N-di-$C_1$-$C_6$-alkylamino, wherein each of $C_1$-$C_6$-alkyl, $C_1$-$C_6$-alkoxy, N—$C_1$-$C_6$-alkoxy-imino-$C_1$-$C_3$-akyl, $C_1$-$C_6$-akylsulfanyl, $C_1$-$C_6$-alkylsulfinyl, $C_1$-$C_6$-alkylsulfonyl, N—$C_1$-$C_6$-alkylamino and N,N-di-$C_1$-$C_6$-akylamino is unsubstituted or substituted with 1 to 5 substituents independently selected from halogen, hydroxy, nitro, amino, cyano, $C_1$-$C_6$-alkoxy, $C_1$-$C_6$-alkoxycarbonyl, hydroxycarbonyl, $C_1$-$C_6$-alkylcarbamoyl, $C_3$-$C_6$-cycloalkylcarbamoyl and phenyl;

T is a 5-membered heteroaryl of formula

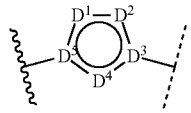

wherein

indicates the bond to the pyrazole group;
$D^1$ is selected from $CR^{6a}$, N, $NR^{6b}$, O and S;
$D^2$ is selected from $CR^{7a}$, N, $NR^{7b}$, O and S;
$D^3$ is C or N;
$D^4$ is selected from $CR^{8a}$, N, $NR^{8b}$, S and O;
$D^5$ is C or N;
with the proviso that at least one of $D^1$, $D^2$, $D^3$, $D^4$ and $D^5$ is selected from N, O and S, and that no more than one of $D^1$, $D^2$ and $D^4$ is O or S, and that at least one of $D^3$ and $D^5$ is C;

$R^{6a}$, $R^{7a}$ and $R^{8a}$ are independently selected from H, halogen, cyano, nitro, amino, $C_1$-$C_6$-alkyl, $C_1$-$C_6$-alkoxy, $C_1$-$C_6$-akylcarbonyl, $C_1$-$C_6$-alkylsulfanyl, $C_1$-$C_6$-alkylsulfinyl and $C_1$-$C_6$-alkylsulfonyl, wherein each of $C_1$-$C_6$-alkyl, $C_1$-$C_6$- alkoxy, $C_1$-$C_6$-alkylcarbonyl, $C_1$-$C_6$-alkylsulfanyl, $C_1$-$C_6$-alkylsulfinyl, $C_1$-$C_6$-alkylsulfonyl is unsubstituted or substituted with 1 to 5 halogen;

$R^{6b}$, $R^{7b}$ and $R^{8b}$ are independently selected from H and $C_1$-$C_6$-akyl, wherein each of $C_1$-$C_6$-alkyl is unsubstituted or substituted with 1 to 5 halogen;

U is selected from —O—, —S—, —SO—, —SO$_2$— and —NR$^{100}$—;

$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloakyl is unsubstituted or substituted with 1 to 8 substituents independently selected from halogen;

$Z^1$ is selected from $C_1$-$C_6$-alkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_2$-$C_6$-alkenyl, $C_2$-$C_6$-alkynyl, —($C_0$-$C_6$-alkyl)-$C_3$-$C_7$ heterocycloalkyl, —($C_0$-$C_6$-alkyl)-$C_3$-$C_6$-cycoalkyl, wherein each of $C_1$-$C_6$-alkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_2$-$C_6$-alkenyl, $C_2$-$C_6$-alkynyl, —($C_0$-$C_6$-alkyl)-$C_3$-$C_7$ heterocycloalkyl, —($C_0$-$C_6$-alkyl)-$C_3$-$C_6$-cycoalkyl is unsubstituted or substituted with 1 to 8 substituents independently selected from halogen, hydroxy, nitro, amino, cyano, $C_1$-$C_6$-alkoxy, $C_1$-$C_6$-alkoxycarbonyl, hydroxycarbonyl, $C_1$-$C_6$-alkylcarbamoyl, $C_3$-$C_6$-cycloalkylcarbamoyl and phenyl;

$Z^2$ is selected from H, halogen, cyano, nitro, amino, $C_1$-$C_6$-alkyl, $C_1$-$C_6$-akylcarbonyl, $C_1$-$C_6$-akylsulfanyl, $C_1$-$C_6$-alkylsulfinyl and $C_1$-$C_6$-alkylsulfonyl, wherein each of $C_1$-$C_6$-alkyl, $C_1$-$C_6$-akylcarbonyl, $C_1$-$C_6$-akylsulfanyl, $C_1$-$C_6$-alkylsulfinyl and $C_1$-$C_6$-alkylsulfonyl is unsubstituted or substituted with 1 to 5 substituents independently selected from halogen, hydroxy, nitro, amino, cyano, $C_1$-$C_6$-alkoxy, $C_1$-$C_3$-alkoxycarbonyl, hydroxycarbonyl, $C_1$-$C_6$-alkylcarbamoyl, $C_3$-$C_6$-cycloalkylcarbamoyl and phenyl;

$Z^3$ is selected from H, $C_1$-$C_6$-akyl, $C_1$-$C_3$-cycloalkyl, $C_1$-$C_6$-alkenyl, $C_1$-$C_6$-alkynyl, aryl and heteroaryl, wherein each of $C_1$-$C_6$-alkyl, $C_1$-$C_6$-cycloakyl, $C_1$-$C_6$-alkenyl, $C_1$-$C_6$-alkynyl, aryl and heteroaryl is unsubstituted or substituted with 1 to 5 substituents independently selected from halogen, hydroxy, nitro, amino, cyano, $C_1$-$C_6$-alkoxy, $C_1$-$C_3$-alkoxycarbonyl, hydroxycarbonyl, $C_1$-$C_3$-alkylcarbamoyl, $C_3$-$C_6$-cycloalkylcarbamoyl and phenyl;

or an agrochemically acceptable salt or N-oxide thereof.

Embodiment 2.1

A compound or salt according to embodiment 1, wherein T is selected from

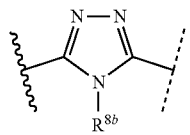
T1

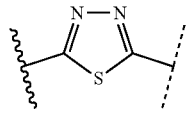
T2

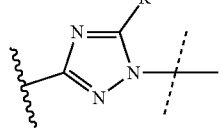
T3

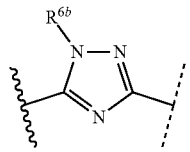
T4

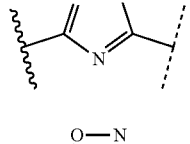
T5

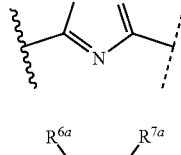
T6

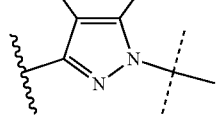
T7

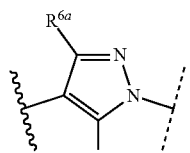
T8

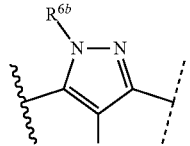
T9

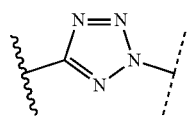
T10

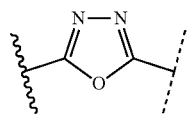
T11

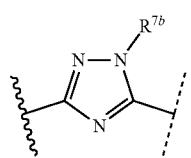
T12

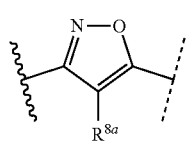
T13

-continued
T14 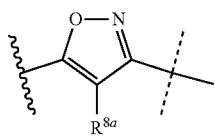
T15 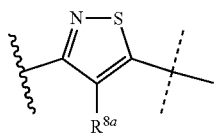
T16 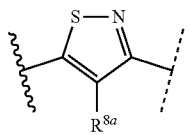
T17 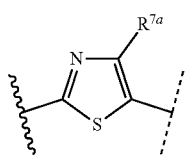
T18 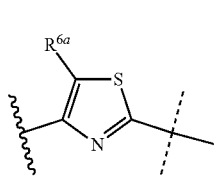
T19 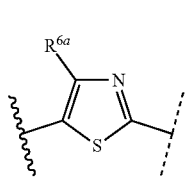
T20 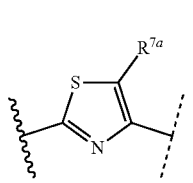
T21 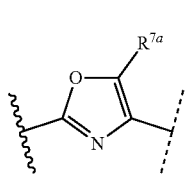
T22 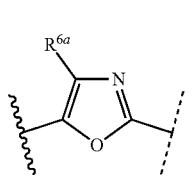
T23 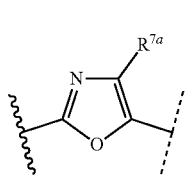
-continued
T24 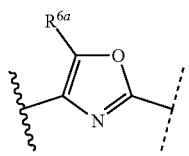
T25 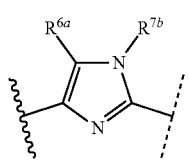
T26 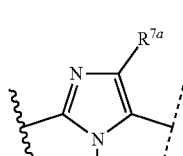
T27 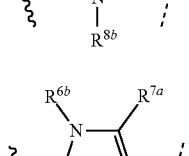
T28 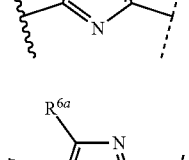
T29 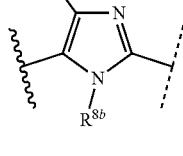
T30 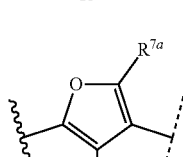
T31 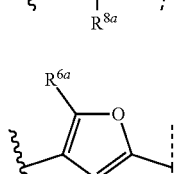
T32 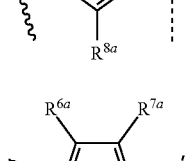
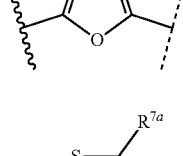

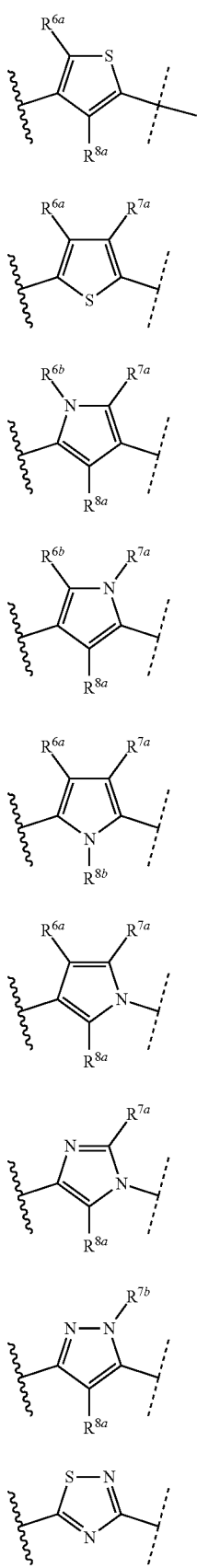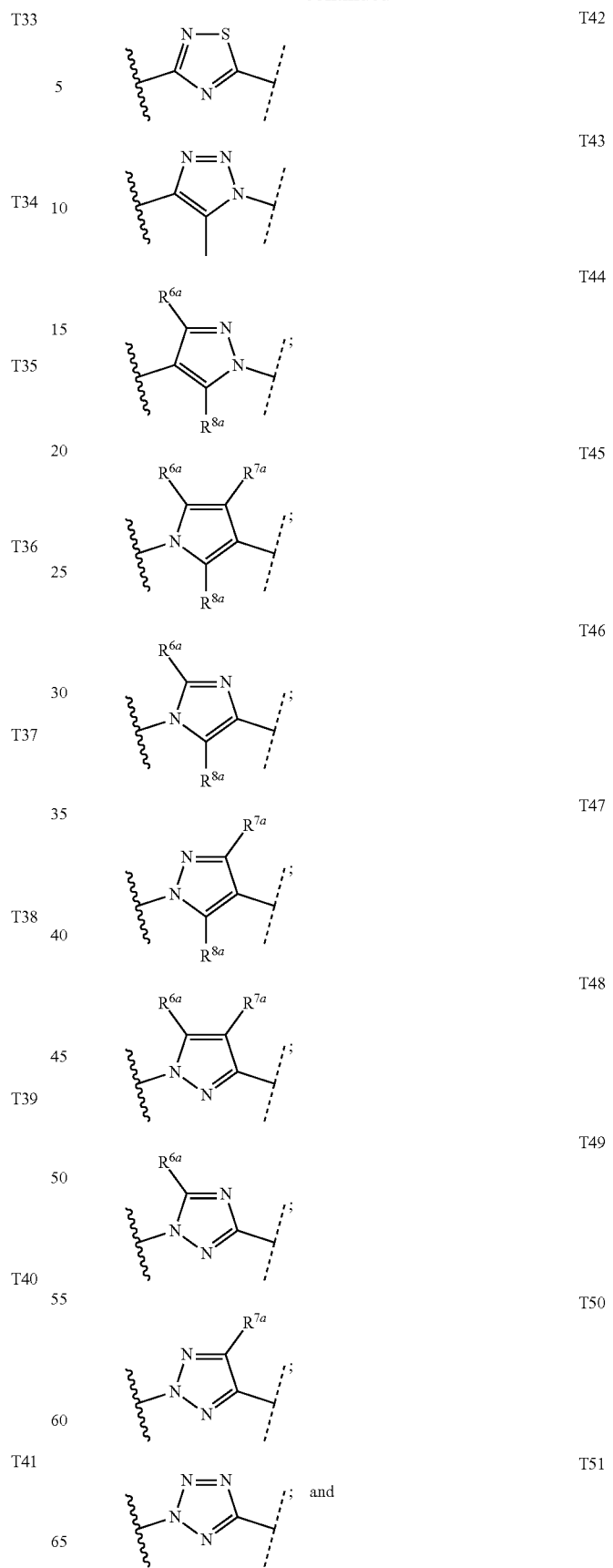

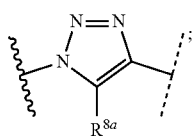
wherein
indicates the bond to the pyrazole group.
Embodiment 3
A compound or salt according to embodiment 1, wherein T is selected from
T2
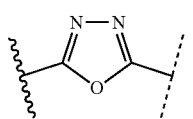
T5
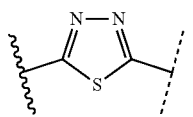
T6
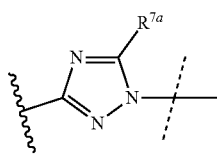
T7
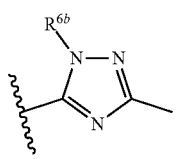
T8
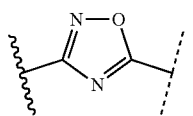
T9
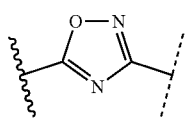
T10
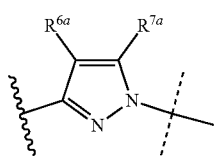
T52
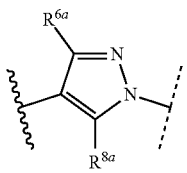
T5
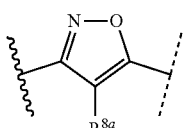
T6
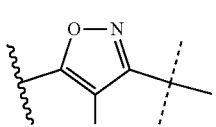
T7
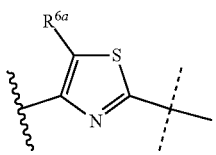
T8
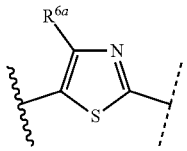
T9
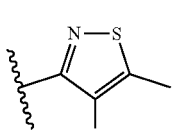
T10
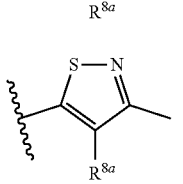
T11
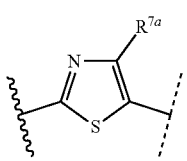
T13
T14
T18
T19
T15
T16
T17
T20
T21

-continued
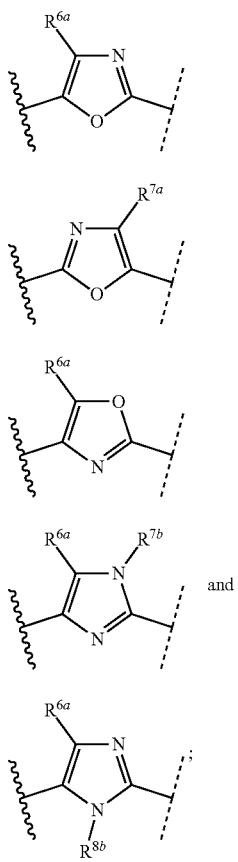
T22
T23
T24
T25
T28
wherein
indicates the bond to the pyrazole group.
Embodiment 4
A compound or salt according to embodiment 1, wherein T is selected from
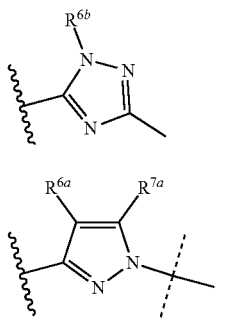
T7
T10
-continued
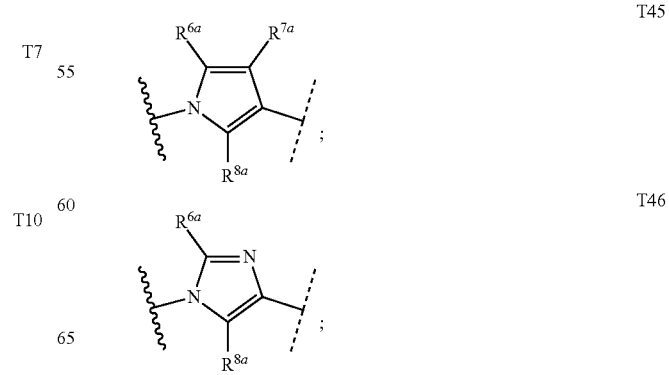
T11
T13
T14
T15
T16
wherein
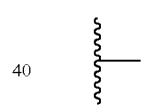
indicates the bond to the pyrazole group.
Embodiment 5
A compound or salt according to embodiment 1, wherein T is selected from
T45
T46

-continued

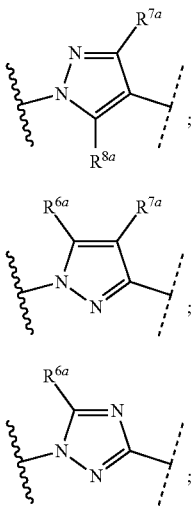

wherein

indicates the bond to the pyrazole group.

Embodiment 5.1

A compound or salt according to embodiment 1, wherein T is selected from

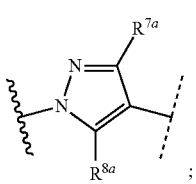

wherein

indicates the bond to the pyrazole group.

Embodiment 6

A compound or salt according to embodiment 1, wherein T is

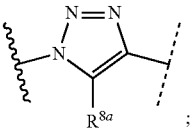

wherein

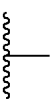

indicates the bond to the pyrazole group.

Embodiment 7

A compound or salt according to any one of embodiments 1 to 6, wherein
$R^1$ is selected from H, methyl, ethyl, n-propyl, isopropyl, n-butyl, isobutyl, s-butyl, t-butyl, propenyl, methoxymethyl, ethoxymethyl, propoxymethyl, methylcarbonyl, ethylcarbonyl, n-propylcarbonyl, isopropylcarbonyl, s-butylcarbonyl, t-butylcarbonyl, methoxycarbonyl, ethoxycarbonyl, n-propoxycarbonyl, isopropoxycarbonyl, s-butoxycarbonyl, t-butoxycarbonyl, cyanomethyl, 2-cyanoethyl, benzyl, 4-methoxybenzyl, pyrid-2-yl-methyl, pyrid-3-yl-methyl, pyrid-4-yl-methyl and 4-chlor-pyrid-3-yl-methyl.

Embodiment 8

A compound or salt according to any one of embodiments 1 to 6, wherein
$R^1$ is selected from H, methyl, ethyl, n-propyl, n-propylcarbonyl and propenyl.

Embodiment 9

A compound or salt according to any one of embodiments 1 to 6, wherein
$R^1$ is H or methyl, in particular H.

Embodiment 10

A compound or salt according to any one of embodiments 1 to 9, wherein
Q is selected from H, hydroxy, HC(=O)—, $C_1$-$C_6$-alkyl, $C_1$-$C_6$-alkoxy, $C_3$-$C_6$ alkenyl, $C_3$-$C_6$ alkynyl, $C_3$-$C_7$ cycloalkyl, $C_3$-$C_7$ heterocycloalkyl, $C_3$-$C_7$ cycloalkyl-$C_1$-$C_3$-alkyl, $C_1$-$C_3$-alkyl-$C_3$-$C_7$ cycloalkyl, aryl($C_0$-$C_3$)-alkyl, heteroaryl($C_0$-$C_3$)-alkyl, N—$C_1$-$C_6$-alkylamino, N—$C_1$-$C_6$-alkylcarbonylamino and N,N-di ($C_1$-$C_6$-alkyl)amino, wherein each of $C_1$-$C_6$-alkyl, $C_1$-$C_6$-alkoxy, $C_3$-$C_6$ alkenyl, $C_3$-$C_6$ alkynyl, $C_3$-$C_7$ cycloalkyl, $C_3$-$C_7$ heterocycloalkyl, $C_3$-$C_7$ cycloalkyl-$C_1$-$C_3$-alkyl, $C_1$-$C_3$-alkyl-$C_3$-$C_7$ cycloalkyl, aryl($C_0$-$C_3$)-alkyl, heteroaryl($C_0$-$C_3$)-alkyl, N—$C_1$-$C_6$-alkylamino, N—$C_1$-$C_6$-alkylcarbonylamino and N,N-di ($C_1$-$C_6$-alkyl)amino is unsubstituted or substituted with 1 to 5 substituents independently selected from halogen, hydroxyl, nitro, amino, cyano, $C_1$-$C_6$-alkoxy, $C_1$-$C_6$-alkoxycarbonyl, hydroxycarbonyl, $C_1$-$C_6$-alkylcarbamoyl, $C_3$-$C_6$-cycloalkylcarbamoyl and phenyl.

Embodiment 11

A compound or salt according to any one of embodiments 1 to 9, wherein
Q is selected from H, methyl, ethyl, n-propyl, 1-cyanocyclopropyl, (E)-1,2,3,3,3-pentafluoroprop-1-enyl, cyanomethyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
1-methylethyl, 1,1-dimethylethyl, 1-methylpropyl, n-butyl, 2-methylpropyl, 2-methylbutyl, hydroxyethyl, 2-hydroxypropyl, cyanomethyl, 2-cyanoethyl, 2-fluoroethyl, 2,2-difluoroethyl, 2,2,2-trifluorethyl, 1-trifluoromethylethyl, 2,2-difluoropropyl, 3,3,3-trifluoropropyl, 2,2-dimethyl-3-fluoropropyl, cyclopropyl, 1-cyano-cyclopropyl, 1-methoxycarbonyl-cyclopropyl, 1-(N-methylcarbamoylcycopropyl, 1-carbamoyl-cyclopropyl, 1-carbamothioyl-cyclopropyl, 1-(N-cyclopropylcarbamoyl)cyclopropyl, cyclopropyl-methyl, cyclobutyl, cyclopentyl, cyclohexyl, 1-cyclopropylethyl, bis(cyclopropyl)methyl, 2,2-dimethylcyclopropyl-methyl, 2-phenylcyclopropyl, 2,2-dichlorocyclopropyl, trans-2-chlorocyclopropyl, cis-2-chlorocyclopropyl, 2,2-difluorocyclopropyl, trans-2-fluorocyclopropyl, cis-2-fluorocyclopropyl, trans-4-hydroxycyclohexyl, 4-trifluoromethylcyclohexyl, prop-2-enyl, 2-methylprop-2-enyl, prop-2-ynyl, 1,1-dimethylbut-2-ynyl, 3-chloro-prop-2-enyl, 3-fluoro-prop-2-enyl, 3,3-dichloro-prop-2-enyl, 3,3-dichloro-1,1-dimethylprop-2-enyl, oxetan-3-yl, thietan-3-yl, 1-oxido-thietan-3-yl, 1,1-dioxido-thietan-3-yl, isoxazol-3-ylmethyl, 1,2,4-triazol-3-ylmethyl, 3-methyloxetan-3-ylmethyl, benzyl, 2,6-difluorophenylmethyl, 3-fluorophenylmethyl, 2-fluorophenylmethyl, 2,5-difluorophenylmethyl, 1-phenylethyl, 4-chlorophenylethyl, 2-trifluoromethylphenylethyl, 1-pyridin-2-ylethyl, pyridin-2-ylmethyl, 5-fluoropyridin-2-ylmethyl, (6-chloro-pyridin-3-yl)methyl, pyrimidin-2-ylmethyl, methoxy, 2-ethoxyethyl, 2-methoxyethyl, 2-(methylsulfanyl)ethyl, 1-methyl-2-(ethylsulfanyl)ethyl, 2-methyl-1-(methylsulfanyl)propan-2-yl, methoxycarbonyl, methoxycarbonylmethyl, $NH_2$, N-ethylamino, N-allylamino, N,N-dimethylamino, N,N-diethylamino, 2-thienylmethyl, isopropyl, isobutyl, methylsulfonyl, methylsulfinyl, 3-(methylsulfanyl)-cyclobutyl, 2-oxo-2[(2,2,2)-trifluoroethyl)amino]ethyl, 1-($CF_3$)cyclopropyl, 2-methylcyclopropyl, 1,1,1-trifluoropropan-2-yl, buta-2,3-dien-1-yl, 3-chloroprop-2-en-1-yl, 3-cyanothientan-3-yl, 3-(methylsulfonyl)cyclobutyl, 4-fluorophenyl, 2-[(methylsulfinyl)methyl]cyclobutyl, 3-methylbutan-2-yl, 2-(methylsulfonyl)cyclobutyl, 2-(dimethylamino)ethyl and 2-methoxyethyl; or
Q is selected from phenyl, naphthyl, pyridazine, pyrazine, pyrimidine, triazine, pyridine, pyrazole, thiazole isothiazole, oxazole, isoxazole, triazole, imidazole, furan, thiophene, pyrrole, oxadiazole, thiadiazole, tetrazole and tetrahydrofuran, each of which is unsubstituted or substituted with 1 to 4 substituents independently selected from V;
V is selected from fluoro, chloro, bromo, iodo, cyano, nitro, methyl, ethyl, difluoromethyl, hydroxyl, trichloromethyl, chlorodifluoromethyl, dichlorofluoromethyl, trifluoromethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl heptafluoro-n-propyl, heptafluoro-isopropyl, nonafluoro-n-butyl, cyclopropyl, cyclobutyl, methoxy, ethoxy, n-propoxy, 1-methylethoxy, fluoromethoxy, difluoromethoxy, chlorodifluoromethoxy, dichloro-fluoromethoxy, trifluoromethoxy, 2,2,2-trifluoroethoxy, 2-chloro-2,2-difluorethoxy, pentafluorethoxy, N-methoxylminomethyl, I-(N-methoxyimino)-ethyl, methylsulfanyl, methylsulfonyl, methylsulfinyl, trifluoromethylsulfonyl, trifluoromethylsulfinyl, trifluoromethylsulfanyl and N,N-dimethylamino.

Embodiment 11.1

A compound or salt according to any one of embodiments 1 to 9, wherein
Q is selected from H, methyl, ethyl, n-propyl, 1-methylethyl, 1,1-dimethylethyl, 1-methylpropyl, n-butyl, 2-methylpropyl, 2-methylbutyl, hydroxyethyl, 2-hydroxypropyl, cyanomethyl, 2-cyanoethyl, 2-fluoroethyl, 2,2-difluoroethyl, 2,2,2-trifluorethyl, 1-trifluoromethylethyl, 2,2-difluoropropyl, 3,3,3-trifluoropropyl, 2,2-dimethyl-3-fluoropropyl, cyclopropyl, 1-cyano-cyclopropyl, 1-methoxycarbonyl-cyclopropyl, 1-(N-methylcarbamoyl)cyclopropyl, 1-carbamoyl-cyclopropyl, 1-carbamothioyl-cyclopropyl, 1-(N-cyclopropylcarbamoyl)cyclopropyl, cyclopropyl-methyl, cyclobutyl, cyclopentyl, cyclohexyl, 1-cyclopropylethyl, bis(cyclopropyl)methyl, 2,2-dimethylcyclopropyl-methyl, 2-phenylcyclopropyl, 2,2-dichlorocyclopropyl, trans-2-chlorocyclopropyl, cis-2-chlorocyclopropyl, 2,2-difluorocyclopropyl, trans-2-fluorocyclopropyl, cis-2-fluorocyclopropyl, trans-4-hydroxycyclohexyl, 4-trifluoromethylcyclohexyl, prop-2-enyl, 2-methylprop-2-enyl, prop-2-ynyl, 1,1-dimethylbut-2-ynyl, 3-chloro-prop-2-enyl, 3-fluoro-prop-2-enyl, 3,3-dichloro-prop-2-enyl, 3,3-dichloro-1,1-dimethylprop-2-enyl, oxetan-3-yl, thietan-3-yl, 1-oxido-thietan-3-yl, 1,1-dioxido-thietan-3-yl, isoxazol-3-ylmethyl, 1,2,4-triazol-3-ylmethyl, 3-methyloxetan-3-ylmethyl, benzyl, 2,6-difluorophenylmethyl, 3-fluorophenylmethyl, 2-fluorophenylmethyl, 2,5-difluorophenylmethyl, 1-phenylethyl, 4-chlorophenylmethyl, 2-trifluoromethylphenylethyl, 1-pyridin-2-ylethyl, pyridin-2-ylmethyl, 5-fluoropyridin-2-ylmethyl, (6-chloro-pyridin-3-yl)methyl, pyrimidin-2-ylmethyl, methoxy, 2-ethoxyethyl, 2-methoxyethyl, 2-(methylsulfanyl)ethyl, 1-methyl-2-(ethylsulfanyl)ethyl, 2-methyl-1-(methylsulfanyl)propan-2-yl, methoxycarbonyl, methoxycarbonylmethyl, $NH_2$, N-ethylamino, N-allylamino, N,N-dimethylamino, N,N-diethylamino, 2-thienylmethyl, isopropyl, isobutyl, methylsulfonyl, methylsulfinyl, 3-(methylsulfanyl)-cyclobutyl, 2-oxo-2[(2,2,2)-trifluoroethyl)amino]ethyl, 1-($CF_3$)cyclopropyl, 2-methylcyclopropyl, 1,1,1-trifluoropropan-2-yl, buta-2,3-dien-1-yl, 3-chloroprop-2-en-1-yl, 3-cyanothientan-3-yl, 3-(methylsulfonyl)cyclobutyl, 4-fluorophenyl, 2-[(methylsulfinyl)methyl]cyclobutyl, 3-methylbutan-2-yl, 2-(methylsulfonyl)cyclobutyl, 2-(dimethylamino)ethyl and 2-methoxyethyl; or
Q is selected from phenyl, naphthyl, pyridazine, pyrazine, pyrimidine, triazine, pyridine, pyrazole, thiazole isothiazole, oxazole, isoxazole, triazole, imidazole, furan, thiophene, pyrrole, oxadiazole, thiadiazole, tetrazole and tetrahydrofuran, each of which is unsubstituted or substituted with 1 to 4 substituents independently selected from V;
V is selected from fluoro, chloro, bromo, iodo, cyano, nitro, methyl, ethyl, difluoromethyl, hydroxyl, trichloromethyl, chlorodifluoromethyl, dichlorofluoromethyl, trifluoromethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl heptafluoro-n-propyl, heptafluoro-isopropyl, nonafluoro-n-butyl, cyclopropyl, cyclobutyl, methoxy, ethoxy, n-propoxy, 1-methylethoxy, fluoromethoxy, difluoromethoxy, chloro-difluoromethoxy, dichloro-fluoromethoxy, trifluoromethoxy, 2,2,2-trifluoroethoxy, 2-chloro-2,2-difluorethoxy, pentafluorethoxy, N-methoxyiminomethyl, 1-(N-methoxyimino)-ethyl, methylsulfanyl, methylsulfonyl, methylsulfinyl, trifluoromethylsulfonyl, trifluoromethylsulfinyl, trifluoromethylsulfanyl and N,N-dimethylamino.

Embodiment 12

A compound or salt according to any one of embodiments 1 to 9, wherein
Q is selected from 1-cyano-cyclopropyl, (E)-1,2,3,3,3-pentafluoroprop-1-enyl, cyanomethyl, benzyl, cyclopropyl, methyl, ethyl, 2-thienylmethyl, carbamothioylcyclopropyl, pyrid-4-yl, 2,2,2-trifluorethyl, methylsulfonyl, thietan-3-yl and 1-carbamoyl-cyclopropyl;

Embodiment 12.1

A compound or salt according to any one of embodiments 1 to 9, wherein
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoyl-cyclopropyl.

Embodiment 13

A compound or salt according to any one of embodiments 1 to 12, wherein
W is O.

Embodiment 14

A compound or salt according to any one of embodiments 1 to 13, wherein
$A^1$ is $CR^2$ or N;
$A^2$ is $CR^3$ or N;
$A^3$ is $CR^4$ or N;
$A^4$ is $CR^5$ or N;
with the proviso that no more than 3 of $A^1$, $A^2$, $A^3$ and $A^4$ are N;
$R^2$ and $R^5$ are independently selected from H, methyl, fluoro and chloro;
$R^3$ and $R^4$ are independently selected from H, fluoro, chloro, bromo, iodo, cyano, nitro, methyl, ethyl, fluoromethyl, difluoromethyl, chlorodifluoromethyl, trifluoromethyl, 2,2,2-trifluoroethyl, methoxy, ethoxy, n-propoxy, 1-methylethoxy, fluoromethoxy, difluoromethoxy, chloro-difluoromethoxy, dichloro-fluoromethoxy, trifluoromethoxy, 2,2,2-trifluoroethoxy, 2-chloro-2,2-difluorethoxy, pentafluoroethoxy, N-methoxyiminomethyl, 1-(N-methoxyimino)-ethyl, methylsulfanyl, trifluoromethylsulfanyl, methylsulfonyl, methylsulfinyl, trifluoromethylsulfonyl and trifluoromethylsulfinyl.

Embodiment 15

A compound or salt according to any one of embodiments 1 to 13, wherein
$A^1$ and $A^4$ are CH;
$A^2$ is CH, CF or N;
$A^3$ is CH or CCl.

Embodiment 15.1

A compound or salt according to any one of embodiments 1 to 13, wherein
$A^1$ and $A^4$ are CH;
$A^2$ is CH or CF;
$A^3$ is CH or CCl.

Embodiment 16

A compound or salt according to any one of embodiments 1 to 15, wherein
$R^{6a}$, $R^{7a}$ and $R^{8a}$ are independently selected from H, halogen, cyano, nitro, amino, methyl, ethyl, propyl, 1-methylethyl, tert-butyl, trifluoromethyl, difluoromethyl, methoxy, ethoxy, trifluoromethoxy, 2,2-difluoroethoxy, 2,2,2-trifluoroethoxy, methylcarbonyl, ethylcarbonyl, trifluoromethylcarbonyl, methylsulfanyl, methylsulfinyl, methylsulfonyl, trifluoromethylsulfonyl, trifluoromethylsulfanyl and trifluoromethylsulfinyl;
$R^{6b}$, $R^{7b}$ and $R^{8b}$ are independently selected from H or methyl.

Embodiment 17

A compound or salt according to any one of embodiments 1 to 15, wherein
$R^{6a}$, $R^{7a}$ and $R^{8a}$ are independently selected from H, methyl and trifluoromethoxy; $R^{6b}$, $R^{7b}$ and $R^{8b}$ are independently selected from H and methyl.

Embodiment 18

A compound or salt according to any one of embodiments 1 to 17, wherein U is —O—.

Embodiment 19

A compound or salt according to any one of embodiments 1 to 17, wherein U is selected from —S—, —SO— and —SO$_2$—.

Embodiment 20

A compound or salt according to any one of embodiments 1 to 17, wherein U is —S—.

Embodiment 21

A compound or salt according to any one of embodiments 1 to 17, wherein U is —SO—.

Embodiment 22

A compound or salt according to any one of embodiments 1 to 17, wherein U is —SO$_2$—.

Embodiment 22.1

A compound or salt according to any one of embodiments 1 to 17, wherein U is —NR$^{100}$—, and R$^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-akylcarbonyl, $C_1$-$C_6$-alkoxycarbonyl and $C_3$-$C_6$-cycloakyl, wherein each of $C_1$-$C_6$-akyl, $C_2$-$C_6$-alkenyl, $C_2$-$C_6$-alkynyl, $C_1$-$C_6$-alkoxy and $C_3$-$C_6$-cycloalkyl is

21 unsubstituted or substituted with 1 to 13 substituents independently selected from halogen.

Embodiment 22.2

A compound or salt according to any one of embodiments 1 to 17, wherein U is —NR$^{100}$—, and R$^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-akylcarbonyl, $C_1$-$C_6$-alkoxycarbonyl and $C_3$-$C_6$-cycloakyl, wherein each of $C_1$-$C_6$-akyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen.

Embodiment 23

A compound or salt according to any one of embodiments 1 to 22, wherein
$Z^1$ is selected from $C_1$-$C_{10}$-alkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_2$-$C_{10}$-alkenyl, $C_2$-$C_{10}$-alkynyl, —($C_0$-$C_6$-alkyl)-$C_3$-$C_7$ heterocycloalkyl, —($C_0$-$C_6$-alkyl)-$C_3$-$C_6$-cycloalkyl and $C_1$-$C_{10}$-alkylsulfonyl, wherein each of $C_1$-$C_{10}$-alkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_2$-$C_{10}$-alkenyl, $C_2$-$C_{10}$-alkynyl, —($C_0$-$C_6$-alkyl)-$C_3$-$C_7$ heterocycloalkyl, —($C_0$-$C_6$-alkyl)-$C_3$-$C_6$-cycloalkyl and $C_1$-$C_{10}$-alkylsulfonyl is unsubstituted or substituted with 1 to 20 substituents independently selected from halogen.

Embodiment 23.1

A compound or salt according to any one of embodiments 1 to 22, wherein
$Z^1$ is selected from $C_1$-$C_6$-alkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_2$-$C_{10}$-alkenyl, $C_2$-$C_6$-alkynyl, —($C_0$-$C_6$-alkyl)-$C_3$-$C_7$ heterocycloalkyl, —($C_0$-$C_6$-alkyl)-$C_3$-$C_6$-cycloalkyl, wherein each of $C_1$-$C_6$-alkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_2$-$C_6$-alkenyl, $C_2$-$C_6$-alkynyl, —($C_0$-$C_6$-alkyl)-$C_3$-$C_7$ heterocycloalkyl, —($C_0$-$C_6$-alkyl)-$C_3$-$C_6$-cycoalkyl is unsubstituted or substituted with 1 to 8 substituents independently selected from halogen.

Embodiment 23.2

A compound or salt according to any one of embodiments 1 to 22, wherein
$Z^1$ is selected from $C_1$-$C_{10}$-alkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_2$-$C_{10}$-alkenyl and $C_1$-$C_{10}$-alkylsulfonyl, wherein each of $C_1$-$C_6$-alkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_2$-$C_{10}$-alkenyl and $C_1$-$C_{10}$-alkylsulfonyl is unsubstituted or substituted with 1 to 20 substituents independently selected from halogen.

Embodiment 23.3

A compound or salt according to embodiment 18, wherein $Z^1$ is selected from $C_1$-$C_{10}$-alkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_2$-$C_{10}$-alkenyl and $C_1$-$C_{10}$-alkylsulfonyl, wherein each of $C_1$-$C_6$-alkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_2$-$C_{10}$-alkenyl and $C_1$-$C_{10}$-alkylsulfonyl is unsubstituted or substituted with 1 to 20 substituents independently selected from halogen.

22

Embodiment 23.4

A compound or salt according to embodiment 18, wherein $Z^1$ is selected from $C_1$-$C_{10}$-alkyl, which is unsubstituted or substituted with 1 to 20 substituents independently selected from halogen.

Embodiment 23.5

A compound or salt according to embodiment 18, wherein $Z^1$ is selected from $C_1$-$C_6$-alkoxy-$C_1$-$C_6$-akyl, which is unsubstituted or substituted with 1 to 20 substituents independently selected from halogen.

Embodiment 23.6

A compound or salt according to embodiment 18, wherein $Z^1$ is selected from $C_1$-$C_6$-alkoxy-$C_1$-$C_6$-alkoxy-$C_1$-$C_6$-akyl, which is unsubstituted or substituted with 1 to 20 substituents independently selected from halogen.

Embodiment 23.7

A compound or salt according to embodiment 18, wherein $Z^1$ is selected from $C_2$-$C_{10}$-alkenyl, which is unsubstituted or substituted with 1 to 20 substituents independently selected from halogen.

Embodiment 23.8

A compound or salt according to embodiment 18, wherein $Z^1$ is selected from $C_1$-$C_{10}$-alkylsulfonyl, which is unsubstituted or substituted with 1 to 20 substituents independently selected from halogen.

Embodiment 23.9

A compound or salt according to any one of embodiments 1 to 17, wherein
U—$Z^1$ is selected from
difluoromethoxy;
2,2,2-trifluoroethoxy;
1,1,2,3,3,3-hexafluoropropoxy;
methoxy;
1,1,2,2-tetrafluoroethoxy;
2-bromo-1,1,2,2-tetrafluoroethoxy;
1,1,2,3,4,4,4-heptafluoro-3-(trifluoromethyl)butoxy;
1,1,2,4,4,4-hexafluoro-3-(trifluoromethyl)but-2-enoxy;
1,1,2-trifluoro-2-(trifluoromethoxy)ethoxy;
trifluoromethylsulfonate;
1,1,2-trifluoro-2-(1,1,2,2,3,3,3-heptafluoropropoxy)ethoxy;
2,2-difluoro-2-[1,1,2,2-tetrafluoro-2-(trifluoromethoxy)ethoxy]ethoxy;
2,2,3,3,4,4,4-heptafluorobutoxy;
5,6,6-trifluorohex-5-enoxy;
2,2,3,3,4,4,5,5,6,6,7,7,8,8,8-pentadecafluorooctoxy;
2,2-difluoroethoxy;
2,2,3,3,4,4,5,5-octafluoropentoxy;
2-(trifluoromethoxy)ethoxy;
2,2,3,3-tetrafluoropropoxy;
1,1,2,2,3,3,3-heptafluoropropoxy;
1,1,2,2,3,3,4,4,4-nonafluorobutane-1-sulfonate;
1,1,2,2,3,3,4,4,5,5,6,6-tridecafluorohexoxy;
1,1,2,2,3,3,4,4,5,5,6,6,7,7,8,8,-heptadeccafluorooctoxy;
2-bromo-1,1-difluoro-ethoxy;
(E)-2,3,3,3-tetrafluoro-1-(trifluoromethyl)prop-1-enoxy;
2-bromo-1,1,2-trifluoro-ethoxy;

2-chloro-1,1,2-trifluoro-ethoxy;
(1E)-1,2-difluorobuta-1,3-dienoxy;
3,4,4-trifluorobut-3-enoxy;
(Z)-1,3,3,3-tetrafluoroprop-1-enoxy;
(Z)-2-fluoro-1-(trifluoromethyl)vinyloxy;
2,2,3,3,4,4,5,5-octafluoropentoxy;
1,1,2,3,4,5,5,5-octafluoro-2-(trifluoromethyl)pent-3-enoxy;
1,2,3,3,3-pentafluoroprop-1-enoxy;
3,3,4,4,5,5,6,6,7,7,8,8-tridecafluorooctylsulfanyl;
2,2,3,3-tetrafluoropropylsulfanyl;
1,1,2,3,3,3-hexafluoropropoxy;
1,1,2-trifluoro-2-(trifluoromethoxy)ethoxy;
trifluoromethylsulfanyl;
1,1,2,2,3,3,3-heptafluoropropylsulfanyl;
1,1,2,3,3,3-hexafluoropropoxy;
1,1,2,3,3-pentachloroallyloxy;
1,1,2,3,3-hexafluoropropoxy;
1,1,2,3,3-pentachloroallyloxy;
1,1,2-trifluoropropoxy;
2,2,2-trifluoroethylamino;
2-bromo-1,1,2-trifluoro-ethoxy; and
2-bromo-2-chloro-1,1-difluoro-ethoxy.

Embodiment 24

A compound or salt according to any one of embodiments 1 to 22, wherein
$Z^1$ is selected from $C_1$-$C_6$-alkyl and $C_1$-$C_6$-alkoxy-$C_1$-$C_6$-alkyl, wherein $C_1$-$C_6$-alkyl is unsubstituted or substituted with 1 to 8 substituents independently selected from halogen.

Embodiment 25

A compound or salt according to any one of embodiments 1 to 22, wherein
$Z^1$ is selected from $C_1$-$C_6$-alkyl, wherein $C_1$-$C_6$-alkyl is unsubstituted or substituted with 1 to 8 fluoro substituents.

Embodiment 26

A compound or salt according to any one of embodiments 1 to 22, wherein
$Z^1$ is selected from —$CF_2H$, —$CF_3$, —$CF_2CFHCF_3$, —$CF_2CF_2CF_3$, —$CF_2CF_2H$, —$CF_2CF_2OCF_3$, —$CH_2CF_2CF_3$, —$CH(CF_3)CH_2CF_3$ and —$CH_2CF_3$ Embodiment 27

A compound or salt according to any one of embodiments 1 to 22, wherein
$Z^1$ is selected from methyl, ethyl, 1,1-dimethylethyl, difluoromethyl, trichloromethyl, chlorodifluoromethyl, dichlorofluoromethyl, trifluoromethyl, bromodichloromethyl, 1-fluoroethyl, 1-fluoro-1-methylethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, heptafluoro-n-propyl, heptafluoro-isopropyl, nonafluoro-n-butyl, cyclopropyl, 1-chlorocyclopropyl, 1-fluorocyclopropyl, 1-bromocyclopropyl, 1-cyano-cyclopropyl, 1-trifluoromethyl-cyclopropyl, cyclobutyl and 2,2-difluoro-1-methyl-cyclopropyl;
$Z^2$ is selected from H, halogen, cyano, nitro, amino, methyl, ethyl, 1,1-dimethylethyl, difluoromethyl, trichloromethyl, chlorodifluoromethyl, dichlorofluoromethyl, trifluoromethyl, bromodichloromethyl, 1-fluoroethyl, 1-fluoro-1-methylethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl heptafluoro-n-propyl, heptafluoro-isopropyl, nonafluoro-n-butyl, methylsulfanyl, methylsulfinyl, methylsulfonyl, ethylthio, ethylsulfinyl, ethylsulfonyl, trifluoromethylsulfanyl, trifluoromethylsulfinyl, trifluoromethylsulfonyl, chloro-difluoromethylsulfanyl, chloro-difluoromethylsulfinyl, chloro-difluoromethylsulfonyl, dichloro-fluoromethylsulfanyl, dichloro-fluoromethylsulfinyl, dichloro-fluoromethylsulfonyl; and
$Z^3$ is selected from H, methyl, ethyl, n-propyl, isopropyl, n-butyl, isobutyl, s-butyl, t-butyl, ethenyl, 1-propenyl, 1-propynyl, 1-butynyl, difluoromethyl, trichloromethyl, chlorodifluoromethyl, dichlorofluoromethyl, trifluoromethyl, 1-fluoroethyl, 1 fluoro-1-methylethyl, 2-fluoroethyl, 2,2-difluoroethyl, 2,2,2-trifluoroethyl, phenyl, 2-chlorophenyl, 3-chlorophenyl, 4-chlorophenyl, 2,5-dichlorophenyl, 3,4-dichlorophenyl, 2,6-dichlorophenyl 2,6dichloro-4-trifluoromethylphenyl, 3-chlor-5-trifluoromethylpyridin-2-yl, 4-$NO_2$-phenyl and 3-chloro-pyridin-2-yl.

Embodiment 28

A compound or salt according to any one of embodiments 1 to 17, wherein
U—$Z_1$ is selected from
difluoromethoxy;
2,2,2-trifluoroethoxy;
1,1,2,3,3,3-hexafluoropropoxy;
methoxy;
1,1,2,2-tetrafluoroethoxy;
2-bromo-1,1,2,2-tetrafluoroethoxy;
1,1,2,3,4,4,4-heptafluoro-3-(trifluoromethyl)butoxy;
1,1,2,4,4,4-hexafluoro-3-(trifluoromethyl)but-2-enoxy;
1,1,2-trifluoro-2-(trifluoromethoxy)ethoxy;
trifluoromethylsulfonate;
1,1,2-trifluoro-2-(1,1,2,2,3,3,3-heptafluoropropoxy)ethoxy;
2,2-difluoro-2-[1,1,2,2-tetrafluoro-2-(trifluoromethoxy)ethoxy]ethoxy;
2,2,3,3,4,4,4-heptafluorobutoxy;
5,6,6-trifluorohex-5-enoxy;
2,2,3,3,4,4,5,5,6,6,7,7,8,8,8-pentadecafluorooctoxy;
2,2-difluoroethoxy;
2,2,3,3,4,4,5,5-octafluoropentoxy;
2-(trifluoromethoxy)ethoxy;
2,2,3,3-tetrafluoropropoxy;
1,1,2,2,3,3,3-heptafluoropropoxy;
1,1,2,2,3,3,4,4,4-nonafluorobutane-1-sulfonate;
1,1,2,2,3,3,4,4,5,5,6,6-tridecafluorohexoxy;
1,1,2,2,3,3,4,4,5,5,6,6,7,7,8,8,8-heptadeccafluorooctoxy;
2-bromo-1,1-difluoro-ethoxy;
(E)-2,3,3,3-tetrafluoro-1-(trifluoromethyl)prop-1-enoxy;
2-bromo-1,1,2-trifluoro-ethoxy;
2-chloro-1,1,2-trifluoro-ethoxy;
(1E)-1,2-difluorobuta-1,3-dienoxy;
3,4,4-trifluorobut-3-enoxy;
(Z)-1,3,3,3-tetrafluoroprop-1-enoxy;
(Z)-2-fluoro-1-(trifluoromethyl)vinyloxy;
2,2,3,3,4,4,5,5-octafluoropentoxy;
1,1,2,3,4,5,5,5-octafluoro-2-(trifluoromethyl)pent-3-enoxy;
1,2,3,3,3-pentafluoroprop-1-enoxy;
3,3,4,4,5,5,6,6,7,7,8,8-tridecafluorooctylsulfanyl;
2,2,3,3-tetrafluoropropylsulfanyl;
1,1,2,3,3,3-hexafluoropropoxy;
1,1,2-trifluoro-2-(trifluoromethoxy)ethoxy;
trifluoromethylsulfanyl;

1,1,2,2,3,3,3-heptafluoropropylsulfanyl;
1,1,2,3,3,3-hexafluoropropoxy;
1,1,2,3,3-pentachloroallyloxy;
1,1,2,3,3,3-hexafluoropropoxy;
1,1,2,3,3-pentachloroallyloxy;
1,1,2-trifluoropropoxy;
2,2,2-trifluoroethylamio;
2-bromo-1,1,2-trifluoro-ethoxy; and
2-bromo-2-chloro-1,1-difluoro-ethoxy;
$Z^2$ is $CF_3$;
$Z^3$ is selected from methyl, ethyl, phenyl, 4-$NO_2$-phenyl and 3-chloro-pyridin-2-yl.

Embodiment 25.1

A compound or salt according to any one of embodiments 1 to 22, wherein
U is —O—;
$Z^1$ is selected from —$CF_2H$, —$CF_2CFHCF_3$, —$CF_2CF_2CF_3$, —$CF_2CF_2H$, —$CF_2CF_2OCF_3$, —$CH_2CF_2CF_3$, —$CH(CF_3)CH_2CF_3$ and —$CH_2CF_3$;
$Z^2$ is $CF_3$;
$Z^3$ is selected from methyl, ethyl, phenyl, 4-$NO_2$-phenyl and 3-chloro-pyridin-2-yl.

Embodiment 29

A compound or salt according to any one of embodiments 1 to 4, wherein
$R^1$ is H;
Q is selected from 1-cyano-cyclopropyl, (E)-1,2,3,3,3-pentafluoroprop-1-enyl, cyanomethyl, benzyl, cyclopropyl, methyl, ethyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ is $CR^2$ or N;
$A^2$ is $CR^3$ or N;
$A^3$ is $CR^4$ or N;
$A^4$ is $CR^5$ or N;
with the proviso that no more than 3 of $A^1$, $A^2$, $A^3$ and $A^4$ are N;
$R^2$ and $R^5$ are independently selected from H, methyl, fluoro and chloro;
$R^3$ and $R^4$ are independently selected from H, fluoro, chloro, bromo, iodo, cyano, nitro, methyl, ethyl, fluoromethyl, difluoromethyl, chlorodifluoromethyl, trifluoromethyl, 2,2,2-trifluoroethyl, methoxy, ethoxy, n-propoxy, 1-methylethoxy, fluoromethoxy, difluoromethoxy, chloro-difluoromethoxy, dichloro-fluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)-ethyl, methylsulfanyl, trifluoromethylsulfanyl, methylsulfonyl, methylsulfinyl, trifluoromethylsulfonyl and trifluoromethylsulfinyl;
U—$Z^1$ is selected from
difluoromethoxy;
2,2,2-trifluoroethoxy;
1,1,2,3,3-hexafluoropropoxy;
methoxy;
1,1,2,2-tetrafluoroethoxy;
2-bromo-1,1,2,2-tetrafluoroethoxy;
1,1,2,3,4,4,4-heptafluoro-3-(trifluoromethyl)butoxy;
1,1,2,4,4,4-hexafluoro-3-(trifluoromethyl)but-2-enoxy;
1,1,2-trifluoro-2-(trifluoromethoxy)ethoxy;
trifluoromethylsulfonate;
1,1,2-trifluoro-2-(1,1,2,2,3,3,3-heptafluoropropoxy)ethoxy;
2,2-difluoro-2-[1,1,2,2-tetrafluoro-2-(trifluoromethoxy)ethoxy]ethoxy;
2,2,3,3,4,4-heptafluorobutoxy;
5,6,6-trifluorohex-5-enoxy;
2,2,3,3,4,4,5,5,6,6,7,7,8,8,8-pentadecafluorooctoxy;
2,2-difluoroethoxy;
2,2,3,3,4,4,5,5-octafluoropentoxy;
2-(trifluoromethoxy)ethoxy;
2,2,3,3-tetrafluoropropoxy;
1,1,2,2,3,3,3-heptafluoropropoxy;
1,1,2,2,3,3,4,4,4-nonafluorobutane-1-sulfonate;
1,1,2,2,3,3,4,4,5,5,6,6-tridecafluorohexoxy;
1,1,2,2,3,3,4,4,5,5,6,6,7,7,8,8,-heptadeccafluorooctoxy;
2-bromo-1,1-difluoro-ethoxy;
(E)-2,3,3,3-tetrafluoro-1-(trifluoromethyl)prop-1-enoxy;
2-bromo-1,1,2-trifluoro-ethoxy;
2-chloro-1,2-trifluoro-ethoxy;
(1E)-1,2-difluorobuta-1,3-dienoxy;
3,4,4-trifluorobut-3-enoxy;
(Z)-1,3,3,3-tetrafluoroprop-1-enoxy;
(Z)-2-fluoro-1-(trifluoromethyl)vinyloxy;
2,2,3,3,4,4,5,5-octafluoropentoxy;
1,1,2,3,4,5,5,5-octafluoro-2-(trifluoromethyl)pent-3-enoxy;
1,2,3,3,3-pentafluoroprop-1-enoxy;
3,3,4,4,5,5,6,6,7,7,8,8,8-tridecafluorooctylsulfanyl;
2,2,3,3-tetrafluoropropylsulfanyl;
1,1,2,3,3,3-hexafluoropropoxy;
1,1,2-trifluoro-2-(trifluoromethoxy)ethoxy;
trifluoromethylsulfanyl;
1,1,2,2,3,3,3-heptafluoropropylsulfanyl;
1,1,2,3,3,3-hexafluoropropoxy;
1,1,2,3,3-pentachloroallyloxy;
1,1,2,3,3,3-hexafluoropropoxy;
1,1,2,3,3-pentachloroallyloxy;
1,1,2-trifluoropropoxy;
2,2,2-trifluoroethylamino;
2-bromo-1,1,2-trifluoro-ethoxy; and
2-bromo-2-chloro-1,1-difluoro-ethoxy;
$Z^2$ is selected from H, halogen, cyano, nitro, amino, methyl, ethyl, 1,1-dimethylethyl, difluoromethyl, trichloromethyl, chlorodifluoromethyl, dichlorofluoromethyl, trifluoromethyl, bromodichloromethyl, 1-fluoroethyl, 1-fluoro-1 methylethyl, 2-fluoroethyl, 2,2-difluoroethyl, 2,2,2-trifluoroethyl, 1,2,2,2-tetrafluoroethyl, 1-chlor-1,2,2,2-tetrafluoroethyl, 2,2,2-trichloroethyl, 2-chloro-2,2-difluoroethyl, 1,1-difluoroethyl, pentafluoroethyl heptafluoro-n-propyl, heptafluoro-isopropyl, nonafluoro-n-butyl, methylsulfanyl, methylsulfinyl, methylsulfonyl, ethylthio, ethylsulfinyl, ethylsulfonyl, trifluoromethylsulfanyl, trifluoromethylsulfinyl, trifluoromethylsulfonyl, chloro-difluoromethylsulfanyl, chloro-difluoromethylsulfinyl, chloro-difluoromethylsulfonyl, dichloro-fluoromethylsulfanyl, dichloro-fluoromethylsulfinyl, dichloro-fluoromethylsulfonyl; and
$Z^3$ is selected from H, methyl, ethyl, n-propyl, isopropyl, n-butyl, isobutyl, s-butyl, t-butyl, ethenyl, 1-propenyl, 1-propynyl, 1-butynyl, difluoromethyl, trichloromethyl, chlorodifluoromethyl, dichlorofluoromethyl, trifluoromethyl, 1-fluoroethyl, 1 fluoro-1-methylethyl, 2-fluoroethyl, 2,2-difluoroethyl, 2,2,2-trifluoroethyl, phenyl, 2-chlorophenyl, 3-chlorophenyl, 4-chlorophenyl, 2,5-dichlorophenyl, 3,4-dichlorophenyl, 2,6-dichlorphenyl 2,6-dichloro-4-trifluoromethylphenyl, 3-chlor-5-trifluoromethylpyridin-2-yl, 4-$NO_2$-phenyl and 3-chloro-pyridin-2-yl.

Embodiment 29.1

A compound or salt according to any one of embodiments 1 to 4, wherein
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ is $CR^2$ or N;
$A^2$ is $CR^3$ or N;
$A^3$ is $CR^4$ or N;
$A^4$ is $CR^5$ or N;
with the proviso that no more than 3 of $A^1$, $A^2$, $A^3$ and $A^4$ are N;
$R^2$ and $R^5$ are independently selected from H, methyl, fluoro and chloro;
$R^3$ and $R^4$ are independently selected from H, fluoro, chloro, bromo, iodo, cyano, nitro, methyl, ethyl, fluoromethyl, difluoromethyl, chlorodifluoromethyl, trifluoromethyl, 2,2,2-trifluoroethyl, methoxy, ethoxy, n-propoxy, 1-methylethoxy, fluoromethoxy, difluoromethoxy, chloro-difluoromethoxy, dichloro-fluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)-ethyl, methylsulfanyl, trifluoromethylsulfanyl, methylsulfonyl, methylsulfinyl, trifluoromethylsulfonyl and trifluoromethylsulfinyl;
U is selected from —O—, —S—, —SO—, —$SO_2$— and —$NR^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from methyl, ethyl, 1,1-dimethylethyl, difluoromethyl, trichloromethyl, chlorodifluoromethyl, dichlorofluoromethyl, trifluoromethyl, bromodichloromethyl, 1-fluoroethyl, 1-fluoro-1-methylethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl heptafluoro-n-propyl, heptafluoro-isopropyl, nonafluoro-n-butyl, cyclopropyl, 1-chlorocyclopropyl, 1-fluoro-cyclopropyl, 1-bromocyclopropyl, 1-cyano-cyclopropyl, 1-trifluoromethyl-cyclopropyl, cyclobutyl and 2,2-difluoro-1-methyl-cyclopropyl;
$Z^2$ is selected from H, halogen, cyano, nitro, amino, methyl, ethyl, 1,1-dimethylethyl, difluoromethyl, trichloromethyl, chlorodifluoromethyl, dichlorofluoromethyl, trifluoromethyl, bromodichloromethyl, 1-fluoroethyl, 1-fluoro-1 methylethyl, 2-fluoroethyl, 2,2-difluoroethyl, 2,2,2-trifluoroethyl, 1,2,2,2-tetrafluoroethyl, 1-chlor-1,2,2,2-tetrafluoroethyl, 2,2,2-trichloroethyl, 2-chloro-2,2-difluoroethyl, 1,1-difluoroethyl, pentafluoroethyl heptafluoro-n-propyl, heptafluoro-isopropyl, nonafluoro-n-butyl, methylsulfanyl, methylsulfinyl, methylsulfonyl, ethylthio, ethylsulfinyl, ethylsulfonyl, trifluoromethylsulfanyl, trifluoromethylsulfinyl, trifluoromethylsulfonyl, chloro-difluoromethylsulfanyl, chloro-difluoromethylsulfinyl, chloro-difluoromethylsulfonyl, dichloro-fluoromethylsulfanyl, dichloro-fluoromethylsulfinyl, dichloro-fluoromethylsulfonyl;
$Z^3$ is selected from H, methyl, ethyl, n-propyl, isopropyl, n-butyl, isobutyl, s-butyl, t-butyl, ethenyl, 1-propenyl, 1-propynyl, 1-butynyl, difluoromethyl, trichloromethyl, chlorodifluoromethyl, 5 dichlorofluoromethyl, trifluoromethyl, 1-fluoroethyl, 1 fluoro-1-methylethyl, 2-fluoroethyl, 2,2-difluoroethyl, 2,2,2-trifluoroethyl, phenyl, 2-chlorophenyl, 3-chlorophenyl, 4-chlorophenyl, 2,5-dichlorophenyl, 3,4-dichlorophenyl, 2,6-dichlorophenyl 2,6-dichloro-4-trifluoromethylphenyl, 3-chlor-5-trifluoromethylpyridin-2-yl, 4-$NO_2$-phenyl and 3-chloro-pyridin-2-yl.

Embodiment 30

A compound or salt according to any one of embodiments 1 to 4, wherein
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ is $CR^2$ or N;
$A^2$ is $CR^3$ or N;
$A^3$ is $CR^4$ or N;
$A^4$ is $CR^5$ or N;
with the proviso that no more than 3 of $A^1$, $A^2$, $A^3$ and $A^4$ are N;
$R^2$ and $R^5$ are independently selected from H, methyl, fluoro and chloro;
$R^3$ and $R^4$ are independently selected from H, fluoro, chloro, bromo, iodo, cyano, nitro, methyl, ethyl, fluoromethyl, difluoromethyl, chlorodifluoromethyl, trifluoromethyl, 2,2,2-trifluoroethyl, methoxy, ethoxy, n-propoxy, 1-methylethoxy, fluoromethoxy, difluoromethoxy, chloro-difluoromethoxy, dichloro-fluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)-ethyl, methylsulfanyl, trifluoromethylsulfanyl, methylsulfonyl, methylsulfinyl, trifluoromethylsulfonyl and trifluoromethylsulfinyl;
U is selected from —O—, —S—, —SO—, —$SO_2$— and —$NR^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —$CF_2H$, —$CF_2CFHCF_3$, —$CF_2CF_2CF_3$, —$CF_2CF_2H$, —$CF_2CF_2OCF_3$, —$CH_2CF_2CF_3$, —$CH(CF_3)CH_2CF_3$ and —$CH_2CF_3$;
$Z^2$ is selected from H, halogen, cyano, nitro, amino, methyl, ethyl, 1,1-dimethylethyl, difluoromethyl, trichloromethyl, chlorodifluoromethyl, dichlorofluoromethyl, trifluoromethyl, bromodichloromethyl, 1-fluoroethyl, 1-fluoro-1 methylethyl, 2-fluoroethyl, 2,2-difluoroethyl, 2,2,2-trifluoroethyl, 1,2,2,2-tetrafluoroethyl, 1-chlor-1,2,2,2-tetrafluoroethyl, 2,2,2-trichloroethyl, 2-chloro-2,2-difluoroethyl, 1,1-difluoroethyl, pentafluoroethyl heptafluoro-n-propyl, heptafluoro-isopropyl, nonafluoro-n-butyl, methylsulfanyl, methylsulfinyl, methylsulfonyl, ethylthio, ethylsulfinyl, ethylsulfonyl, trifluoromethylsulfanyl, trifluoromethylsulfinyl, trifluoromethylsulfonyl, chloro-difluoromethylsulfanyl, chloro-difluoromethylsulfinyl, chloro-difluoromethylsulfonyl, dichloro-fluoromethylsulfanyl, dichloro-fluoromethylsulfinyl, dichloro-fluoromethylsulfonyl;
$Z^3$ is selected from H, methyl, ethyl, n-propyl, isopropyl, n-butyl, isobutyl, s-butyl, t-butyl, ethenyl, 1-propenyl, 1-propynyl, 1-butynyl, difluoromethyl, trichloromethyl, chlorodifluoromethyl, dichlorofluoromethyl, trifluoromethyl, 1-fluoroethyl, 1 fluoro-1-methylethyl, 2-fluoroethyl, 2,2-difluoroethyl, 2,2,2-trifluoroethyl, phenyl, 2-chlorophenyl, 3-chlorophenyl, 4-chlorophenyl, 2,5-dichlorophenyl, 3,4-dichlorophenyl, 2,6-dichlorophenyl 2,6-dichloro-4-trifluoromethylphenyl, 3-chlor-5-trifluoromethylpyridin-2-yl, 4-$NO_2$-phenyl and 3-chloro-pyridin-2-yl.

Embodiment 31

A compound or salt according to any one of embodiments 1 to 4, wherein
$R^{6a}$, $R^{7a}$ and $R^{8a}$ are independently selected from H, methyl and trifluoromethoxy;
$R^{6b}$, $R^{7b}$ and $R^{8b}$ are independently selected from H and methyl.
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is —O—;
$Z^1$ is selected from —$CF_2H$, —$CF_2CFHCF_3$, —$CF_2CF_2CF_3$, —$CF_2CF_2H$, —$CF_2CF_2OCF_3$, —$CH_2CF_2CF_3$, —$CH(CF_3)CH_2CF_3$ and —$CH_2CF_3$;
$Z^2$ is $CF_3$;
$Z^3$ is selected from methyl, ethyl, phenyl, 4-$NO_2$-phenyl and 3-chloropyridin-2-yl.

Embodiment 32

A compound or salt according to any one of embodiments 1 to 4, wherein
$R^{6a}$, $R^{7a}$ and $R^{8a}$ are independently selected from H, methyl and trifluoromethoxy;
$R^{6b}$, $R^{7b}$ and $R^{8b}$ are independently selected from H and methyl.
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is —S—;
$Z^1$ is selected from —$CF_2H$, —$CF_2CFHCF_3$, —$CF_2CF_2CF_3$, —$CF_2CF_2H$, —$CF_2CF_2OCF_3$, —$CH_2CF_2CF_3$, —$CH(CF_3)CH_2CF_3$ and —$CH_2CF_3$;
$Z^2$ is $CF_3$;
$Z^3$ is selected from methyl, ethyl, phenyl, 4-$NO_2$-phenyl and 3-chloropyridin-2-yl.

Embodiment 33

A compound or salt according to any one of embodiments 1 to 4, wherein
$R^{6a}$, $R^{7a}$ and $R^{8a}$ are independently selected from H, methyl and trifluoromethoxy;
$R^{6b}$, $R^{7b}$ and $R^{8b}$ are independently selected from H and methyl.
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is —SO—;
$Z^1$ is selected from —$CF_2H$, —$CF_2CFHCF_3$, —$CF_2CF_2CF_3$, —$CF_2CF_2H$, —$CF_2CF_2OCF_3$, —$CH_2CF_2CF_3$, —$CH(CF_3)CH_2CF_3$ and —$CH_2CF_3$.
$Z^2$ is $CF_3$;
$Z^3$ is selected from methyl, ethyl, phenyl, 4-$NO_2$-phenyl and 3-chloropyridin-2-yl.

Embodiment 34

A compound or salt according to any one of embodiments 1 to 4, wherein
$R^{6a}$, $R^{7a}$ and $R^{8a}$ are independently selected from H, methyl and trifluoromethoxy;
$R^{6b}$, $R^{7b}$ and $R^{8b}$ are independently selected from H and methyl.
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is -$SO_2$—;
$Z^1$ is selected from —$CF_2H$, —$CF_2CFHCF_3$, —$CF_2CF_2CF_3$, —$CF_2CF_2H$, —$CF_2CF_2OCF_3$, —$CH_2CF_2CF_3$, —$CH(CF_3)CH_2CF_3$ and —$CH_2CF_3$;
$Z_2$ is $CF_3$;
$Z^3$ is selected from methyl, ethyl, phenyl, 4-$NO_2$-phenyl and 3-chloropyridin-2-yl.

Embodiment 34.1

A compound or salt according to any one of embodiments 1 to 4, wherein
$R^{6a}$, $R^{7a}$, and $R^{8a}$ are independently selected from H, methyl and trifluoromethoxy;
$R^{6b}$, $R^{7b}$ and $R^{8b}$ are independently selected from H and methyl.
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is —$NR^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —$CF_2H$, —$CF_2CFHCF_3$, —$CF_2CF_2CF_3$, —$CF_2CF_2H$, —$CF_2CF_2OCF_3$, —$CH_2CF_2CF_3$, —$CH(CF_3)CH_2CF_3$ and —$CH_2CF_3$;
$Z^2$ is $CF_3$;

$Z^3$ is selected from methyl, ethyl, phenyl, 4-NO$_2$-phenyl and 3-chloropyridin-2-yl.

Embodiment 35

A compound or salt according to embodiment 1, wherein T is

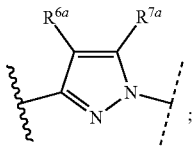

;

$R^{6a}$ and $R^{7a}$ are independently selected from H, methyl and trifluoromethoxy;
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —SO$_2$— and —NR$^{100}$—;
$R^{100}$ is selected from H, C$_1$-C$_6$-alkyl, C$_2$-C$_6$-alkenyl, C$_2$-C$_6$-alkynyl, C$_1$-C$_6$-alkoxy, C$_1$-C$_6$-alkylcarbonyl, C$_1$-C$_6$-alkoxycarbonyl and C$_3$-C$_6$-cycloalkyl, wherein each of C$_1$-C$_6$-alkyl, C$_2$-C$_6$-alkenyl, C$_2$-C$_6$-alkynyl, C$_1$-C$_6$-alkoxy and C$_3$-C$_6$-cycloalkyl is unsubstituted or substituted with 1 to 8 substituents independently selected from halogen;
$Z^1$ is selected from —CF$_2$H, —CF$_2$CFHCF$_3$, —CF$_2$CF$_2$CF$_3$, —CF$_2$CF$_2$H, —CF$_2$CF$_2$OCF$_3$, —CH$_2$CF$_2$CF$_3$, —CH(CF$_3$)CH$_2$CF$_3$ and —CH$_2$CF$_3$;
$Z^2$ is CF$_3$;
$Z^3$ is selected from methyl and ethyl.

Embodiment 36

A compound or salt according to embodiment 1, wherein T is

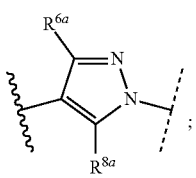

;

$R^{6a}$ and $R^{8a}$ are independently selected from H, methyl and trifluoromethoxy;
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —SO$_2$— and —NR$^{100}$—;
$R^{100}$ is selected from H, C$_1$-C$_6$-alkyl, C$_2$-C$_6$-alkenyl, C$_2$-C$_6$-alkynyl, C$_1$-C$_6$-alkoxy, C$_1$-C$_6$-alkylcarbonyl, C$_1$-C$_6$-alkoxycarbonyl and C$_3$-C$_6$-cycloalkyl, wherein each of C$_1$-C$_6$-alkyl, C$_2$-C$_6$-alkenyl, C$_2$-C$_6$-alkynyl, C$_1$-C$_6$-alkoxy and C$_3$-C$_6$-cycloalkyl is unsubstituted or substituted with 1 to 8 substituents independently selected from halogen;
$Z^1$ is selected from —CF$_2$H, —CF$_2$CFHCF$_3$, —CF$_2$CF$_2$CF$_3$, —CF$_2$CF$_2$H, —CF$_2$CF$_2$OCF$_3$, —CH$_2$CF$_2$CF$_3$, —CH(CF$_3$)CH$_2$CF$_3$ and —CH$_2$CF$_3$;
$Z^2$ is CF$_3$;
$Z^3$ is selected from methyl and ethyl.

Embodiment 37

A compound or salt according to embodiment 1, wherein T is

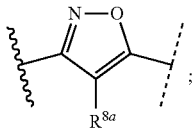

;

$R^{8a}$ is selected from H, methyl and trifluoromethoxy;
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —SO$_2$— and —NR$^{100}$—;
$R^{100}$ is selected from H, C$_1$-C$_6$-alkyl, C$_2$-C$_6$-alkenyl, C$_2$-C$_6$-alkynyl, C$_1$-C$_6$-alkoxy, C$_1$-C$_6$-alkylcarbonyl, C$_1$-C$_6$-alkoxycarbonyl and C$_3$-C$_6$-cycloalkyl, wherein each of C$_1$-C$_6$-alkyl, C$_2$-C$_6$-alkenyl, C$_2$-C$_6$-alkynyl, C$_1$-C$_6$-alkoxy and C$_3$-C$_6$-cycloalkyl is unsubstituted or substituted with 1 to 8 substituents independently selected from halogen;
$Z^1$ is selected from —CF$_2$H, —CF$_2$CFHCF$_3$, —CF$_2$CF$_2$CF$_3$, —CF$_2$CF$_2$H, —CF$_2$CF$_2$OCF$_3$, —CH$_2$CF$_2$CF$_3$, —CH(CF$_3$)CH$_2$CF$_3$ and —CH$_2$CF$_3$;
$Z^2$ is CF$_3$;
$Z^3$ is selected from methyl and ethyl.

Embodiment 38

A compound or salt according to embodiment 1, wherein T is

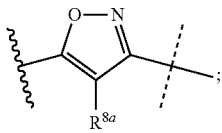

;

$R^{8a}$ is selected from H, methyl and trifluoromethoxy;
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;

W is O;
A¹ and A4 are CH;
A² is CH or CF;
A³ is CH or CCl;
U is selected from —O—, —S—, —SO—, —SO₂— and —NR¹⁰⁰—;
R¹⁰⁰ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
Z¹ is selected from —CF₂H, —CF₂CFHCF₃, —CF₂CF₂CF₃, —CF₂CF₂H, —CF₂CF₂OCF₃, —CH₂CF₂CF₃, —CH(CF₃)CH₂CF₃ and —CH₂CF₃;
Z² is CF₃;
Z³ is selected from methyl and ethyl.

Embodiment 39

A compound or sat according to embodiment 1, wherein T is

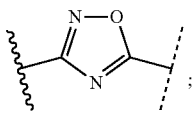

R¹ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
A¹ and A4 are CH;
A² is CH or CF;
A³ is CH or CCl;
U is selected from —O—, —S—, —SO—, —SO₂— and —NR¹⁰⁰—;
R¹⁰⁰ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
Z¹ is selected from —CF₂H, —CF₂CFHCF₃, —CF₂CF₂CF₃, —CF₂CF₂H, —CF₂CF₂OCF₃, —CH₂CF₂CF₃, —CH(CF₃)CH₂CF₃ and —CH₂CF₃;
Z² is CF₃;
Z³ is selected from methyl and ethyl.

Embodiment 40

A compound or salt according to embodiment 1, wherein T is

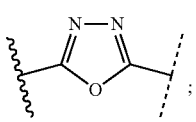

R¹ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
A¹ and A4 are CH;
A² is CH or CF;
A³ is CH or CCl;
U is selected from —O—, —S—, —SO—, —SO₂— and —NR¹⁰⁰—;
R¹⁰⁰ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
Z¹ is selected from —CF₂H, —CF₂CFHCF₃, —CF₂CF₂CF₃, —CF₂CF₂H, —CF₂CF₂OCF₃, —CH₂CF₂CF₃, —CH(CF₃)CH₂CF₃ and —CH₂CF₃;
Z² is CF₃;
Z³ is selected from methyl and ethyl.

Embodiment 41

A compound or sat according to embodiment 1, wherein T is

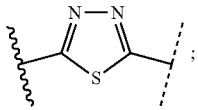

R¹ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
A¹ and A4 are CH;
A² is CH or CF;
A³ is CH or CCl;
U is selected from —O—, —S—, —SO—, —SO₂— and —NR¹⁰⁰—;
R¹⁰⁰ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
Z¹ is selected from —CF₂H, —CF₂CFHCF₃, —CF₂CF₂CF₃, —CF₂CF₂H, —CF₂CF₂OCF₃, —CH₂CF₂CF₃, —CH(CF₃)CH₂CF₃ and —CH₂CF₃;
Z² is CF₃;
Z³ is selected from methyl and ethyl.

Embodiment 42

A compound or salt according to embodiment 1, wherein T is

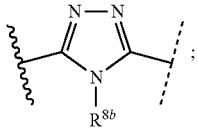

$R^{8b}$ is selected from H, methyl and trifluoromethoxy;
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —SO$_2$— and —NR$^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —CF$_2$H, —CF$_2$CFHCF$_3$, —CF$_2$CF$_2$CF$_3$, —CF$_2$CF$_2$H, —CF$_2$CF$_2$OCF$_3$, —CH$_2$CF$_2$CF$_3$, —CH(CF$_3$)CH$_2$CF$_3$ and —CH$_2$CF$_3$;
$Z^2$ is CF$_3$;
$Z^3$ is selected from methyl and ethyl.

Embodiment 44

A compound or sat according to embodiment 1, wherein T is

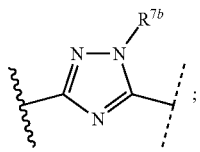

$R^{7D}$ is selected from H, methyl and trifluoromethoxy;
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —SO$_2$— and —NR$^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —CF$_2$H, —CF$_2$CFHCF$_3$, —CF$_2$CF$_2$CF$_3$, —CF$_2$CF$_2$H, —CF$_2$CF$_2$OCF$_3$, —CH$_2$CF$_2$CF$_3$, —CH(CF$_3$)CH$_2$CF$_3$ and —CH$_2$CF$_3$;
$Z^2$ is CF$_3$;
$Z^3$ is selected from methyl and ethyl.

Embodiment 45

A compound or salt according to embodiment 1, wherein T is

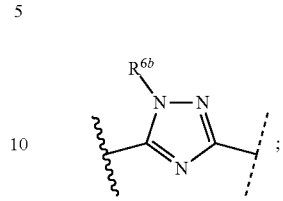

$R^b$ is selected from H, methyl and trifluoromethoxy;
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —SO$_2$— and —NR$^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —CF$_2$H, —CF$_2$CFHCF$_3$, —CF$_2$CF$_2$CF$_3$, —CF$_2$CF$_2$H, —CF$_2$CF$_2$OCF$_3$, —CH$_2$CF$_2$CF$_3$, —CH(CF$_3$)CH$_2$CF$_3$ and —CH$_2$CF$_3$;
$Z^2$ is CF$_3$;
$Z^3$ is selected from methyl and ethyl.

Embodiment 46

A compound or salt according to embodiment 1, wherein T is

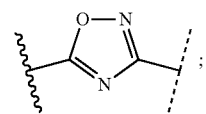

$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —SO$_2$— and —NR$^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;

$Z^1$ is selected from —CF$_2$H, —CF$_2$CFHCF$_3$, —CF$_2$CF$_2$CF$_3$, —CF$_2$CF$_2$H, —CF$_2$CF$_2$OCF$_3$, —CH$_2$CF$_2$CF$_3$, —CH(CF$_3$)CH$_2$CF$_3$ and —CH$_2$CF$_3$;
$Z^2$ is CF$_3$;
$Z^3$ is selected from methyl and ethyl.

Embodiment 47

A compound or sat according to embodiment 1, wherein T is

$R^{6b}$ and $R^{7a}$ are independently selected from H, methyl and trifluoromethoxy;
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and $A4$ are CH;
$A^2$ is CH or CF;
$A^3$ is CH or CCl;
U is selected from —O—, —S—, —SO—, —SO$_2$— and —NR$^{100}$—;
$R^{100}$ is selected from H, C$_1$-C$_6$-alkyl, C$_2$-C$_6$-alkenyl, C$_2$-C$_6$-alkynyl, C$_1$-C$_6$-alkoxy, C$_1$-C$_6$-alkylcarbonyl, C$_1$-C$_6$-alkoxycarbonyl and C$_3$-C$_6$-cycloalkyl, wherein each of C$_1$-C$_6$-alkyl, C$_2$-C$_6$-alkenyl, C$_2$-C$_6$-alkynyl, C$_1$-C$_6$-alkoxy and C$_3$-C$_6$-cycloalkyl is unsubstituted or substituted with 1 to 8 substituents independently selected from halogen;
$Z^1$ is selected from —CF$_2$H, —CF$_2$CFHCF$_3$, —CF$_2$CF$_2$CF$_3$, —CF$_2$CF$_2$H, —CF$_2$CF$_2$OCF$_3$, —CH$_2$CF$_2$CF$_3$, —CH(CF$_3$)CH$_2$CF$_3$ and —CH$_2$CF$_3$;
$Z^2$ is CF$_3$;
$Z^3$ is selected from methyl and ethyl.

Embodiment 48

A compound or salt according to embodiment 1, wherein T is

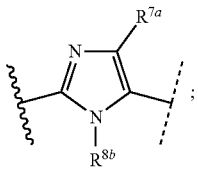

$R^{7a}$ and $R^{8b}$ are selected from H, methyl and trifluoromethoxy;
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and $A4$ are CH;
$A^2$ is CH or CF;
$A^3$ is CH or CCl;
U is selected from —O—, —S—, —SO—, —SO$_2$— and —NR$^{100}$—;
$R^{100}$ is selected from H, C$_1$-C$_6$-alkyl, C$_2$-C$_6$-alkenyl, C$_2$-C$_6$-alkynyl, C$_1$-C$_6$-alkoxy, C$_1$-C$_6$-alkylcarbonyl, C$_1$-C$_6$-alkoxycarbonyl and C$_3$-C$_6$-cycloalkyl, wherein each of C$_1$-C$_6$-alkyl, C$_2$-C$_6$-alkenyl, C$_2$-C$_6$-alkynyl, C$_1$-C$_6$-alkoxy and C$_3$-C$_6$-cycloalkyl is unsubstituted or substituted with 1 to 8 substituents independently selected from halogen;
$Z^1$ is selected from —CF$_2$H, —CF$_2$CFHCF$_3$, —CF$_2$CF$_2$CF$_3$, —CF$_2$CF$_2$H, —CF$_2$CF$_2$OCF$_3$, —CH$_2$CF$_2$CF$_3$, —CH(CF$_3$)CH$_2$CF$_3$ and —CH$_2$CF$_3$;
$Z^2$ is CF$_3$;
$Z^3$ is selected from methyl and ethyl.

Embodiment 49

A compound or sat according to embodiment 1, wherein T is

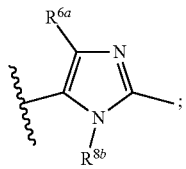

$R^6$ and $R^{8b}$ are independently selected from H, methyl and trifluoromethoxy;
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and $A4$ are CH;
$A^2$ is CH or CF;
$A^3$ is CH or CCl;
U is selected from —O—, —S—, —SO—, —SO$_2$— and —NR$^{100}$—;
$R^{100}$ is selected from H, C$_1$-C$_6$-alkyl, C$_2$-C$_6$-alkenyl, C$_2$-C$_6$-alkynyl, C$_1$-C$_6$-alkoxy, C$_1$-C$_6$-alkylcarbonyl, C$_1$-C$_6$-alkoxycarbonyl and C$_3$-C$_6$-cycloalkyl, wherein each of C$_1$-C$_6$-alkyl, C$_2$-C$_6$-alkenyl, C$_2$-C$_6$-alkynyl, C$_1$-C$_6$-alkoxy and C$_3$-C$_6$-cycloalkyl is unsubstituted or substituted with 1 to 8 substituents independently selected from halogen;
$Z^1$ is selected from —CF$_2$H, —CF$_2$CFHCF$_3$, —CF$_2$CF$_2$CF$_3$, —CF$_2$CF$_2$H, —CF$_2$CF$_2$OCF$_3$, —CH$_2$CF$_2$CF$_3$, —CH(CF$_3$)CH$_2$CF$_3$ and —CH$_2$CF$_3$;
$Z^2$ is CF$_3$;
$Z^3$ is selected from methyl and ethyl.

Embodiment 50

A compound or salt according to embodiment 1, wherein T is

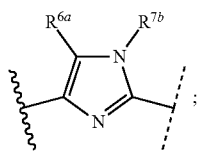

$R^{6a}$ and $R^{7b}$ are independently selected from H, methyl and trifluoromethoxy;
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —SO$_2$— and —NR$^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —CF$_2$H, —CF$_2$CFHCF$_3$, —CF$_2$CF$_2$CF$_3$, —CF$_2$CF$_2$H, —CF$_2$CF$_2$OCF$_3$, —CH$_2$CF$_2$CF$_3$, —CH(CF$_3$)CH$_2$CF$_3$ and —CH$_2$CF$_3$;
$Z^2$ is CF$_3$;
$Z^3$ is selected from methyl and ethyl.

Embodiment 51

A compound or salt according to embodiment 1, wherein T is

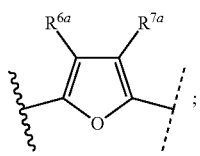

$R^{6a}$ and $R^{7a}$ are independently selected from H, methyl and trifluoromethoxy;
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —SO$_2$— and —NR$^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —CF$_2$H, —CF$_2$CFHCF$_3$, —CF$_2$CF$_2$CF$_3$, —CF$_2$CF$_2$H, —CF$_2$CF$_2$OCF$_3$, —CH$_2$CF$_2$CF$_3$, —CH(CF$_3$)CH$_2$CF$_3$ and —CH$_2$CF$_3$;
$Z^2$ is CF$_3$;
$Z^3$ is selected from methyl and ethyl.

Embodiment 52

A compound or sat according to embodiment 1, wherein T is

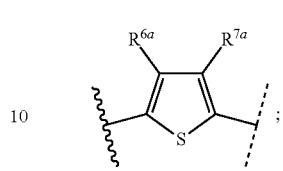

$R^{6a}$ and $R^{7a}$ are independently selected from H, methyl and trifluoromethoxy;
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —SO$_2$— and —NR$^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —CF$_2$H, —CF$_2$CFHCF$_3$, —CF$_2$CF$_2$CF$_3$, —CF$_2$CF$_2$H, —CF$_2$CF$_2$OCF$_3$, —CH$_2$CF$_2$CF$_3$, —CH(CF$_3$)CH$_2$CF$_3$ and —CH$_2$CF$_3$;
$Z^2$ is CF$_3$;
$Z^3$ is selected from methyl and ethyl.

Embodiment 53

A compound or salt according to embodiment 1, wherein T is

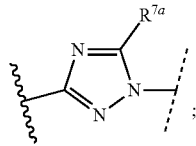

$R^7$, is selected from H, methyl and trifluoromethoxy;
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —SO$_2$— and —NR$^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —$CF_2H$, —$CF_2CFHCF_3$, —$CF_2CF_2CF_3$, —$CF_2CF_2H$, —$CF_2CF_2OCF_3$, —$CH_2CF_2CF_3$, —$CH(CF_3)CH_2CF_3$ and —$CH_2CF_3$;
$Z^2$ is $CF_3$;
$Z^3$ is selected from methyl and ethyl.

Embodiment 54

A compound or sat according to embodiment 1, wherein T is

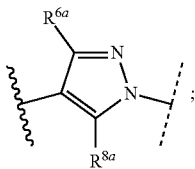

$R^{6a}$ and $R^{8a}$ are independently selected from H, methyl and trifluoromethoxy;
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —$SO_2$— and —$NR^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —$CF_2H$, —$CF_2CFHCF_3$, —$CF_2CF_2CF_3$, —$CF_2CF_2H$, —$CF_2CF_2OCF_3$, —$CH_2CF_2CF_3$, —$CH(CF_3)CH_2CF_3$ and —$CH_2CF_3$;
$Z_2$ is $CF_3$;
$Z^3$ is selected from methyl and ethyl.

Embodiment 55

A compound or salt according to embodiment 1, wherein T is

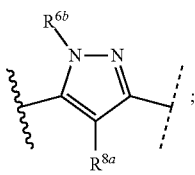

$R^b$ and RU are independently selected from H, methyl and trifluoromethoxy;
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —$SO_2$— and —$NR^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —$CF_2H$, —$CF_2CFHCF_3$, —$CF_2CF_2CF_3$, —$CF_2CF_2H$, —$CF_2CF_2OCF_3$, —$CH_2CF_2CF_3$, —$CH(CF_3)CH_2CF_3$ and —$CH_2CF_3$;
$Z^2$ is $CF_3$;
$Z^3$ is selected from methyl and ethyl.

Embodiment 56

A compound or salt according to embodiment 1, wherein T is

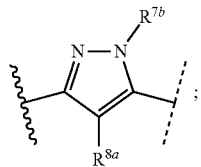

$R^{7b}$ and $R^{8a}$ are independently selected from H, methyl and trifluoromethoxy;
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —$SO_2$— and —$NR^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —$CF_2H$, —$CF_2CFHCF_3$, —$CF_2CF_2CF_3$, —$CF_2CF_2H$, —$CF_2CF_2OCF_3$, —$CH_2CF_2CF_3$, —$CH(CF_3)CH_2CF_3$ and —$CH_2CF_3$;
$Z^2$ is $CF_3$;
$Z^3$ is selected from methyl and ethyl.

Embodiment 57

A compound or sat according to embodiment 1, wherein T is

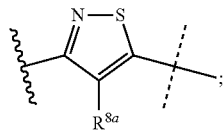

$R^{8a}$ is selected from H, methyl and trifluoromethoxy;
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —SO$_2$— and —NR$^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —CF$_2$H, —CF$_2$CFHCF$_3$, —CF$_2$CF$_2$CF$_3$, —CF$_2$CF$_2$H, —CF$_2$CF$_2$OCF$_3$, —CH$_2$CF$_2$CF$_3$, —CH(CF$_3$)CH$_2$CF$_3$ and —CH$_2$CF$_3$;
$Z^2$ is CF$_3$;
$Z^3$ is selected from methyl and ethyl.

Embodiment 58

A compound or salt according to embodiment 1, wherein T is

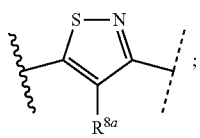

$R^{8a}$ is selected from H, methyl and trifluoromethoxy;
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —SO$_2$— and —NR$^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —CF$_2$H, —CF$_2$CFHCF$_3$, —CF$_2$CF$_2$CF$_3$, —CF$_2$CF$_2$H, —CF$_2$CF$_2$OCF$_3$, —CH$_2$CF$_2$CF$_3$, —CH(CF$_3$)CH$_2$CF$_3$ and —CH$_2$CF$_3$;
$Z^2$ is CF$_3$;
$Z^3$ is selected from methyl and ethyl.

Embodiment 59

A compound or sat according to embodiment 1, wherein T is

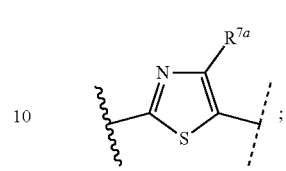

$R^{7a}$ is selected from H, methyl and trifluoromethoxy;
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —SO$_2$— and —NR$^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —CF$_2$H, —CF$_2$CFHCF$_3$, —CF$_2$CF$_2$CF$_3$, —CF$_2$CF$_2$H, —CF$_2$CF$_2$OCF$_3$, —CH$_2$CF$_2$CF$_3$, —CH(CF$_3$)CH$_2$CF$_3$ and —CH$_2$CF$_3$;
$Z^2$ is CF$_3$;
$Z^3$ is selected from methyl and ethyl.

Embodiment 60

A compound or salt according to embodiment 1, wherein T is

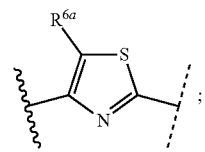

$R^{6a}$ is selected from H, methyl and trifluoromethoxy;
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —SO$_2$— and —NR$^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —$CF_2H$, —$CF_2CFHCF_3$, —$CF_2CF_2CF_3$, —$CF_2CF_2H$, —$CF_2CF_2OCF_3$, —$CH_2CF_2CF_3$, —$CH(CF_3)CH_2CF_3$ and —$CH_2CF_3$;
$Z^2$ is $CF_3$;
$Z^3$ is selected from methyl and ethyl.

Embodiment 61

A compound or salt according to embodiment 1, wherein T is

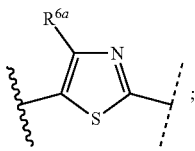

$R^{6a}$ is selected from H, methyl and trifluoromethoxy;
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —$SO_2$— and —$NR^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —$CF_2H$, —$CF_2CFHCF_3$, —$CF_2CF_2CF_3$, —$CF_2CF_2H$, —$CF_2CF_2OCF_3$, —$CH_2CF_2CF_3$, —$CH(CF_3)CH_2CF_3$ and —$CH_2CF_3$;
$Z^2$ is $CF_3$;
$Z^3$ is selected from methyl and ethyl.

Embodiment 62

A compound or sat according to embodiment 1, wherein T is

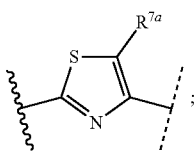

$R^{7a}$ is selected from H, methyl and trifluoromethoxy;
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —$SO_2$— and —$NR^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —$CF_2H$, —$CF_2CFHCF_3$, —$CF_2CF_2CF_3$, —$CF_2CF_2H$, —$CF_2CF_2OCF_3$, —$CH_2CF_2CF_3$, —$CH(CF_3)CH_2CF_3$ and —$CH_2CF_3$;
$Z^2$ is $CF_3$;
$Z^3$ is selected from methyl and ethyl.

Embodiment 63

A compound or salt according to embodiment 1, wherein T is

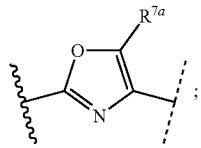

$R^{7a}$ is selected from H, methyl and trifluoromethoxy;
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —$SO_2$— and —$NR^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —$CF_2H$, —$CF_2CFHCF_3$, —$CF_2CF_2CF_3$, —$CF_2CF_2H$, —$CF_2CF_2OCF_3$, —$CH_2CF_2CF_3$, —$CH(CF_3)CH_2CF_3$ and —$CH_2CF_3$;
$Z^2$ is $CF_3$;
$Z^3$ is selected from methyl and ethyl.

Embodiment 64

A compound or sat according to embodiment 1, wherein T is

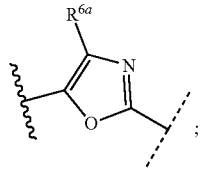

$R^{6a}$ is selected from H, methyl and trifluoromethoxy;
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —SO$_2$— and —NR$^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —CF$_2$H, —CF$_2$CFHCF$_3$, —CF$_2$CF$_2$CF$_3$, —CF$_2$CF$_2$H, —CF$_2$CF$_2$OCF$_3$, —CH$_2$CF$_2$CF$_3$, —CH(CF$_3$)CH$_2$CF$_3$ and —CH$_2$CF$_3$;
$Z^2$ is CF$_3$;
$Z^3$ is selected from methyl and ethyl.

Embodiment 65

A compound or salt according to embodiment 1, wherein T is

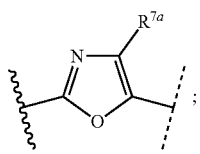

$R^{7a}$ s selected from H, methyl and trifluoromethoxy;
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —SO$_2$— and —NR$^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —CF$_2$H, —CF$_2$CFHCF$_3$, —CF$_2$CF$_2$CF$_3$, —CF$_2$CF$_2$H, —CF$_2$CF$_2$OCF$_3$, —CH$_2$CF$_2$CF$_3$, —CH(CF$_3$)CH$_2$CF$_3$ and —CH$_2$CF$_3$;
$Z^2$ is CF$_3$;
$Z^3$ is selected from methyl and ethyl.

Embodiment 66

A compound or salt according to embodiment 1, wherein T is

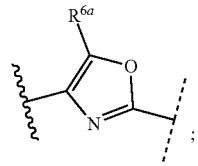

R is selected from H, methyl and trifluoromethoxy;
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —SO$_2$— and —NR$^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —CF$_2$H, —CF$_2$CFHCF$_3$, —CF$_2$CF$_2$CF$_3$, —CF$_2$CF$_2$H, —CF$_2$CF$_2$OCF$_3$, —CH$_2$CF$_2$CF$_3$, —CH(CF$_3$)CH$_2$CF$_3$ and —CH$_2$CF$_3$;
$Z^2$ is CF$_3$;
$Z^3$ is selected from methyl and ethyl.

Embodiment 67

A compound or sat according to embodiment 1, wherein T is

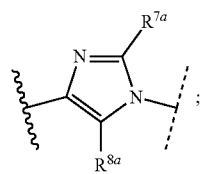

$R^{7a}$ and $R^{8a}$ are independently selected from H, methyl and trifluoromethoxy;
$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —SO$_2$— and —NR$^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$- alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —$CF_2H$, —$CF_2CFHCF_3$, —$CF_2CF_2CF_3$, —$CF_2CF_2H$, —$CF_2CF_2OCF_3$, —$CH_2CF_2CF_3$, —$CH(CF_3)CH_2CF_3$ and —$CH_2CF_3$;
$Z^2$ is $CF_3$;
$Z^3$ is selected from methyl and ethyl.

Embodiment 68

A compound or salt according to embodiment 1, wherein T is

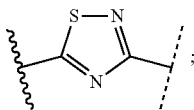

;

$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —$SO_2$— and —$NR^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —$CF_2H$, —$CF_2CFHCF_3$, —$CF_2CF_2CF_3$, —$CF_2CF_2H$, —$CF_2CF_2OCF_3$, —$CH_2CF_2CF_3$, —$CH(CF_3)CH_2CF_3$ and —$CH_2CF_3$;
$Z^2$ is $CF_3$;
$Z^3$ is selected from methyl and ethyl.

Embodiment 69

A compound or sat according to embodiment 1, wherein T is

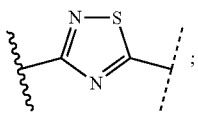

;

$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —$SO_2$— and —$NR^{100}$—; $R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —$CF_2H$, —$CF_2CFHCF_3$, —$CF_2CF_2CF_3$, —$CF_2CF_2H$, —$CF_2CF_2OCF_3$, —$CH_2CF_2CF_3$, —$CH(CF_3)CH_2CF_3$ and —$CH_2CF_3$;
$Z^2$ is $CF_3$;
$Z^3$ is selected from methyl and ethyl.

Embodiment 70

A compound or salt according to embodiment 1, wherein T is

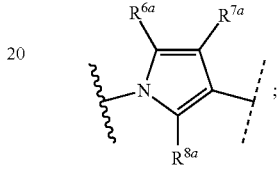

;

$R^1$ is H;
$R^{6a}$, $R^{7a}$ and $R^{8a}$ are independently selected from H, methyl and trifluoromethoxy;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —$SO_2$— and —$NR^{100}$—; $R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —$CF_2H$, —$CF_2CFHCF_3$, —$CF_2CF_2CF_3$, —$CF_2CF_2H$, —$CF_2CF_2OCF_3$, —$CH_2CF_2CF_3$, —$CH(CF_3)CH_2CF_3$ and —$CH_2CF_3$;
$Z^2$ is $CF_3$;
$Z^3$ is selected from methyl and ethyl.

Embodiment 71

A compound or salt according to embodiment 1, wherein T is

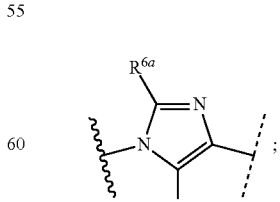

;

$R^1$ is H;
$R^{6a}$ and $R^{8a}$ are independently selected from H, methyl and trifluoromethoxy;

51

Q is selected from 1-cyano-cyclopropyl, (E)-1,2,3,3,3-pentafluoroprop-1-enyl, cyanomethyl, benzyl, cyclopropyl, methyl, ethyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
$U—Z^1$ is selected from
difluoromethoxy;
2,2,2-trifluoroethoxy;
1,1,2,3,3,3-hexafluoropropoxy;
methoxy;
1,1,2,2-tetrafluoroethoxy;
2-bromo-1,1,2,2-tetrafluoroethoxy;
1,1,2,3,4,4,4-heptafluoro-3-(trifluoromethyl)butoxy;
1,1,2,4,4,4-hexafluoro-3-(trifluoromethyl)but-2-enoxy;
1,1,2-trifluoro-2-(trifluoromethoxy)ethoxy;
trifluoromethylsulfonate;
1,1,2-trifluoro-2-(1,1,2,2,3,3,3-heptafluoropropoxy)ethoxy;
2,2-difluoro-2-[1,1,2,2-tetrafluoro-2-(trifluoromethoxy)ethoxy]ethoxy;
2,2,3,3,4,4,4-heptafluorobutoxy;
5,6,6-trifluorohex-5-enoxy;
2,2,3,3,4,4,5,5,6,6,7,7,8,8,8-pentadecafluorooctoxy;
2,2-difluoroethoxy;
2,2,3,3,4,4,5,5-octafluoropentoxy;
2-(trifluoromethoxy)ethoxy;
2,2,3,3-tetrafluoropropoxy;
1,1,2,2,3,3,3-heptafluoropropoxy;
1,1,2,2,3,3,4,4,4-nonafluorobutane-1-sulfonate;
1,1,2,2,3,3,4,4,5,5,6,6,6-tridecafluorohexoxy;
1,1,2,2,3,3,4,4,5,5,6,6,7,7,8,8,8-heptadeccafluorooctoxy;
2-bromo-1,1-difluoro-ethoxy;
(E)-2,3,3,3-tetrafluoro-1-(trifluoromethyl)prop-1-enoxy;
2-bromo-1,1,2-trifluoro-ethoxy;
2-chloro-1,1,2-trifluoro-ethoxy;
(1E)-1,2-difluorobuta-1,3-dienoxy;
3,4,4-trifluorobut-3-enoxy;
(Z)-1,3,3,3-tetrafluoroprop-1-enoxy;
(Z)-2-fluoro-1-(trifluoromethyl)vinyloxy;
2,2,3,3,4,4,5,5-octafluoropentoxy;
1,1,2,3,4,5,5,5-octafluoro-2-(trifluoromethyl)pent-3-enoxy;
1,2,3,3,3-pentafluoroprop-1-enoxy;
3,3,4,4,5,5,6,6,7,7,8,8,8-tridecafluorooctylsulfanyl;
2,2,3,3-tetrafluoropropylsulfanyl;
1,1,2,3,3,3-hexafluoropropoxy;
1,1,2-trifluoro-2-(trifluoromethoxy)ethoxy;
trifluoromethylsulfanyl;
1,1,2,2,3,3,3-heptafluoropropylsulfanyl;
1,1,2,3,3,3-hexafluoropropoxy;
1,1,2,3,3-pentachloroallyloxy;
1,1,2,3,3,3-hexafluoropropoxy;
1,1,2,3,3-pentachloroallyloxy;
1,1,2-trifluoropropoxy;
2,2,2-trifluoroethylamio;
2-bromo-1,1,2-trifluoro-ethoxy;
$Z^2$ is $CF_3$;
$Z^3$ is selected from methyl and ethyl.

52

Embodiment 72

A compound or salt according to embodiment 1, wherein T is

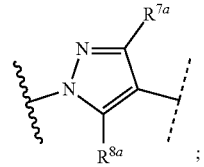

$R^1$ is H;
$R^{7a}$ and $R^{8a}$ are independently selected from H, methyl and trifluoromethoxy;
Q is selected from 1-cyano-cyclopropyl, (E)-1,2,3,3,3-pentafluoroprop-1-enyl, cyanomethyl, benzyl, cyclopropyl, methyl, ethyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
$U—Z^1$ is selected from
difluoromethoxy;
2,2,2-trifluoroethoxy;
1,1,2,3,3,3-hexafluoropropoxy;
methoxy;
1,1,2,2-tetrafluoroethoxy;
2-bromo-1,1,2,2-tetrafluoroethoxy;
1,1,2,3,4,4,4-heptafluoro-3-trifluoromethyl)butoxy;
1,1,2,4,4,-hexafluoro-3-(trifluoromethyl)but-2-enoxy;
1,1,2-trifluoro-2-(trifluoromethoxy)ethoxy;
trifluoromethylsulfonate;
1,1,2-trifluoro-2-(1,1,2,2,3,3,3-heptafluoropropoxy)ethoxy;
2,2-difluoro-2-[1,1,2,2-tetrafluoro-2-(trifluoromethoxy)ethoxy]ethoxy;
2,2,3,3,4,4,4-heptafluorobutoxy;
5,6,6-trifluorohex-5-enoxy;
2,2,3,3,4,4,5,5,6,6,7,7,8,8,8-pentadecafluorooctoxy;
2,2-difluoroethoxy;
2,2,3,3,4,4,5,5-octafluoropentoxy;
2-(trifluoromethoxy)ethoxy;
2,2,3,3-tetrafluoropropoxy;
1,1,2,2,3,3,3-heptafluoropropoxy;
1,1,2,2,3,3,4,4,4-nonafluorobutane-1-sulfonate;
1,1,2,2,3,3,4,4,5,5,6,6,6-tridecafluorohexoxy;
1,1,2,2,3,3,4,4,5,5,6,6,7,7,8,8,8-heptadeccafluorooctoxy;
2-bromo-1,1-difluoro-ethoxy;
(E)-2,3,3,3-tetrafluoro-1-(trifluoromethyl)prop-1-enoxy;
2-bromo-1,1,2-trifluoro-ethoxy;
2-chloro-1,1,2-trifluoro-ethoxy;
(1E)-1,2-difluorobuta-1,3-dienoxy;
3,4,4-trifluorobut-3-enoxy;
(Z)-1,3,3,3-tetrafluoroprop-1-enoxy;
(Z)-2-fluoro-1-(trifluoromethyl)vinyloxy;
2,2,3,3,4,4,5,5-octafluoropentoxy;
1,1,2,3,4,5,5,5-octafluoro-2-(trifluoromethyl)pent-3-enoxy;
1,2,3,3,3-pentafluoroprop-1-enoxy;
3,3,4,4,5,5,6,6,7,7,8,8,8-tridecafluorooctylsulfanyl;
2,2,3,3-tetrafluoropropylsulfanyl;
1,1,2,3,3,3-hexafluoropropoxy;
1,1,2-trifluoro-2-(trifluoromethoxy)ethoxy;
trifluoromethylsulfanyl;

1,1,2,2,3,3,3-heptafluoropropylsulfanyl;
1,1,2,3,3,3-hexafluoropropoxy;
1,1,2,3,3,3-pentachloroallyloxy;
1,1,2,3,3,3-hexafluoropropoxy;
1,1,2,3,3,3-pentachloroallyloxy;
1,1,2-trifluoropropoxy;
2,2,2-trifluoroethylamino;
2-bromo-1,1,2-trifluoro-ethoxy;
$Z^2$ is $CF_3$;
$Z^3$ is selected from methyl and ethyl.

Embodiment 72.1

A compound or salt according to embodiment 1, wherein T is

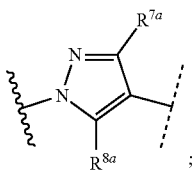

$R^1$ is H;
$R^{7a}$ and $R^{8a}$ are independently selected from H, methyl and trifluoromethoxy;
Q is selected from 1-cyano-cyclopropyl, (E)-1,2,3,3,3-pentafluoroprop-1-enyl, cyanomethyl, benzyl, cyclopropyl, methyl, ethyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —SO$_2$— and —NR$^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —CF$_2$H, —CF$_2$CFHCF$_3$, —CF$_2$CF$_2$CF$_3$, —CF$_2$CF$_2$H, —CF$_2$CF$_2$OCF$_3$, —CH$_2$CF$_2$CF$_3$, —CH(CF$_3$)CH$_2$CF$_3$ and —CH$_2$CF$_3$;
$Z^2$ is $CF_3$;
$Z^3$ is selected from methyl and ethyl.

Embodiment 72.2

A compound or salt according to embodiment 1, wherein T is

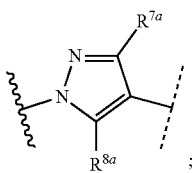

$R^1$ is H;
$R^{7a}$ and $R^{8a}$ are independently selected from H, methyl and trifluoromethoxy;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —SO$_2$— and —NR$^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —CF$_2$H, —CF$_2$CFHCF$_3$, —CF$_2$CF$_2$CF$_3$, —CF$_2$CF$_2$H, —CF$_2$CF$_2$OCF$_3$, —CH$_2$CF$_2$CF$_3$, —CH(CF$_3$)CH$_2$CF$_3$ and —CH$_2$CF$_3$;
$Z^2$ is $CF_3$;
$Z^3$ is selected from methyl and ethyl.

Embodiment 73

A compound or salt according to embodiment 1, wherein T is

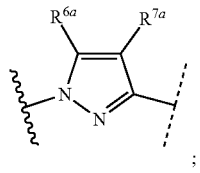

$R^1$ is H;
$R^{6a}$ and $R^{7a}$ are independently selected from H, methyl and trifluoromethoxy;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —SO$_2$— and —NR$^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —CF$_2$H, —CF$_2$CFHCF$_3$, —CF$_2$CF$_2$CF$_3$, —CF$_2$CF$_2$H, —CF$_2$CF$_2$OCF$_3$, —CH$_2$CF$_2$CF$_3$, —CH(CF$_3$)CH$_2$CF$_3$ and —CH$_2$CF$_3$;
$Z^2$ is $CF_3$;
$Z^3$ is selected from methyl and ethyl.

Embodiment 74

A compound or salt according to embodiment 1, wherein T is

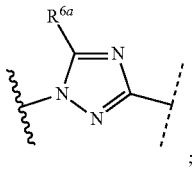
;

$R^1$ is H;
$R^{6a}$ is selected from H, methyl and trifluoromethoxy;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —SO$_2$— and —NR$^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —CF$_2$H, —CF$_2$CFHCF$_3$, —CF$_2$CF$_2$CF$_3$, —CF$_2$CF$_2$H, —CF$_2$CF$_2$OCF$_3$, —CH$_2$CF$_2$CF$_3$, —CH(CF$_3$)CH$_2$CF$_3$ and —CH$_2$CF$_3$;
$Z^2$ is CF$_3$;
$Z^3$ is selected from methyl and ethyl.

Embodiment 75

A compound or salt according to embodiment 1, wherein T is

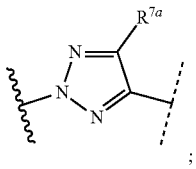
;

$R^1$ is H;
$R^{7a}$ is selected from H, methyl and trifluoromethoxy;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —SO$_2$— and —NR$^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —CF$_2$H, —CF$_2$CFHCF$_3$, —CF$_2$CF$_2$CF$_3$, —CF$_2$CF$_2$H, —CF$_2$CF$_2$OCF$_3$, —CH$_2$CF$_2$CF$_3$, —CH(CF$_3$)CH$_2$CF$_3$ and —CH$_2$CF$_3$;
$Z^2$ is CF$_3$;
$Z^3$ is selected from methyl and ethyl.

Embodiment 76

A compound or salt according to embodiment 1, wherein T is

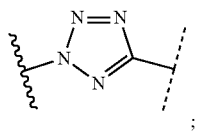
;

$R^1$ is H;
Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
$A^1$ and A4 are CH;
$A^2$ is CH or CF;
$A^3$ is CH or CCl;
U is selected from —O—, —S—, —SO—, —SO$_2$— and —NR$^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;
$Z^1$ is selected from —CF$_2$H, —CF$_2$CFHCF$_3$, —CF$_2$CF$_2$CF$_3$, —CF$_2$CF$_2$H, —CF$_2$CF$_2$OCF$_3$, —CH$_2$CF$_2$CF$_3$, —CH(CF$_3$)CH$_2$CF$_3$ and —CH$_2$CF$_3$;
$Z^2$ is CF$_3$;
$Z^3$ is selected from methyl and ethyl.

Embodiment 77

A compound or salt according to embodiment 1, wherein T is

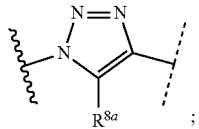
;

R¹ is H;

R⁸ᵃ is selected from H, methyl and trifluoromethoxy;

Q is selected from 1-cyano-cyclopropyl, benzyl, cyclopropyl, 2-thienylmethyl, carbamothioylcyclopropyl, pyrid-4-yl, 2,2,2-trifluorethyl, methylsulfonyl, thietan-3-yl and 1-carbamoylcyclopropyl;

W is O;

A¹ and A4 are CH;

A² is CH or CF;

A³ is CH or CCl;

U is selected from —O—, —S—, —SO—, —SO₂— and —NR¹⁰⁰—;

R¹⁰⁰ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 8 substituents independently selected from halogen;

Z¹ is selected from —CF₂H, —CF₂CFHCF₃, —CF₂CF₂CF₃, —CF₂CF₂H, —CF₂CF₂OCF₃, —CH₂CF₂CF₃, —CH(CF₃)CH₂CF₃ and —CH₂CF₃;

Z² is CF₃;

Z³ is selected from methyl and ethyl.

Embodiment 78

A compound or salt according to embodiment 1, wherein the compound is selected from any one of example 1 to 87

| Example No. | Structure | Chemical name |
| --- | --- | --- |
| 1 | 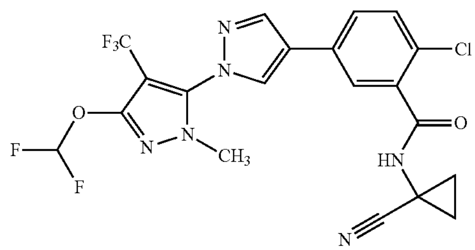 [SMILES: Cn1nc(OC(F)F)c(C(F)(F)F)c1-n1cc(-c2ccc(Cl)c(C(=O)NC3(C#N)CC3)c2)cn1] | 2-chloro-N-(1-cyanocyclopropyl)-5-[1-[5-[(Z)-2-fluoro-1-(trifluoromethyl)vinyloxy]-2-methyl-4-(trifluoromethyl)pyrazol-3-yl]pyrazol-4-yl]benzamide (Example 1); |
| 2 | 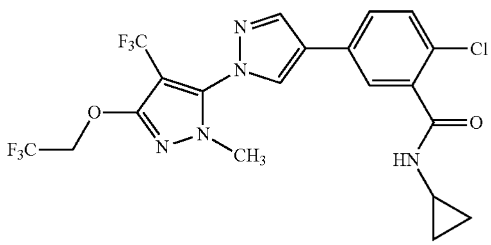 [SMILES: Cn1nc(OCC(F)(F)F)c(C(F)(F)F)c1-n1cc(-c2ccc(Cl)c(C(=O)NC3CC3)c2)cn1] | 2-chloro-N-cyclopropyl-5-[1-[2-methyl-5-(2,2,2-trifluoroethoxy)-4-(trifluoromethyl)pyrazol-3-yl]pyrazol-4-yl]benzamide (Example 2); |
| 3 | 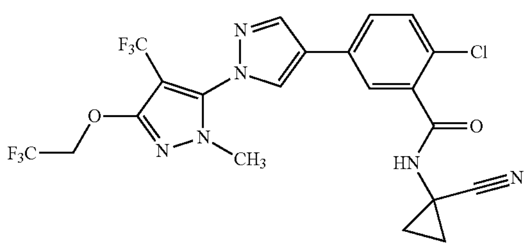 [SMILES: Cn1nc(OCC(F)(F)F)c(C(F)(F)F)c1-n1cc(-c2ccc(Cl)c(C(=O)NC3(C#N)CC3)c2)cn1] | 2-chloro-N-(1-cyanocyclopropyl)-5-[1-[2-methyl-5-(2,2,2-trifluoroethoxy)-4-(trifluoromethyl)pyrazol-3-yl]pyrazol-4-yl]benzamide (Example 3); |
| 4 | 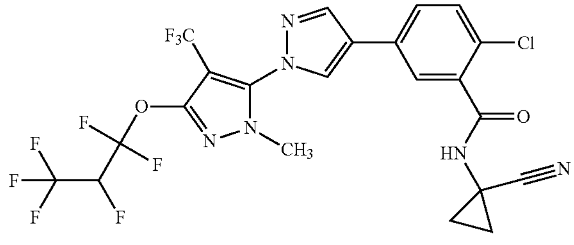 [SMILES: Cn1nc(OC(F)(F)C(F)C(F)(F)F)c(C(F)(F)F)c1-n1cc(-c2ccc(Cl)c(C(=O)NC3(C#N)CC3)c2)cn1] | 2-chloro-N-(1-cyanocyclopropyl)-5-[1-[5-(1,1,2,3,3,3-hexafluoropropoxy)-2-methyl-4-(trifluoromethyl)pyrazol-3-yl]pyrazol-4-yl]benzamide (Example 4); |

-continued

| Example No. | Structure | Chemical name |
|---|---|---|
| 5 | 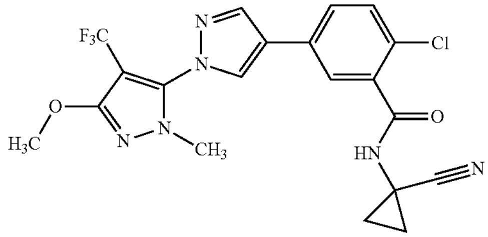 [SMILES: COc1nn(C)c(-n2cc(-c3ccc(Cl)c(C(=O)NC4(C#N)CC4)c3)cn2)c1C(F)(F)F] | 2-chloro-N-(1-cyanocyclopropyl)-5-[1-[5-methoxy-2-methyl-4-(trifluoromethyl)pyrazol-3-yl]pyrazol-4-yl]benzamide (Example 5); |
| 6 | 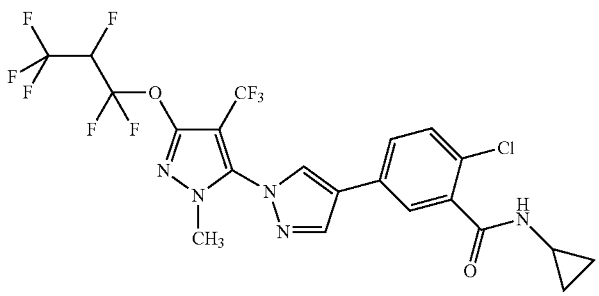 [SMILES: Cn1nc(OC(F)(F)C(F)C(F)(F)F)c(C(F)(F)F)c1-n1cc(-c2ccc(Cl)c(C(=O)NC3CC3)c2)cn1] | 2-chloro-N-cyclopropyl-5-[1-[5-(1,1,2,3,3,3-hexafluoropropoxy)-2-methyl-4-(trifluoromethyl)pyrazol-3-yl]pyrazol-4-yl]benzamide (Example 6); |
| 7 | 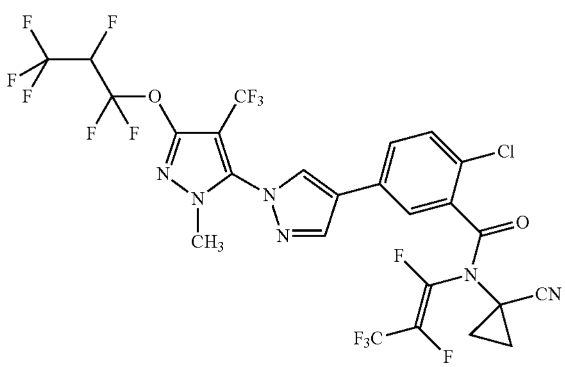 [SMILES: Cn1nc(OC(F)(F)C(F)C(F)(F)F)c(C(F)(F)F)c1-n1cc(-c2ccc(Cl)c(C(=O)N(/C(F)=C(\F)C(F)(F)F)C3(C#N)CC3)c2)cn1] | 2-chloro-N-(1-cyanocyclopropyl)-5-[1-[5-(1,1,2,3,3,3-hexafluoropropoxy)-2-methyl-4-(trifluoromethyl)pyrazol-3-yl]pyrazol-4-yl]-N-[(E)-1,2,3,3,3-pentafluoroprop-1-enyl]benzamide (Example 7); |
| 8 | 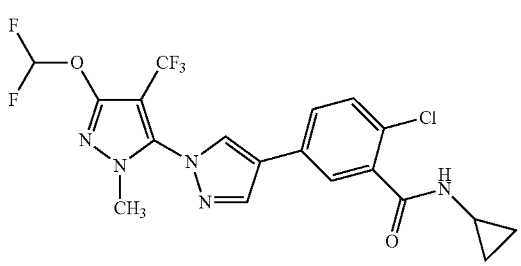 [SMILES: Cn1nc(OC(F)F)c(C(F)(F)F)c1-n1cc(-c2ccc(Cl)c(C(=O)NC3CC3)c2)cn1] | 2-chloro-N-cyclopropyl-5-[1-[5-(difluoromethoxy)-2-methyl-4-(trifluoromethyl)pyrazol-3-yl]pyrazol-4-yl]benzamide (Example 8); |
| 9 | 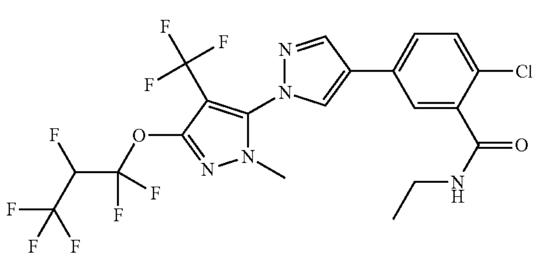 [SMILES: CCNC(=O)c1cc(-c2cnn(-c3c(C(F)(F)F)c(OC(F)(F)C(F)C(F)(F)F)nn3C)c2)ccc1Cl] | 2-chloro-N-ethyl-5-[1-[5-(1,1,2,3,3,3-hexafluoropropoxy)-2-methyl-4-(trifluoromethyl)pyrazol-3-yl]pyrazol-4-yl]benzamide (Example 9); |

| Example No. | Structure | Chemical name |
|---|---|---|
| 10 | 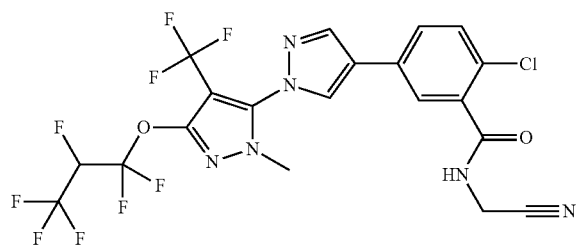 [SMILES: Cn1nc(OC(F)(F)C(F)C(F)(F)F)c(C(F)(F)F)c1-n1cc(-c2ccc(Cl)c(C(=O)NCC#N)c2)cn1] | 2-chloro-N-(cyanomethyl)-5-[1-[5-(1,1,2,3,3,3-hexafluoropropoxy)-2-methyl-4-(trifluoromethyl)pyrazol-3-yl]pyrazol-4-yl]benzamide (Example 10); |
| 11 | 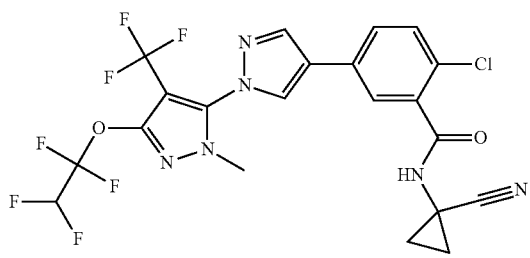 [SMILES: Cn1nc(OC(F)(F)C(F)F)c(C(F)(F)F)c1-n1cc(-c2ccc(Cl)c(C(=O)NC3(C#N)CC3)c2)cn1] | 2-chloro-N-(1-cyanocyclopropyl)-5-[1-[2-methyl-5-(1,1,2,2-tetrafluoroethoxy)-4-(trifluoromethyl)pyrazol-3-yl]pyrazol-4-yl]benzamide (Example 11); |
| 12 | 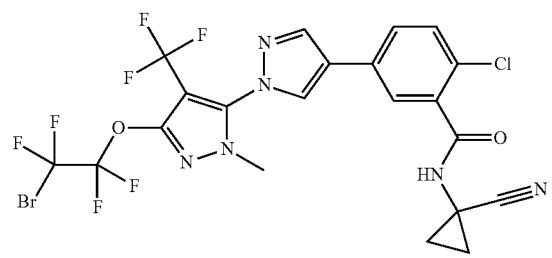 [SMILES: Cn1nc(OC(F)(F)C(F)(F)Br)c(C(F)(F)F)c1-n1cc(-c2ccc(Cl)c(C(=O)NC3(C#N)CC3)c2)cn1] | 5-[1-[5-(2-bromo-1,1,2,2-tetrafluoroethoxy)-2-methyl-4-(trifluoromethyl)pyrazol-3-yl]pyrazol-4-yl]-2-chloro-N-(1-cyanocyclopropyl)benzamide (Example 12); |
| 13 | 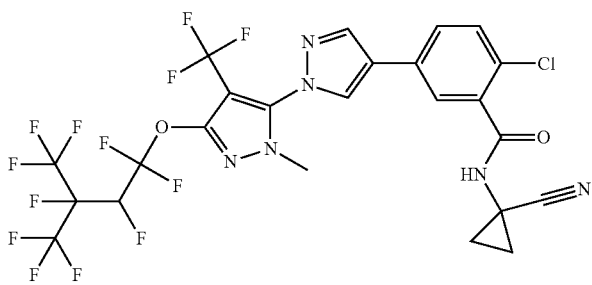 [SMILES: Cn1nc(OC(F)(F)C(F)C(F)(C(F)(F)F)C(F)(F)F)c(C(F)(F)F)c1-n1cc(-c2ccc(Cl)c(C(=O)NC3(C#N)CC3)c2)cn1] | 2-chloro-N-(1-cyanocyclopropyl)-5-[1-[5-[1,1,2,3,4,4,4-heptafluoro-3-(trifluoromethyl)butoxy]-2-methyl-4-(trifluoromethyl)pyrazol-3-yl]pyrazol-4-yl]benzamide (Example 13); |
| 14 | 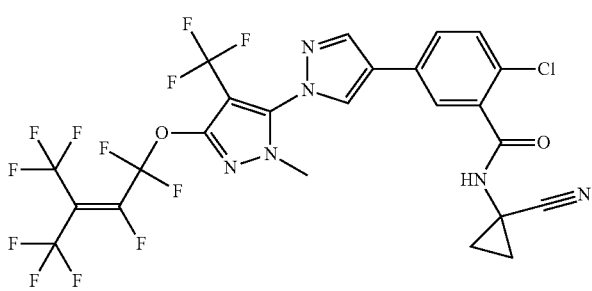 [SMILES: Cn1nc(OC(F)(F)C(F)=C(C(F)(F)F)C(F)(F)F)c(C(F)(F)F)c1-n1cc(-c2ccc(Cl)c(C(=O)NC3(C#N)CC3)c2)cn1] | 2-chloro-N-(1-cyanocyclopropyl)-5-[1-[5-[1,1,2,4,4,4-hexafluoro-3-(trifluoromethyl)but-2-enoxy]-2-methyl-4-(trifluoromethyl)pyrazol-3-yl]pyrazol-4-yl]benzamide (Example 14); |

-continued

| Example No. | Structure | Chemical name |
|---|---|---|
| 15 | 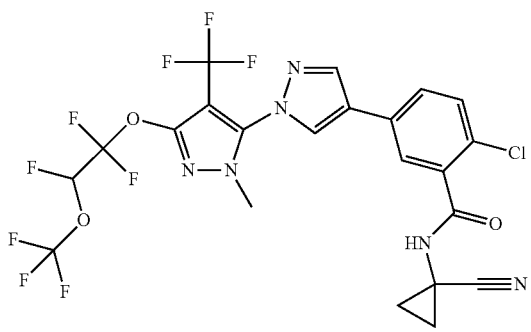 [SMILES: Cn1nc(OC(F)(F)C(F)OC(F)(F)F)c(C(F)(F)F)c1-n1cc(-c2ccc(Cl)c(C(=O)NC3(C#N)CC3)c2)cn1] | 2-chloro-N-(1-cyanocyclopropyl)-5-[1-[2-methyl-4-(trifluoromethyl)-5-[1,1,2-trifluoro-2-(trifluoromethoxy)ethoxy]pyrazol-3-yl]pyrazol-4-yl]benzamide (Example 15); |
| 16 | 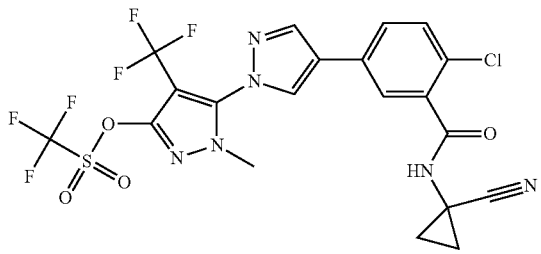 [SMILES: Cn1nc(OS(=O)(=O)C(F)(F)F)c(C(F)(F)F)c1-n1cc(-c2ccc(Cl)c(C(=O)NC3(C#N)CC3)c2)cn1] | [5-[4-[4-chloro-3-[(1-cyanocyclopropyl)carbamoyl]phenyl]pyrazol-1-yl]-1-methyl-4-(trifluoromethyl)pyrazol-3-yl]trifluoromethanesulfonate (Example 16); |
| 17 | 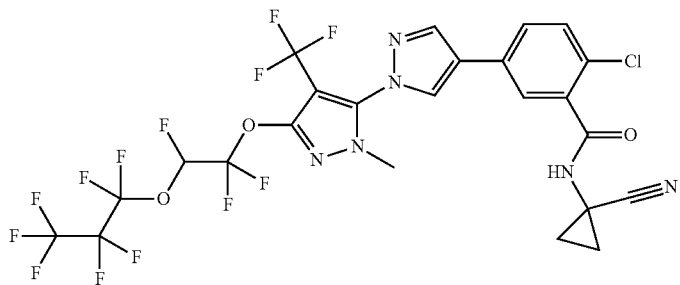 [SMILES: Cn1nc(OC(F)(F)C(F)OC(F)(F)C(F)(F)C(F)(F)F)c(C(F)(F)F)c1-n1cc(-c2ccc(Cl)c(C(=O)NC3(C#N)CC3)c2)cn1] | 2-chloro-N-(1-cyanocyclopropyl)-5-[1-[2-methyl-5-[1,1,2-trifluoro-2-(1,1,2,2,3,3,3-heptafluoropropoxy)ethoxy]-4-(trifluoromethyl)pyrazol-3-yl]pyrazol-4-yl]benzamide (Example 17); |
| 18 | 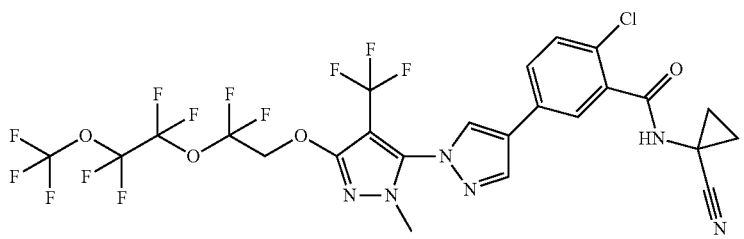 [SMILES: Cn1nc(OCC(F)(F)OC(F)(F)C(F)(F)OC(F)(F)F)c(C(F)(F)F)c1-n1cc(-c2ccc(Cl)c(C(=O)NC3(C#N)CC3)c2)cn1] | 2-chloro-N-(1-cyanocyclopropyl)-5-[1-[5-[2,2-difluoro-2-[1,1,2,2-tetrafluoro-2-(trifluoromethoxy)ethoxy]ethoxy]-2-methyl-4-(trifluoromethyl)pyrazol-3-yl]pyrazol-4-yl]benzamide (Example 18); |
| 19 | 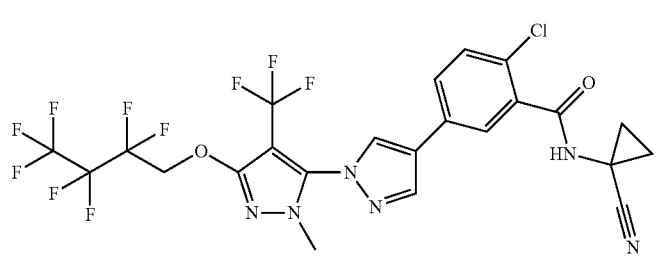 [SMILES: Cn1nc(OCC(F)(F)C(F)(F)C(F)(F)F)c(C(F)(F)F)c1-n1cc(-c2ccc(Cl)c(C(=O)NC3(C#N)CC3)c2)cn1] | 2-chloro-N-(1-cyanocyclopropyl)-5-[1-[5-(2,2,3,3,4,4,4-heptafluorobutoxy)-2-methyl-4-(trifluoromethyl)pyrazol-3-yl]pyrazol-4-yl]benzamide (Example 19); |

| Example No. | Structure | Chemical name |
|---|---|---|
| 20 | 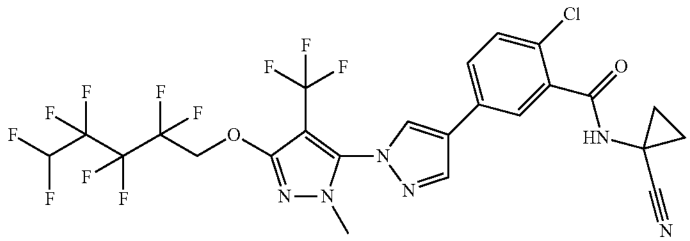 [SMILES: Cn1nc(OCC(F)(F)C(F)(F)C(F)(F)C(F)F)c(C(F)(F)F)c1-n1cc(-c2ccc(Cl)c(C(=O)NC3(C#N)CC3)c2)cn1] | 2-chloro-N-(1-cyanocyclopropyl)-5-[1-[2-methyl-5-(2,2,3,3,4,4,5,5-octafluoropentoxy)-4-(trifluoromethyl)pyrazol-3-yl]pyrazol-4-yl]benzamide (Example 20); |
| 21 | 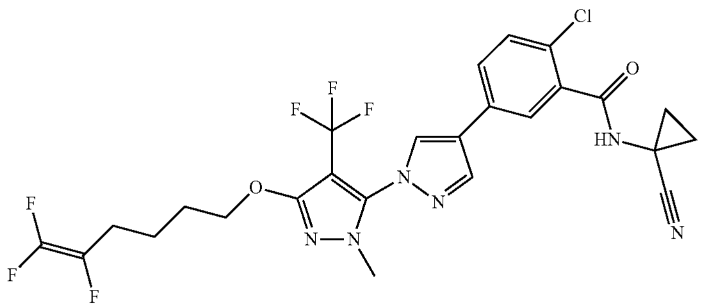 [SMILES: Cn1nc(OCCCCC(F)=C(F)F)c(C(F)(F)F)c1-n1cc(-c2ccc(Cl)c(C(=O)NC3(C#N)CC3)c2)cn1] | 2-chloro-N-(1-cyanocyclopropyl)-5-[1-[2-methyl-5-(5,6,6-trifluorohex-5-enoxy)-4-(trifluoromethyl)pyrazol-3-yl]pyrazol-4-yl]benzamide (Example 21); |
| 22 | 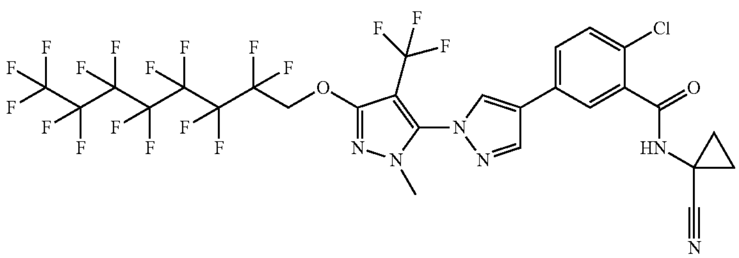 [SMILES: Cn1nc(OCC(F)(F)C(F)(F)C(F)(F)C(F)(F)C(F)(F)C(F)(F)C(F)(F)F)c(C(F)(F)F)c1-n1cc(-c2ccc(Cl)c(C(=O)NC3(C#N)CC3)c2)cn1] | 2-chloro-N-(1-cyanocyclopropyl)-5-[1-[2-methyl-5-(2,2,3,3,4,4,5,5,6,6,7,7,8,8,8-pentadecafluorooctoxy)-4-(trifluoromethyl)pyrazol-3-yl]pyrazol-4-yl]benzamide (Example 22); |
| 23 | 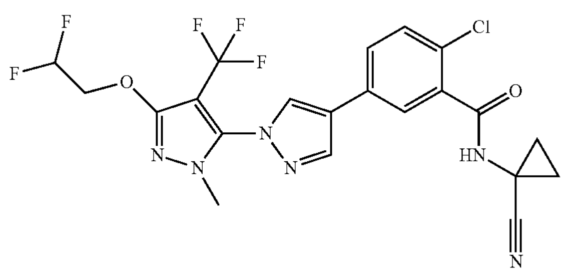 [SMILES: Cn1nc(OCC(F)F)c(C(F)(F)F)c1-n1cc(-c2ccc(Cl)c(C(=O)NC3(C#N)CC3)c2)cn1] | 2-chloro-N-(1-cyanocyclopropyl)-5-[1-[5-(2,2-difluoroethoxy)-2-methyl-4-(trifluoromethyl)pyrazol-3-yl]pyrazol-4-yl]benzamide (Example 23); |
| 24 | 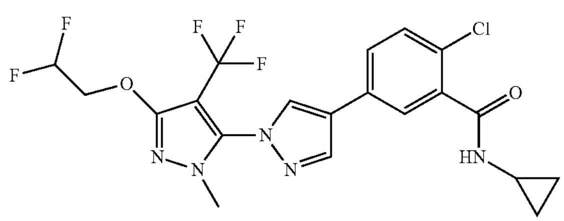 [SMILES: Cn1nc(OCC(F)F)c(C(F)(F)F)c1-n1cc(-c2ccc(Cl)c(C(=O)NC3CC3)c2)cn1] | 2-chloro-N-cyclopropyl-5-[1-[5-(2,2-difluoroethoxy)-2-methyl-4-(trifluoromethyl)pyrazol-3-yl]pyrazol-4-yl]benzamide (Example 24); |
| 25 | 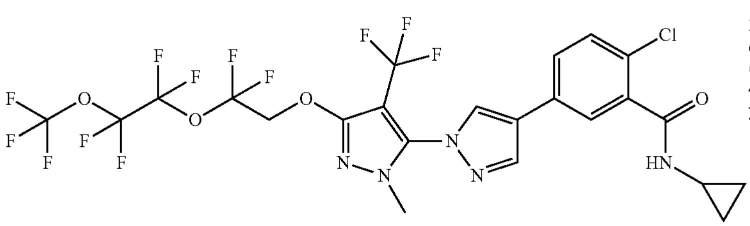 [SMILES: Cn1nc(OCC(F)(F)OC(F)(F)C(F)(F)OC(F)(F)F)c(C(F)(F)F)c1-n1cc(-c2ccc(Cl)c(C(=O)NC3CC3)c2)cn1] | 2-chloro-N-cyclopropyl-5-[1-[5-[2,2-difluoro-2-[1,1,2,2-tetrafluoro-2-(trifluoromethoxy)ethoxy]ethoxy]-2-methyl-4-(trifluoromethyl)pyrazol-3-yl]pyrazol-4-yl]benzamide (Example 25); |

-continued

| Example No. | Structure | Chemical name |
|---|---|---|
| 26 | 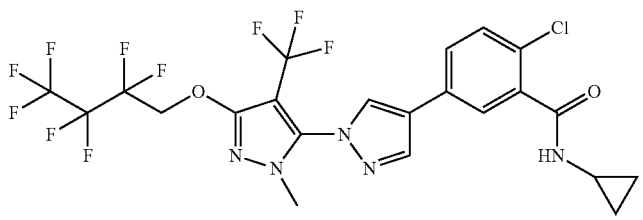 [SMILES: Cn1nc(OCC(F)(F)C(F)(F)C(F)(F)F)c(C(F)(F)F)c1-n1cc(-c2ccc(Cl)c(C(=O)NC3CC3)c2)cn1] | 2-chloro-N-cyclopropyl-5-[1-[5-(2,2,3,3,4,4,4-heptafluorobutoxy)-2-methyl-4-(trifluoromethyl)pyrazol-3-yl]pyrazol-4-yl]benzamide (Example 26); |
| 27 | 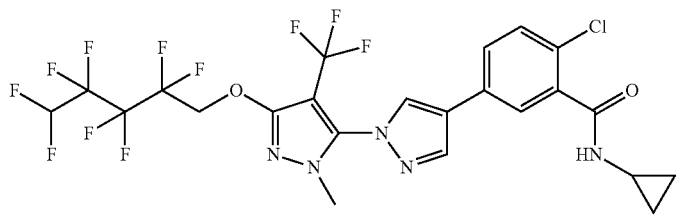 [SMILES: Cn1nc(OCC(F)(F)C(F)(F)C(F)(F)C(F)F)c(C(F)(F)F)c1-n1cc(-c2ccc(Cl)c(C(=O)NC3CC3)c2)cn1] | 2-chloro-N-cyclopropyl-5-[1-[2-methyl-5-(2,2,3,3,4,4,5,5-octafluoropentoxy)-4-(trifluoromethyl)pyrazol-3-yl]pyrazol-4-yl]benzamide (Example 27); |
| 28 | 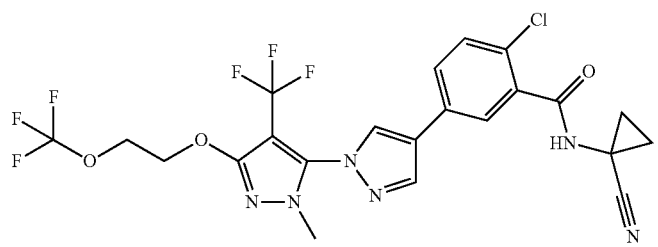 [SMILES: Cn1nc(OCCOC(F)(F)F)c(C(F)(F)F)c1-n1cc(-c2ccc(Cl)c(C(=O)NC3(C#N)CC3)c2)cn1] | 2-chloro-N-(1-cyanocyclopropyl)-5-[1-[2-methyl-5-[2-(trifluoromethoxy)ethoxy]-4-(trifluoromethyl)pyrazol-3-yl]pyrazol-4-yl]benzamide (Example 28); |
| 29 | 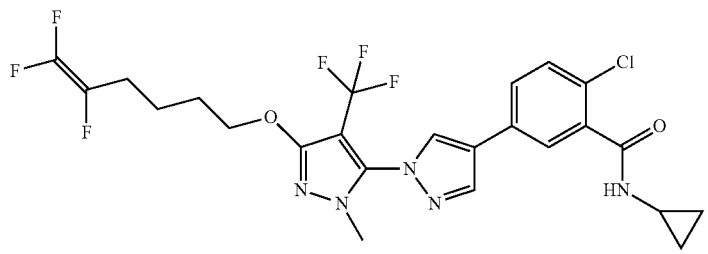 [SMILES: Cn1nc(OCCCCC(F)=C(F)F)c(C(F)(F)F)c1-n1cc(-c2ccc(Cl)c(C(=O)NC3CC3)c2)cn1] | 2-chloro-N-cyclopropyl-5-[1-[2-methyl-5-(5,6,6-trifluorohex-5-enoxy)-4-(trifluoromethyl)pyrazol-3-yl]pyrazol-4-yl]benzamide (Example 29); |
| 30 | 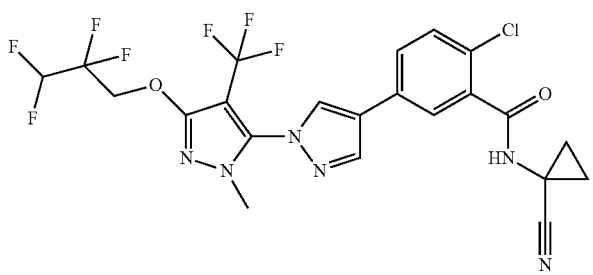 [SMILES: Cn1nc(OCC(F)(F)C(F)F)c(C(F)(F)F)c1-n1cc(-c2ccc(Cl)c(C(=O)NC3(C#N)CC3)c2)cn1] | 2-chloro-N-(1-cyanocyclopropyl)-5-[1-[2-methyl-5-(2,2,3,3-tetrafluoropropoxy)-4-(trifluoromethyl)pyrazol-3-yl]pyrazol-4-yl]benzamide (Example 30); |
| 31 | 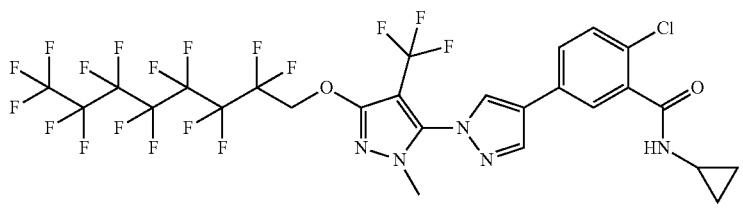 [SMILES: Cn1nc(OCC(F)(F)C(F)(F)C(F)(F)C(F)(F)C(F)(F)C(F)(F)C(F)(F)F)c(C(F)(F)F)c1-n1cc(-c2ccc(Cl)c(C(=O)NC3CC3)c2)cn1] | 2-chloro-N-cyclopropyl-5-[1-[2-methyl-5-(2,2,3,3,4,4,5,5,6,6,7,7,8,8,8-pentadecafluorooctoxy)-4-(trifluoromethyl)pyrazol-3-yl]pyrazol-4-yl]benzamide (Example 31); |

| Example No. | Structure | Chemical name |
|---|---|---|
| 32 | 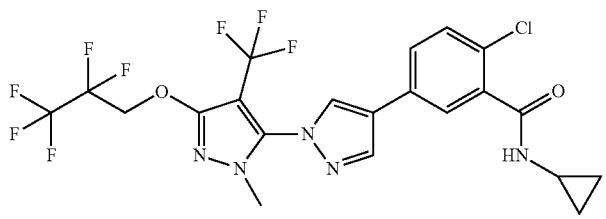 [SMILES: Cn1nc(OCC(F)(F)C(F)(F)F)c(C(F)(F)F)c1-n1cc(-c2ccc(Cl)c(C(=O)NC3CC3)c2)cn1] | 2-chloro-N-cyclopropyl-5-[1-[2-methyl-5-(2,2,3,3,3-pentafluoropropoxy)-4-(trifluoromethyl)pyrazol-3-yl]pyrazol-4-yl]benzamide (Example 32); |
| 33 | 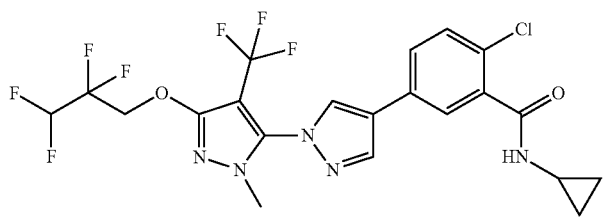 [SMILES: Cn1nc(OCC(F)(F)C(F)F)c(C(F)(F)F)c1-n1cc(-c2ccc(Cl)c(C(=O)NC3CC3)c2)cn1] | 2-chloro-N-cyclopropyl-5-[1-[2-methyl-5-(2,2,3,3-tetrafluoropropoxy)-4-(trifluoromethyl)pyrazol-3-yl]pyrazol-4-yl]benzamide (Example 33); |
| 34 | 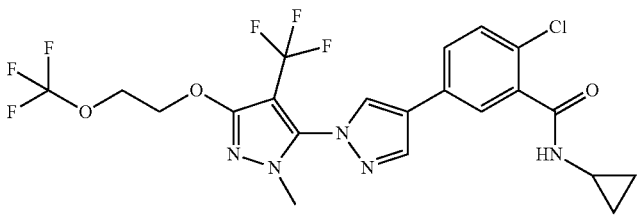 [SMILES: Cn1nc(OCCOC(F)(F)F)c(C(F)(F)F)c1-n1cc(-c2ccc(Cl)c(C(=O)NC3CC3)c2)cn1] | 2-chloro-N-cyclopropyl-5-[1-[2-methyl-5-[2-(trifluoromethoxy)ethoxy]-4-(trifluoromethyl)pyrazol-3-yl]pyrazol-4-yl]benzamide (Example 34); |
| 35 | 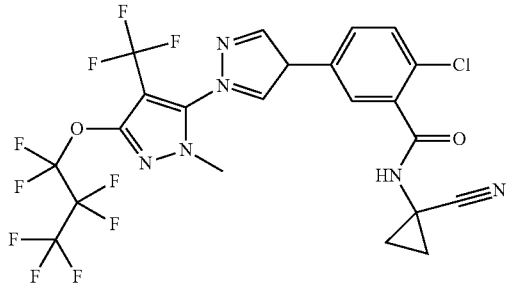 | 2-chloro-N-(1-cyanocyclopropyl)-5-[1-[5-(1,1,2,2,3,3,3-heptafluoropropoxy)-2-methyl-4-(trifluoromethyl)pyrazol-3-yl]pyrazol-4-yl]benzamide (Example 35); |
| 36 | 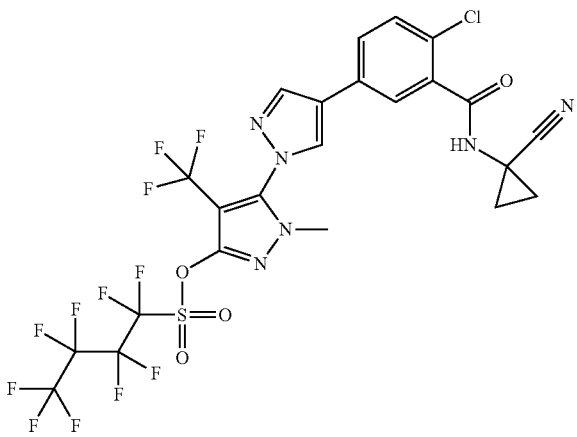 [SMILES: Cn1nc(OS(=O)(=O)C(F)(F)C(F)(F)C(F)(F)C(F)(F)F)c(C(F)(F)F)c1-n1cc(-c2ccc(Cl)c(C(=O)NC3(C#N)CC3)c2)cn1] | [5-[4-[4-chloro-3-(cyanocyclopropyl-carbamoyl)phenyl]pyrazol-1-yl]-1-methyl-4-(trifluoromethyl)pyrazol-3-yl]1,1,2,2,3,3,4,4,4-nonafluorobutane-1-sulfonate (Example 36); |

-continued

| Example No. | Structure | Chemical name |
|---|---|---|
| 37 | 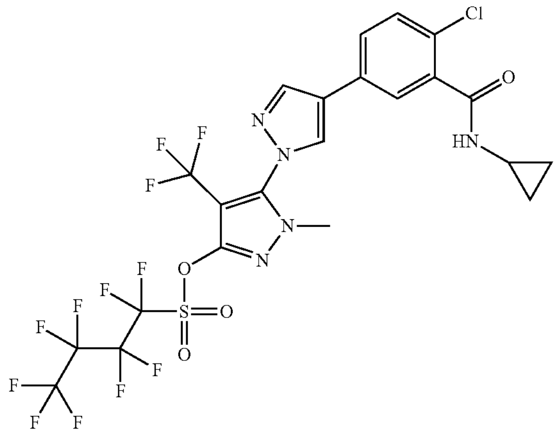 [SMILES: Cn1nc(OS(=O)(=O)C(F)(F)C(F)(F)C(F)(F)C(F)(F)F)c(C(F)(F)F)c1-n1cc(-c2ccc(Cl)c(C(=O)NC3CC3)c2)cn1] | [5-[4-[4-chloro-3-(cyclopropylcarbamoyl)phenyl]pyrazol-1-yl]-1-methyl-4-(trifluoromethyl)pyrazol-3-yl] 1,1,2,2,3,3,4,4,4-nonafluorobutane-1-sulfonate (Example 37); |
| 38 | 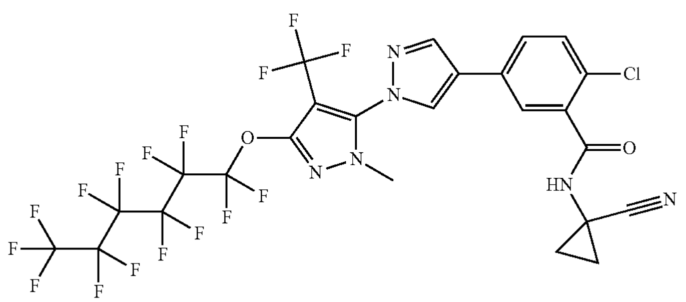 [SMILES: Cn1nc(OC(F)(F)C(F)(F)C(F)(F)C(F)(F)C(F)(F)C(F)(F)F)c(C(F)(F)F)c1-n1cc(-c2ccc(Cl)c(C(=O)NC3(C#N)CC3)c2)cn1] | 2-chloro-N-(1-cyanocyclopropyl)-5-[1-[2-methyl-5-(1,1,2,2,3,3,4,4,5,5,6,6,6-tridecafluorohexoxy)-4-(trifluoromethyl)pyrazol-3-yl]pyrazol-4-yl]benzamide (Example 38); |
| 39 | 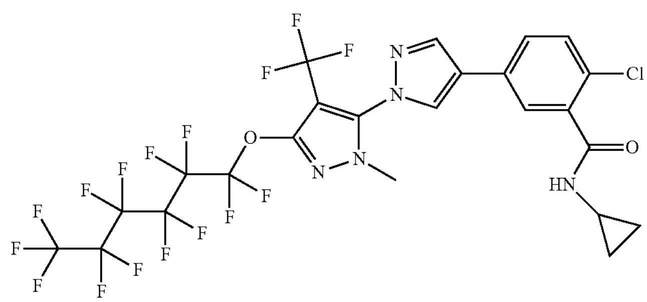 [SMILES: Cn1nc(OC(F)(F)C(F)(F)C(F)(F)C(F)(F)C(F)(F)C(F)(F)F)c(C(F)(F)F)c1-n1cc(-c2ccc(Cl)c(C(=O)NC3CC3)c2)cn1] | 2-chloro-N-cyclopropyl-5-[1-[2-methyl-5-(1,1,2,2,3,3,4,4,5,5,6,6,6-tridecafluorohexoxy)-4-(trifluoromethyl)pyrazol-3-yl]pyrazol-4-yl]benzamide (Example 39); |
| 40 | 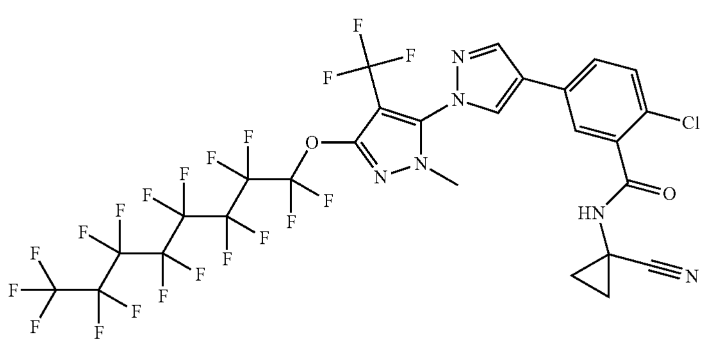 [SMILES: Cn1nc(OC(F)(F)C(F)(F)C(F)(F)C(F)(F)C(F)(F)C(F)(F)C(F)(F)C(F)(F)F)c(C(F)(F)F)c1-n1cc(-c2ccc(Cl)c(C(=O)NC3(C#N)CC3)c2)cn1] | 2-chloro-N-(1-cyanocyclopropyl)-5-[1-[5-(1,1,2,2,3,3,4,4,5,5,6,6,7,7,8,8,8-heptadecafluorooctoxy)-2-methyl-4-(trifluoromethyl)pyrazol-3-yl]pyrazol-4-yl]benzamide (Example 40); |

| Example No. | Structure | Chemical name |
|---|---|---|
| 41 | 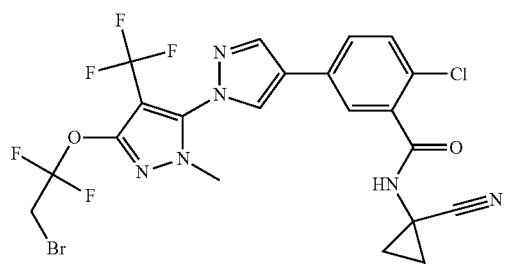 [SMILES: Cn1nc(OC(F)(F)CBr)c(C(F)(F)F)c1-n1cc(-c2ccc(Cl)c(C(=O)NC3(C#N)CC3)c2)cn1] | 5-[1-[5-(2-bromo-1,1-difluoro-ethoxy)-2-methyl-4-(trifluoromethyl)pyrazol-3-yl]pyrazol-4-yl]-2-chloro-N-(1-cyanocyclopropyl)benzamide (Example 41); |
| 42 | 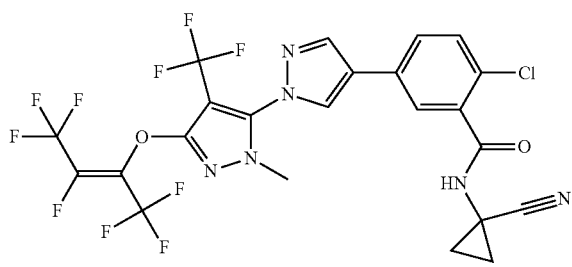 [SMILES: Cn1nc(O/C(=C(/F)C(F)(F)F)C(F)(F)F)c(C(F)(F)F)c1-n1cc(-c2ccc(Cl)c(C(=O)NC3(C#N)CC3)c2)cn1] | 2-chloro-N-(1-cyanocyclopropyl)-5-[1-[2-methyl-5-[(E)-2,3,3,3-tetrafluoro-1-(trifluoromethyl)prop-1-enoxy]-4-(trifluoromethyl)pyrazol-3-yl]pyrazol-4-yl]benzamide (Example 42); |
| 43 | 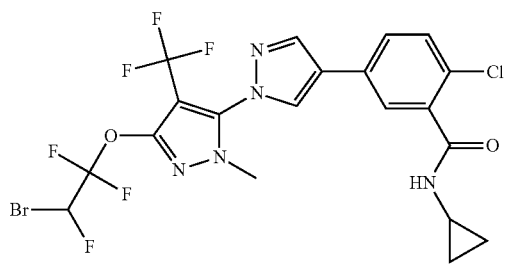 [SMILES: Cn1nc(OC(F)(F)C(F)Br)c(C(F)(F)F)c1-n1cc(-c2ccc(Cl)c(C(=O)NC3CC3)c2)cn1] | 5-[1-[5-(2-bromo-1,1,2-trifluoro-ethoxy)-2-methyl-4-(trifluoromethyl)pyrazol-3-yl]pyrazol-4-yl]-2-chloro-N-cyclopropyl-benzamide (Example 43); |
| 44 | 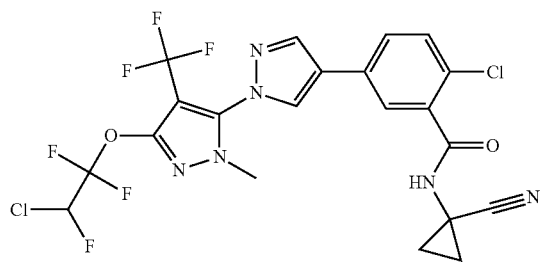 [SMILES: Cn1nc(OC(F)(F)C(F)Cl)c(C(F)(F)F)c1-n1cc(-c2ccc(Cl)c(C(=O)NC3(C#N)CC3)c2)cn1] | 2-chloro-5-[1-[5-(2-chloro-1,1,2-trifluoro-ethoxy)-2-methyl-4-(trifluoromethyl)pyrazol-3-yl]pyrazol-4-yl]-N-(1-cyanocyclopropyl)benzamide (Example 44); |
| 45 | 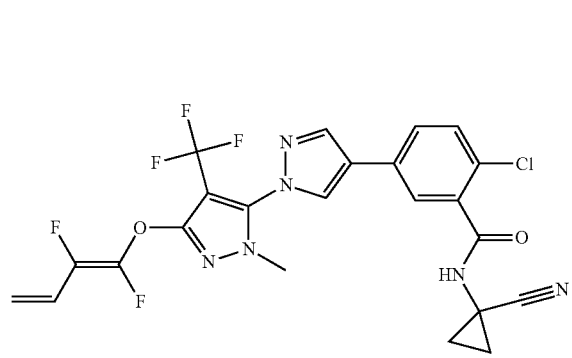 [SMILES: C=C/C(F)=C(\F)Oc1nn(C)c(-n2cc(-c3ccc(Cl)c(C(=O)NC4(C#N)CC4)c3)cn2)c1C(F)(F)F] | 2-chloro-N-(1-cyanocyclopropyl)-5-[1-[5-[(1E)-1,2-difluorobuta-1,3-dienoxy]-2-methyl-4-(trifluoromethyl)pyrazol-3-yl]pyrazol-4-yl]benzamide (Example 45); |

-continued

| Example No. | Structure | Chemical name |
|---|---|---|
| 46 | 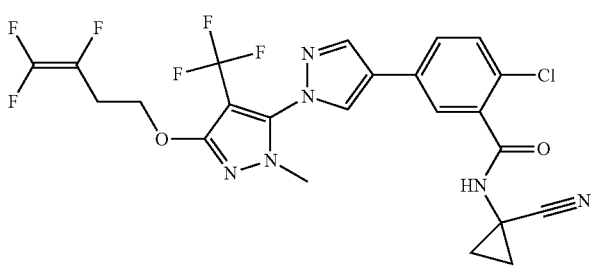 [SMILES: Cn1nc(OCCC(F)=C(F)F)c(C(F)(F)F)c1-n1cc(-c2ccc(Cl)c(C(=O)NC3(C#N)CC3)c2)cn1] | 2-chloro-N-(1-cyanocyclopropyl)-5-[1-[2-methyl-5-(3,4,4-trifluorobut-3-enoxy)-4-(trifluoromethyl)pyrazol-3-yl]pyrazol-4-yl]benzamide (Example 46); |
| 47 | 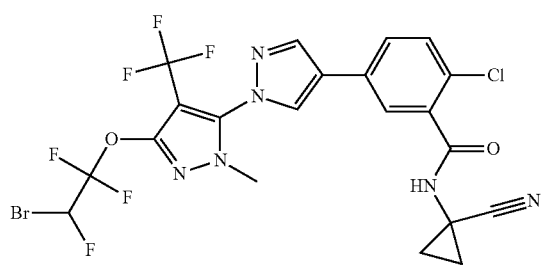 | 5-[1-[5-(2-bromo-1,1,2-trifluoro-ethoxy)-2-methyl-4-(trifluoromethyl)pyrazol-3-yl]pyrazol-4-yl]-2-chloro-N-(1-cyanocyclopropyl)benzamide (Example 47); |
| 48 | 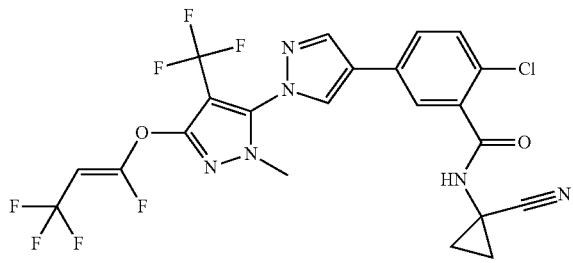 [SMILES: Cn1nc(O/C(F)=C/C(F)(F)F)c(C(F)(F)F)c1-n1cc(-c2ccc(Cl)c(C(=O)NC3(C#N)CC3)c2)cn1] | 2-chloro-N-(1-cyanocyclopropyl)-5-[1-[2-methyl-5-[(Z)-1,3,3,3-tetrafluoroprop-1-enoxy]-4-(trifluoromethyl)pyrazol-3-yl]pyrazol-4-yl]benzamide (Example 48); |
| 49 | 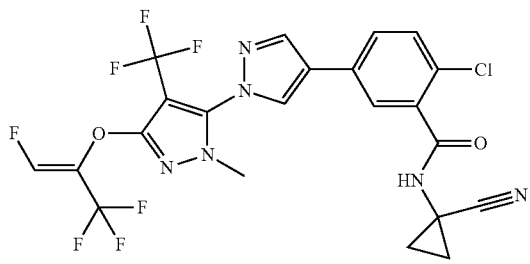 [SMILES: Cn1nc(O/C(=C\F)C(F)(F)F)c(C(F)(F)F)c1-n1cc(-c2ccc(Cl)c(C(=O)NC3(C#N)CC3)c2)cn1] | 2-chloro-N-(1-cyanocyclopropyl)-5-[1-[5-[(Z)-2-fluoro-1-(trifluoromethyl)vinyloxy]-2-methyl-4-(trifluoromethyl)pyrazol-3-yl]pyrazol-4-yl]benzamide (Example 49); |
| 50 | 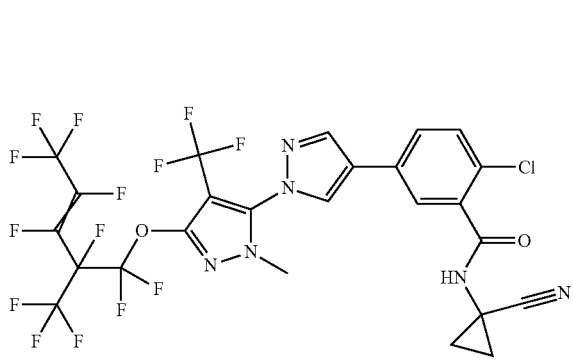 [SMILES: Cn1nc(OC(F)(F)C(F)(C(F)=C(F)C(F)(F)F)C(F)(F)F)c(C(F)(F)F)c1-n1cc(-c2ccc(Cl)c(C(=O)NC3(C#N)CC3)c2)cn1] | 2-chloro-N-(1-cyanocyclopropyl)-5-[1-[2-methyl-5-[(E or Z)-1,1,2,3,4,5,5,5-octafluoro-2-(trifluoromethyl)pent-3-enoxy]-4-(trifluoromethyl)pyrazol-3-yl]pyrazol-4-yl]benzamide (Example 50) |

-continued

| Example No. | Structure | Chemical name |
|---|---|---|
| 51 | 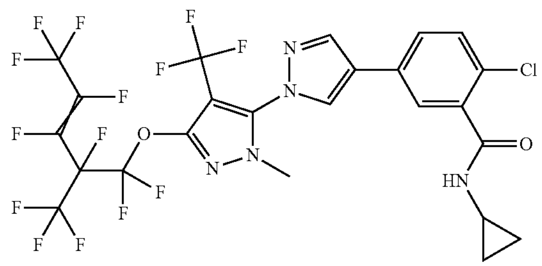 [SMILES: Cn1nc(OC(F)(F)C(F)(C(F)=C(F)C(F)(F)F)C(F)(F)F)c(C(F)(F)F)c1-n1cc(-c2ccc(Cl)c(C(=O)NC3CC3)c2)cn1] | 2-chloro-N-cyclopropyl-5-[1-[2-methyl-5-[(E or Z)-1,1,2,3,4,5,5,5-octafluoro-2-(trrfluoromethyl)pent-3-enoxy]-4-(trifluoromethyl)pyrazol-3-yl]pyrazol-4-yl]benzamide (Example 51) |
| 52 | 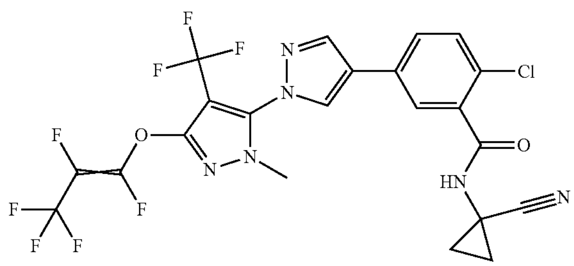 [SMILES: Cn1nc(OC(F)=C(F)C(F)(F)F)c(C(F)(F)F)c1-n1cc(-c2ccc(Cl)c(C(=O)NC3(C#N)CC3)c2)cn1] | 2-chloro-N-(1-cyanocyclopropyl)-5-[1-[2-methyl-5-[(E or Z)-1,2,3,3,3-pentafluoroprop-1-enoxy]-4-(trifluoromethyl)pyrazol-3-yl]pyrazol-4-yl]benzamide |
| 53 | 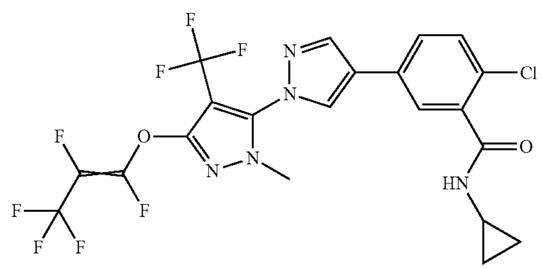 [SMILES: Cn1nc(OC(F)=C(F)C(F)(F)F)c(C(F)(F)F)c1-n1cc(-c2ccc(Cl)c(C(=O)NC3CC3)c2)cn1] | 2-chloro-N-cyclopropyl-5-[1-[2-methyl-5-[(E or Z)-1,2,3,3,3-pentafluoroprop-1-enoxy]-4-(trifluoromethyl)pyrazol-3-yl]pyrazol-4-yl]benzamide |
| 54 | 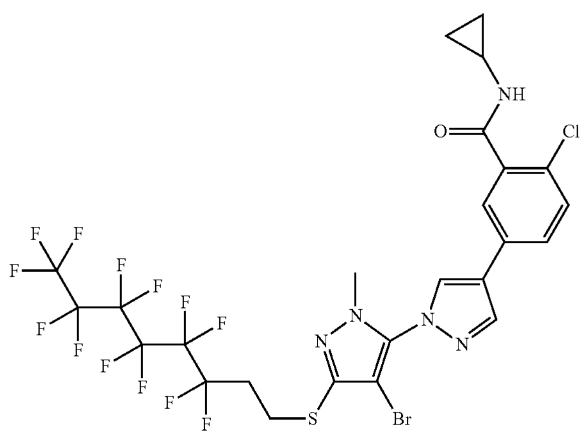 [SMILES: Cn1nc(SCCC(F)(F)C(F)(F)C(F)(F)C(F)(F)C(F)(F)C(F)(F)F)c(Br)c1-n1cc(-c2ccc(Cl)c(C(=O)NC3CC3)c2)cn1] | 5-[1-[4-bromo-2-methyl-5-(3,3,4,4,5,5,6,6,7,7,8,8,8-tridecafluorooctylsulfanyl)pyrazol-3-yl]pyrazol-4-yl]-2-chloro-N-cyclopropyl-benzamide |
| 55 | 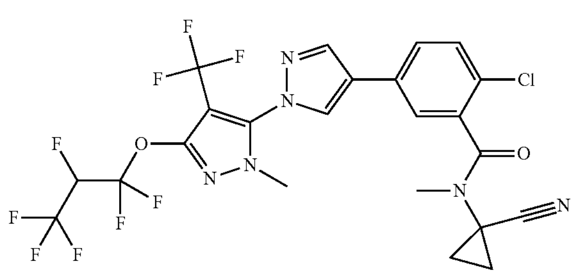 [SMILES: CN(C(=O)c1cc(-c2cnn(-c3c(C(F)(F)F)c(OC(F)(F)C(F)C(F)(F)F)nn3C)c2)ccc1Cl)C1(C#N)CC1] | 2-chloro-N-(1-cyanocyclopropyl)-5-[1-[5-(1,1,2,3,3,3-hexafluoropropoxy)-2-methyl-4-(trifluoromethyl)pyrazol-3-yl]pyrazol-4-yl]-N-methyl-benzamide |

-continued

| Example No. | Structure | Chemical name |
|---|---|---|
| 56 | 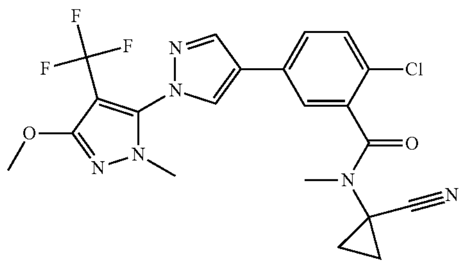 [SMILES: COc1nn(C)c(-n2cc(-c3ccc(Cl)c(C(=O)N(C)C4(C#N)CC4)c3)cn2)c1C(F)(F)F] | 2-chloro-N-(1-cyanocyclopropyl)-5-[1-[5-methoxy-2-methyl-4-(trifluoromethyl)pyrazol-3-yl]pyrazol-4-yl]-N-methyl-benzamide |
| 57 | 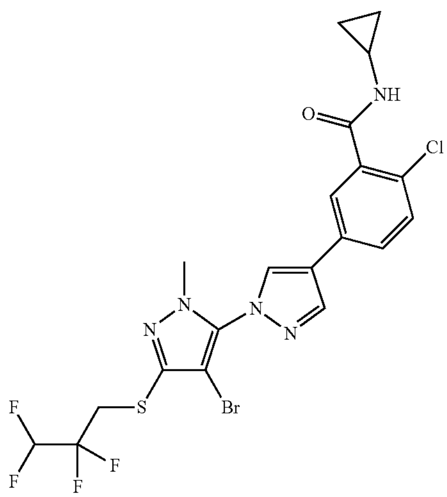 [SMILES: Cn1nc(SCC(F)(F)C(F)F)c(Br)c1-n1cc(-c2ccc(Cl)c(C(=O)NC3CC3)c2)cn1] | 5-[1-[4-bromo-2-methyl-5-(2,2,3,3-tetrafluoropropylsulfanyl)pyrazol-3-yl]pyrazol-4-yl]-2-chloro-N-cyclopropyl-benzamide |
| 58 | 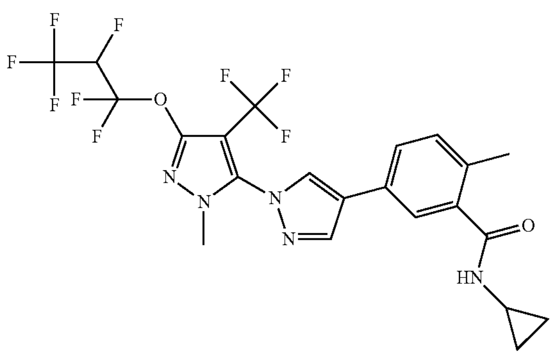 [SMILES: Cc1ccc(-c2cnn(-c3c(C(F)(F)F)c(OC(F)(F)C(F)C(F)(F)F)nn3C)c2)cc1C(=O)NC1CC1] | N-cyclopropyl-5-[1-[5-(1,1,2,3,3,3-hexafluoropropoxy)-2-methyl-4-(trifluoromethyl)pyrazol-3-yl]pyrazol-4-yl]-2-methyl-benzamide |
| 59 | 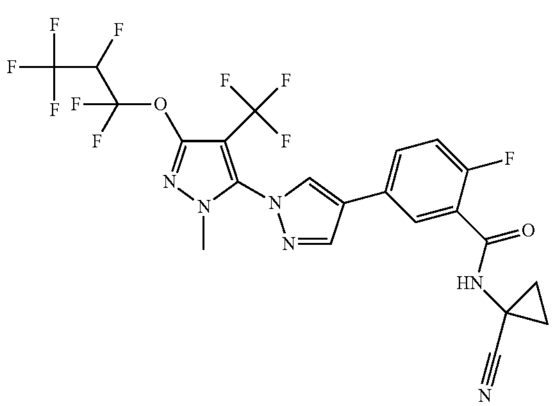 [SMILES: Cn1nc(OC(F)(F)C(F)C(F)(F)F)c(C(F)(F)F)c1-n1cc(-c2ccc(F)c(C(=O)NC3(C#N)CC3)c2)cn1] | N-(1-cyanocyclopropyl)-2-fluoro-5-[1-[5-(1,1,2,3,3,3-hexafluoropropoxy)-2-methyl-4-(trifluoromethyl)pyrazol-3-yl]pyrazol-4-yl]benzamide |

| Example No. | Structure | Chemical name |
|---|---|---|
| 60 | 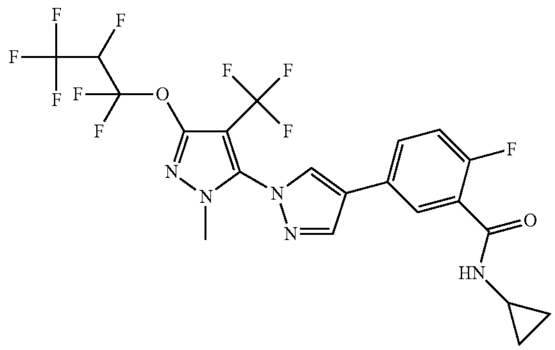 [SMILES: Cn1nc(OC(F)(F)C(F)C(F)(F)F)c(C(F)(F)F)c1-n1cc(-c2ccc(F)c(C(=O)NC3CC3)c2)cn1] | N-cyclopropyl-2-fluoro-5-[1-[5-(1,1,2,3,3,3-hexafluoropropoxy)-2-methyl-4-(trifluoromethyl)pyrazol-3-yl]pyrazol-4-yl]benzamide |
| 61 | 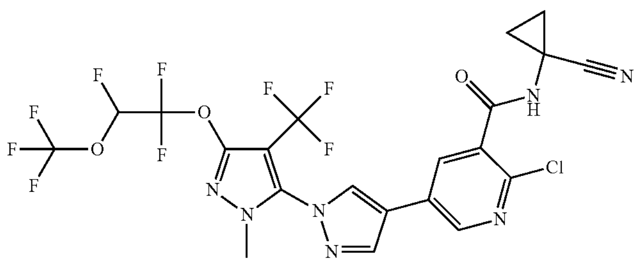 [SMILES: Cn1nc(OC(F)(F)C(F)OC(F)(F)F)c(C(F)(F)F)c1-n1cc(-c2cnc(Cl)c(C(=O)NC3(C#N)CC3)c2)cn1] | 2-chloro-N-(1-cyanocyclopropyl)-5-[1-[2-methyl-4-(trifluoromethyl)-5-[1,1,2-trifluoro-2-(trifluoromethoxy)ethoxy]pyrazol-3-yl]pyrazol-4-yl]pyridine-3-carboxamide |
| 62 | 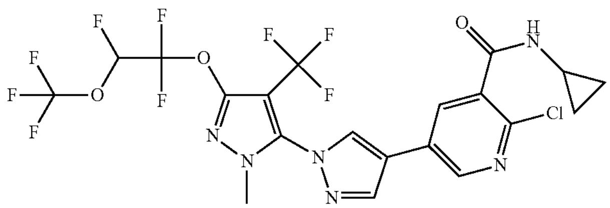 [SMILES: Cn1nc(OC(F)(F)C(F)OC(F)(F)F)c(C(F)(F)F)c1-n1cc(-c2cnc(Cl)c(C(=O)NC3CC3)c2)cn1] | 2-chloro-N-cyclopropyl-5-[1-[2-methyl-4-(trifluoromethyl)-5-[1,1,2-trifluoro-2-(trifluoromethoxy)ethoxy]pyrazol-3-yl]pyrazol-4-yl]pyridine-3-carboxamide |
| 63 | 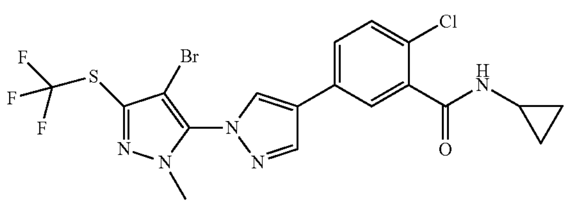 [SMILES: Cn1nc(SC(F)(F)F)c(Br)c1-n1cc(-c2ccc(Cl)c(C(=O)NC3CC3)c2)cn1] | 5-[1-[4-bromo-2-methyl-5-(trifluoromethylsulfanyl)pyrazol-3-yl]pyrazol-4-yl]-2-chloro-N-cyclopropyl-benzamide |
| 64 | 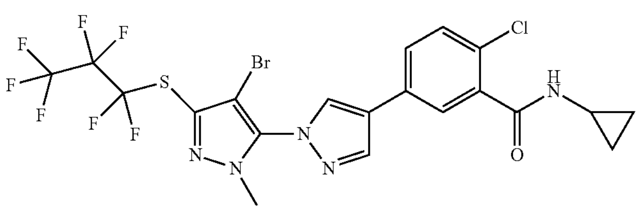 [SMILES: Cn1nc(SC(F)(F)C(F)(F)C(F)(F)F)c(Br)c1-n1cc(-c2ccc(Cl)c(C(=O)NC3CC3)c2)cn1] | 5-[1-[4-bromo-5-(1,1,2,2,3,3,3-heptafluoropropylsulfanyl)-2-methyl-pyrazol-3-yl]pyrazol-4-yl]-2-chloro-N-cyclopropyl-benzamide |
| 65 | 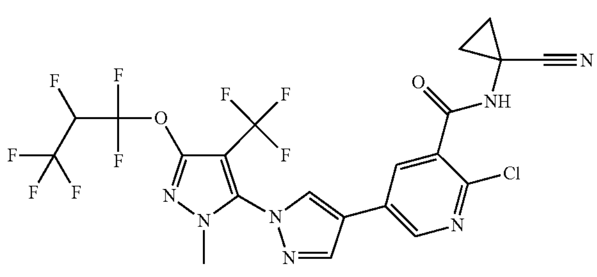 [SMILES: Cn1nc(OC(F)(F)C(F)C(F)(F)F)c(C(F)(F)F)c1-n1cc(-c2cnc(Cl)c(C(=O)NC3(C#N)CC3)c2)cn1] | 2-chloro-N-(1-cyanocyclopropyl)-5-[1-[5-(1,1,2,3,3,3-hexafluoropropoxy)-2-methyl-4-(trifluoromethyl)pyrazol-3-yl]pyrazol-4-yl]pyridine-3-carboxamide |

-continued

| Example No. | Structure | Chemical name |
|---|---|---|
| 66 | 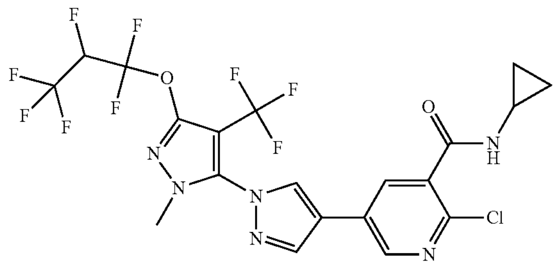 [SMILES: Cn1nc(OC(F)(F)C(F)C(F)(F)F)c(C(F)(F)F)c1-n1cc(-c2cnc(Cl)c(C(=O)NC3CC3)c2)cn1] | 2-chloro-N-cyclopropyl-5-[1-[5-(1,1,2,3,3,3-hexafluoropropoxy)-2-methyl-4-(trifluoromethyl)pyrazol-3-yl]pyrazol-4-yl]pyridine-3-carboxamide |
| 67 | 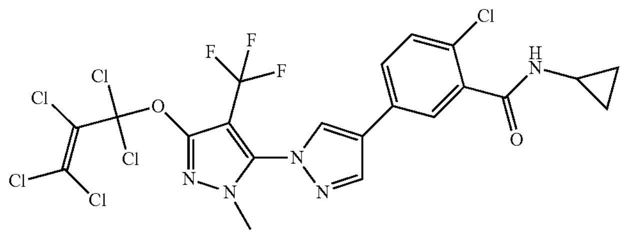 [SMILES: Cn1nc(OC(Cl)(Cl)C(Cl)=C(Cl)Cl)c(C(F)(F)F)c1-n1cc(-c2ccc(Cl)c(C(=O)NC3CC3)c2)cn1] | 2-chloro-N-cyclopropyl-5-[1-[2-methyl-5-(1,1,2,3,3-pentachloroallyloxy)-4-(trifluoromethyl)pyrazol-3-yl]pyrazol-4-yl]benzamide |
| 68 | 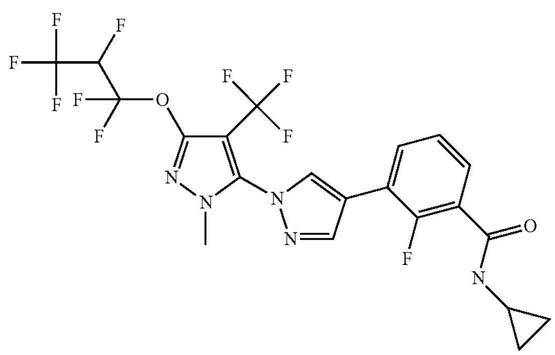 [SMILES: Cn1nc(OC(F)(F)C(F)C(F)(F)F)c(C(F)(F)F)c1-n1cc(-c2cccc(C(=O)NC3CC3)c2F)cn1] | N-cyclopropyl-2-fluoro-3-[1-[5-(1,1,2,3,3,3-hexafluoropropoxy)-2-methyl-4-(trifluoromethyl)pyrazol-3-yl]pyrazol-4-yl]benzamide |
| 69 | 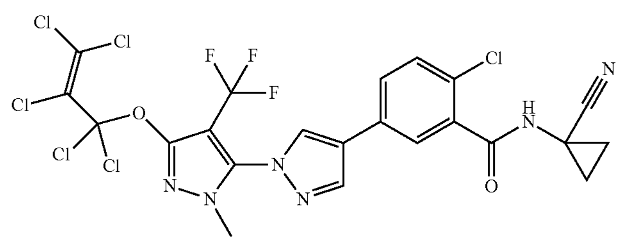 [SMILES: Cn1nc(OC(Cl)(Cl)C(Cl)=C(Cl)Cl)c(C(F)(F)F)c1-n1cc(-c2ccc(Cl)c(C(=O)NC3(C#N)CC3)c2)cn1] | 2-chloro-N-(1-cyanocyclopropyl)-5-[1-[2-methyl-5-(1,1,2,3,3-pentachloroallyloxy)-4-(trifluoromethyl)pyrazol-3-yl]pyrazol-4-yl]benzamide |
| 70 | 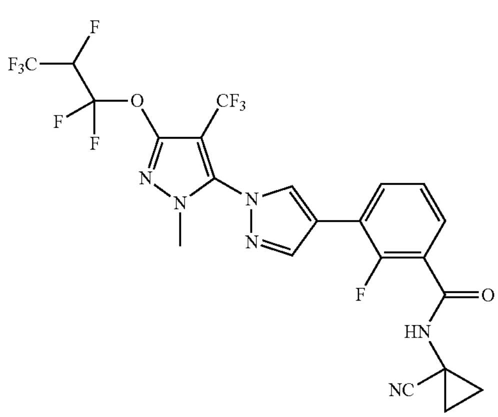 [SMILES: Cn1nc(OC(F)(F)C(F)C(F)(F)F)c(C(F)(F)F)c1-n1cc(-c2cccc(C(=O)NC3(C#N)CC3)c2F)cn1] | 3-[1-[2,4-dimethyl-5-(1,1,2-trifluoropropoxy)pyrazol-3-yl]pyrazol-4-yl]-2-fluoro-N-(1-cyanocyclopropyl)benzamide |

-continued

| Example No. | Structure | Chemical name |
|---|---|---|
| 71 | 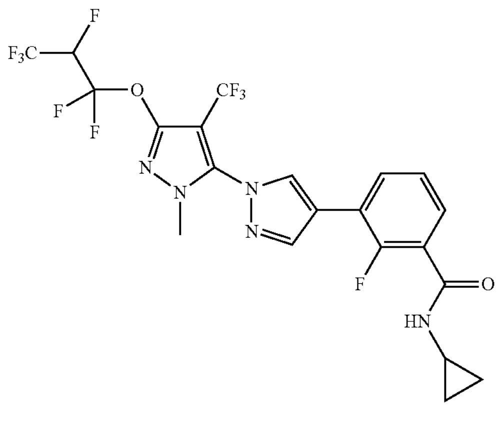 [SMILES: Cn1nc(OC(F)(F)C(F)C(F)(F)F)c(C(F)(F)F)c1-n1cc(-c2cccc(C(=O)NC3CC3)c2F)cn1] | N-cyclopropyl-3-[1-[2,4-dimethyl-5-(1,1,2-trifluoropropoxy)pyrazol-3-yl]pyrazol-4-yl]-2-fluoro-benzamide |
| 72 | 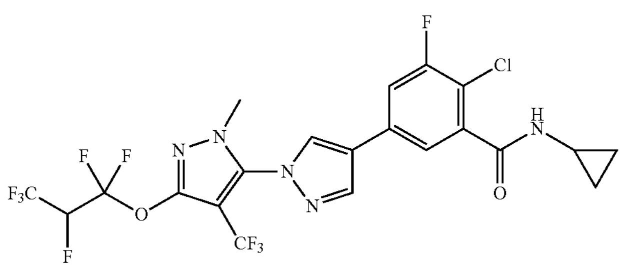 [SMILES: Cn1nc(OC(F)(F)C(F)C(F)(F)F)c(C(F)(F)F)c1-n1cc(-c2cc(F)c(Cl)c(C(=O)NC3CC3)c2)cn1] | 2-chloro-N-cyclopropyl-5-[1-[2,4-dimethyl-5-(1,1,2-trifluoropropoxy)pyrazol-3-yl]pyrazol-4-yl]-3-fluoro-benzamide |
| 73 | 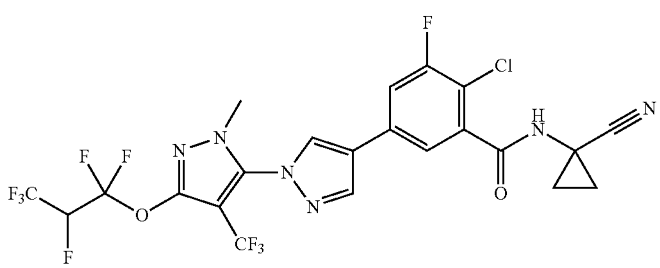 [SMILES: Cn1nc(OC(F)(F)C(F)C(F)(F)F)c(C(F)(F)F)c1-n1cc(-c2cc(F)c(Cl)c(C(=O)NC3(C#N)CC3)c2)cn1] | 2-chloro-N-(1-cyanocyclopropyl)-5-[1-[2,4-dimethyl-5-(1,1,2-trifluoropropoxy)pyrazol-3-yl]pyrazol-4-yl]-3-fluoro-benzamide |
| 74 | 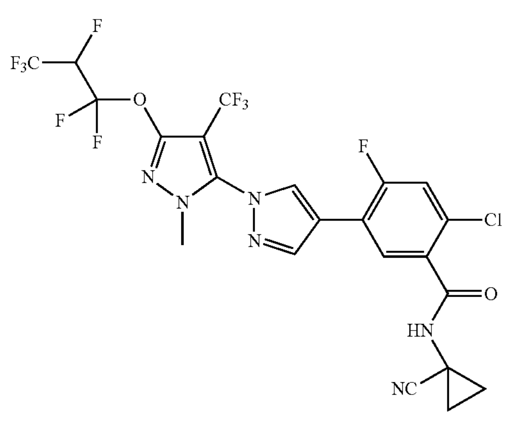 | 2-chloro-5-[1-[2,4-dimethyl-5-(1,1,2-trifluoropropoxy)pyrazol-3-yl]pyrazol-4-yl]-4-fluoro-N-(1-cyanocyclopropyl)benzamide |

-continued
| Example No. | Structure | Chemical name |
|---|---|---|
| 75 | 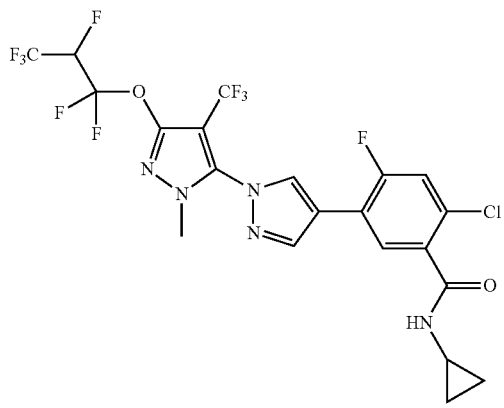 [SMILES: Cn1nc(OC(F)(F)C(F)C(F)(F)F)c(C(F)(F)F)c1-n1cc(-c2cc(C(=O)NC3CC3)c(Cl)cc2F)cn1] | 2-chloro-N-cyclopropyl-5-[1-[2,4-dimethyl-5-(1,1,2-trifluoropropoxy)pyrazol-3-yl]pyrazol-4-yl]-4-fluoro-benzamide |
| 76 | 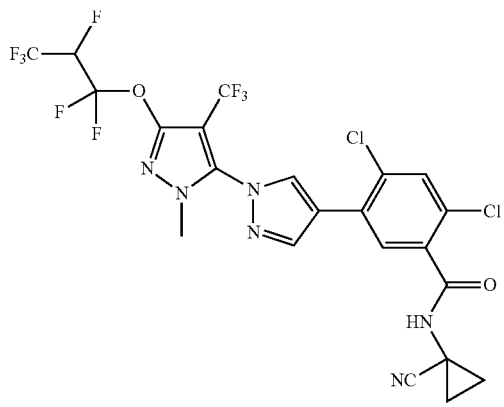 [SMILES: Cn1nc(OC(F)(F)C(F)C(F)(F)F)c(C(F)(F)F)c1-n1cc(-c2cc(C(=O)NC3(C#N)CC3)c(Cl)cc2Cl)cn1] | 2,4-dichloro-5-[1-[2,4-dimethyl-5-(1,1,2-trifluoropropoxy)pyrazol-3-yl]pyrazol-4-yl]-N-(1-cyanocyclopropyl)benzamide |
| 77 | 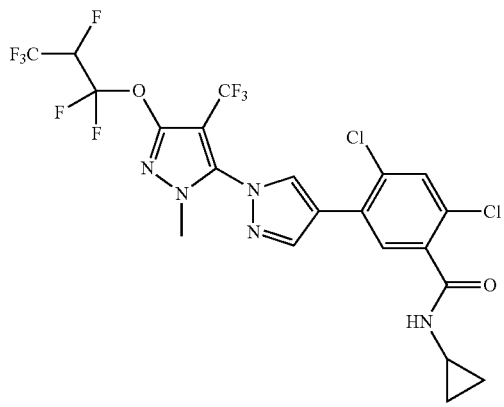 [SMILES: Cn1nc(OC(F)(F)C(F)C(F)(F)F)c(C(F)(F)F)c1-n1cc(-c2cc(C(=O)NC3CC3)c(Cl)cc2Cl)cn1] | 2,4-dichloro-N-cyclopropyl-5-[1-[2,4-dimethyl-5-(1,1,2-trifluoropropoxy)pyrazol-3-yl]pyrazol-4-yl]benzamide |

-continued

| Example No. | Structure | Chemical name |
|---|---|---|
| 78 | 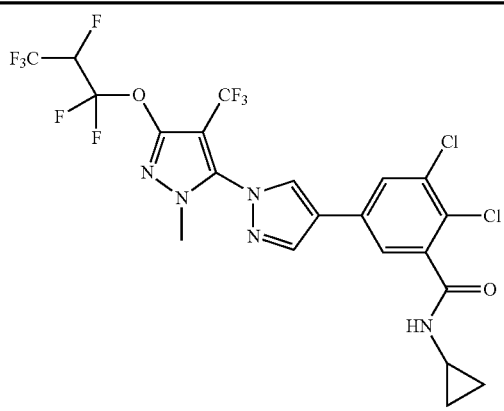 | 2,3-dichloro-N-cyclopropyl-5-[1-[2,4-dimethyl-5-(1,1,2-trifluoropropoxy)pyrazol-3-yl]pyrazol-4-yl]benzamide |
| 79 | 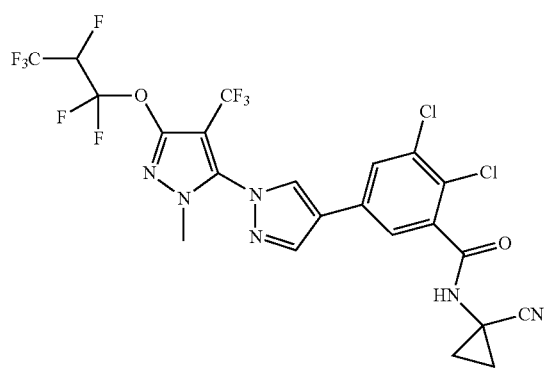 [SMILES: Cn1nc(OC(F)(F)C(F)C(F)(F)F)c(C(F)(F)F)c1-n1cc(-c2cc(Cl)c(Cl)c(C(=O)NC3(C#N)CC3)c2)cn1] | 2,3-dichloro-5-[1-[2,4-dimethyl-5-(1,1,2-trifluoropropoxy)pyrazol-3-yl]pyrazol-4-yl]-N-(1-cyanocyclopropyl)benzamide |
| 80 | 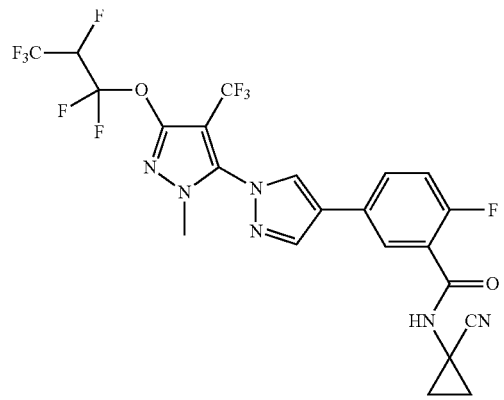 [SMILES: Cn1nc(OC(F)(F)C(F)C(F)(F)F)c(C(F)(F)F)c1-n1cc(-c2ccc(F)c(C(=O)NC3(C#N)CC3)c2)cn1] | 5-[1-[2,4-dimethyl-5-(1,1,2-trifluoropropoxy)pyrazol-3-yl]pyrazol-4-yl]-2-fluoro-N-(1-cyanocyclopropyl)benzamide |
| 81 | 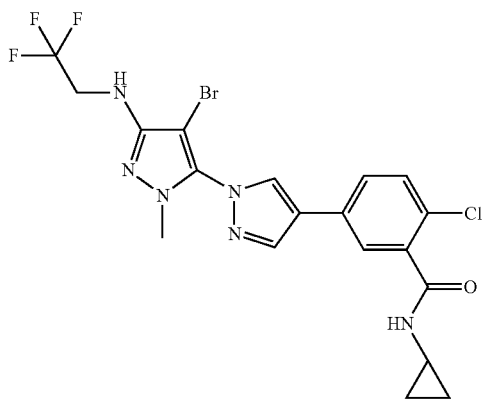 [SMILES: Cn1nc(NCC(F)(F)F)c(Br)c1-n1cc(-c2ccc(Cl)c(C(=O)NC3CC3)c2)cn1] | 5-[1-[4-bromo-2-methyl-5-(2,2,2-trifluoroethylamino)pyrazol-3-yl]pyrazol-4-yl]-2-chloro-N-cyclopropyl-benzamide |

-continued

| Example No. | Structure | Chemical name |
|---|---|---|
| 82 | 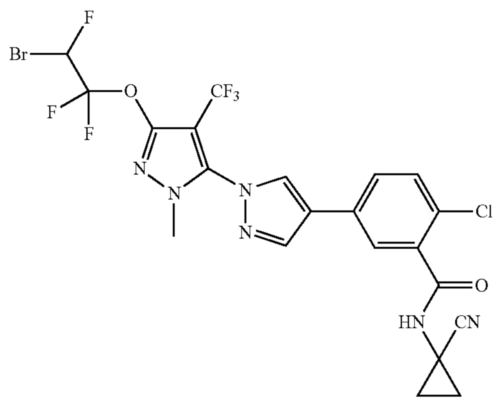 [SMILES: Cn1nc(OC(F)(F)C(F)Br)c(C(F)(F)F)c1-n1cc(-c2ccc(Cl)c(C(=O)NC3(C#N)CC3)c2)cn1] | 5-[1-[5-(2-bromo-1,1,2-trifluoro-ethoxy)-2,4-dimethyl-pyrazol-3-yl]pyrazol-4-yl]-2-chloro-N-(1-cyanocyclopropyl)benzamide |
| 83 | 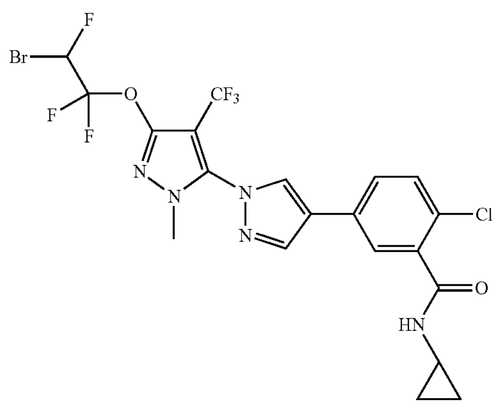 | 5-[1-[5-(2-bromo-1,1,2-trifluoro-ethoxy)-2,4-dimethyl-pyrazol-3-yl]pyrazol-4-yl]-2-chloro-N-cyclopropyl-benzamide |
| 84 | 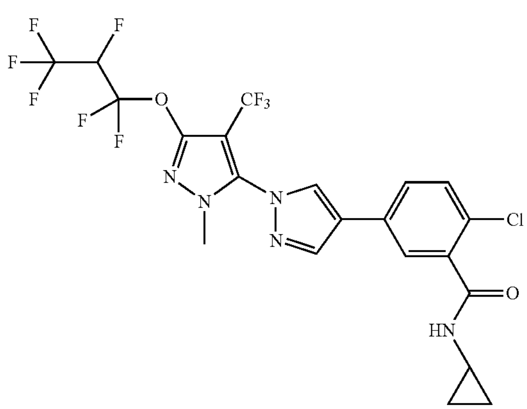 [SMILES: Cn1nc(OC(F)(F)C(F)C(F)(F)F)c(C(F)(F)F)c1-n1cc(-c2ccc(Cl)c(C(=O)NC3CC3)c2)cn1] | 2-chloro-N-cyclopropyl-5-[1-[5-(1,1,2,3,3,3-hexafluoropropoxy)-2,4-dimethyl-pyrazol-3-yl]triazol-4-yl]benzamide |

| Example No. | Structure | Chemical name |
|---|---|---|
| 85 | 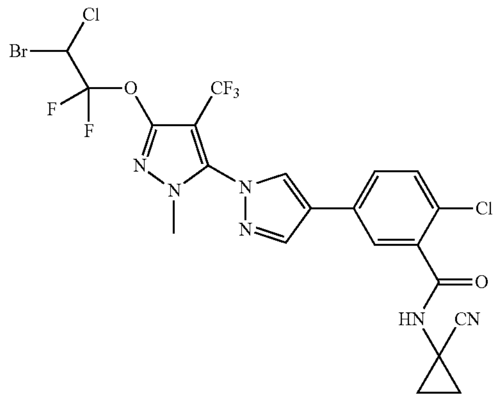 [SMILES: Cn1nc(OC(F)(F)C(Cl)Br)c(C(F)(F)F)c1-n1cc(-c2ccc(Cl)c(C(=O)NC3(C#N)CC3)c2)cn1] | 5-[1-[5-(2-bromo-2-chloro-1,1-difluoro-ethoxy)-2,4-dimethyl-pyrazol-3-yl]pyrazol-4-yl]-2-chloro-N-(1-cyanocyclopropyl)benzamide |
| 86 | 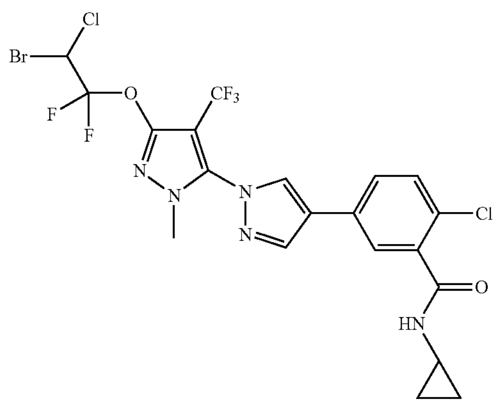 [SMILES: Cn1nc(OC(F)(F)C(Cl)Br)c(C(F)(F)F)c1-n1cc(-c2ccc(Cl)c(C(=O)NC3CC3)c2)cn1] | 5-[1-[5-(2-bromo-2-chloro-1,1-difluoro-ethoxy)-2,4-dimethyl-pyrazol-3-yl]pyrazol-4-yl]-2-chloro-N-cyclopropyl-benzamide |
| 87 | | 2-chloro-N-cyclopropyl-5-[1-(5-methoxy-2,4-dimethyl-pyrazol-3-yl)triazol-4-yl]benzamide | or an agrochemically acceptable salt or N-oxide thereof.

As used herein, when one embodiment refers to several other embodiments by using the term "according to any one of", for example "according to any one of embodiments 1 to 23", then said embodiment refers not only to embodiments indicated by integers such as 1 and 2 but also to embodiments indicated by numbers with a decimal component such as 23.1, 23.2, 23.3, 23.4, 23.20, 23.25, 23.30.

Definitions

The term "Alkyl" as used herein—in isolation or as part of a chemical group—represents straight-chain or branched hydrocarbons, preferably with 1 to 6 carbon atoms, for example methyl, ethyl, n-propyl, isopropyl, n-butyl, isobutyl, s-butyl, t-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylpropyl, 1,3-dimethylbutyl, 1,4-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl and 2-ethylbutyl. Alkyl groups with 1 to 4 carbon atoms are preferred, for example methyl, ethyl, n-propyl, isopropyl, n-butyl, isobutyl, s-butyl or t-butyl.

The term "Alkenyl"—in isolation or as part of a chemical group—represents straight-chain or branched hydrocarbons, preferably with 2 to 6 carbon atoms and at least one double bond, for example vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl- 3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1, 2-trimethyl-2-propenyl, 1-ethyl-1-methyl-2-propenyl and 1-ethyl-2-methyl-2-propenyl. Alkenyl groups with 2 to 4 carbon atoms are preferred, for example 2-propenyl, 2-butenyl or 1-methyl-2-propenyl.

The term "alkynyl"—in isolation or as part of a chemical group—represents straight-chain or branched hydrocarbons, preferably with 2 to 6 carbon atoms and at least one triple bond, for example 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-3-butynyl, 1,2-dimethyl-3-butynyl, 2,2-dimethyl-3-butynyl, 1-ethyl-3-butynyl, 2-ethyl-3-butynyl, 1-ethyl-1-methyl, 1,2-propynyl and 2,5-hexadiynyl. Alkynyls with 2 to 4 carbon atoms are preferred, for example ethynyl, 2-propynyl or 2-butynyl-2-propynyl.

The term "cycloalkyl" In isolation or as part of a chemical group—represents saturated or partially unsaturated mono-, bi- or tricyclic hydrocarbons, preferably 3 to 10 carbon atoms, for example cyclopropyl, cyclobutyl, cyclopentyl, cyclohexyl, cycloheptyl, cyclooctyl, bicyclo[2.2.1]heptyl, bicyclo[2.2.2]octyl or adamantyl.

Cycloalkyls with 3, 4, 5, 6 or 7 carbon atoms are preferred, for example cyclopropyl or cyclobutyl.

The term "heterocycloalkyl"—in isolation or as part of a chemical group—represents saturated or partially unsaturated mono-, bi- or tricyclic hydrocarbons, preferably 3 to 10 carbon atoms, for example cyclopropyl, cyclobutyl, cyclopentyl, cyclohexyl, cycloheptyl, cyclooctyl, bicyclo[2.2.1]heptyl, bicyclo[2.2.2]octyl or adamantyl, wherein one or more of the ring atoms, preferably 1 to 4, more preferably 1, 2 or 3 of the ring atoms are independently selected from N, O, S, P, B, Si and Se, more preferably N, O and S, wherein no O atoms can be located next to each other.

The term "Alkylcycloalkyl" represents mono-, bi- or tricyclic alkylcycloalkyl, preferably with 4 to 10 or 4 to 7 carbon atoms, for example ethylcyclopropyl, isopropylcyclobutyl, 3-methylcyclopentyl and 4-methyl-cyclohexyl. Alkylcycloalkyls with 4, 5 or 7 carbon atoms are preferred, for example ethylcyclopropyl or 4-methyl-cyclohexyl.

The term "cycloalkylalkyl" represents mono, bi- or tricyclic cycloalkylalkyls, preferably 4 to 10 or 4 to 7 carbon atoms, for example cyclopropylmethyl, cyclobutylmethyl, cyclopentylmethyl, cyclohexylmethyl and cyclopentylethyl. Cycloalkylalkyls with 4, 5 or 7 carbon atoms are preferred, for example cyclopropylmethyl or cyclobutylmethyl.

The term "halogen" represents fluoro, chloro, bromo or iodo, particularly fluoro, chloro or bromo. The chemical groups which are substituted with halogen, for example haloalkyl, halocycloalkyl, haloalkyloxy, haloalkylsulfanyl, haloalkylsulfinyl or haloalkylsulfonyl are substituted one or up to the maximum number of substituents with halogen. If "alkyl", "alkenyl" or "alkynyl" are substituted with halogen, the halogen atoms can be the same or different and can be bound at the same carbon atom or different carbon atoms.

The term "halocycloalkyl" represents mono-, bi- or tricyclic halocycloalkyl, preferably with 3 to 10 carbon atoms, for example 1-fluoro-cyclopropyl, 2-fluoro-cyclopropyl or 1-fluoro-cyclobutyl. Preferred halocycloalkyl have 3, 5 or 7 carbon atoms.

The term "haloalkyl", "haloalkenyl" or "haloalkynyl" represents alkyls, alkenyls or alkynyls substituted with halogen, preferably with 1 to 9 halogen atoms that are the same or different, for example monohaloalkyls (=monohaloalkyl) like $CH_2CH_2Cl$, $CH_2CH_2F$, $CHClCH_3$, $CHFCH_3$, $CH_2Cl$, $CH_2F$; perhaloalkyls like $CCl_3$ or $CF_3$ or $CF_2CF_3$; polyhaloalkyls like $CHF_2$, $CH_2F$, $CH_2CHFCl$, $CF_2CF_2H$, $CH_2CF_3$. The same applies for haloalkenyl and other groups substituted by halogen.

Examples of haloalkoxy are for example $OCF_3$, $OCHF_2$, $OCH_2F$, $OCF_2CF_3$, $OCH_2CF_3$, $OCF_3$, $OCHF_2$, $OCH_2F$, $OCF_2CF_3$, $OCH_2CF_3$.

Further examples of haloalkyls are trichloromethyl, chlorodifluoromethyl, dichlorofluoromethyl, 1-fluoroethyl, 2-fluoroethyl, 2,2-difluoroethyl, 2,2,2-trifluorethyl, 2,2,2-trichloroethyl, 2-chloro-2,2-difluoroethyl, pentafluoroethyl and pentafluoro-t-butyl.

Haloalkyls having 1 to 4 carbon atoms and 1 to 9, preferably 1 to 5 of the same or different halogen atoms selected from fluoro, chloro or bromo, are preferred.

Haloalkyls having 1 or 2 carbon atoms and 1 to 5 of the same or different halogen atoms selected from fluoro or chloro, for example difluoromethyl, trifluoromethyl or 2,2-difluoroethyl, are particularly preferred.

The term "hydroxyalkyl" represents straight or branched chain alcohols, preferably with 1 to 6 carbon atoms, for example methanol, ethanol, n-propanol, isopropanol, n-butanol, isobutanol, s-butanol and t-butanol. Hydroxyalkyls having 1 to 4 carbon atoms are preferred.

The term "alkoxy" represents straight or branched chain O-alkyl, preferably having 1 to 6 carbon atoms, for example methoxy, ethoxy, n-propoxy, isopropoxy, n-butoxy, isobutoxy, s-butoxy and t-butoxy. Alkoxy having 1 to 4 carbon atoms are preferred.

The term "haloalkoxy" represents straight or branched chain O-alkyl substituted with halogen, preferably with 1 to 6 carbon atoms, for example difluoromethoxy, trifluoromethoxy, 2,2-difluoroethoxy, 1,1,2,2-tetrafluoroethoxy, 2,2,2-Trifluoroethoxy and 2-Chloro-1,1,2-trifluoroethoxy.

Haloalkoxy having 1 to 4 carbon atoms are preferred.

The term "alkylsulfanyl" represents straight or branched chain S-alkyl, preferably with 1 to 6 carbon atoms, for example methylthio, ethylthio, n-propylthio, isopropylthio, n-butylthio, isobutylthio, s-butylthio and t-butylthio. Alkylsulfanyl having 1 to 4 carbon atoms are preferred. Examples for haloalkylsulfanyl, i.e. with halogen substituted alkylsulfanyl, are for example difluoromethylthio, trifluoromethylthio, trichloromethylthio, chlorodifluoromethylthio, 1-fluoroethylthio, 2-fluoroethylthio, 2,2-difluoroethylthio, 1,1,2,2-tetrafluoroethylthio, 2,2,2-trifluoroethylthio or 2-chloro-1,1,2-trifluoroethylthio.

The term "alkylsulfinyl" represents straight or branched chain alkylsulfinyl, preferably having 1 to 6 carbon atoms, for example methylsulfinyl, ethylsulfinyl, n-propylsulfinyl, isopropylsulfinyl, n-butylsulfinyl, isobutylsulfinyl, s-butylsulfinyl and t-butylsulfinyl.

Alkylsulfinyls having 1 to 4 carbon atoms are preferred.

Examples of haloalkylsulfinyls, i.e. with halogen substituted alkylsulfinyls, are difluoromethylsulfinyl, trifluoromethylsulfinyl, trichloromethylsulfinyl, chlorodifluoromethylsulfinyl, 1-fluoroethylsulfinyl, 2-fluoroethylsulfinyl, 2,2-difluoroethylsulfinyl, 1,1,2,2-tetrafluoroethylsulfinyl, 2,2,2-trifluoroethylsulfinyl and 2-chloro-1,1,2-trifluoroethylsulfinyl.

The term "alkylsulfonyl" represents straight or branched chain alkylsulfonyl, preferably having 1 to 6 carbon atoms, for example methylsulfonyl, ethylsulfonyl, n-propylsulfonyl, isopropylsulfonyl, n-butylsulfonyl, isobutylsulfonyl, s-butylsulfonyl and t-butylsulfonyl.

Alkylsulfonyls having 1 to 4 carbon atoms are preferred.

Examples of haloalkylsulfonyls, i.e. with halogen substituted alkylsulfonyls, are for example difluoromethylsulfonyl, trifluoromethylsulfonyl, trichloromethylsulfonyl, chlorodfluoromethylsulfonyl, 1-fluoroethylsulfonyl, 2-fluoroethylsulfonyl, 2,2-difluoroethylsulfonyl, 1,1,2,2-tetrafluoroethylsulfonyl, 2,2,2-trifluoroethylsulfonyl and 2-chloro-1,1,2-trifluorethylsulfonyl.

The term "alkylcarbonyl" represents straight or branched chain akyl-C(=O), preferably having 2 to 7 carbon atoms, for example methylcarbonyl, ethylcarbonyl, n-propylcarbonyl, isopropylcarbonyl, s-butylcarbonyl and t-butylcarbonyl.

Alkylcarbonyls having 1 to 4 carbon atoms are preferred.

The term "cycloalkylcarbonyl" represents cycloalkyl-carbonyl, preferably 3 to 10 carbon atoms in the cycloakyl part, for example cyclopropylcarbonyl, cyclobutylcarbonyl, cyclopentylcarbonyl, cyclohexyl-carbonyl, cycloheptyl-carbonyl, cyclooctylcarbonyl, bicyclo[2.2.1]heptyl, bicyclo[2.2.2]octylcarbonyl and adamantylcarbonyl. Cycloalkyl-carbonyls having 3, 5 or 7 carbon atoms in the cycloalkyl part are preferred.

The term "alkoxycarbonyl"—in isolation or as part of a chemical group—represents straight or branched chain alkoxycarbonyl, preferably having 1 to 6 carbon atoms or 1 to 4 carbon atoms in the alkoxy part, for example methoxycarbonyl, ethoxycarbonyl, n-propoxycarbonyl, isopropoxycarbonyl, s-butoxycarbonyl and t-butoxycarbonyl.

The term "alkylaminocarbonyl" represents straight or branched chain alkylaminocarbonyl having preferably 1 to 6 carbon atoms or 1 to 4 carbon atoms in the alkyl part, for example methylaminocarbonyl, ethylaminocarbonyl, n-proylaminocarbonyl, isopropyl-aminocarbonyl, s-butylaminocarbonyl and t-butylaminocarbonyl.

The term "N,N-Dialkylamino-carbonyl" represents straight or branched chain N,N-diakylaminocarbonyl with preferably 1 to 6 carbon atoms or 1 to 4 carbon atoms in the akyl part, for example N,N-Dimethylamino-carbonyl, N,N-diethylamino-carbonyl, N,N-di(n-propylamino)-carbonyl, N,N-di-(isopropylamino)-carbonyl and N,N-di-(s-butylamino)-carbonyl.

The term "aryl" represents a mono-, bi- or polycydical aromatic system with preferably 6 to 14, more preferably 6 to 10 ring-carbon atoms, for example phenyl, naphthyl, anthryl, phenanthrenyl, preferably phenyl. "Aryl" also represents polycyclic systems, for example tetrahydronaphtyl, indenyl, Indanyl, fluorenyl, biphenyl. Arylalkyls are examples of substituted aryls, which may be further substituted with the same or different substituents both at the aryl or alkyl part. Benzyl and 1-phenylethyl are examples of such arylalkyls.

The term "heterocyclyl", "heterocyclic ring" or "heterocyclic ring system" represents a carbocyclic ring system with at least one ring, in which ring at least one carbon atom is replaced by a heteroatom, preferably selected from N, O, S, P, B, SI, Se, and which ring is saturated, unsaturated or partially saturated, and which ring is unsubstituted or substituted with a substituent Z, wherein the connecting bond is located at a ring atom. Unless otherwise defined, the heterocyclic ring has preferably 3 to 9 ring atoms, preferably 3 to 6 ring atoms, and one or more, preferably 1 to 4, more preferably 1, 2 or 3 heteroatoms in the heterocyclic ring, preferably selected from N, O, and S, wherein no O atoms can be located next to each other. The heterocyclic rings normally contain no more than 4 nitrogens, and/or no more than 2 oxygen atoms and/or no more than 2 sulfur atoms. In case that the heterocyclic substituent or the heterocyclic ring are further substituted, it can be further annulated with other heterocyclic rings.

The term "heterocyclic" also includes polycyclic systems, for example 5-aza-bicyclo[3.2.1]octanyl or 1-aza-bicyclo[2.2.1]heptyl.

The term "heterocycldic" also includes spirocyclic systems, for example 1-oxa-5-aza-spiro[2.3]hexyl. Examples of heterocyclyls are for example piperidinyl, piperazinyl, morpholinyl, thiomorpholinyl, dihydropyranyl, tetrahydropyranyl, dioxanyl, pyrrolinyl, pyrrolidinyl, imidazolinyl, Imidazolidinyl, thiazolidinyl, oxazolidinyl, dioxolanyl, dioxolyl, pyrazolidinyl, tetrahydrofuranyl, dihydrofuranyl, oxetanyl, oxiranyl, azetidinyl, aziridinyl, oxazetidinyl, oxaziridinyl, oxazepanyl, oxazinanyl, azepanyl, oxopyrrolidinyl, dioxopyrrolidinyl, oxomorpholinyl, oxopiperazinyl and oxepanyl.

Particularly important are heteroaryls, i.e. heteroaromatic systems.

The term "heteroaryl" represents heteroaromatic groups, i.e. completely unsaturated aromatic heterocyclic groups, which fall under the above definition of heterocycls. "Heteroaryls" with 5 to 7-membered rings with 1 to 3, preferably 1 or 2 of the same or different heteroatoms selected from N, O, and S. Examples of "heteroaryls" are furyl, thienyl, pyrazolyl, imidazolyl, 1,2,3- and 1,2,4-triazolyl, isoxazolyl, thiazolyl, isothiazolyl, 1,2,3-, 1,3,4-, 1,2,4- and 1,2,5-oxadiazolyl, azepinyl, pyrrolyl, pyridyl, pyridazinyl, pyrimidinyl, pyrazinyl, 1,3,5-, 1,2,4- and 1,2,3-triazinyl, 1,2,4-, 1,3,2-, 1,3,6- and 1,2,6-oxazinyl, oxepinyl, thiepinyl, 1,2,4-triazolonyl and 1,2,4-diazepinyl.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloakyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl.

Alkoxy is, for example, methoxy, ethoxy, propoxy, i-propoxy, n-butoxy, isobutoxy, sec-butoxy and tert-butoxy and also the isomeric pentyloxy and hexyloxy radicals.

Alkoxyalkyl groups preferably have a chain length of 1 to 6 carbon atoms.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkoxycarbonyl is for example methoxycarbonyl (which is $C_1$alkoxycarbonyl), ethoxycarbonyl, propoxycarbonyl, isopropoxycarbonyl, n-butoxycarbonyl, tert-butoxycarbonyl, n-pentoxycarbonyl or hexoxycarbonyl.

The cycloalkyl groups preferably have from 3 to 6 ring carbon atoms, for example cyclopropyl, cyclobutyl, cyclopentyl and cyclohexyl.

A compound according to any one of embodiments 1 to 78 which has at least one basic centre can form, for example, acid addition salts, for example with strong inorganic acids such as mineral acids, for example perchloric acid, sulfuric acid, nitric acid, nitrose acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. A compounds according to any one of embodiments 1 to 20 which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

Compounds according to any one of embodiments 1 to 78 also include hydrates which may be formed during the salt formation.

The compounds according to any one of embodiments 1 to 78 may be made by a variety of methods well known to a person skilled in the art or as shown in Schemes 1 to 4. Further instructions regarding the preparation can be found in WO2015/067646, WO2015/150442, WO2014/122083 and WO2012/107434.

For example, compounds of formula (Ia) or (Ib) can be prepared, for example, according to Scheme 1,

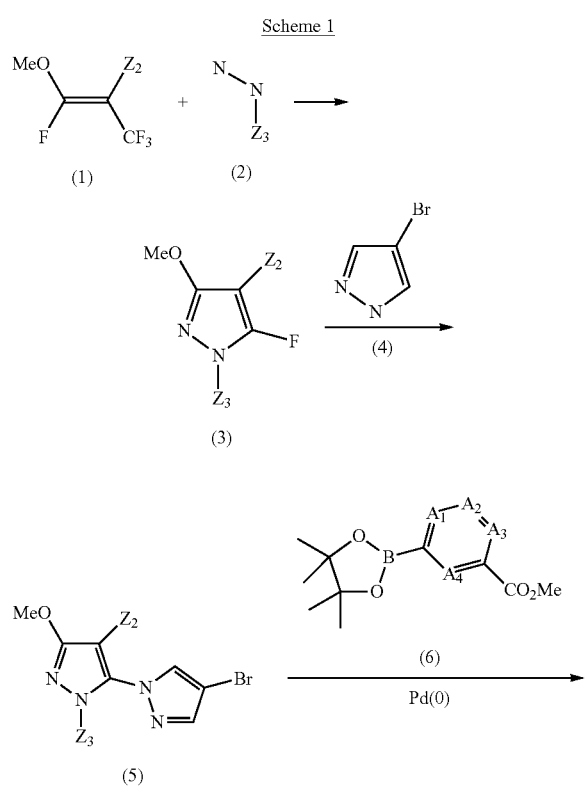

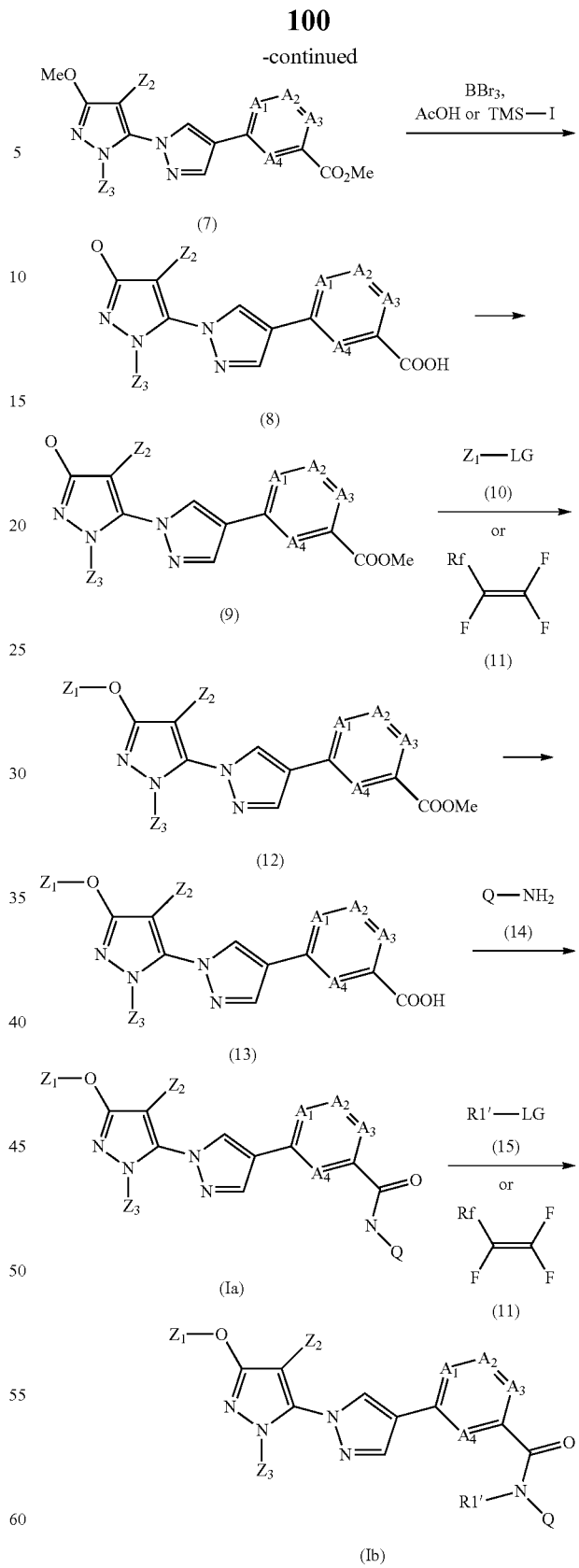

wherein $R^1$, Q, $A^1$, $A^2$, $A^3$, $A^4$, $Z^1$, $Z^2$, and $Z^3$ are as defined in any one of embodiments 1 to 78, $R^{1'}$ is as $R^1$ but not H, LG represents a leaving group such as Cl, Br, I, OMs (—OSO$_2$CH$_3$), OTs (—OSO$_2$—C or OTf and Rf is F or a fluorinated $C_{1-10}$alkyl. Compounds of formula (1), (2), (4), (6), (10), (11), (14) or (15) are commercially available or are known from the chemistry literature. Compound of formula (3) can be prepared according to processes described in WO12/158413 p. 371.

Compounds of formula (Ic) or (Id) can be prepared, for example, according to Scheme 2,

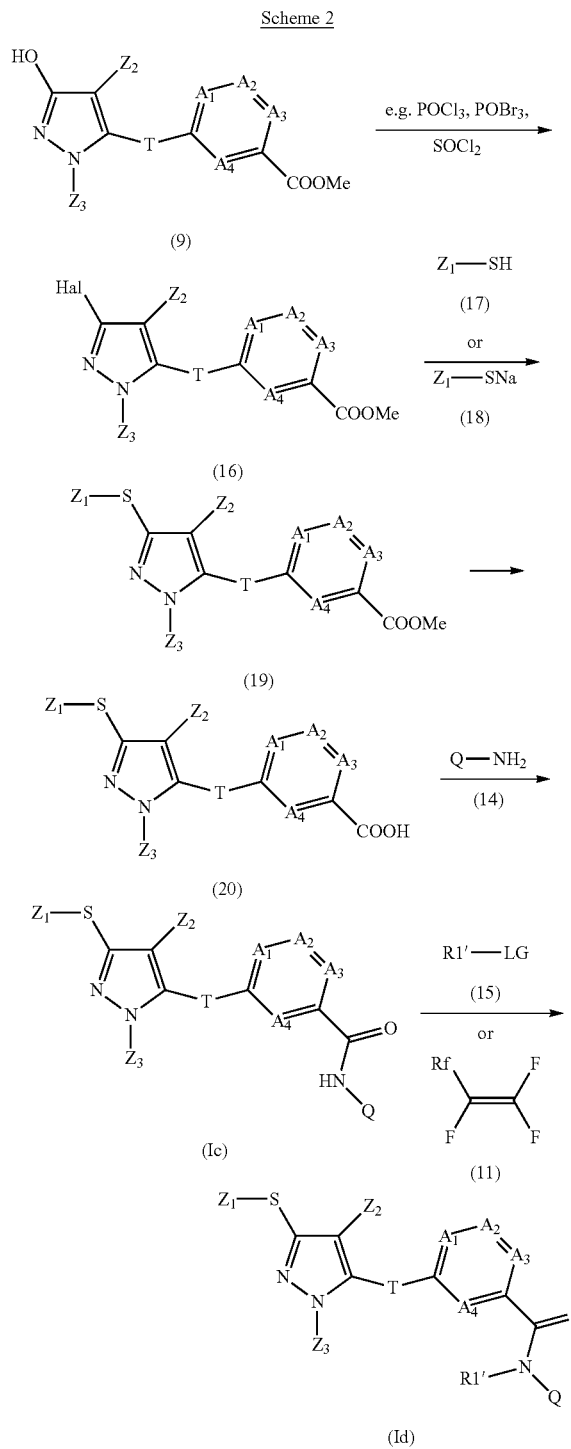

Scheme 2

(9), (16), (19), (20), (Ic), (Id)

LG represents a leaving group such as Cl, Br, I, OMs, OTs or OTf and Rf is F or a fluorinated $C_{1-10}$alkyl, Hal is an halogen such as Cl or Br. Compounds of formula (17) and (18) are commercially available or are known from the chemistry literature.

Compounds of formula (Ie) or (If) can be prepared, for example, according to Scheme 3,

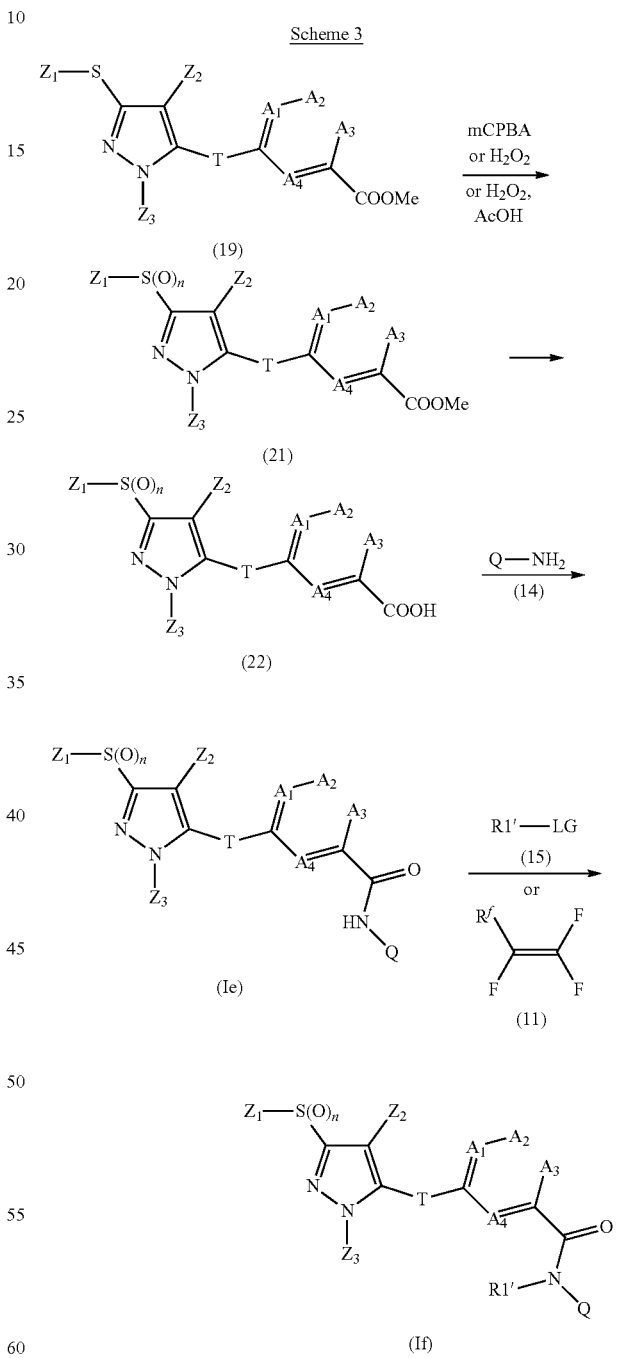

Scheme 3

(19), (21), (22), (Ie), (If)

wherein $R^1$, Q, T, $A^1$, $A^2$, $A^3$, $A^4$, $Z^1$, $Z^2$, and $Z^3$ are as defined in any one of embodiments 1 to 78, $R^{1'}$ is as $R^1$ but not H, LG represents a leaving group such as Cl, Br, I, OMs, OTs or OTf and Rf is F or a fluorinated $C_{1-10}$alkyl, n is 1 or 2.

wherein $R^1$, Q, T, $A^1$, $A^2$, $A^3$, $A^4$, $Z^1$, $Z^2$, and $Z^3$ are as defined in any one of embodiments, $R^{1'}$ is as $R^1$ but not H, Compounds of formula (Ig) or (Ih) can be prepared, for example, according to Scheme 4,

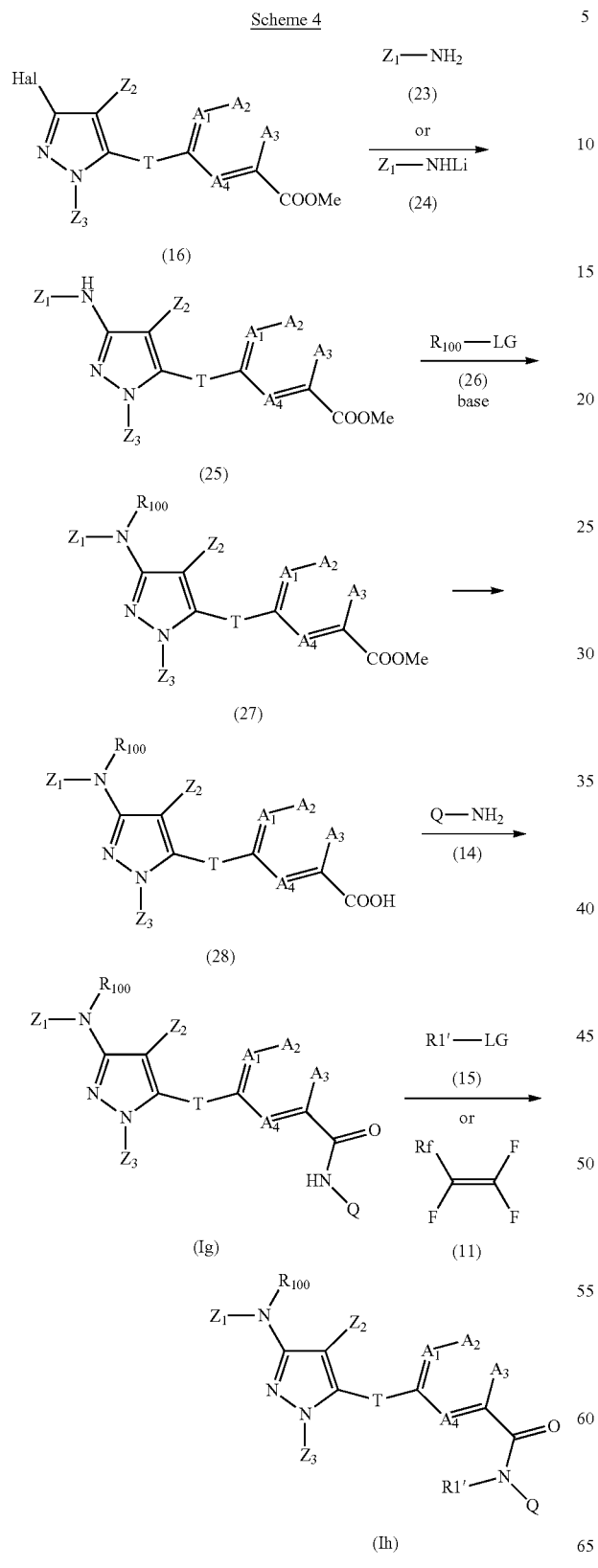

wherein $R^1$, $R^{100}$, Q, T, $A^1$, $A^2$, $A^3$, $A^4$, $Z^1$, $Z^2$, and $Z^3$ are as defined in any one of embodiments 1 to 78, $R^{1'}$ is as $R^1$ but not H, LG represents a leaving group such as Cl, Br, I, OMs, OTs or OTf and Rf is F or a fluorinated $C_{1-10}$alkyl, Hal is an halogen such as Cl or Br. Compounds of formula (23), (24) and (26) are commercially available or are known from the chemistry literature.

Compounds of formula (II) can be prepared, for example, according to Scheme 5,

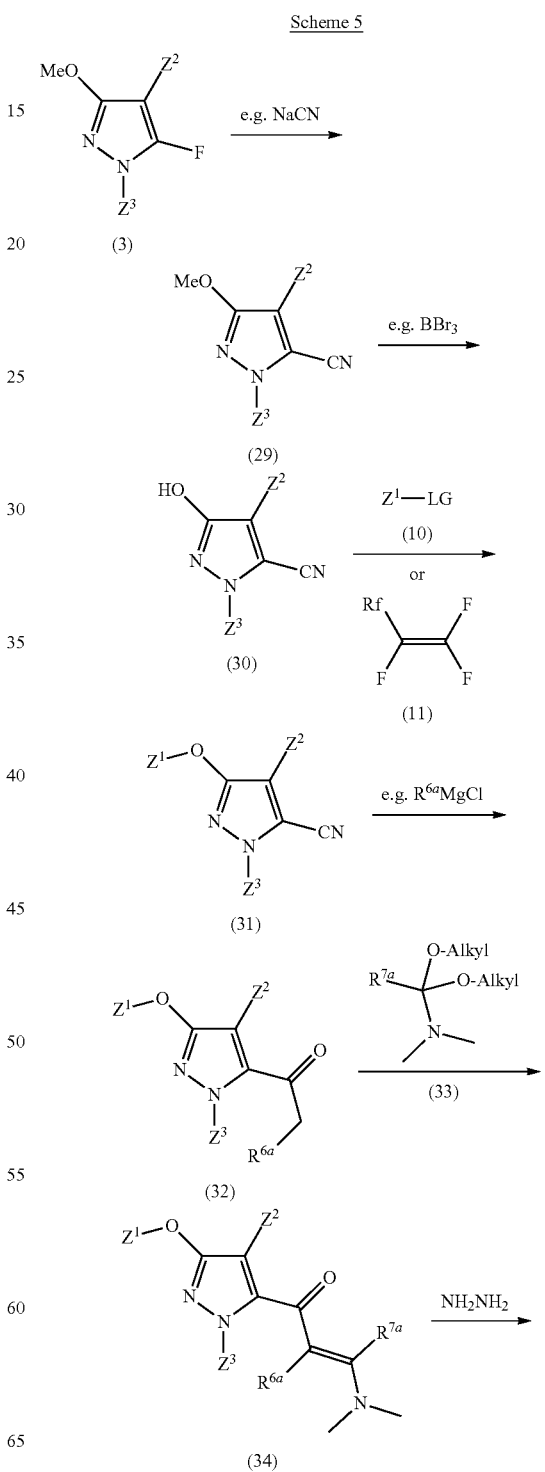

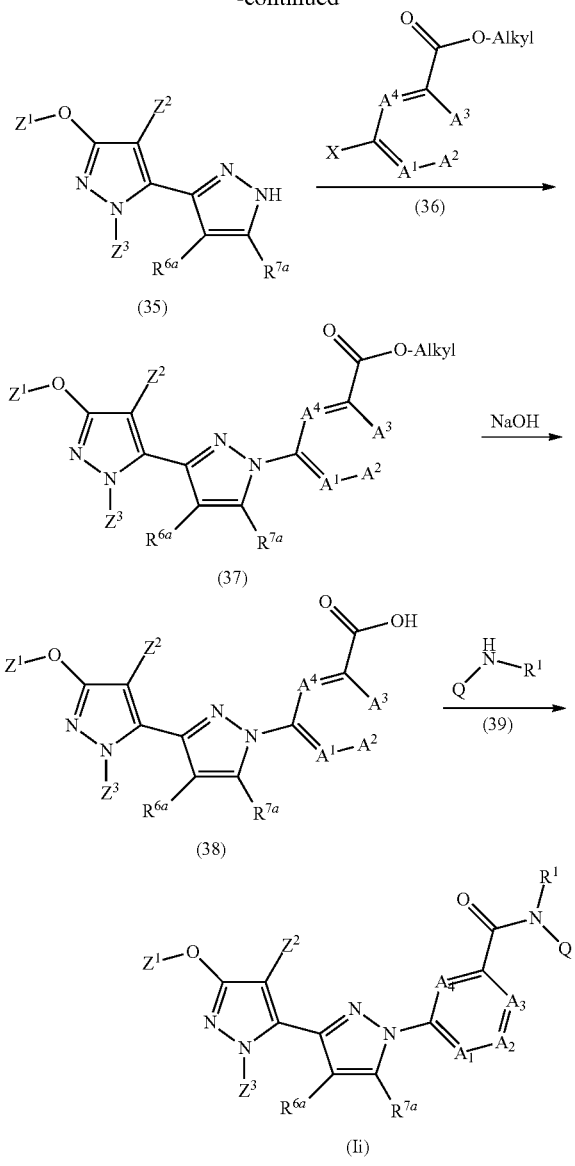

(35)

(37)

(38)

(Ii)

literature methods from compounds (38) and (39) via known peptide coupling methods (for example WO2010/051926 and WO2010/133312). Compounds (39) are known or may be prepared according to known methods.

Compounds of formula (Ii) can be prepared, for example, according to Scheme 6,

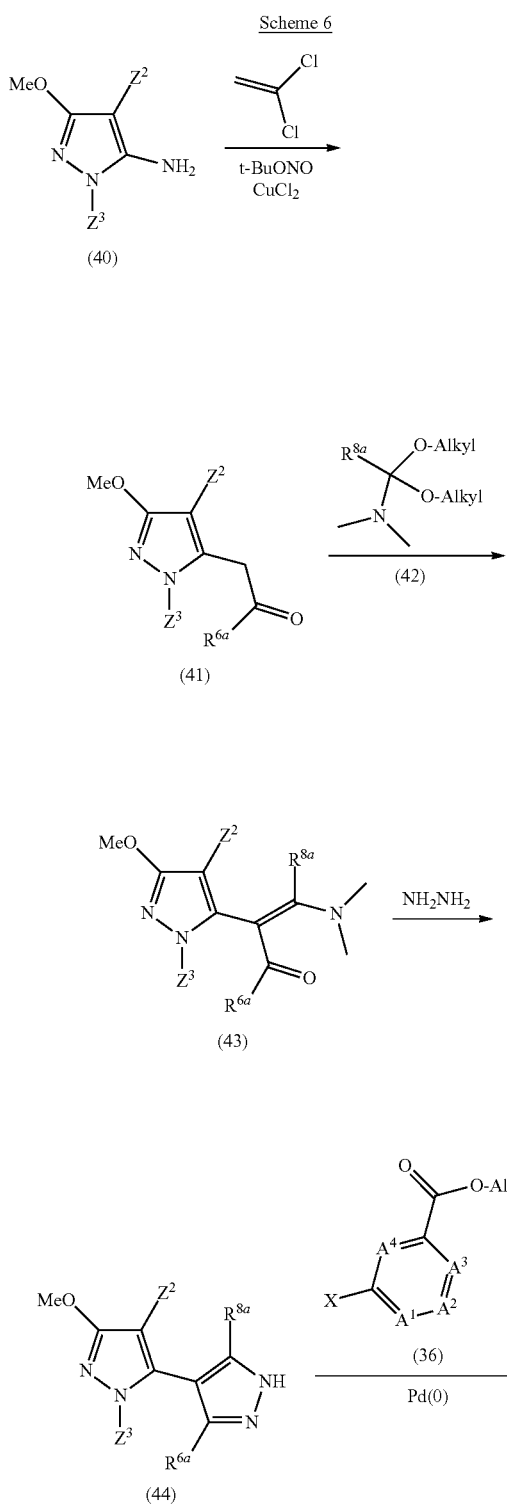

Scheme 6

(40)

(41)

(43)

(44)

wherein $R^1$, $R^{6a}$, $R^7$, Q, $A^1$, $A^2$, $A^3$, $A^4$, $Z^1$, $Z^2$, and $Z^3$ are as defined in any one of embodiments 1 to 78, LG represents a leaving group such as Cl, Br, I, OMs, OTs or OTf and Rf is F or a fluorinated $C_{1-10}$alkyl, X represents Cl, Br, I or a boronic acid/boronic acid ester group. Compounds of formula (33) and (36) are commercially available or are known from the chemistry literature.

Compounds (34) may be prepared in analogy to literature methods from compounds (32) and carbonic acid amide acetal compounds (33) (for example WO2006/044505, compound 60, part A; WO2012/4604, intermediate 2). Compounds (35) may be prepared in analogy to literature methods from compounds (34) and hydrazine (for example WO2013/009791, p. 50, example 43; WO2004/099146, p. 75-76). Compounds (37) may be prepared in analogy to literature methods from compounds (35) and (36) (for example WO2013/009791, p. 50, example 44, X=Br). Compounds (38) may be prepared in analogy to literature methods from compound (37) via ester cleavage (for example WO2010/051926 or WO2010/133312). Compounds of formula (I) may be prepared in analogy to

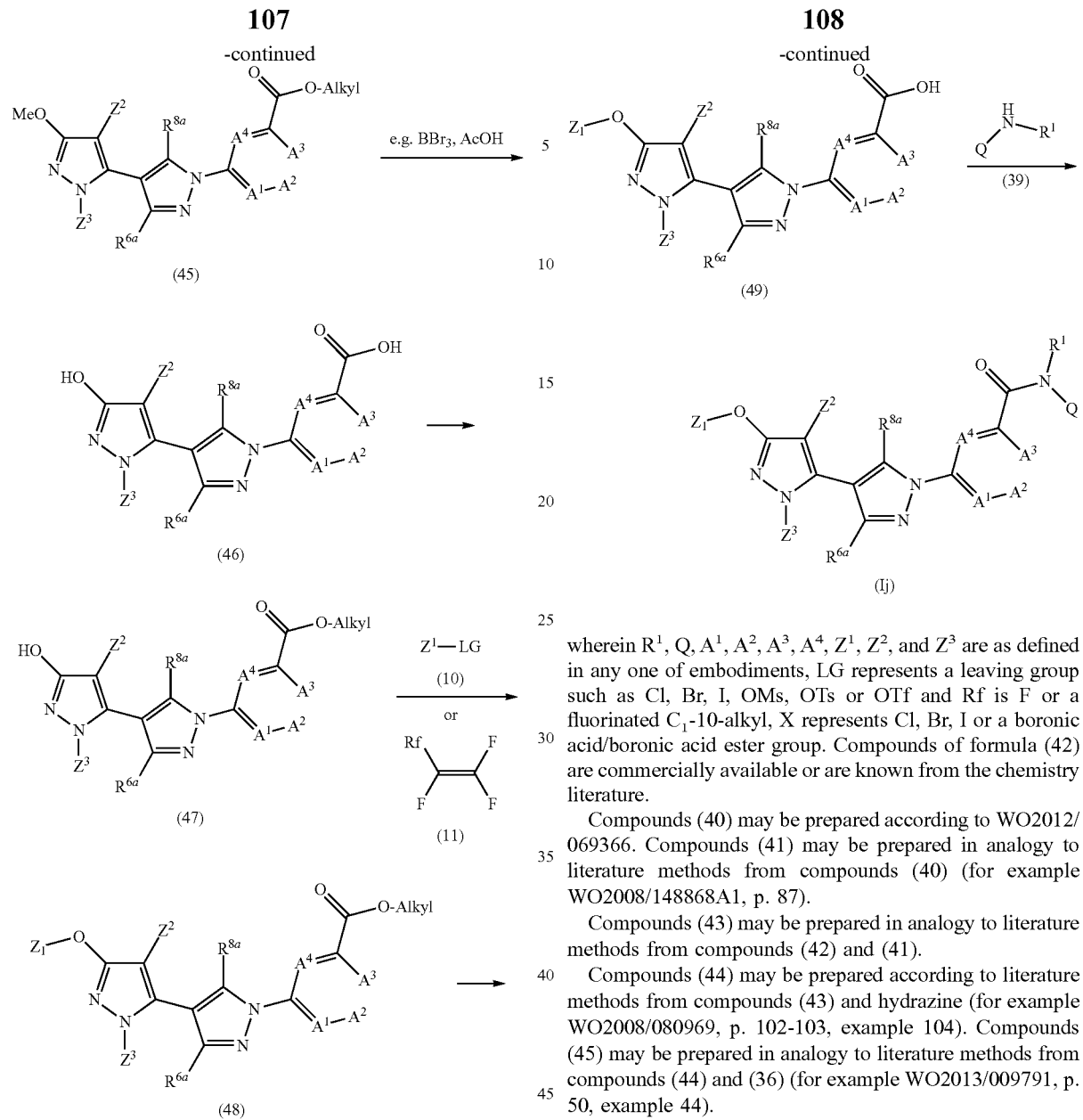

wherein $R^1$, Q, $A^1$, $A^2$, $A^3$, $A^4$, $Z^1$, $Z^2$, and $Z^3$ are as defined in any one of embodiments, LG represents a leaving group such as Cl, Br, I, OMs, OTs or OTf and Rf is F or a fluorinated $C_1$-10-alkyl, X represents Cl, Br, I or a boronic acid/boronic acid ester group. Compounds of formula (42) are commercially available or are known from the chemistry literature.

Compounds (40) may be prepared according to WO2012/069366. Compounds (41) may be prepared in analogy to literature methods from compounds (40) (for example WO2008/148868A1, p. 87).

Compounds (43) may be prepared in analogy to literature methods from compounds (42) and (41).

Compounds (44) may be prepared according to literature methods from compounds (43) and hydrazine (for example WO2008/080969, p. 102-103, example 104). Compounds (45) may be prepared in analogy to literature methods from compounds (44) and (36) (for example WO2013/009791, p. 50, example 44).

Compounds of formula (Ik) can be prepared, for example, according to Scheme 7,

Scheme 7

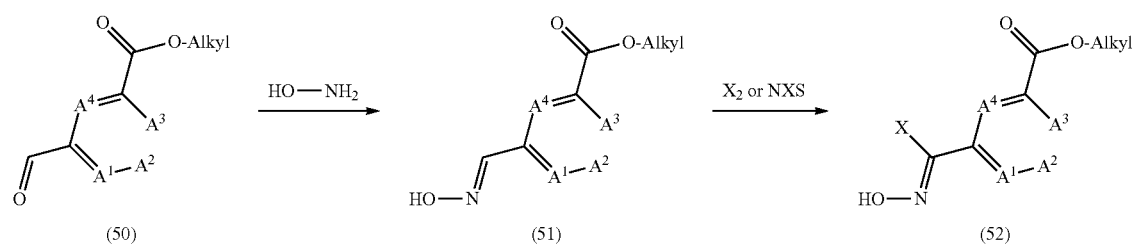

-continued

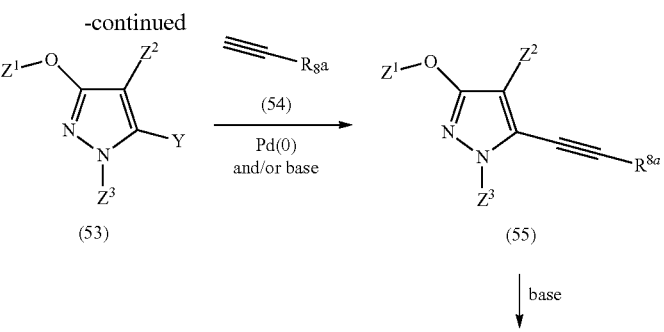

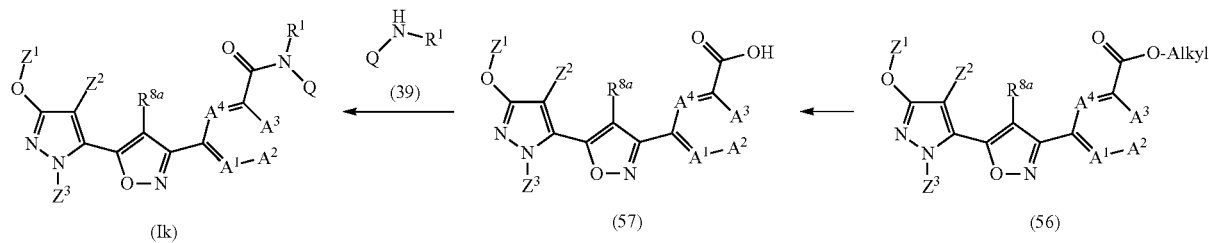

wherein $R^1$, $R^{8a}$, Q, $A^1$, $A^2$, $A^3$, $A^4$, $Z^1$, $Z^2$, and $Z^3$ are as defined in any one of embodiments, Y represents a leaving group such as Cl, Br, I or triflate. Compounds of formula (54) and (50) are commercially available or are known from the chemistry literature.

Compounds (51) may be prepared in analogy to literature methods from compounds (50). For example, known methods for the preparation of oximes from aldehydes may be used (for example H. Metzger in Houben-Weyl, Band X/4, p. 55 ff, Georg Thieme Verlag Stuttgart, 1968). Compounds (52) may be prepared in analogy to literature methods by reacting them with halogenating agents such as $Cl_2$, $Br_2$, $I_2$, N-chlorosuccinimide, N-bromosuccinimide, N-iodosuccinimide, etc. Compounds (56) may be prepared in analogy to literature methods by reacting compounds (52) with (55) in the presence of a transition metal catalyst such as paladium or copper and a suitable base (for example Chinchilla, Rafael et al., Chemical Reviews, 2007, 40(10), p. 5084-5121; Chinchilla, Rafael et al., Chemical Reviews, 2007, 107(3), p. 874-922). Compounds (53) can be prepared according to known methods (for example see pages 8-10 of EP1253128). If $R^{8a}$ is H, then a suitable protecting group can be used instead of $R^{8a}$. Suitable protecting groups are for example trimethylsilyl, triethylsilyl and dimethylhydroxymethyl. Further suitable protecting groups and methods for introducing and removing such protecting groups are described in literature (for example see "Greene's protective groups in organic synthesis", $4^{th}$ edition, P. G. M. Wuts, T. W. Greene, John Wiley & Sons, Inc., Hoboken, N.J., 2007, p. 927-933).

Compounds of formula (IL) can be prepared, for example, according to Scheme 8,

Scheme 8

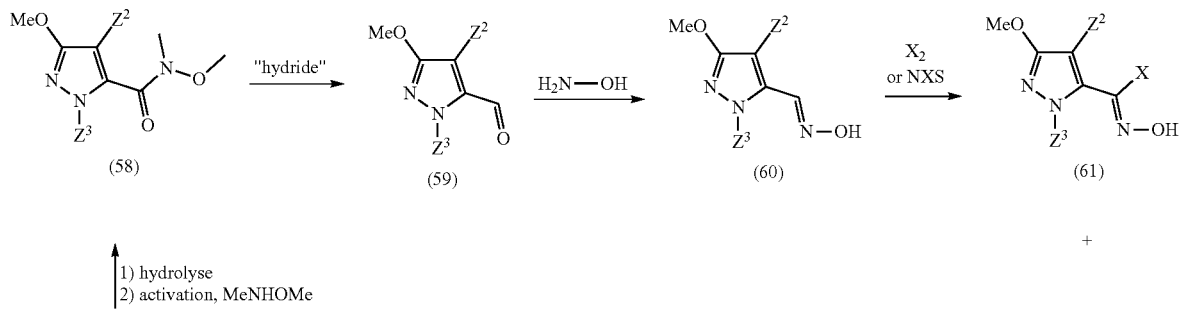

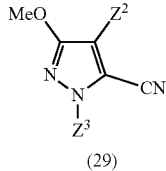
(29)

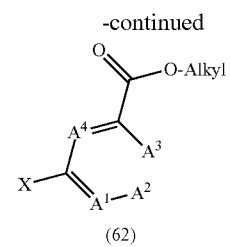
(62)

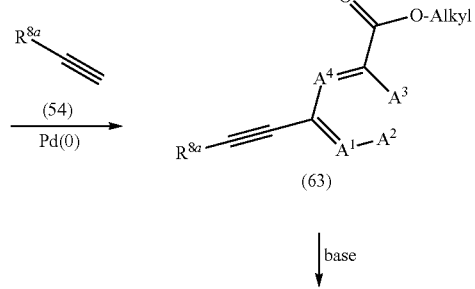
(54) → (63)

| base

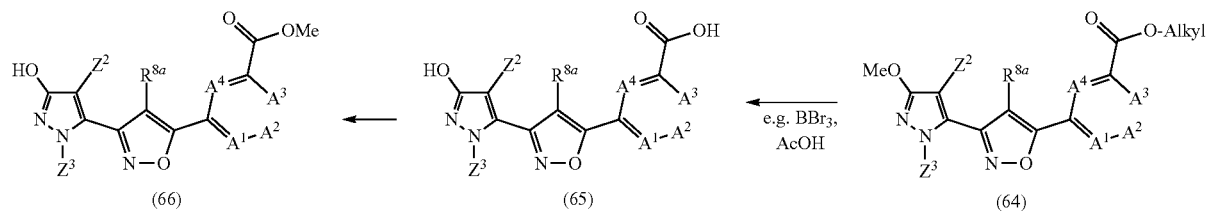
(66)  (65)  (64)

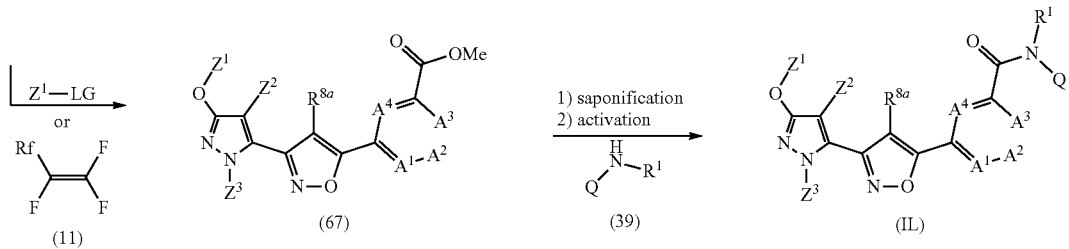
(11)  (67)  (39)  (IL)

wherein $R^1$, $R^{8a}$, Q, $A^1$, $A^2$, $A^3$, $A^4$, $Z^1$, $Z^2$, and $Z^3$ are as defined in any one of embodiments, LG represents a leaving group such as Cl, Br, I, OMs, OTs or OTf and Rf is F or a fluorinated $C_1$-10-alkyl, X represents Cl, Br, I or a boronic acid/boronic acid ester group. Compounds of formula (54) are commercially available or are known from the chemistry literature.

Compounds (62) are known or may be prepared in analogy to literature methods. Compounds (63) may be prepared by reacting compounds (62) with compounds (54) according to literature methods (for example WO2012/175474, p. 117-118). Compounds (61) may be prepared in analogy to literature (for example US2011/53904, p. 19) or by reacting compounds (58) with a hydride source also according to known methods. Compounds (60) may be prepared in analogy to literature methods for the preparation of oximes from aldehyde compounds (59) (for example H. Metzger in Houben-Weyl, Band X/4, p. 55 ff, Georg Thieme Verlag Stuttgart 1968). Compounds (61) may be prepared according to literature methods by reacting compounds (60) with a suitable halogenating agent such as $Cl_2$, $Br_2$, $I_2$, N-chlorosuccinimde, N-bromosuccinimide, N-iodosuccinimide, etc. Compounds (64) may be prepared in analogy to literature methods by reacting compounds (61) with compounds (63) in the presence of a suitable base (see WO2015/067646, p. 138-141). The last five reaction steps to obtain compounds (II) from compounds of formula (64) may be carried out as previously described in Scheme 6.

Compounds of formula (Im) can be prepared, for example, according to Scheme 9,

Scheme 9

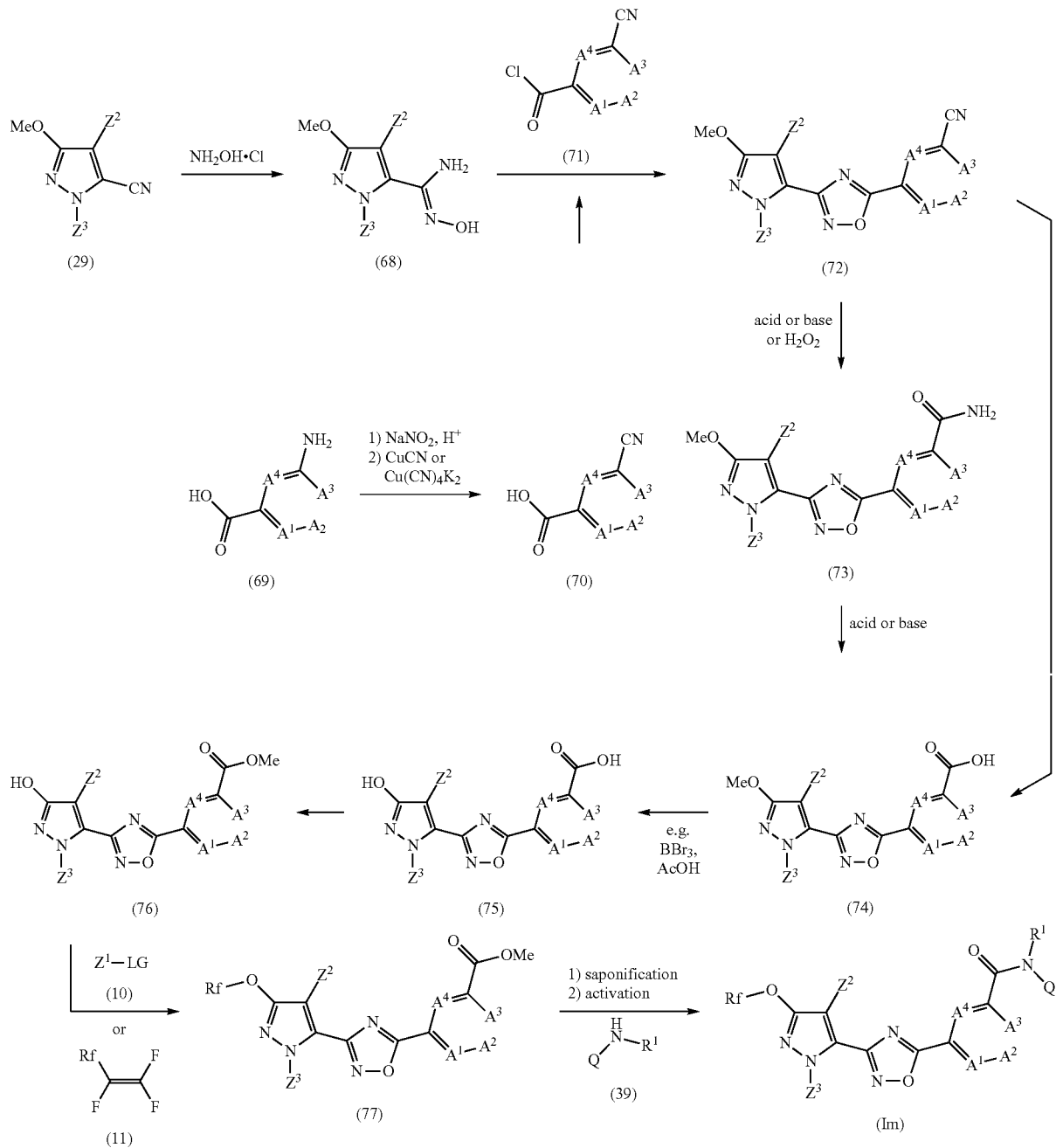

wherein $R^1$, Q, $A^1$, $A^2$, $A^3$, $A^4$, Z, $Z^2$, and $Z^3$ are as defined in any one of embodiments 1 to 78, LG represents a leaving group such as Cl, Br, I, OMs, OTs or OTf and Rf is F or a fluorinated $C_{1-10}$-alkyl.

Compounds of formula (69) are commercially available or are known from the chemistry literature.

Compound (68) can be prepared in analogy to WO10/078905 or WO2010/078910. Compound (72) can be prepared in analogy to Quian U et al, *Org. Lett.* 2014, 16, 1622 or WO2012/166951. Compound (74) can be prepared in analogy to WO2011/088181. The final steps to obtain compounds (77) and then compounds of formula (Im) may be carried out as previously described in Scheme 6.

Compounds of formula (In) can be prepared, for example, according to Scheme 10.

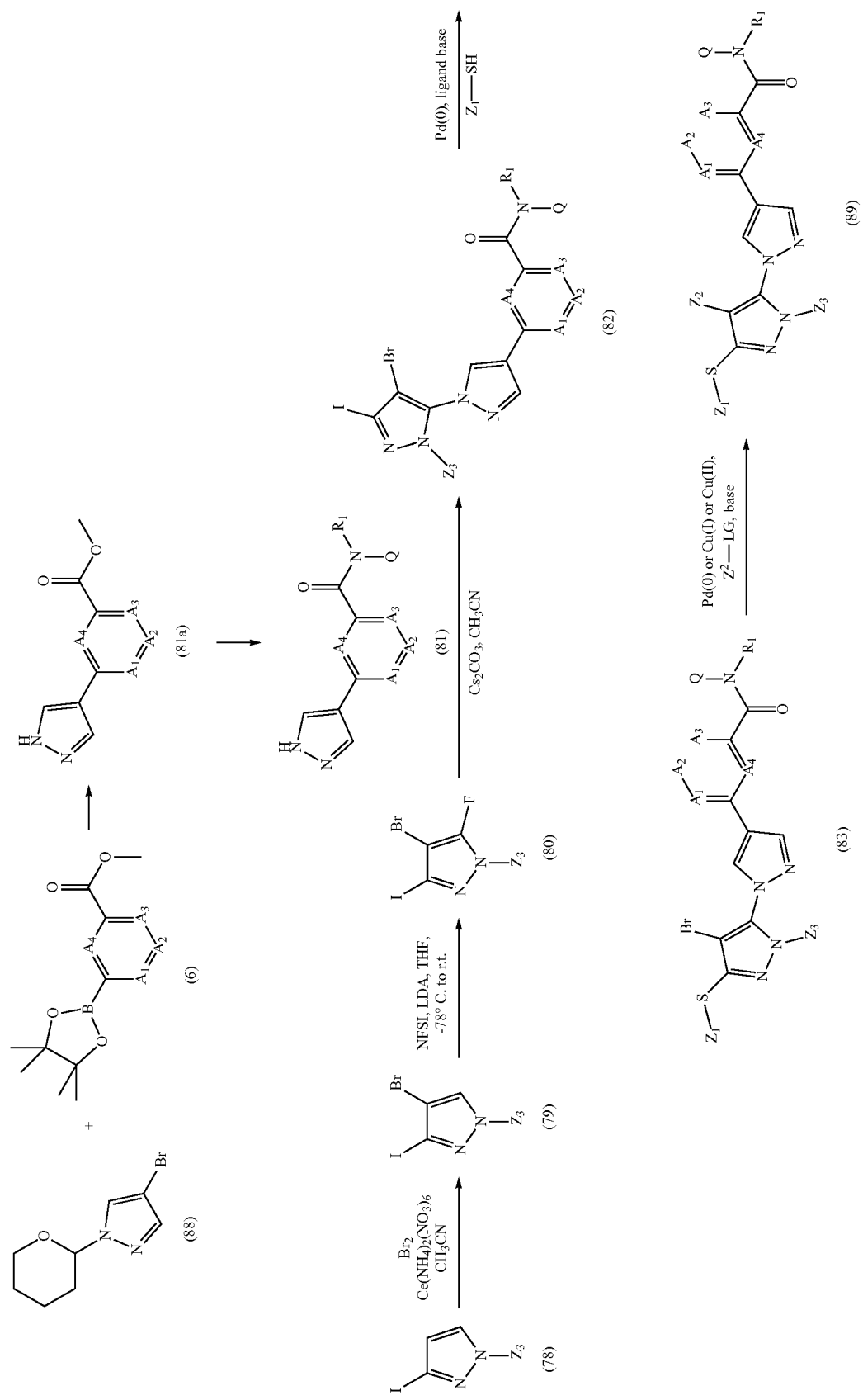

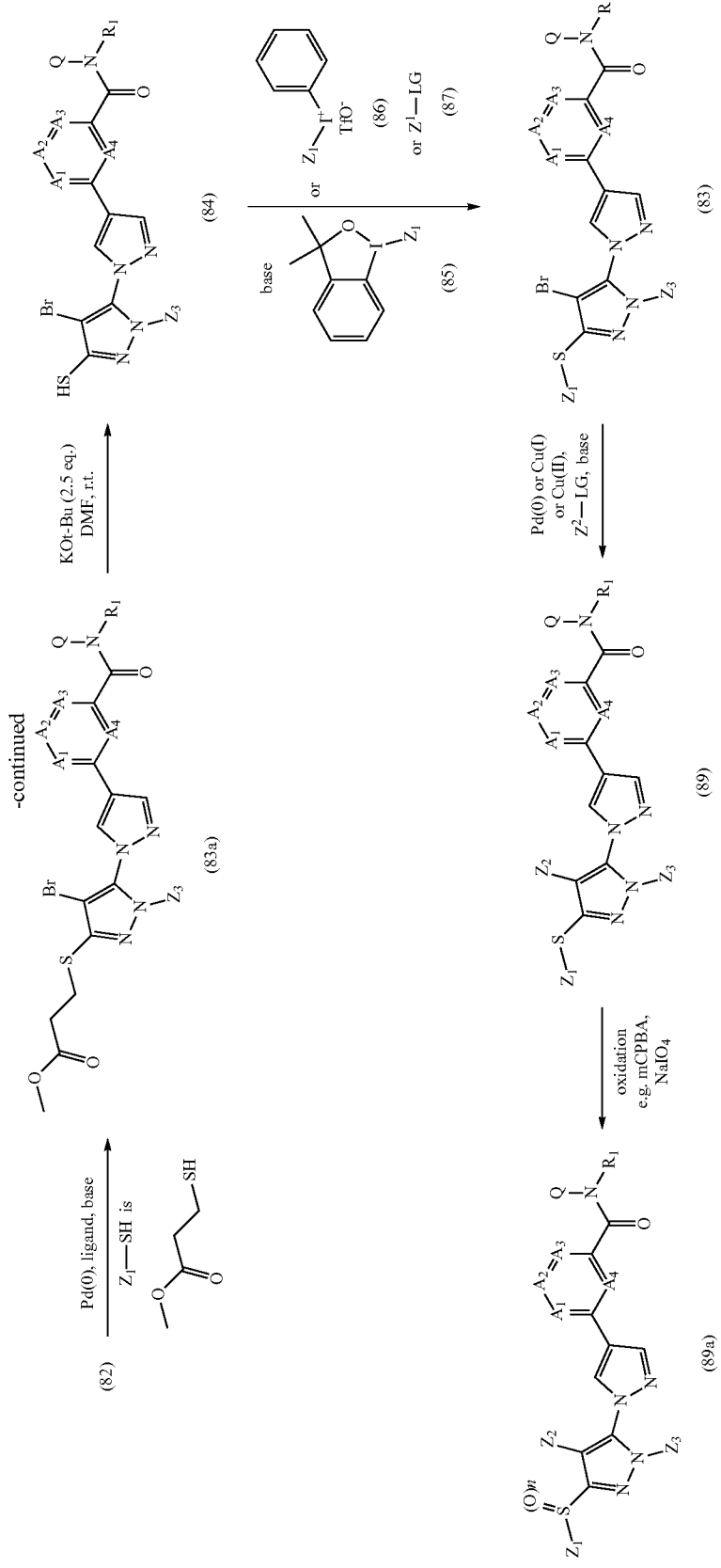

wherein $R^1$, Q, $A^1$, $A^2$, $A^3$, $A^4$, $Z^1$, $Z^2$, and $Z^3$ are as defined in any one of embodiments 1 to 78, LG represents a leaving group such as Cl, Br, I, OMs, OTs or OTf. Compounds of formula (78) are commercially available or are known from the chemistry literature.

Compound (80) can be prepared by metalation of compound (79) followed by reaction with an electrophilic fluorine source such as e.g. NSFI, pyridinium salts or Selectfluor. Compound (83) can be prepared from compound (82) and compound $Z^1$—SH under Pd (0) catalysis in the presence of a phosphine or a carbene ligand in analogy to WO09/149837 (Bayer Schering Pharma). Similarly, compound (83a) can be prepared from compound (82) and methyl 3-sulfanypropanoate under Pd (0) catalysis in the presence of a phosphine or a carbene ligand. Compound (84) can be prepared from compound (83a) by a retro-Michael reaction, as described e.g. In A. Kahehi, S. Ito, H. Isawa, T. Takashima, Chem. Pharm. Bull. 1990, 38(10), 2662. Compounds (83) can be obtained by reacting a compound of formula (84) with a Togni-type reagent (85) (e.g. I. Kieltsch, P. Eisenberger, and A. Togni, Angew. Chem. Int. Ed. 2007, 46, 754), a iodonium salt (86) (described e.g. in WO2009/051245) or a compound $Z^1$-LG (87). Compound (89) can be obtained by cross-coupling of compound (83) with $Z^2$-LG in the presence of Pd(0) or a Cu(I) or a Cu(II) salt in the presence or in the absence of a ligand.

Compound (81) can be prepared from compound (81a) according to standard synthetic practice.

Compound (81a) can be prepared from known protected 3-bromo pyrazole (88) and compound (6) described in scheme 1 by standard Suzuki cross-coupling.

Compounds of formula (Io) can be prepared, for example, according to Scheme 11,

Scheme 11

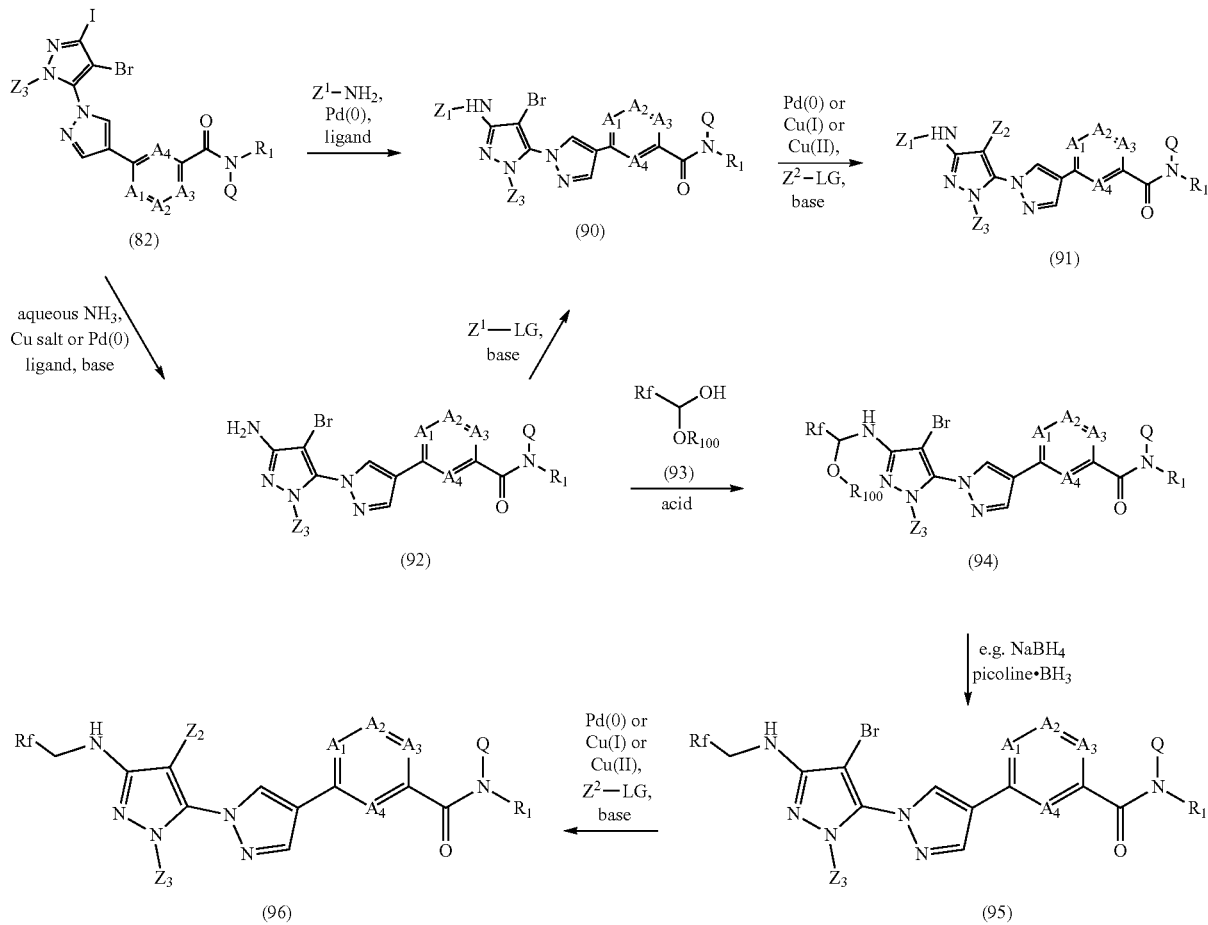

wherein $R^1$, Q, $A^1$, $A^2$, $A^3$, $A^4$, $Z^1$, $Z^2$, and $Z^3$ are as defined in any one of embodiments 1 to 78, LG represents a leaving group such as Cl, Br, I, OMs, OTs or OTf. Compounds of formula (82) can be prepared according to scheme 10.

Compound (90) can be obtained by cross-coupling of compounds (82) with $Z^1$—$NH_2$, as described in J. Hartwig et al., J. Am. Chem. Soc. 2015, 137, 8460. Compound (91) can be obtained by cross-coupling of compound (90) with $Z^2$-LG in the presence of Pd(0) or a Cu(I) or a Cu(II) salt in the presence or in the absence of a ligand. Compound (92) can be prepared by cross-coupling of compound (82) with aqueous ammonia under Pd(0) or Cu(I) or Cu(II) salt catalysis, as described in M. Taillefer et al. Angew. Chem. Int. Ed., 2009, 48, 337 or J. Hartwig et al., J. Am. Chem. Soc. 2009, 131, 11049 or D. Ma et al., J. Org. Chem. 2009, 74, 4542 or D. Ma et al, Org. Lett. 2015, 17, 5934. Compounds (90) can be obtained by reacting a compound of formula (92) with a compound $Z^1$-LG in the presence of a base. Alternatively, compound (94) can be obtained in analogy to in H.

Mimura et al., *J. Fluor. Chem.*, 2010, 131, 477, by reacting compound (92) with a hemi-acetal of formula (93), where Rf is a fluorinated $C_{1-10}$-alkyl (possibly containing one O atom) and $R^{200}$ is a $C_{1-4}$ alkyl rest. Reduction of compound (94) with a reductant such as e.g. $NaBH_4$ or picoline.$BH_3$ gives a compound of formula (95), in analogy to in H. Mimura et al., *J. Fluor. Chem.*, 2010, 131,477. Compound (96) can be obtained by cross-coupling of compound (95) with $Z^2$-LG in the presence of Pd(0) or a Cu(I) or a Cu(II) salt in the presence or in the absence of a ligand.

A compound according to any one of embodiments 1 to 78 can be converted in a manner known per se into another compound according to any one of embodiments 1 to 78 by replacing one or more substituents of the starting compound according to any one of embodiments 1 to 78 in the customary manner by (an)other substituent(s) according to the invention.

Depending on the choice of the reaction conditions and starting materials which are suitable in each case, k is possible, for example, in one reaction step only to replace one substituent by another substituent according to the invention, or a plurality of substituents can be replaced by other substituents according to the invention in the same reaction step.

Salts of compounds of formula (I) can be prepared in a manner known per se. Thus, for example, acid addition salts of compounds according to any one of embodiments 1 to 78 are obtained by treatment with a suitable acid or a suitable ion exchanger reagent and salts with bases are obtained by treatment with a suitable base or with a suitable ion exchanger reagent.

Salts of compounds according to any one of embodiments 1 to 78 can be converted in the customary manner into the free compounds, acid addition salts, for example, by treatment with a suitable basic compound or with a suitable ion exchanger reagent and salts with bases, for example, by treatment with a suitable acid or with a suitable ion exchanger reagent.

Salts of compounds according to any one of embodiments 1 to 78 can be converted in a manner known per se into other salts of compounds according to any one of embodiments 1 to 78, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds according to any one of embodiments 1 to 78, which have sat-forming properties can be obtained in free form or in the form of salts.

The compounds according to any one of embodiments 1 to 78 and, where appropriate, the tautomers thereof, in each case in free form or in salt form, can be present in the form of one of the stereoisomers which are possible or as a mixture of these, for example in the form of pure stereoisomers, such as antipodes and/or diastereomers, or as stereoisomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure stereoisomers and also to all stereoisomer mixtures which are possible and is to be understood in each case in this sense hereinabove and hereinbelow, even when stereochemical details are not mentioned specifically in each case.

Diastereomer mixtures or racemate mixtures of compounds according to any one of embodiments 1 to 78, in free form or in salt form, which can be obtained depending on which starting materials and procedures have been chosen can be separated in a known manner into the pure diastereomers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable stereoisomer mixtures, but also by generally known methods of diastereoselective or enantioselective synthesis, for example by carrying out the process according to the invention with starting materials of a suitable stereochemistry.

N-oxides can be prepared by reacting a compound according to any one of embodiments 1 to 78 with a suitable oxidizing agent, for example the $H_2O_2$/urea adduct in the presence of an acid anhydride, e.g. trifluoroacetic anhydride. Such oxidations are known from the literature, for example from J. Med. Chem., 32 (12), 2561-73, 1989 or WO 00/15615.

It is advantageous to isolate or synthesize in each case the biologically more effective stereoisomer, for example enantiomer or diastereomer, or stereoisomer mixture, for example enantiomer mixture or diastereomer mixture, if the individual components have a different biological activity.

The compounds according to any one of embodiments 1 to 78 and, where appropriate, the tautomers thereof, in each case in free form or in salt form, can, if appropriate, also be obtained in the form of hydrates and/or include other solvents, for example those which may have been used for the crystallization of compounds which are present in solid form.

The following Examples illustrate, but do not limit, the invention.

The compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, 6 ppm, 3 ppm, 1.5 ppm or 0.8 ppm.

The present invention also provides intermediates useful for the preparation of compounds according to any one of embodiments 1 to 78. Certain intermediates are novel and as such form a further aspect of the invention.

One group of novel intermediates are compounds of formula (II)

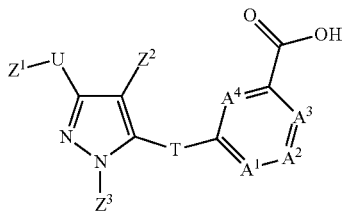
(II)

wherein $A^1$, $A^2$, $A^3$, $A^4$, T, U, $Z^1$, $Z^2$ and $Z^3$ are as defined in any one of embodiments 1 to 78. The preferences for $A^1$, $A^2$, $A^3$, $A^4$, T, U, $Z^1$, $Z^2$ and Z are the same as the preferences set out for the corresponding substituents of a compound according to any one of embodiments 1 to 78.

Another group of novel intermediates are compounds of formula (III)

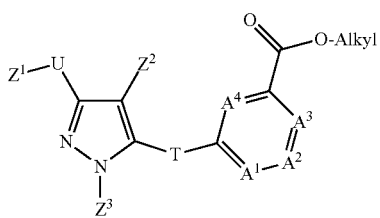
(III)

wherein $A^1$, $A^2$, $A^3$, $A^4$, T, U, $Z^1$, $Z^2$, $Z^3$ and alkyl are as defined in any one of embodiments 1 to 78. The preferences for $A^1$, $A^2$, $A^3$, $A^4$, T, $Z^1$, $Z^2$, Z are the same as the preferences set out for the corresponding substituents of a compound according to any one of embodiments 1 to 78.

The compounds according to any one of embodiments 1 to 78 are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as Insects or representatives of the order Acarina. The insecticidal or acaricidal activity of the active ingredients according to the invention can manifest itself directly, i. e. In destruction of the pests, which takes place either immediately or only after some time has elapsed, for example during ecdysis, or indirectly, for example in a reduced oviposition and/or hatching rate.

Examples of the above mentioned animal pests are:
from the order Acarina, for example,
*Acallus* spp, *Aculus* spp, *Acaricalus* spp, *Aceria* spp, *Acarus siro*, *Amblyomma* spp., *Argas* spp., *Boophilus* spp., *Brevipalpus* spp., *Bryobia* spp, *Calipitrimerus* spp., *Chorioptes* spp., *Dermanyssus gallnae*, *Dermatophagoldes* spp, *Eotetranychus* spp, *Eriophyes* spp., *Hemlarsonemus* spp, *Hyalomma* spp., *Ixodes* spp., *Olygonychus* spp, *Omlhodoros* spp., *Polyphagotarsone latus*, *Panonychus* spp., *Phyllocoptruta olevora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,
*Haematopinus* spp., *Unognathus* spp., *Pediculus* spp., *Pemphigus* spp. and *Phylloxera* spp.;
from the order Coleoptera, for example,
*Agriotes* spp., *Amphimalon majale*, *Anomala orlentalis*, *Anthonomus* spp., *Aphodius* spp, *Astylus atromaculatus*, *Ataenius* spp, *Atomaria Nnearis*, *Chaetocnema tiblalis*, *Cerotoma* spp, *Conoderus* spp, *Cosmopolites* spp., *Cotlnsnlida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampel*, *Lagria vilosa*, *Leptinotarsa decemUneata*, *Lissorhoptrus* spp., *Liogenys* spp, *Maecolaspis* spp, *Maladera castanea*, *Megascells* spp, *Melighetes aeneus*, *Melolontha* spp., *Myochrous armatus*, *Orycaephlus* spp., *Otiorhynchus* spp., *Phylophaga* spp, *Phlyctinus* spp., *Popilla* spp., *Psylliodes* spp., *Rhyssomatus aubtlis*, *Rhizopertha* spp., *Scarabeidae*, *Sitophilus* spp., *Sitotroga* spp., *Somaticus* spp, *Sphenophorus* spp, *Stemechus subsignatus*, *Tenebrio* spp., *Tribolum* spp. and *Trogoderma* spp.;
from the order Diptera, for example,
*Aedes* spp., *Anopheles* spp, *Antherigona soccata*, *Bactrocea oleae*, *Bblo hortulanus*, *Bradysia* spp, *CalNphora erythrocephala*, *Ceratltis* spp., *Chrysomyla* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Lirlomyza* spp., *Lucilla* spp., *Melanagromyza* spp., *Musca* spp., *Oestrus* spp., *Orseolla* spp., *Osdnella frit*, *Pegomyla hyoscyami*, *Phorbia* spp., *Rhagoletis* spp, *Rivela quadrifasciata*, *Scatella* spp, *Sciara* spp., *Stomoxys* spp., *Tabanus* spp., *Tannia* spp. and *Tipula* spp.;
from the order Hemiptera, for example,
*Acanthocoris scabrator*, *Acrostemum* spp, *Adelphocoris Ilneolatus*, *Amblypelta nitida*, *Bathycoella thalassina*, *Blissus* spp, *Cimex* spp., *Clavigralla tomentosicollis*, *Creontlades* spp, *Distantlella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilelus*, *Leptocorisa* spp., *Lygus* spp, *Margarodes* spp, *Murgantla histrionic*, *Neomegalotomus* spp, *Nesidiocoris tenuis*, *Nezara* spp., *Nysius simulans*, *Oebalus insularis*, *Piesma* spp., *Piezodorus* spp, *Rhodnius* spp., *Sahbergela singularis*, *Scaptocoris castanea*, *Scotinophara* spp., *Thyanta* spp, *Triatoma* spp., *Vatiga Iludens*;
*Acyrthoslum pisum*, *Adalges* spp, *Agallilana ensigera*, *Agonoscena targioni*, *Aleurodicus* spp, *Aleurocanthus* spp, *Aleurolobus barodensis*, *Aleurothrixus floccosus*, *Aleyrodes brassicae*, *Amarasca biguttula*, *Amrlodus atkinsoni*, *Aonidlela* spp., *Aphididae*, *Aphis* spp., *Aspidiotus* spp., *Aulacorthum solani*, *Bactericera cockerelli*, *Bemisla* spp, *Brachycaudus* spp, *Brevicoryne brassicae*, *Cacopsylla* spp, *Cavarela aegopodii* spp., *Ceroplaster* spp., *Chrysomphalus aonidium*, *Chrysomphalus dictyospermi*, *Cicadela* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp, *Empoasca* spp., *Eriosoma larigerum*, *Erythroneura* spp., *Gascardia* spp., *Glycaspis brimblecombel*, *Hyadaphis pseudobrassicae*, *Hyalopterus* spp, *Hyperomyzus pallidus*, *Idioscopus clypealls*, *Jacoblasca lybica*, *Laodelphax* spp., *Lecanium comi*, *Lepidosaphes* spp., *Lopaphis erysimi*, *Lyogenys maidis*, *Macrosiphum* spp., *Mahanarva* spp, *Metcalfa pruinosa*, *Metopolophium dirhodum*, *Myndus crudus*, *Myzus* spp., *Neotoxoptera* sp, *Nephotettix* spp., *Nilaparvata* spp., *Nippolachnus piri Mats*, *Odonaspis ruthae*, *Oregma lanigera Zehnter*, *Parabemisla myricae*, *Paratrioza cockerelli*, *Parlatoria* spp.,

*Pemphigus* spp., *Peregrinus maidis*, *Perklinsela* spp, *Phorodon humul*, *Phylloxera* spp, *Planococcus* spp., *Pseudaulacaspis* spp., *Pseudococcus* spp., *Pseudatomoscels seriatus*, *Psylla* spp., *PuMnaria aethiopica*, *Quadraspidlotus* spp., *Quesada gigas*, *Recilia dorsalis*, *Rhopalosiphum* spp., *Saissetia* spp., *Scapholdeus* spp., *Schizaphis* spp., *Sitobion* spp., *Sogatela furcifera*, *Spissistilus festinus*, *Tarophagus Proserpina*, *Toxoptera* spp, *Trialeurodes* spp, *Tridiscus sporoboll*, *Trionymus* spp, *Trioza erytreae*, *Unaspis citd*, *Zygina flammigera*, *Zyginidia scutelaris;*
from the order Hymenoptera, for example,
*Acromyrmex*, *Arge* spp, *Atta* spp., *Cephus* spp., *Diprion* spp., *Diprionidae*, *GHpinia polytoma*, *Hoplocampa* spp., *Lasius* spp., *Monomorlum pharaonis*, *Neodiprion* spp., *Pogonomyrmex* spp, *Slenopsis invicta*, *Solenopsis* spp. and *Vespa* spp.;
from the order Isoptera, for example,
*Coptotermes* spp, *Comitemes cumulans*, *Inciskermes* spp, *Macrotermes* spp, *Mastotermes* spp, *Microtermes* spp, *Reticullermes* spp.; *Solenopsis geminate*
from the order Lepidoptera, for example,
*Acleris* spp., *Adoxophyes* spp., *Aegeria* spp., *Agrotis* spp., *Alabama argilaceae*, *Amylois* spp., *Anticarsia gemmatals*, *Archips* spp., *Argyresthia* spp, *Argyrotaenla* spp., *Autographa* spp., *Bucculatrix thurberlella*, *Busseola fusca*, *Cadra cautella*, *Carposina nipponensis*, *Chilo* spp., *Choristoneura* spp., *Chrysoteuchia toplaria*, *Clysia ambiguela*, *Cnaphalocrocis* spp., *Cnephasla* spp., *Cochylis* spp., *Coleophora* spp., *Collas lesbia*, *Cosmophia flava*, *Crambus* spp, *Crocidolomia binotalis*, *Cryptophlebla leucotreta*, *Cydalima perspectals*, *Cydla* spp., *Diaphanla perspectalls*, *Dlatraea* spp., *Diparopsis castanea*, *Earlas* spp., *Eldana saccharina*, *Ephestia* spp., *Epinotia* spp, *Estigmene acrea*, *Etela zinckinella*, *Eucosma* spp., *Eupoecila ambiguella*, *Euproctis* spp., *Euxoa* spp., *Feltia jaculiferia*, *Grapholla* spp., *Hedya nubiferana*, *Helothis* spp., *Helula undalis*, *Herpetogramma* spp, *Hyphantria cunea*, *Keiferia lycopersicella*, *Lasmopalpus lignosellus*, *Leucoptera scitella*, *Lithocollethis* spp., *Lobesla botrana*, *Loxostege bifidalis*, *Lymantria* spp., *Lyonetia* spp., *Malacosoma* spp., *Mamestra brassicae*, *Manduca sexta*, *Mythimna* spp, *Noctua* spp, *Operophtera* spp., *Omiodes Indica*, *Ostrinia nubilalis*, *Pammene* spp., *Pandemis* spp., *Panols flammea*, *Papalpema nebris*, *Pectinophora gossypiela*, *Perileucoptera coffeella*, *Pseudaletia unipuncta*, *Phthorimaea operculela*, *Peris rapae*, *Pieris* spp., *Plutella xylostella*, *Prays* spp., *Pseudoplusla* spp, *Rachiplusla nu*, *Richia albicosta*, *Scirpophaga* spp., *Sesamia* spp., *Sparganothis* spp., *Spodoptera* spp., *Sylepta derogate*, *Synanthedon* spp., *Thaumetopoea* spp., *Tortrix* spp., *Trichoplusla ni*, *Tuta absoluta*, and *Yponomeuta* spp.;
from the order Mallophaga, for example,
*Damalinea* spp. and *Trichodectes* spp.;
from the order Oithoptera, for example,
*Blatta* spp., *Blattella* spp., *Gryllotalpa* spp., *Leucophaea maderae*, *Locusta* spp., *Neocurtila hexadactyla*, *Periplaneta* spp., *Scapteriscus* spp, and *Schistocerca* spp.;
from the order Psocoptera, for example,
*Uposcells* spp.;
from the order Siphonaptera, for example,
*Ceratophylus* spp., *Ctenocephalides* spp. and *Xenopsylla cheopis;*
from the order Thysanoptera, for example,
*Caliothrips phaseoi*, *Franklinlella* spp, *Helothrips* spp, *Hercinothrips* spp., *Parthenothrips* spp, *Scirtothdlps aurantll*, *Sericothrips variabils*, *Taeniothrips* spp., *Thrips* spp;
from the order Thysanura, for example, *Lepisma saccharina*.

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals.

The active ingredients according to the invention are especially suitable for controlling *Aphis craccivora*, *Diabrotica balteata*, *Hellothis virescens*, *Myzus persicae*, *Plutella xylostela and Spodoptera ittoralls* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo supressalis* (preferably in rice).

In a further aspect, the invention may also relate to a method of controlling damage to plant and parts thereof by plant parasitic nematodes (Endoparasitic-, Semlendoparasltio- and Ectoparasltic nematodes), especially plant parasitic nematodes such as root knot nematodes, *Meloidogyne hapla*, *Meloidogyne incognita*, *Meloidogyne javanica*, *Meloidogyne arenaria* and other *Meloidogyne* species; cyst-forming nematodes, *Globodera rostochiensis* and other *Globodera* species; *Heterodera avenae*, *Heterodera glycines*, *Heterodera schachtii*, *Heterodera trifolii*, and other *Heterodera* species; Seed gall nematodes, *Anguina* species; Stem and folar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor*, *Ditylenchus dipsaci* and other *Ditylenchus* species; Awl nematodes, *Dolichodorus* species; Spiral nematodes, *Heliocotylenchus mulicinctus* and other *Helicotylenchus* species; Sheath and sheathoid nematodes, *Hemicycliophora* species and *Hemicriconemodes* species; *Hirshmanniella* species; Lance nematodes, *Hopioalmus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus*, *Pratylenchus penetrans*, *Pratylenchus curvitatus*, *Pratylenchus goodeyi* and other *Pratylenchus* species; Burrowing nematodes, *Radopholus simlis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dublus* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonla* spp., *Melinius* spp., *Punctodera* spp., and *Quinisulcius* spp.

The compounds according to any one of embodiments 1 to 78 may also have activity against the molluscs. Examples of which include, for example, Ampullaridae; *Arion* (*A. ater, A. circumscriptus, A. hortensis, A. rufus*); Bradybaenidae (*Bradybaena fruticum*); Cepaea (*C. hortensis, C. Nemoralls*); ochlodina; *Deroceras* (*D. agrestis, D. empiricorum, D. laeve, D. reticulatum*); Discus (*D. rotundatus*); Euomphalla; Galba (*G. trunculata*); Helicella (*H. Itala, H. obvia*); Helicidae *Helicigona arbustorum*); Helicodiscus; Helix (*H. aperta*); Limax (*L. cinereoniger, L. flavus, L. marginatus, L. maximus, L. tenelus*); Lymnaea; *Milax* (*M. gagates, M. marginatus, M. sowerbyi*); Opeas; *Pomacea* (*P. canaticulata*); Vallonla and Zanitoldes.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophius*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stibene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO93/07278, WO95/34656, EP-A-0 427 529, EP-A-451 878 and WO 03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 338® (cotton variety that expresses a Cry1Ac toxin); Bolgard I® (cotton variety that expresses a Cry1Ac toxin); Bolgard 116 (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hoblt 27, F-31 790 St. Sauveur, France, registration number C/FR/96/05/10. Genetically modified *Zea mays* which has been rendered resistant to attack by the European corn borer (*Ostrinia nubilalis* and *Sesamla nonagroides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalls* and *Sesamia nonagolides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 883 Maize from Monsanto Europe SA. 270-272 Avenue de Tervuren, B-1150 Brussels, Belgium, registration number C/DE/02/9. MON 863 expresses a Cry3Bb1 toxin and has resistance to certain Coleoptera Insects.

5. IPC 531 Cotton from Monsanto Europe SA. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera Insects and of the PAT protein for achieving tolerance to the herbicide glufosinate ammonium.

7. NK603×MON 810 Maize from Monsanto Europe SA. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO95/33818 and EP-A-0 353 191. The methods of producing such transgenic plants are generally known to the person skilled in the art and are described, for example, in the publications mentioned above.

Crops may also be modified for enhanced resistance to fungal (for example *Fusarium, Anthracnose*, or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerant to abiotic stress include those that have enhanced tolerance to drought, high salt, high temperature, chill, frost, or light radiation, for example through expression of NF—YB or other proteins known in the art.

Antipathogenic substances which can be expressed by such transgenic plants include, for example, ion channel blockers, such as blockers for sodium and calcium channels, for example the viral KP1, KP4 or KP6 toxins; stibene synthases; bibenzyl syntheses; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO95/33818) or protein or polypeptide factors involved in plant pathogen defence (so-called "plant disease resistance genes", as described in WO 03/000906).

Further areas of use of the compostions according to the invention are the protection of stored goods and store rooms and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compostons to a substrate such as non-woven or a fabric material in the form of (or which can be used in the manufacture of) netting, clothing, bedding, curtains and tents.

In another embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compostions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO2006/128870, EP 1724392, WO2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B:

TABLE A

Examples of exotic woodborers of economic importance.

| Family | Species | Host or Crop Infested |
|---|---|---|
| Buprestidae | Agrilus planipennis | Ash |
| Cerambycidae | Anoplura glabripennis | Hardwoods |
|  | Xylosandrus crassiusculus | Hardwoods |
| Scolytidae | X. mutilatus | Hardwoods |
|  | Tomicus piniperda | Conifers |

TABLE B

Examples of native woodborers of economic importance.

| Family | Species | Host or Crop Infested |
|---|---|---|
| Buprestidae | *Agrilus anxius* | Birch |
| | *Agrilus politus* | Willow, Maple |
| | *Agrilus sayi* | Bayberry, Sweetfern |
| | *Agrilus vittaticolllis* | Apple, Pear, Cranberry, Serviceberry, Hawthorn |
| | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
| | *Texania campestris* | Basswood, Beech, Maple, Oak, Sycamore, Willow, Yellow-poplar |
| Cerambycidae | *Goes pulverulentus* | Beech, Elm, Nuttall, Willow, Black oak, Cherrybark oak, Water oak, Sycamore |
| | *Goes tigrinus* | Oak |
| | *Neoclytus acuminatus* | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
| | *Neoptychodes trilineatus* | Fig, Alder, Mulberry, Willow, Netleaf hackberry |
| | *Oberea ocellata* | Sumac, Apple, Peach, Plum, Pear, Currant, Blackberry |
| | *Oberea tripunctata* | Dogwood, Viburnum, Elm, Sourwood, Blueberry, Rhododendron, Azalea, Laurel, Poplar, Willow, Mulberry |
| | *Oncideres cingulata* | Hickory, Pecan, Persimmon, Elm, Sourwood, Basswood, Honeylocust, Dogwood, Eucalyptus, Oak, Hackberry, Maple, Fruit trees |
| | *Saperda calcarata* | Poplar |
| | *Strophiona nitens* | Chestnut, Oak, Hickory, Walnut, Beech, Maple |
| Scolytidae | *Corthylus columbianus* | Maple, Oak, Yellow-poplar, Beech, Boxelder, Sycamore, Birch, Basswood, Chestnut, Elm |
| | *Dendroctonus frontalis* | Pine |
| | *Dryocoetes betulae* | Birch, Sweetgum, Wild cherry, Beech, Pear |
| | *Monarthrum fasciatum* | Oak, Maple, Birch, Chestnut, Sweetgum, Blackgum, Poplar, Hickory, Mimosa, Apple, Peach, Pine |
| | *Phloeotribus liminaris* | Peach, Cherry, Plum, Black cherry, Elm, Mulberry, Mountain-ash |
| | *Pseudopityophthorus pruinosus* | Oak, American beech, Black cherry, Chickasaw plum, Chestnut, Maple, Hickory, Hornbeam, Hophornbeam |
| Sesiidae | *Paranthrene simulans* | Oak, American chestnut |
| | *Sannina uroceriformis* | Persimmon |
| | *Synanthedon exitiosa* | Peach, Plum, Nectarine, Cherry, Apricot, Almond, Black cherry |
| | *Synanthedon pictipes* | Peach, Plum, Cherry, Beach, Black Cherry |
| | *Synanthedon rubrofascia* | Tupelo |
| | *Synanthedon scitula* | Dogwood, Pecan, Hickory, Oak, Chestnut, Beech, Birch, Black cherry, Elm, Mountain-ash, Viburnum, Willow, Apple, Loquat, Ninebark, Bayberry |
| | *Vitacea polistiformis* | Grape |

In the hygiene sector, the compostions according to the invention are active against ectoparasites such as hard ticks, soft ticks, mange mites, harvest miles, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Wemeckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyla* spp., *Culicoides* spp., *Chrysops* spp., *Hybomitra* spp., *Atylotus* spp., *Tabanus* spp., *Haematopota* spp., *Phlipomyla* spp., *Braula* spp., *Musca* spp., *Hydrotaea* spp., *Stomoxys* spp., *Haematobla* spp., *Morella* spp., *Fannia* spp., *Glossina* spp., *Caliphora* spp., *Luclia* spp., *Chrysomyla* spp., *Wohfahrtia* spp., *Sarcophaga* spp., *Oestrus* spp., *Hypoderma* spp., *Gasterophilus* spp., *Hippobosca* spp., *Lipoptena* spp and *Melophagus* spp.

Of the order Siphonapterida, for example *Pulex* spp., *Ctenocephaldes* spp., *Xenopsylla* spp., *Ceratophylus* spp.

Of the order Heteropterida, for example *Cimex* spp., *Triatoma* spp., *Rhodnius* spp., *Panstrongylus* spp.

Of the order Blattarida, for example *Blatta orientalis, Periplaneta americana, Blattelagermanica* and *Supella* spp.

Of the subclass Acaria (Acarida) and the orders Meta- and Meso-*stigmata*, for example *Argas* spp., *Omithodorus* spp., *Otoblus* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Railletla* spp., *Pneumonyssus* spp., *Stemostoma* spp. and *Varroa* spp.

Of the orders Actinedida (Prostigmata) and Acaridida (Astigmata), for example *Acarapis* spp., *Cheyletiella* spp., *Omithocheyletia* spp., *Myobla* spp., *Psorergatesspp., Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodles* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anoblum punctatum, Xestoblum rufovillosum, Ptilinuspecticomis, Dendroblum pertinex, Emoblus mollis, Prioblum carpini, Lydus brunneus, Lyctus africanus, Lyctus planicolis, Lyctus linearis, Lyctus pubescens, Trogoxylon aequale, Minthesrugicolls, Xyleborus spec., Tryptodendron spec., Apate monachus, Bostrychus capucins, Heterobostrychus brunneus, Sinoxylon* spec. and *Dinoderus minutus*, and also hymenopterans such as *Sirex juvencus, Urocerus gigas, Urocerus gigas taignus* and *Urocerus augur*, and termites such as *Kalotermes flavicolis, Cryptotermes brevis, Heterotermes indicola, Reticultermes flavipes, Reticulitermes santonensis, Reticultermes lucifugus, Mastotermes darwiniensis, Zootermopsis nevadensis* and *Coptotermes formosanus*, and bristletails such as *Lepisma saccharina*.

In one aspect, the invention therefore also relates to pesticidal compositions such as emulsifiable concentrates, suspension concentrates, microemulsions, oil dispersibles, directly sprayable or dilutable solutions, spreadable pastes, dilute emulsions, soluble powders, dispersible powders, wettable powders, dusts, granules or encapsulations in polymeric substances, which comprise—at least—one of the active ingredients according to any one of embodiments 1 to 78 and which are to be selected to suit the intended aims and the prevailing circumstances. In these compositions, the active ingredient is employed in pure form, a solid active ingredient for example in a specific particle size, or, preferably, together with—at least—one of the auxiliaries conventionally used in the art of formulation, such as extenders, for example solvents or solid carriers, or such as surface-active compounds (surfactants).

Examples of suitable solvents are: unhydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, sophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Sold carriers which are used for example for dusts and dispersible powders are, as a rule, ground natural minerals such as calcite, talc, kaolin, montmorllionite or attapulgite. To improve the physical properties, it is also possible to add highly disperse silicas or highly disperse absorbtive polymers.

Suitable adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopolypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylphenoxypolyethoxyethanol, polyethylene glycol or octylphenoxypolyethoxyethanol. Also suitable are fatty acid esters of polyoxyethylene sorbitan, such as polyoxyethylene sorbian trioleate.

The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethylammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and a fatty acid radical of approximately 8 to approximately 22 C atoms. Examples of alkylarylsulfonates are the sodium, calcium or triethanolammonium salts of decylbenzenesulfonic acid, of dibutylnaphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids.

As a rule, the compostions comprise 0.1 to 99%, especially 0.1 to 95%, of active ingredient and 1 to 99.9%, especially 5 to 99.9%, of at least one solid or liquid adjuvant, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compostions which have substantially lower concentrations of active ingredient.

Typically, a pre-mix formulation for foliar application comprises 0.1 to 99.9%, especially 1 to 95%, of the desired ingredients, and 99.9 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Normally, a tank-mix formulation for seed treatment application comprises 0.25 to 80%, especially 1 to 75%, of the desired ingredients, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation.

Typically, a pre-mix formulation for seed treatment application comprises 0.5 to 99.9%, especially 1 to 95%, of the desired ingredients, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Whereas commercial products will preferably be formulated as concentrates (e.g., pre-mix composition (formulation)), the end user will normally employ dilute formulations (e.g., tank mix composition).

Preferred seed treatment pre-mix formulations are aqueous suspension concentrates. The formulation can be applied to the seeds using conventional treating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art.

In general, the pre-mix compositions of the invention contain 0.5 to 99.9 especially 1 to 95, advantageously 1 to 50%, by mass of the desired ingredients, and 99.5 to 0.1, especially 99 to 5%, by mass of a solid or liquid adjuvant (including, for example, a solvent such as water), where the auxiliaries (or adjuvant) can be a surfactant in an amount of 0 to 50, especially 0.5 to 40%, by mass based on the mass of the pre-mix formulation.

Examples of foliar formulation types for pre-mix compositions are:
GR: Granules
WP: wettable powders
WG: water dispersable granules (powders)
SG: water soluble granules
SL: soluble concentrates
EC: emulsifiable concentrate
EW emulsions, oil in water
ME: micro-emulsion
SC: aqueous suspension concentrate
CS: aqueous capsule suspension
OD: oil-based suspension concentrate, and
SE: aqueous suspo-emulsion.
Whereas, examples of seed treatment formulation types for pre-mix compositions are:
WS: wettable powders for seed treatment slurry
LS: solution for seed treatment
ES: emulsions for seed treatment
FS: suspension concentrate for seed treatment
WG: water dispersible granules, and
CS: aqueous capsule suspension.

Examples of formulation types suitable for tank-mix compositions are solutions, dilute emulsions, suspensions, or a mixture thereof, and dusts.

Preferred compositions are composed in particular as follows (%=percent by weight):
Emulsifiable Concentrates:
active ingredient: 1 to 95%, preferably 5 to 20%
surfactant: 1 to 30%, preferably 10 to 20%
solvent: 5 to 98%, preferably 70 to 85%
Dusts:
active ingredient: 0.1 to 10%, preferably 0.1 to 1%
solid carrier 99.9 to 90%, preferably 99.9 to 99%
Suspension Concentrates:
active ingredient: 5 to 75%, preferably 10 to 50%
water: 94 to 24%, preferably 88 to 30% surfactant: 1 to 40%, preferably 2 to 30%

Wettable Powders:

active ingredient: 0.5 to 90%, preferably 1 to 80% surfactant: 0.5 to 20%, preferably 1 to 15% solid carrier 5 to 99%, preferably 15 to 98%

Granulates:

active ingredient: 0.5 to 30%, preferably 3 to 15% solid carrier 99.5 to 70%, preferably 97 to 85%

EXAMPLES

The following compounds according to embodiment 1 may be prepared according to the methods described herein or according to known methods.

Experimental

The following examples are intended to illustrate the invention and are not to be construed as being limitations thereon.

"Mp" means melting point in ° C. $^1$H NMR measurements were recorded on a Brucker 400 MHz spectrometer, chemical shifts are given in ppm relevant to a TMS standard. Spectra measured in deuterated solvents as indicated.

LC MS Method A: Standard:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector.

Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 0% B, 100% A; 1.2-1.5 min 100% B; Flow (ml/min) 0.85.

LC MS Method B: Standard Long:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector.

Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 0% B, 100% A; 2.7-3.0 min 100% B; Flow (ml/min) 0.85.

LC MS Method C: Unpolar:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector.

Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 40% B, 60% A; 1.2-1.5 min 100% B; Flow (ml/min) 0.85.

LC MS Method D: UPLC2. Standard Long Gradient Column 1

SQ Detector 2 from Waters

Ionisation method: Electrospray

Polarity: positive ions

Capillary (kV) 3.5, Cone (V) 30.00, Extractor (V) 3.00, Source Temperature (° C.) 150, Desolvation Temperature (° C.) 400, Cone Gas Flow (L/Hr) 60, Desolvation Gas Flow (L/Hr) 700

Mass range: 140 to 800 Da

DAD Wavelength range (nm): 210 to 400

Method Waters ACQUITY UPLC with the following HPLC gradient conditions (Solvent A: Water/Methanol 9:1,0.1% formic acid and Solvent B: Acetonitrile, 0.1% formic acid)

| Time (minutes) | A (%) | B (%) | Flow rate (ml/min) |
|---|---|---|---|
| 0 | 100 | 0 | 0.75 |
| 2.5 | 0 | 100 | 0.75 |
| 2.8 | 0 | 100 | 0.75 |
| 3.0 | 100 | 0 | 0.75 |

Type of column: Waters ACQUITY UPLC HSS T3; Column length: 30 mm; Internal diameter of column: 2.1 mm; Particle Size: 1.8 micron; Temperature: 60° C.

Example 1: 2-Chloro-N-(1-cyanocyclopropyl-5-[1-[5-(difluoromethoxy)-2-methyl-4-(trifluoromethyl)pyrazol-3-yl]pyrazol-4-yl]benzamide a) Preparation of 5-fluoro-3-methoxy-1-methyl-4-(trifluoromethyl)pyrazole

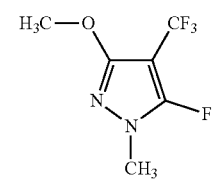

A mixture of methylhydrazine (1.32 ml, 24.6 mmol) and triethylamine (3.15 ml, 22.4 mmol) in 12 mi of ethanol was added dropwise at 25° C.-30° C. to a solution of 1-methoxy-(perfluoro-2-methyl-1-propene) (3.32 ml, 22.4 mmol) in 8 ml of ethanol. The addition was exothermic and the reaction was stirred overnight at room temperature. The ethanol was carefully evaporated, residue was diluted with tert-butyl methyl ether, and the organic layer was washed with water, brine, dried over sodium sulfate, filtrated and evaporated to give the crude product as yellow oil.

¹H NMR (400 MHz, CDCl₃) δ ppm 3.61 (d, J=0.73 Hz, 3H) 3.90 (s, 3H).

GC/MS (electrospray): m/z=198 [M+1].

b) Preparation of 5-(4-bromopyrazol-1-yl)-3-methoxy-1-methyl-4-(trifluoromethyl)pyrazole

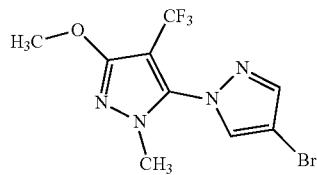 [SMILES: COc1nn(C)c(-n2cc(Br)cn2)c1C(F)(F)F]

Under Argon, 5-fluoro-3-methoxy-1-methyl-4-(trifluoromethyl)pyrazole (2.9 g, 11.7 mmol), 4-bromo-1H-pyrazole (2.11 g, 14.1 mmol) and potassium carbonate (3.43 g, 24.6 mmol) were dissolved in 35 ml THF. The yellow solution was heated over 3 days at 80° C. The mixture was then diluted with tert-butyl methyl ether, quenched with 15 ml of water, extracted 2 times with 20 ml of tert-butyl methyl ether, the organic phase was washed with brine, dried over sodium sulfate, filtrated and evaporated. The crude resin obtained (4.76 g) was purified over silica to give 5-(4-bromopyrazol-1-yl)-3-methoxy-1-methyl-4-(trifluoromethyl)pyrazole.

¹H NMR (400 MHz, CDCl₃) δ ppm 3.59 (s, 3H) 3.98 (s, 3H) 7.66 (s, 1H) 7.77 (s, 1H). GC/MS (electrospray): m/z=326 [M+1].

c) Synthesis of 2-chloro-5-[1-[5-methoxy-2-methyl-4-(trifluoromethyl)pyrazol-3-yl]pyrazol-4-yl]benzoic acid

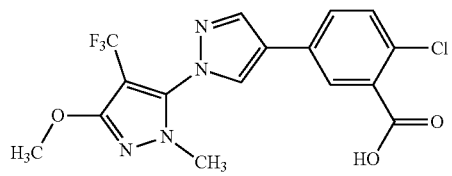 [SMILES: COc1nn(C)c(-n2cc(-c3ccc(Cl)c(C(=O)O)c3)cn2)c1C(F)(F)F]

In a 3-neck round bottom flask under argon, 5-(4-bromopyrazol-1-yl)-3-methoxy-1-methyl-4-(trifluoromethyl)pyrazole (1.81 g, 5.01 mmol), methyl 2-chloro-5-(4,4,5,5-tetramethyl-1,3,2-dioxaborolan-2-yl)benzoate (1.56 g, 5.26 mmol) and sodium hydrogen carbonate 1M (15 ml, 15 mmol) were dissolved in 30 ml of 2-propanol. The mixture was purged with argon for 5 min. After that, tetrakis(triphenylphosphine)palladium(0) (177 mg, 0.15 mmol) was added and the mixture was heated at 100° C. overnight. The mixture was filtrated, evaporated, diluted with ethyl acetate, quenched with 10 ml of sodium hydroxide 2N, and extracted 2 times with ethyl acetate. The water phase was acidified to pH 2 using hydrochloride acid 10% and extracted 3 times with 20 ml of ethyl acetate, the organic phase was washed with brine, dried over sodium sulfate, filtrated and evaporated to give 2-chloro-5-[1-[5-methoxy-2-methyl-4-(trifluoromethyl)pyrazol-3-yl]pyrazol-4-yl]benzoic acid as a yellow resin.

¹H NMR (400 MHz, CDCl₃) δ ppm 3.62-3.68 (m, 3H) 4.00 (s, 3H) 7.52-7.56 (m, 1H) 7.60-7.64 (m, 1H) 7.91 (s, 1H) 8.11 (d, J=0.73 Hz, 1H) 8.14 (d, J=2.20 Hz, 1H).

LC-MS: t_R=1.00 min, m/z=399 [M−1], 401 [M+1].

d) Preparation of 2-chloro-5-[1-[5-hydroxy-2-methyl-4-(trifluoromethyl)pyrazol-3-yl]pyrazol-4-yl]benzoic acid

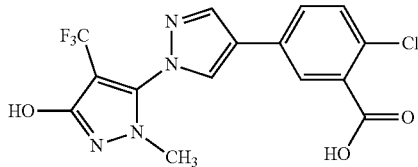 [SMILES: Cn1nc(O)c(C(F)(F)F)c1-n1cc(-c2ccc(Cl)c(C(=O)O)c2)cn1]

2-Chloro-5-[1-[5-methoxy-2-methyl-4-(trifluoromethyl)pyrazol-3-yl]pyrazol-4-yl]benzoic acid (1.99 g, 4.57 mmol) in a 33% solution HBr in AcOH (12.4 ml) was stirred under argon in a thick glass microwave tube. The colorless solution was heated at 60° C. overnight. After dilution with tert-butyl methyl ether, the solution was quenched with saturated sodium hydrogen carbonate. The water phase was acidified to pH 2 with 10% HCl and extracted with 3 times with 20 ml of ethyl acetate; the organic phase was washed with brine, dried over sodium sulfate, filtrated and evaporated. The crude beige product was purified to give 2-chloro-5-[1-[5-hydroxy-2-methyl-4-(trifluoromethyl)pyrazol-3-yl]pyrazol-4-yl]benzoic acid as white crystals.

¹H NMR (400 MHz, CD₃OD) δ ppm 3.28-3.36 (m, 3H) 3.51-3.56 (m, 3H) 7.54 (d, J=8.44 Hz, 1H) 7.78 (dd, J=8.25, 2.38 Hz, 1H) 8.11 (d, J=2.20 Hz, 1H) 8.28 (s, 1H) 8.40 (s, 1H)

LC-MS: t_R=0.85 min, m/z=385 [M−1], 387 [M+1].

e) Preparation of methyl 2-chloro-5-[1-[5-hydroxy-2-methyl-4-(trifluoromethyl)pyrazol-3-yl]pyrazol-4-yl]benzoate

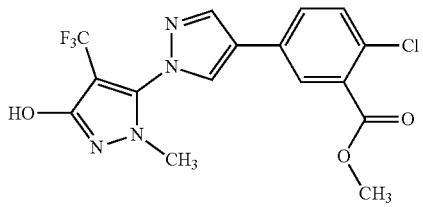 [SMILES: COC(=O)c1cc(-c2cnn(-c3c(C(F)(F)F)c(O)nn3C)c2)ccc1Cl]

2-Chloro-5-[1-[5-methoxy-2-methyl-4-(trifluoromethyl)pyrazol-3-yl]pyrazol-4-yl]benzoic acid (885 mg, 2.06 mmol) was dissolved in 15 ml of methanol and 2 drops conc. sulfuric acid were added. The solution was heated at 40° C. over 3 days. The mixture was evaporated, diluted with 10 ml of water and 15 ml ethyl acetate, quenched with a saturated solution of sodium hydrogen carbonate. The water phase was extracted 2 times with 15 ml of ethyl acetate, the organic phase was washed with brine, dried over sodium sulfate, filtrated and evaporated. The residue was purified on silica gel to give methyl 2-chloro-5-[1-[5-hydroxy-2-methyl-4-(trifluoromethyl)pyrazol-3-yl]pyrazol-4-yl]benzoate as white crystals.

¹H NMR (400 MHz, CDCl₃) δ ppm 3.69 (s, 3H) 3.98 (s, 3H) 7.49-7.53 (m, 1H) 7.56-7.60 (m, 1H) 7.94 (s, 1H) 7.98 (d, J=2.20 Hz, 1H) 8.11 (s, 1H)

LC-MS: $t_R$=0.96 min, m/z=399 [M−1], 401 [M+1].

f) Preparation of methyl 2-chloro-5-[1-[5-(difluoromethoxy)-2-methyl-4-(trifluoromethyl)pyrazol-3-yl]pyrazol-4-yl]benzoate

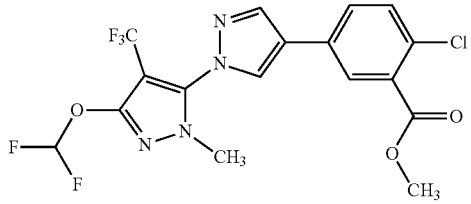 [SMILES: COC(=O)c1cc(-c2cnn(-c3c(C(F)(F)F)c(OC(F)F)nn3C)c2)ccc1Cl]

To a solution of methyl 2-chloro-5-[1-[5-hydroxy-2-methyl-4-(trifluoromethyl)pyrazol-3-yl]pyrazol-4-yl]benzoate (85 mg, 0.202 mmol) in 1.5 ml DMF was added chlorodifluoroacetic acid (87.1 µl, 1.01 mmol) and potassium carbonate (281 mg, 2.02 mmol) under argon. The cloudy solution was heated to 80° C. overnight. The mixture was filtrated, quenched with HCl 1N, and extracted with 3 times with 10 ml tert-butyl methyl ether. The organic layer was washed with brine, dried over sodium sulfate, filtrated. The residue was purified over silica gel to give methyl 2-chloro-5-[1-[5-(difluoromethoxy)-2-methyl-4-(trifluoromethyl)pyrazol-3-yl]pyrazol-4-yl]benzoate.

¹H NMR (400 MHz, CDCl₃) δ ppm 3.72 (s, 3H) 3.97 (s, 3H) 7.49-7.52 (m, 1H) 7.55-7.59 (m, 1H) 7.92 (s, 1H) 7.97 (d, J=2.20 Hz, 1H) 8.11 (s, 1H).

LC-MS: $t_R$=1.12 min, m/z=449 [M−1], 450 [M+1].

g) Preparation of 2-chloro-5-[1-[5-(difluoromethoxy)-2-methyl-4-(trifluoromethyl)pyrazol-3-yl]pyrazol-4-yl]benzoic acid

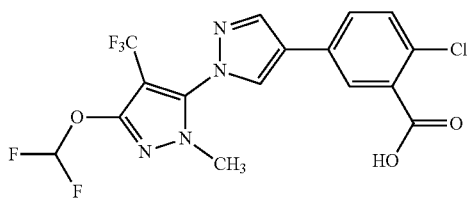 [SMILES: Cn1nc(OC(F)F)c(C(F)(F)F)c1-n1cc(-c2ccc(Cl)c(C(=O)O)c2)cn1]

Methyl 2-chloro-5-[1-[5-(difluoromethoxy)-2-methyl-4-(trifluoromethyl)pyrazol-3-yl]pyrazol-4-yl]benzoate (71 mg, 0.151 mmol) was dissolved in a mixture of THF and water (4 ml, 3/1). To this colorless solution was added LiOH monohydrate (7.12 mg, 0.166 mmol) and the yellow solution was allowed to stirred over night at RT. The mixture was acidified with HCl 2N and evaporated. The residue was diluted with 10 ml of water and 15 ml of ethyl acetate. The water phase was extracted with two times with 15 ml of ethyl acetate, and the organic phases were washed with brine, dried over Na₂SO₄, filtrated and evaporated to give 2-chloro-5-[1-[5-(difluoromethoxy)-2-methyl-4-(trifluoromethyl)pyrazol-3-yl]pyrazol-4-yl]benzoic acid as white crystals.

¹H NMR (400 MHz, CDCl₃) δ ppm 3.73 (s, 3H) 7.54-7.58 (m, 1H) 7.61-7.65 (m, 1H) 7.94 (s, 1H) 8.13-8.18 (m, 2H).

LC-MS: $t_R$=0.99 min, m/z=435 [M−1], 437 [M+1].

h) Preparation of 2-chloro-N-(1-cyanocyclopropyl)-5-[1-[5-(difluoromethoxy)-2-methyl-4-(trifluoromethyl)pyrazol-3-yl]pyrazol-4-yl]benzamide

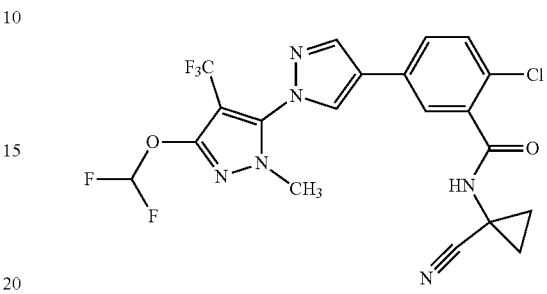

To a mixture of 2-chloro-5-[1-[5-(difluoromethoxy)-2-methyl-4-(trifluoromethyl)pyrazol-3-yl]pyrazol-4-yl]benzoic acid (70 mg, 0.154 mmol), 1-amino-1-cyano-cyclopropane-HCl (37 mg, 0.308 mmol), 4-dimethyl amino pyridine (29 mg, 0.231 mmol), 1-(3-dimethylaminopropyl)-3-ethyl-carbodiimide hydrochloride (33 mg, 0.169 mmol) and 3-hydroxytriazolo[4,5-b]pyridine (24 mg, 0.169 mmol) in 5 ml dichloromethane was added pyridine (14 µl, 0.169 mmol) and the mixture was stirred overnight at room temperature. The mixture was diluted with dichloromethane, quenched with water, the organic phase was washed successively with water and with brine. The organic phase was dried over magnesium sulfate, filtrated and evaporated. The residue was purified by flash chromatography to give 2-chloro-N-(1-cyanocyclopropyl)-5-[1-[5-(difluoromethoxy)-2-methyl-4-(trifluoromethyl)pyrazol-3-yl]pyrazol-4-yl]benzamide as a colorless resin.

¹H NMR (400 MHz, CDCl₃) δ ppm 1.41-1.45 (m, 2H) 1.66-1.71 (m, 2H) 3.23 (s, 1H) 3.72 (s, 3H) 7.07 (s, 1H) 7.44 (d, J=8.44 Hz, 1H) 7.56 (dd, J=8.44, 2.20 Hz, 1H) 7.92 (d, J=2.20 Hz, 1H) 7.95 (s, 1H) 8.11-8.12 (m, 1H).

LC-MS: $t_R$=1.00 min, m/z=499 [M−1], 500 [M+1].

Example 2: 2-Chloro-N-cyclopropyl-5-[1-[2-methyl-5-(2,2,2-trifluoroethoxy)-4-(trifluoromethyl)pyrazol-3-yl]pyrazol-4-yl]benzamide a) Preparation of 2-chloro-5-[1-[2-methyl-5-(2,2,2-trifluoroethoxy)-4-(trifluoromethyl)pyrazol-3-yl]pyrazol-4-yl]benzoic acid

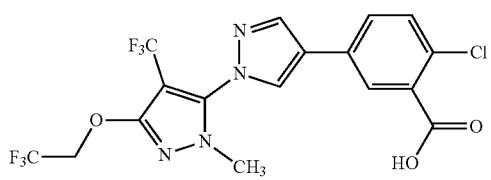 [SMILES: Cn1nc(OCC(F)(F)F)c(C(F)(F)F)c1-n1cc(-c2ccc(Cl)c(C(=O)O)c2)cn1]

Under argon, sodium hydride in mineral oil (10.4 mg, 0.261 mmol) was suspended in 1 ml DMF and a solution of methyl 2-chloro-5-[1-[5-hydroxy-2-methyl-4-(trifluoromethyl)pyrazol-3-yl]pyrazol-4-yl]benzoate (prepared in example 1, step e) (100 mg, 0.237 mmol) in 1.5 ml DMF was added dropwise at 25°–30° C. The yellow solution was stirred 30 min at room temperature. The mixture was cooled to 5° C. before adding dropwise 2,2,2-trifluoroethyltriflate (38 µl, 0.261 mmol). The dark blue solution was allowed to warm at room temperature. More sodium hydride in mineral oil (10.4 mg, 0.261 mmol) was added and the mixture was stirred for 30 min, before adding 2,2,2-trifluoroethyltriflate (38 µl, 0.261 mmol). The mixture was quenched with water and lithium hydroxide (10.2 mg, 0.237 mmol) was added. The mixture was stirred overnight at room temperature. The mixture was poured on 5 ml of water, and extracted with 3 times with 10 ml of tert-butyl methyl ether. The organic layer was washed with brine, dried over $Na_2SO_4$, filtrated and evaporated to give 2-chloro-5-[1-[2-methyl-5-(2,2,2-trifluoroethoxy)-4-(trifluoromethyl)pyrazol-3-yl]pyrazol-4-yl]benzoic acid as a resin.

$^1$H NMR (400 MHz, $CDCl_3$) δ ppm 3.67 (s, 3H) 4.69 (q, J=8.19 Hz, 2H) 7.53-7.57 (m, 1H) 7.60-7.65 (m, 1H) 7.93 (s, 1H) 8.11-8.17 (m, 2H)

LC-MS: $t_R$=1.04 min, m/z=467 [M−1], 469 [M+1].

b) Preparation 2-chloro-N-cyclopropyl-5-[1-[2-methyl-5-(2,2,2-trifluoroethoxy)-4-(trifluoromethyl)pyrazol-3-yl]pyrazol-4-yl]benzamide

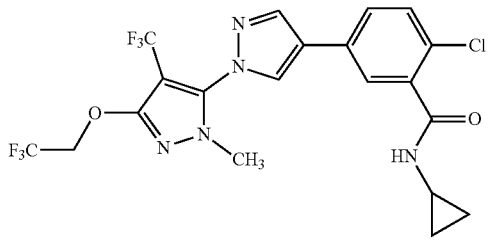 [SMILES: Cn1nc(OCC(F)(F)F)c(C(F)(F)F)c1-n1cc(-c2ccc(Cl)c(C(=O)NC3CC3)c2)cn1]

A mixture of 2-chloro-5-[1-[2-methyl-5-(2,2,2-trifluoroethoxy)-4-(trifluoromethyl)pyrazol-3-yl]pyrazol-4-yl]benzoic acid (60 mg, 0.115 mmol), cyclopropylamine (9 µl, 0.127 mmol), 1-(3-dimethylaminopropyl)-3-ethylcarbodiimide hydrochloride (25 mg, 0.127 mmol), 3-hydroxytriazolo[4,5-b]pyridine (18 mg, 0.127 mmol) in 5 ml of dichloromethane was stirred at room temperature. To this yellow solution was added 4-dimethylaminopyridine (21 mg, 0.173 mmol) and the reaction mixture was stirred overnight at room temperature. The mixture was diluted with dichloromethane, quenched with HCl 2 N; the organic phase was washed successively with water and brine, dried over magnesium sulfate, filtrated and evaporated to give after purification on silica gel 2-chloro-N-cyclopropyl-5-[1-[2-methyl-5-(2,2,2-trifluoroethoxy)-4-(trifluoromethyl)pyrazol-3-yl]pyrazol-4-yl]benzamide as white crystals.

$^1$H NMR (400 MHz, $CDCl_3$) δ ppm 0.65-0.70 (m, 2H) 0.89-0.94 (m, 2H) 2.96 (tq, J=7.15, 3.67 Hz, 1H) 3.64-3.68 (m, 3H) 4.69 (q, J=8.07 Hz, 2H) 6.39 (br. s., 1H) 7.41-7.44 (m, 1H) 7.48-7.52 (m, 1H) 7.85 (d, J=2.20 Hz, 1H) 7.89 (s, 1H) 8.08 (s, 1H).

LC-MS: $t_R$=1.05 min, m/z=506 [M−1], 508 [M+1].

MP: 167°–169° C.

Example 3: 2-Chloro-N-(1-cyanocyclopropyl)-5-[1-[2-methyl-5-(2,2,2-trifluoroethoxy)-4-(trifluoromethyl)pyrazol-3-yl]pyrazol-4-yl]benzamide

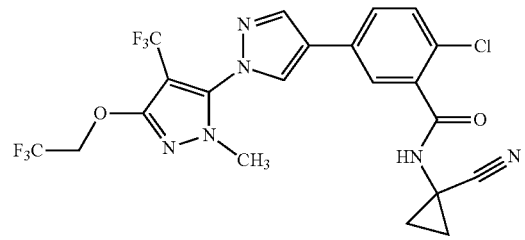 [SMILES: Cn1nc(OCC(F)(F)F)c(C(F)(F)F)c1-n1cc(-c2ccc(Cl)c(C(=O)NC3(C#N)CC3)c2)cn1]

A mixture of 2-chloro-5-[1-[2-methyl-5-(2,2,2-trifluoroethoxy)-4-(trifluoromethyl)pyrazol-3-yl]pyrazol-4-yl] benzoic acid (prepared in example 2, step a) (60 mg, 0.115 mmol), 1-amino-1-cyano-cyclopropane-HCl (28 mg, 0.23 mmol), 4-dimethylaminopyridine (21 mg, 0.173 mmol), 1-(3-dimethylaminopropyl)-3-ethylcarbodiimide hydrochloride (25 mg, 0.127 mmol) and 3-hydroxytriazolo[4,5-b]pyridine (18 mg, 0.127 mmol) in 5 ml of dichloromethane was stirred at room temperature. To this yellow solution was added pyridine (10 µl, 0.127 mmol) and the mixture was stirred overnight at room temperature. The mixture was diluted with dichloromethane, quenched with a solution of hydrochloride acid 2N, the organic phase was washed successively with water and once with brine, dried over magnesium sulfate, filtrated and evaporated to give after purification on silica gel 2-chloro-N-(1-cyanocyclopropyl)-5-[1-[2-methyl-5-(2,2,2-trifluoroethoxy)-4-(trifluoromethyl)pyrazol-3-yl]pyrazol-4-yl]benzamide as white crystals.

$^1$H NMR (400 MHz, $CDCl_3$) δ ppm 1.40-1.44 (m, 2H) 1.68-1.72 (m, 2H) 3.66 (s, 3H) 4.69 (q, J=8.19 Hz, 2H) 6.92 (s, 1H) 7.45 (d, J=8.44 Hz, 1H) 7.56 (dd, J=8.25, 2.38 Hz, 1H) 7.90-7.95 (m, 2H) 8.10 (s, 1H)

LC-MS: $t_R$=1.04 min, m/z=531 [M−1], 533 [M+1].

MP: 190°–192° C.

Example 4: 2-Chloro-N-(1-cyanocyclopropyl)-5-[1-[5-(1,1,2,3,3,3-hexafluoropropoxy)-2-methyl-4-(trifluoromethyl)pyrazol-3-yl]pyrazol-4-yl]benzamide a) Preparation of 2-chloro-N-(1-cyanocyclopropyl)-5-[1-[5-hydroxy-2-methyl-4-(trifluoromethyl)pyrazol-3-yl]pyrazol-4-yl]benzamide

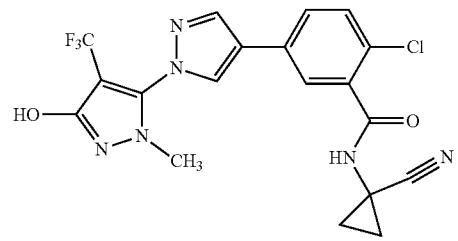 [SMILES: Cn1nc(O)c(C(F)(F)F)c1-n1cc(-c2ccc(Cl)c(C(=O)NC3(C#N)CC3)c2)cn1]

A mixture of 2-chloro-5-[1-[5-hydroxy-2-methyl-4-(trifluoromethyl)pyrazol-3-yl]pyrazol-4-yl]benzoic acid (Prepared in example 1, step d) (300 mg, 0.698 mmol), 3-(ethyliminomethylideneamino)-N,N-dimethylpropan-1-amine; hydrochloride (150 mg, 0.768 mmol), 1-amino-1-cyano-cyclopropane-HCl (211 mg, 1.75 mmol) and 3-hydroxytriazolo[4,5-b]pyridine (107 mg, 0.768 mmol) in 10 ml of dichloromethane was stirred at room temperature. To this yellow solution was added 4-dimethylaminopyridine (215 mg, 1.75 mmol) and mixture was stirred overnight at room temperature until complete conversion. The mixture was diluted with dichloromethane, quenched with HCl 2N, the organic phase was washed successively with water and once with brine, dried over MgSO$_4$, filtrated and evaporated to give after a purification on silica gel 2-chloro-N-(1-cyanocyclopropyl)-5-[1-[5-hydroxy-2-methyl-4-(trifluoromethyl)pyrazol-3-yl]pyrazol-4-yl]benzamide as white crystals.

$^1$H NMR (400 MHz, CD$_3$OD) δ ppm 1.27-1.31 (m, 2H) 1.48-1.52 (m, 2H) 3.42 (s, 3H) 7.40 (d, J=8.07 Hz, 1H) 7.63-7.67 (m, 2H) 8.18 (d, J=0.73 Hz, 1H) 8.29 (s, 1H)

LC-MS: t$_R$=0.88 min, m/z=449 [M−1], 451 [M+1].

b) Preparation of 2-chloro-N-(1-cyanocyclopropyl)-5-[1-[5-(1,1,2,3,3,3-hexafluoropropoxy)-2-methyl-4-(trifluoromethyl)pyrazol-3-yl]pyrazol-4-yl]benzamide

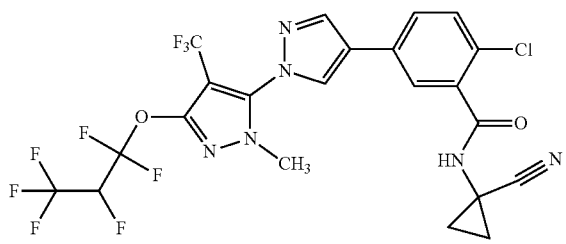 [SMILES: Cn1nc(OC(F)(F)C(F)C(F)(F)F)c(C(F)(F)F)c1-n1cc(-c2ccc(Cl)c(C(=O)NC3(C#N)CC3)c2)cn1]

In a sealed tube, a mixture of 2-chloro-N-(1-cyanocyclopropyl)-5-[1-[5-hydroxy-2-methyl-4-(trifluoromethyl)pyrazol-3-yl]pyrazol-4-yl]benzamide (29 mg, 0.0611 mmol), triethylamine (22 µl, 0.153 mmol) were stirred in 1 ml DMF and cooled to −10° C. Hexafluoropropene (93 mg, 0.611 mmol) was passed through the solution at −10° C. After 15 min the tube was sealed and the mixture was stirred at room temperature. The mixture was diluted with tert-butyl methyl ether, quenched with a saturated solution of ammonium chloride. The organic layer was washed with water, brine, dried over sodium sulfate, filtrated and evaporated to give after purification on silica gel 2-chloro-N-(1-cyanocyclopropyl)-5-[1-[5-(1,1,2,3,3,3-hexafluoropropoxy)-2-methyl-4-(trifluoromethyl)pyrazol-3-yl]pyrazol-4-yl]benzamide as a yellow resin.

$^1$H NMR (400 MHz, CDCl$_3$) δ ppm 1.41-1.44 (m, 2H) 1.68-1.72 (m, 2H) 3.79 (s, 3H) 5.08-5.27 (m, 1H) 6.94 (s, 1H) 7.46 (d, J=8.07 Hz, 1H) 7.56 (dd, J=8.44, 2.20 Hz, 1H) 7.92-7.97 (m, 2H) 8.13 (s, 1H)

LC-MS: t$_R$=1.17 min, m/z=599 [M−1], 601 [M+1].

Example 5: 2-Chloro-N-(1-cyanocyclopropyl)-5-[1-[5-methoxy-2-methyl-4-(trifluoromethyl)pyrazol-3-yl]pyrazol-4-yl]benzamide a) Preparation of 2-chloro-5-[1-[5-methoxy-2-methyl-4-(trifluoromethyl)pyrazol-3-yl]pyrazol-4-yl] benzoyl chloride

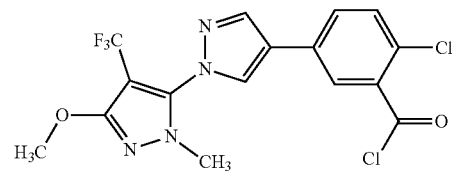 [SMILES: COc1nn(C)c(-n2cc(-c3ccc(Cl)c(C(=O)Cl)c3)cn2)c1C(F)(F)F]

Under argon, 2-chloro-5-[1-[5-methoxy-2-methyl-4-(trifluoromethyl)pyrazol-3-yl]pyrazol-4-yl]benzoic acid (prepared in example 1, step c) (32 mg, 0.0759 mmol) was stirred in 3 ml dichloromethane. To this solution was added 1 drop DMF followed by oxalyl chloride (8 µl, 0.091 mmol). The mixture was allow to stir at room temperature up to completion and the mixture was evaporated to dryness to give 2-chloro-5-[1-[5-methoxy-2-methyl-4-(trifluoromethyl)pyrazol-3-yl]pyrazol-4-yl]benzoyl chloride.

LC-MS: t$_R$=1.14 min, m/z (methyl ester)=415 [M+1].

b) Preparation of 2-chloro-N-(1-cyanocyclopropyl)-5-[1-[5-methoxy-2-methyl-4-(trifluoromethyl)pyrazol-3-yl]pyrazol-4-yl]benzamide

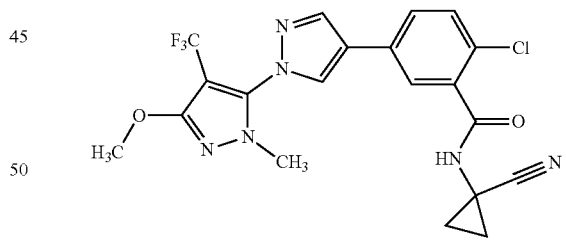

Under argon, 1-amino-1-cyano-cyclopropane-HCl (9 mg, 0.0744 mmol) and pyridine (16 µl, 0.186 mmol) were dissolved in 2 ml of THF. To this solution was dropwise added 2-chloro-5-[1-[5-methoxy-2-methyl-4-(trifluoromethyl)pyrazol-3-yl]pyrazol-4-yl]benzoyl chloride (32 mg, 0.744 mmol) at room temperature and stirred overnight. The mixture was diluted with tert-butyl methyl ether, quenched with a saturated solution of sodium hydrogen carbonate. The organic layer was washed with water, brine, dried over sodium sulfate, filtrated and evaporated to give after purification on silica gel 2-chloro-N-(1-cyanocyclopropyl)-5-[1-[5-methoxy-2-methyl-4-(trifluoromethyl)pyrazol-3-yl]pyrazol-4-yl]benzamide.

¹H NMR (400 MHz, CDCl₃) δ ppm 1.43-1.44 (m, 2H) 1.67-1.71 (m, 2H) 3.64 (s, 3H) 4.00 (s, 3H) 6.91 (s, 1H) 7.42-7.46 (m, 1H) 7.54-7.57 (m, 1H) 7.89-7.94 (m, 2H) 8.08 (s, 1H).

LC-MS: $t_R$=1.00 min, m/z=463 [M+1], 465 [M+1].

Example 6: 5-[1-[4-bromo-2-methyl-5-(trifluoromethylsulfanyl)pyrazol-3-yl]pyrazol-4-yl]-2-chloro-N-cyclopropyl-benzamide a) Preparation of methyl 2-chloro-5-(1-tetrahydropyran-2-ylpyrazol-4-yl)benzoate

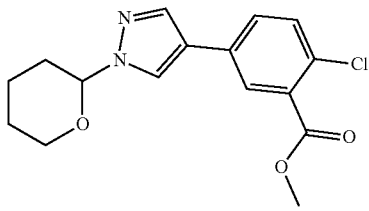 [SMILES: COC(=O)c1cc(-c2cnn(C3CCCCO3)c2)ccc1Cl]

To a solution of 4-bromo-1-tetrahydropyran-2-yl-pyrazole (0.108 g) in isopropanol (7 mL) was added methyl 2-chloro-5-(4,4,5,5-tetramethyl-1,3,2-dioxaborolan-2-yl)benzoate (0.1386 g) and an aqueous solution of sodium bicarbonate (1M, 1.4 mL). The reaction mixture was degassed with argon and then tetrakis(triphenylphosphine)palladium (0) was added (16.2 mg). The reaction mixture was then heated to 100° C. for 4 hours and cooled down to room temperature. The reaction mixture was partitioned between water and AcOEt. The aqueous phase was extracted with AcOEt twice, the combined organic layers were dried on Na₂SO₄ and concentrated under vacuum. The crude material was purified by flash chromatography (Cyclohexane/AcOEt) to give methyl 2-chloro-5-(1-tetrahydropyran-2-ylpyrazol-4-yl)benzoate as a colourless oil.

1H NMR (400 MHz, CDCl₃) δ ppm 1.58-1.79 (m, 4H) 2.09-2.18 (m, 2H) 3.68-3.79 (m, 1H) 3.95 (s, 3H) 4.05-4.15 (m, 1H) 5.38-5.44 (m, 1H) 7.43 (d, 1H) 7.52 (dd, 1H) 7.82 (s, 1H) 7.90 (s, 1H) 7.93 (d, 1H).

b) Preparation of methyl 2-chloro-5-(1H-pyrazol-4-yl)benzoate

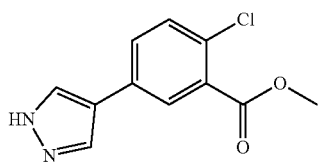 [SMILES: COC(=O)c1cc(-c2cn[nH]c2)ccc1Cl]

To a solution of methyl 2-chloro-5-(1-tetrahydropyran-2-ylpyrazol-4-yl)benzoate (2.5 g) in tetrahydrofuran (31 mL) was added concentrated hydrochloric acid (36% in water, 2.3 mL). The reaction mixture was stirred at 55° C. for 30 minutes and cooled down to room temperature. The reaction mixture was diluted with AcOEt, washed with saturated aqueous NaHCO₃ and with brine. The combined organic layers were dried over Na₂SO₄ and concentrated under vacuum. The crude material was purified by flash chroma-tography (Cyclohexane/AcOEt) to give methyl 2-chloro-5-(1H-pyrazol-4-yl)benzoate as a white solid.

1H NMR (400 MHz, CDCl₃) δ ppm 3.97 (s, 3H) 7.45 (d, 1H) 7.55 (dd, 1H) 7.90 (s, 2H) 7.96 (d, 1H).

c) Preparation of 2-chloro-5-(1H-pyrazol-4-yl)benzoic acid

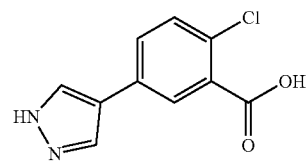 [SMILES: O=C(O)c1cc(-c2cn[nH]c2)ccc1Cl]

Methyl 2-chloro-5-(1H-pyrazol-4-yl)benzoate (2 g) was dissolved in dioxane (10 ml) and water (4 ml). NaOH pellets (0.372 g) were added at r.t. and the reaction mixture was stirred overnight at r.t. The reaction mixture was then concentrated under vacuum and diluted with some water. This basic solution was washed with methyl tert-butyl ether and was then acidified with HCl 1N. Precipitation of 2-chloro-5-(1H-pyrazol-4-yl)benzoic acid occurred. The solid was rinsed with water and dried on the filter. The solid was redissolved in CH₂Cl₂/methanol and dried on MgSO₄. The solution was then concentrated under vacuum to give 2-chloro-5-(1H-pyrazol-4-yl)benzoic acid as white crystals.

Melting point: 227-229° C.

d) Preparation of 2-chloro-N-cyclopropyl-5-(1H-pyrazol-4-yl)benzamide

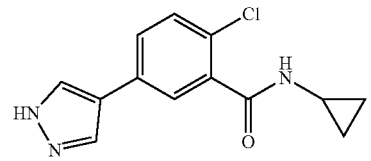 [SMILES: O=C(NC1CC1)c1cc(-c2cn[nH]c2)ccc1Cl]

2-Chloro-5-(1H-pyrazol-4-yl)benzoic acid (825 mg) was dissolved in DMA and (3 mL). Then cyclopropylamine (0.280 mL), Hunig's base (1.59 mL) were added at r.t. and the reaction mixture was stirred at r.t. for 10 minutes. The mixture was cooled down with an icebath and BOP-Cl (1.037 g) was added in 1 portion. The icebath was removed and the light suspension stirred for 8 h at 55° C. then at r.t. overnight. As the reaction was not completed, cyclopropylamine (0.127 mL), Huenig's base (0.318 mL) and BOP—Cl (0.471 g) were added and the reaction mixture was heated again to 55° C. for 6 hours. The reaction mixture was poured into water. The precipitation of white cristals occurred.

After stirring for 10 minutes, the solid was filtered off and dried on filter. It was triturated in petrol ether to provide 2-chloro-N-cyclopropyl-5-(1H-pyrazol-4-yl)benzamide as white crystals.

Melting point: 102-103° C.

e) Preparation of 4-bromo-3-iodo-1-methyl-pyrazole

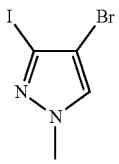

A solution of 3-iodo-1-methyl-pyrazole (4.2 mL) in acetonitrile (76 mL) was mixed with cerium ammonium nitrate (10 g) and bromine (1.9 mL) at room temperature under argon. The reaction mixture was then stirred at room temperature for 2 h. The reaction mixture was poured onto a mixture of water/AcOEt. The aqueous phase was extracted twice with AcOEt. Then the gathered organic phases were washed twice with sodium bicarbonate, washed again with brine. The organic phase was finally dried on MgSO$_4$ concentrated to dryness to give crude material which was purified via flash chromatography (Cyclohexane/AcOEt) to afford 4-bromo-3-iodo-1-methyl-pyrazole as an orange oil.

1H NMR (400 MHz, CDCl$_3$) δ ppm 3.93 (s, 3H) 7.31 (s, 1H).

f) Preparation of 4-bromo-5-fluoro-3-iodo-1-methyl-pyrazole

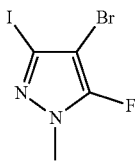

To a solution of 4-bromo-3-iodo-1-methyl-pyrazole (9.23 g) in tetrahydrofuran (183 mL) was added at −78° C. a solution of LDA (2M in THF/heptane/ethylbenzene, 24.1 mL). The reaction mixture was stirred for 1 h at −78° C. Then N-(benzenesulfonyl)-N-fluoro-benzenesulfonamide (20.9 g) in 65 mL of THF was added dropwise at −78° C. After 4 hours, the reaction mixture was warmed up to 0° C. then quenched with saturated aqueous NH$_4$Cl. The aqueous phase was extracted with AcOEt, the latter being washed again with NH$_4$Cl. The organic phase was dried on MgSO$_4$ and evaporated. The crude residue was triturated with dichloromethane, and the filtrate was further purified by flash chromatography (Cyclohexane/AcOEt) to give 4-bromo-5-fluoro-3-iodo-1-methyl-pyrazole as a white solid.

1H NMR (400 MHz, CDCl$_3$) δ ppm 3.79 (d, 3H).

g) Preparation of 5-[1-(4-bromo-5-iodo-2-methyl-pyrazol-3-yl)pyrazol-4-yl]-2-chloro-N-cyclopropyl-benzamide

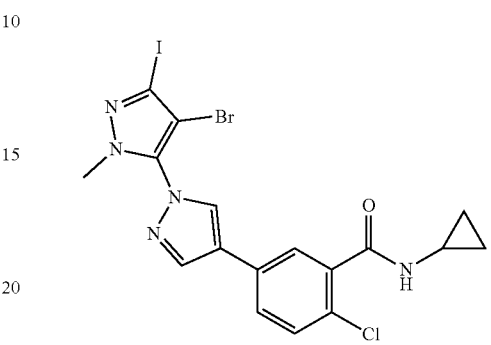

To a solution of 2-chloro-N-cyclopropyl-5-(1H-pyrazol-4-yl)benzamide (2.46 g, example 6d) in acetonitrile (62.7 mL) was added cesium carbonate (5.89 g). Then 4-bromo-5-fluoro-3-iodo-1-methyl-pyrazole (2.73 g) was added and the suspension was heated to 80° C. for 15 min. The reaction mixture was poured on water and extracted twice with AcOEt. The combined organic layers were dried (MgSO$_4$), and concentrated. The crude material was purified by flash chromatography (Cyclohexane/AcOEt) to give 5-[1-(4-bromo-5-iodo-2-methyl-pyrazol-3-yl)pyrazol-4-yl]-2-chloro-N-cyclopropyl-benzamide as an off white solid.

1H NMR (400 MHz, DMSO-d6) δ ppm 0.51-0.57 (m, 2H) 0.67-0.74 (m, 2H) 2.84 (tq, 1H) 3.75 (s, 3H) 7.52 (d, 1H) 7.73-7.79 (m, 2H) 8.50 (s, 1H) 8.52 (d, 1H) 8.75 (s, 1H).

h) Preparation of methyl 3-[4-bromo-5-[4-[4-chloro-3-(cyclopropylcarbamoyl)phenyl]pyrazol-1-yl]-1-methyl-pyrazol-3-yl]sulfanylpropanoate

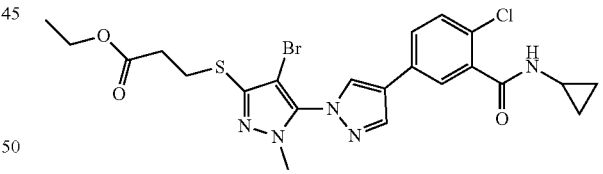

5-[1-(4-bromo-5-iodo-2-methyl-pyrazol-3-yl)pyrazol-4-yl]-2-chloro-N-cyclopropyl-benzamide (0.1 g) and Xant-Phos (5.3 mg) were dissolved in dry dioxane (2 mL). Hunig's base (64 µL) was added to the reaction mixture. The solution was degased with argon using argon and vacuum cycles. Methyl 3-sulfanylpropanoate (41 µL) and Pd$_2$(dba)$_3$ (4.2 mg) were added successively to the reaction mixture. The reaction was hermetically sealed in a microwave vial and irradiated under microwaves at 120° C. for 40 minutes. The reaction mixture was cooled down, concentrated under vacuum and the crude residue was purified by flash chromatography (Cyclohexane/AcOEt) to afford methyl 3-[4-bromo-5-[4-[4-chloro-3-(cyclopropylcarbamoyl)phenyl] pyrazol-1-yl]-1-methyl-pyrazol-3-yl]sulfanylpropanoate as a yellow gum.

1H NMR (400 MHz, CDCl₃) δ ppm 0.64-0.71 (m, 2H) 0.87-0.95 (m, 2H) 2.78 (t, 2H) 2.95 (tq, 1H) 3.25 (t, 2H) 3.71 (s, 3H) 3.86 (s, 3H) 6.44 (br s, 1H) 7.42 (d, 1H) 7.51 (dd, 1H) 7.86 (d, 1H) 8.02 (s, 1H) 8.07 (s, 1H).

i) Preparation of 5-[1-(4-bromo-2-methyl-5-sulfanyl-pyrazol-3-yl)pyrazol-4-yl]-2-chloro-N-cyclopropyl-benzamide

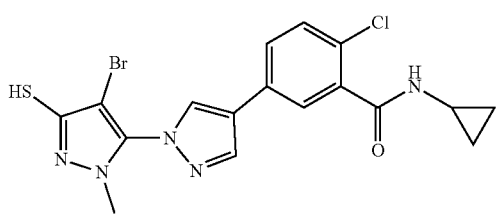 [SMILES: Cn1nc(S)c(Br)c1-n1cc(-c2ccc(Cl)c(C(=O)NC3CC3)c2)cn1]

Methyl 3-[4-bromo-5-[4-[4-chloro-3-(cyclopropylcarbamoyl)phenyl]pyrazol-1-yl]-1-methyl-pyrazol-3-yl]sulfanylpropanoate (0.430 g) was dissolved in dry DMF (4 mL) and KOtBu (0.228 g) was added to the solution which immediately turned from a clear yellow solution to a dark red solution. After 8.5 hours at r.t. under argon, there was only partial conversion. Therefore more KOtBu (0.1 g) was added, and the reaction mixture was stirred at r.t. under argon overnight. The reaction mixture was neutralized with aqueous HCl 1N. The aqueous phase was extracted with methyl tert-butyl ether three times. The combined organic phases were washed with water twice, dried over MgSO₄ and concentrated under vacuum. The crude residue was purified by flash chromatography (Cyclohexane/AcOEt) to afford 5-[1-(4-bromo-2-methyl-5-sulfanyl-pyrazol-3-yl)pyrazol-4-yl]-2-chloro-N-cyclopropyl-benzamide as a yellow gum.

1H NMR (400 MHz, CDCl₃) δ ppm 0.65-0.72 (m, 2H) 0.87-0.95 (m, 2H) 2.92-2.99 (m, 2H) 3.92 (s, 3H) 6.49 (br s, 1H) 7.42 (d, 1H) 7.52 (dd, 1H) 7.86 (d, 1H) 8.05 (s, 1H) 8.10 (s, 1H).

j) Preparation of 5-[1-[4-bromo-2-methyl-5-(trifluoromethylsulfanyl)pyrazol-3-yl]pyrazol-4-yl]-2-chloro-N-cyclopropyl-benzamide

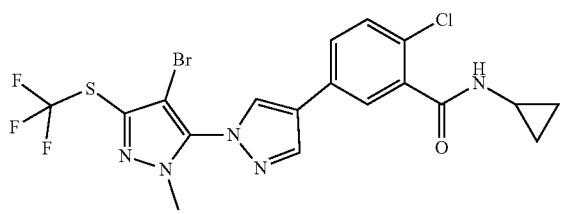 [SMILES: Cn1nc(SC(F)(F)F)c(Br)c1-n1cc(-c2ccc(Cl)c(C(=O)NC3CC3)c2)cn1]

5-[1-(4-bromo-2-methyl-5-sulfanyl-pyrazol-3-yl)pyrazol-4-yl]-2-chloro-N-cyclopropyl-benzamide (0.110 g) was dissolved in dichloromethane (4 mL) and the solution was cooled down to −78° C. 3,3-dimethyl-1-(trifluoromethyl)-1,2-benziodoxole (Togni's reagent, 0.113 g) was dissolved in 2 mL of dichloromethane and this solution was added dropwise to the reaction mixture at −78° C. which was then allowed to warm up slowly to r.t. As some oxidation by-products were visible the day after, tris(2-carboxyethyl)phosphine hydrochloride (TCEP HCl) was added: first 10 mg of TCEP HCl, 30 minutes later 30 mg more of TCEP HCl, and 1 hour later 30 mg more of TCEP HCl. The reaction mixture was stirred at r.t. for 2 more hours. Since conversion was not complete, some more Togni's reagent (30 mg) was added at r.t. and the reaction mixture was stirred at r.t. overnight. The reaction mixture was then quenched with water, the aqueous phase was extracted 3 times with dichloromethane. The combined organic phases were dried over MgSO₄ and concentrated under vacuum. The crude material was purified by flash chromatography (Cyclohexane/AcOEt) to afford 5-[1-[4-bromo-2-methyl-5-(trifluoromethylsulfanyl) pyrazol-3-yl]pyrazol-4-yl]-2-chloro-N-cyclopropyl-benzamide as a yellow gum.

1H NMR (400 MHz, CDCl₃) δ ppm 0.65-0.72 (m, 2H) 0.91-0.95 (m, 2H) 2.97 (tq, 1H) 3.98 (s, 3H) 6.42 (br s, 1H) 7.44 (d, 1H) 7.54 (dd, 1H) 7.89 (d, 1H) 8.08 (s, 1H) 8.12 (s, 1H).

Example 7: 5-[1-[4-bromo-2-methyl-5-(2,2,2-trifluoroethylamino)pyrazol-3-yl]pyrazol-4-yl]-2-chloro-N-cyclopropyl-benzamide a) Preparation of 5-[1-(5-amino-4-bromo-2-methyl-pyrazol-3-yl)pyrazol-4-yl]-2-chloro-N-cyclopropyl-benzamide

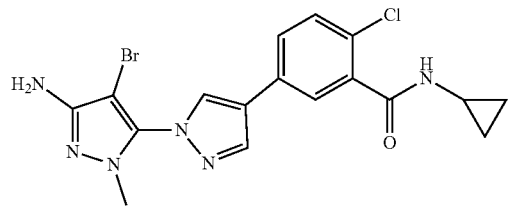 [SMILES: Cn1nc(N)c(Br)c1-n1cc(-c2ccc(Cl)c(C(=O)NC3CC3)c2)cn1]

An argon flushed microwave vial was charged with 5-[1-(4-bromo-5-iodo-2-methyl-pyrazol-3-yl)pyrazol-4-yl]-2-chloro-N-cyclopropyl-benzamide (0.2 g, example 6 g), cesium carbonate (0.2384 g), Cu(acac)₂ (10 mg). The vial was then evacuated and flushed again with argon before the addition of acetylacetone (0.015 mL), DMF (2 mL), and aqueous ammonia (28%, 0.237 mL). The vial was sealed and heated to 80° C. for 24 hours. As the reaction was incomplete, aqueous ammonia (28%, 0.237 mL) was added and the vial was sealed and heated again to 80° C. for 24 hours. Then the vial was heated under microwave irradiation at 120° C. for 30 minutes. The reaction mixture was filtered on Cellite, the latter being washed with dichloromethane. The organic phase was washed twice with water. The aqueous phase was extracted 5 times with dichloromethane. The combined organic phases were dried over magnesium sulfate and concentrated under reduced pressure. The crude material was purified by flash chromatography (Cyclohexane/AcOEt) to afford 5-[1-(5-amino-4-bromo-2-methyl-pyrazol-3-yl)pyrazol-4-yl]-2-chloro-N-cyclopropyl-benzamide as a brown solid.

1H NMR (400 MHz, CDCl₃) δ ppm 0.63-0.72 (m, 2H) 0.85-0.95 (m, 2H) 2.90-3.00 (m, 1H) 3.72 (s, 3H) 5.36-5.94 (br s, 2H) 6.51 (br s, 1H) 7.39 (d, 1H) 7.48 (dd, 1H) 7.82 (d, 1H) 7.86 (s, 1H) 7.99 (s, 1H).

b) Preparation of 5-[1-[4-bromo-2-methyl-5-[(2,2,2-trifluoro-1-methoxy-ethyl)amino]pyrazol-3-yl]pyrazol-4-yl]-2-chloro-N-cyclopropyl-benzamide

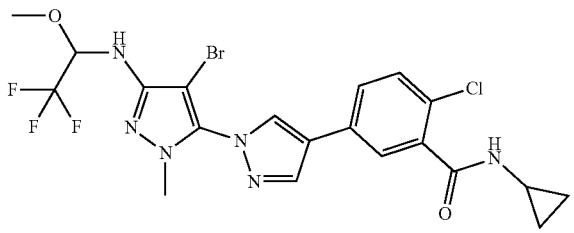 [SMILES: COC(Nc1nn(C)c(-n2cc(-c3ccc(Cl)c(C(=O)NC4CC4)c3)cn2)c1Br)C(F)(F)F]

5-[1-(5-amino-4-bromo-2-methyl-pyrazol-3-yl)pyrazol-4-yl]-2-chloro-N-cyclopropyl-benzamide (15 mg) was dissolved in MeOH (0.2 mL) in a vial, p-toluenesulfonic acid hydrate (0.3 mg) and trifluoroacetaldehyde ethyl hemiacetal (5 µL) was added to the reaction mixture. The vial was sealed and the reaction was heated to 70° C. for 2.5 hours. The reaction mixture was cooled down and quenched with aqueous NaHCO₃. The aqueous phase was extracted with AcOEt 3 times. The combined organic phases were dried over MgSO₄ and concentrated under vacuum. This crude material was directly engaged into the next step.
LC-MS (A): tR=1.02 min, m/z=547.

c) Preparation of 5-[1-[4-bromo-2-methyl-5-(2,2,2-trifluoroethylamino)pyrazol-3-yl]pyrazol-4-yl]-2-chloro-N-cyclopropyl-benzamide

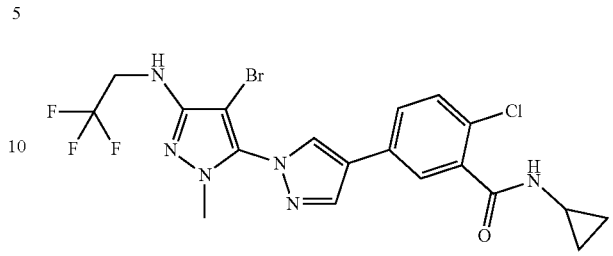

Crude 5-[1-[4-bromo-2-methyl-5-[(2,2,2-trifluoro-1-methoxy-ethyl)amino]pyrazol-3-yl]pyrazol-4-yl]-2-chloro-N-cyclopropyl-benzamide (0.01 g) was suspended in acetic acid (0.20 mL) and 2-picoline borane complex (2.4 mg) was added. The reaction mixture was stirred at r.t. for 16 hours. Since conversion was not complete 2-picoline borane complex (2.4 mg) was added and the reaction mixture was heated to reflux. The reaction mixture was poured on saturated aqueous NaHCO₃. The aqueous phase was extracted with AcOEt 3 times. The combined organic phases were dried over MgSO₄ and concentrated under vacuum. This crude material was purified by flash chromatography (Cyclohexane/AcOEt) to afford 5-[1-[4-bromo-2-methyl-5-(2,2,2-trifluoroethylamino)pyrazol-3-yl]pyrazol-4-yl]-2-chloro-N-cyclopropyl-benzamide.
LC-MS (A): tR=0.99 min, m/z=517.

The following compounds were prepared in analogy with Examples 1 to 7.

TABLE 1

Examples of compounds of formula (I)

| Ex. No. | Structure | (NMR (400 MHz, CDCl₃) δ ppm), LC MS (method) | mp (° C.) |
|---|---|---|---|
| 1 | 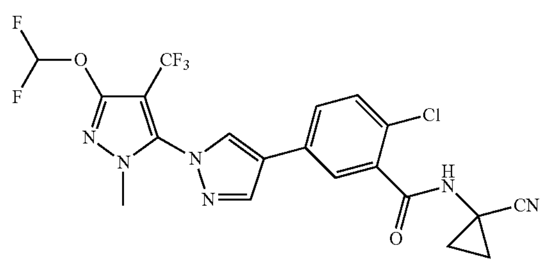 [SMILES: Cn1nc(OC(F)F)c(C(F)(F)F)c1-n1cc(-c2ccc(Cl)c(C(=O)NC3(C#N)CC3)c2)cn1] | 1.41-1.45 (m, 2 H) 1.66-1.71 (m, 2 H) 3.23 (s, 1 H) 3.72 (s, 3 H) 7.07 (s, 1 H) 7.44 (d, J = 8.44 Hz, 1 H) 7.56 (dd, J = 8.44, 2.20 Hz, 1 H) 7.92 (d, J = 2.20 Hz, 1 H) 7.95 (s, 1 H) 8.11-8.12 (m, 1 H). LC-MS (A): $t_R$ = 1.00 min, m/z = 499 [M − 1], 500 [M + 1] | |
| 2 | 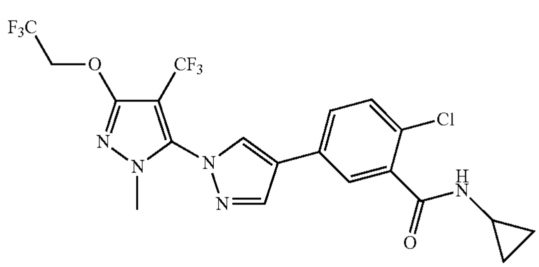 [SMILES: Cn1nc(OCC(F)(F)F)c(C(F)(F)F)c1-n1cc(-c2ccc(Cl)c(C(=O)NC3CC3)c2)cn1] | 0.65-0.70 (m, 2 H) 0.89-0.94 (m, 2H) 2.96 (tq, J = 7.15, 3.67 Hz, 1 H) 3.64-3.68 (m, 3 H) 4.69 (q, J = 8.07 Hz, 2 H) 6.39 (br. s., 1 H) 7.41-7.44 (m, 1 H) 7.48-7.52 (m, 1 H) 7.85 (d, J = 2.20 Hz, 1 H) 7.89 (s, 1 H) 8.08 (s, 1 H). LC-MS (A): $t_R$ = 1.05 min, m/z = 506 [M − 1], 508 [M + 1] | 167-9 |

TABLE 1-continued

Examples of compounds of formula (I)

| Ex. No. | Structure | (NMR (400 MHz, CDCl₃) δ ppm), LC MS (method) | mp (° C.) |
|---|---|---|---|
| 3 | 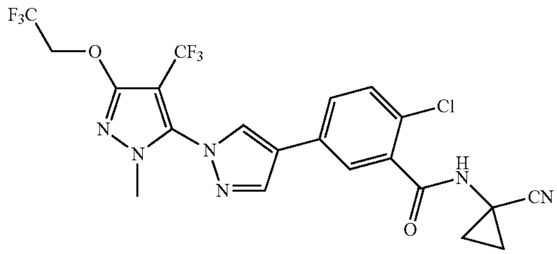 [SMILES: Cn1nc(OCC(F)(F)F)c(C(F)(F)F)c1-n1cc(-c2ccc(Cl)c(C(=O)NC3(C#N)CC3)c2)cn1] | 1.40-1.44 (m, 2 H) 1.68-1.72 (m, 2 H) 3.66 (s, 3 H) 4.69 (q, J = 8.19 Hz, 2 H) 6.92 (s, 1 H) 7.45 (d, J = 8.44 Hz, 1 H) 7.56 (dd, J = 8.25, 2.38 Hz, 1 H) 7.90-7.95 (m, 2 H) 8.10 (s, 1 H) LC-MS (A): t$_R$ = 1.04 min, m/z = 531 [M − 1], 533 [M + 1] | 190-2 |
| 4 | 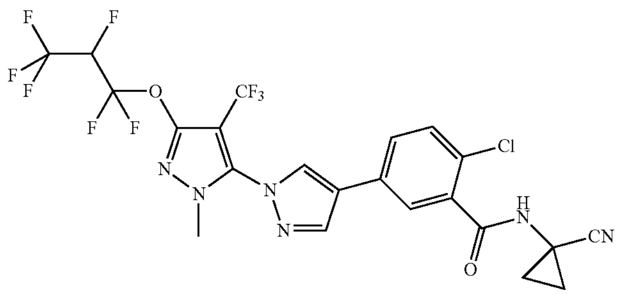 [SMILES: Cn1nc(OC(F)(F)C(F)C(F)(F)F)c(C(F)(F)F)c1-n1cc(-c2ccc(Cl)c(C(=O)NC3(C#N)CC3)c2)cn1] | 1.41-1.44 (m, 2 H) 1.68-1.72 (m, 2 H) 3.79 (s, 3 H) 5.08-5.27 (m, 1 H) 6.94 (s, 1 H) 7.46 (d, J = 8.07 Hz, 1 H) 7.56 (dd, J = 8.44, 2.20 Hz, 1 H) 7.92-7.97 (m, 2H) 8.13 (s, 1 H) LC-MS (A): t$_R$ = 1.17 min, m/z = 599 [M − 1], 601 [M + 1] | |
| 5 | 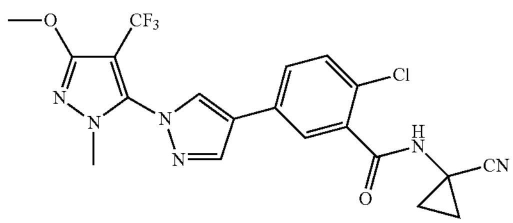 [SMILES: COc1nn(C)c(-n2cc(-c3ccc(Cl)c(C(=O)NC4(C#N)CC4)c3)cn2)c1C(F)(F)F] | 1.43-1.44 (m, 2 H) 1.67-1.71 (m, 2 H) 3.64 (s, 3 H) 4.00 (s, 3 H) 6.91 (s, 1 H) 7.42-7.46 (m, 1 H) 7.54-7.57 (m, 1 H) 7.89-7.94 (m, 2 H) 8.08 (s, 1 H). LC-MS (A): t$_R$ = 1.00 min, m/z = 463 [M + 1], 465 [M + 1] | |
| 6 | 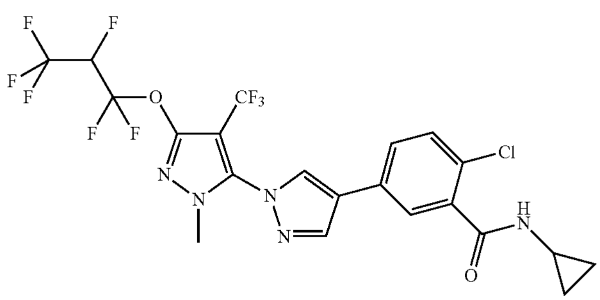 [SMILES: Cn1nc(OC(F)(F)C(F)C(F)(F)F)c(C(F)(F)F)c1-n1cc(-c2ccc(Cl)c(C(=O)NC3CC3)c2)cn1] | LC-MS (A): t$_R$ = 1.10 min, m/z = 731 [M − 1], 576 [M + 1] | |
| 7 | 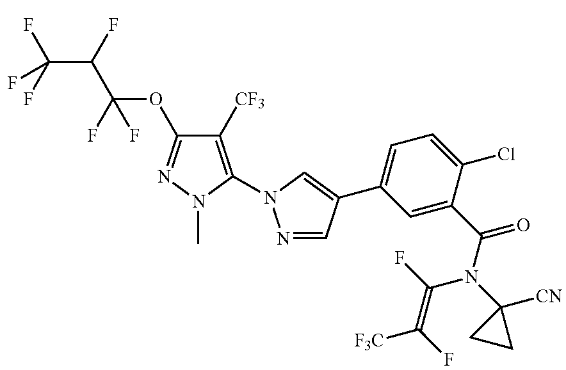 [SMILES: Cn1nc(OC(F)(F)C(F)C(F)(F)F)c(C(F)(F)F)c1-n1cc(-c2ccc(Cl)c(C(=O)N(/C(F)=C(\F)C(F)(F)F)C3(C#N)CC3)c2)cn1] | LC-MS (A): t$_R$ = 1.26 min, m/z = 731 [M − 1], 733 [M + 1] | |

TABLE 1-continued

Examples of compounds of formula (I)

| Ex. No. | Structure | (NMR (400 MHz, CDCl$_3$) δ ppm), LC MS (method) | mp (° C.) |
|---|---|---|---|
| 8 | 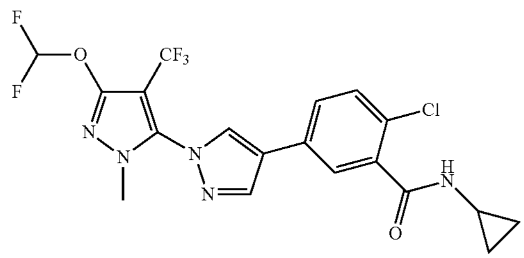 [SMILES: Cn1nc(OC(F)F)c(C(F)(F)F)c1-n1cc(-c2ccc(Cl)c(C(=O)NC3CC3)c2)cn1] | | |
| 9 | 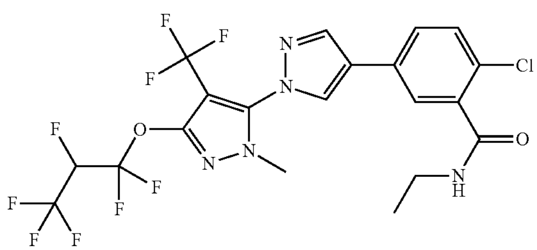 [SMILES: CCNC(=O)c1cc(-c2cnn(-c3c(C(F)(F)F)c(OC(F)(F)C(F)C(F)(F)F)nn3C)c2)ccc1Cl] | LC-MS (A): t$_R$ = 1.09 min, m/z = 564 [M + 1] | |
| 10 | 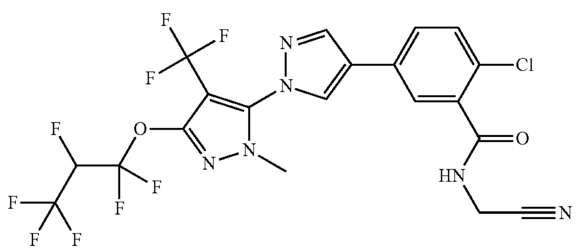 [SMILES: Cn1nc(OC(F)(F)C(F)C(F)(F)F)c(C(F)(F)F)c1-n1cc(-c2ccc(Cl)c(C(=O)NCC#N)c2)cn1] | LC-MS (A): t$_R$ = 1.06 min, m/z = 575 [M + 1] | |
| 11 | 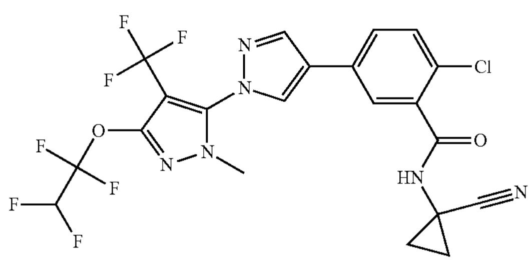 [SMILES: Cn1nc(OC(F)(F)C(F)F)c(C(F)(F)F)c1-n1cc(-c2ccc(Cl)c(C(=O)NC3(C#N)CC3)c2)cn1] | LC-MS (A): t$_R$ = 1.03 min, m/z = 550 [M + 1] | |
| 12 | 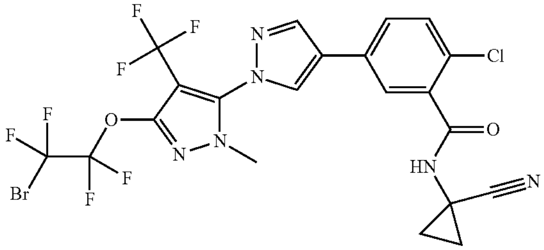 [SMILES: Cn1nc(OC(F)(F)C(F)(F)Br)c(C(F)(F)F)c1-n1cc(-c2ccc(Cl)c(C(=O)NC3(C#N)CC3)c2)cn1] | LC-MS (A): t$_R$ = 1.13 min, m/z = 629, 631 [M + 1] | |

TABLE 1-continued

Examples of compounds of formula (I)

| Ex. No. | Structure | (NMR (400 MHz, CDCl₃) δ ppm), LC MS (method) | mp (° C.) |
|---|---|---|---|
| 13 | 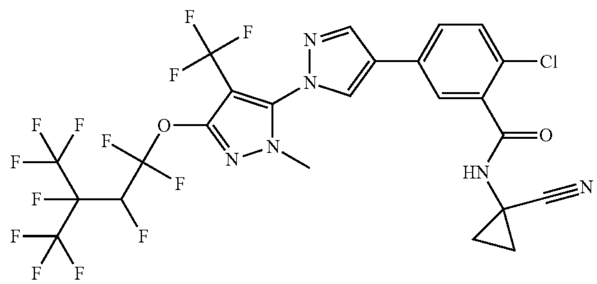 [SMILES: Cn1nc(OC(F)(F)C(F)C(F)(C(F)(F)F)C(F)(F)F)c(C(F)(F)F)c1-n1cc(-c2ccc(Cl)c(C(=O)NC3(C#N)CC3)c2)cn1] | LC-MS (A): $t_R$ = 1.19 min, m/z = 701 [M + 1] | |
| 14 | 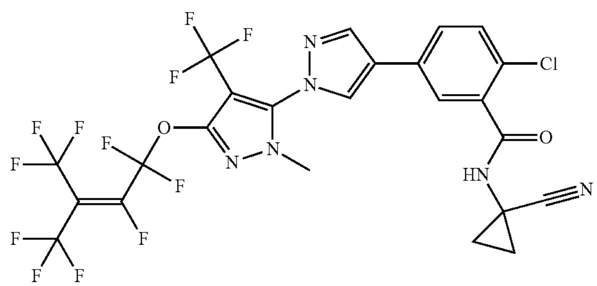 [SMILES: Cn1nc(OC(F)(F)C(F)=C(C(F)(F)F)C(F)(F)F)c(C(F)(F)F)c1-n1cc(-c2ccc(Cl)c(C(=O)NC3(C#N)CC3)c2)cn1] | LC-MS (A): $t_R$ = 1.17 min, m/z = 681 [M + 1] | |
| 15 | 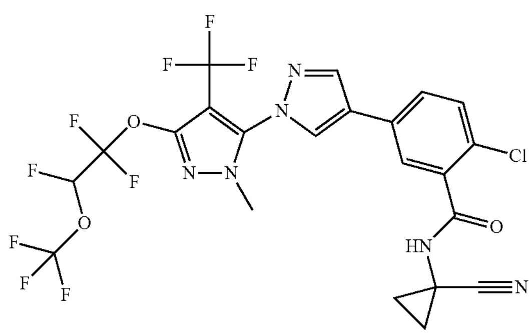 [SMILES: Cn1nc(OC(F)(F)C(F)OC(F)(F)F)c(C(F)(F)F)c1-n1cc(-c2ccc(Cl)c(C(=O)NC3(C#N)CC3)c2)cn1] | LC-MS (A): $t_R$ = 1.10 min, m/z = 616 733 [M + 1] | |
| 16 | 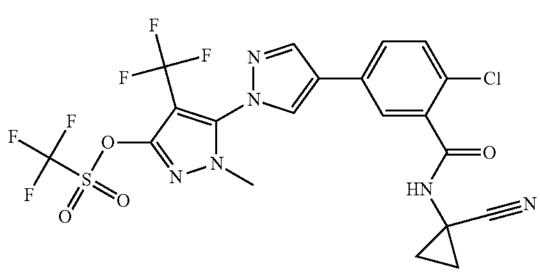 [SMILES: Cn1nc(OS(=O)(=O)C(F)(F)F)c(C(F)(F)F)c1-n1cc(-c2ccc(Cl)c(C(=O)NC3(C#N)CC3)c2)cn1] | LC-MS (A): $t_R$ = 1.09 min, m/z = 583 [M + 1] | |
| 17 | 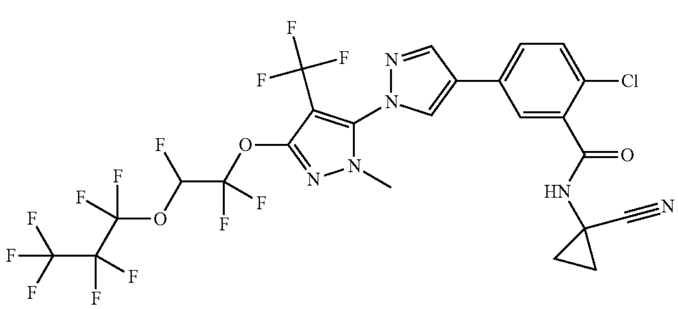 [SMILES: Cn1nc(OC(F)(F)C(F)OC(F)(F)C(F)(F)C(F)(F)F)c(C(F)(F)F)c1-n1cc(-c2ccc(Cl)c(C(=O)NC3(C#N)CC3)c2)cn1] | LC-MS (A): $t_R$ = 1.18 min, m/z = 717 [M + 1] | |

TABLE 1-continued

Examples of compounds of formula (I)

| Ex. No. | Structure | (NMR (400 MHz, CDCl₃) δ ppm), LC MS (method) | mp (° C.) |
|---|---|---|---|
| 18 | 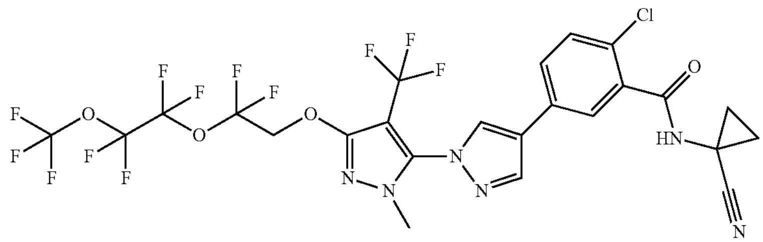 [SMILES: Cn1nc(OCC(F)(F)OC(F)(F)C(F)(F)OC(F)(F)F)c(C(F)(F)F)c1-n1cc(-c2ccc(Cl)c(C(=O)NC3(C#N)CC3)c2)cn1] | LC-MS (D): $t_R$ = 2.01 min, m/z = 715 [M + 1] | |
| 19 | 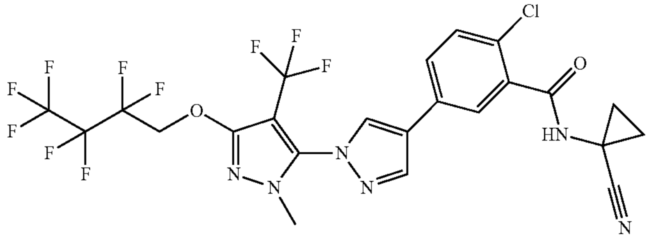 [SMILES: Cn1nc(OCC(F)(F)C(F)(F)C(F)(F)F)c(C(F)(F)F)c1-n1cc(-c2ccc(Cl)c(C(=O)NC3(C#N)CC3)c2)cn1] | LC-MS (D): $t_R$ = 1.88 min, m/z = 633 [M + 1] | |
| 20 | 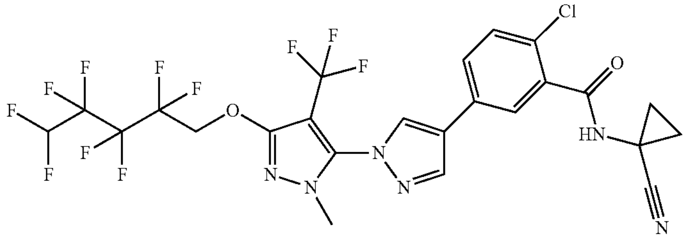 [SMILES: Cn1nc(OCC(F)(F)C(F)(F)C(F)(F)C(F)F)c(C(F)(F)F)c1-n1cc(-c2ccc(Cl)c(C(=O)NC3(C#N)CC3)c2)cn1] | LC-MS (D): $t_R$ = 1.82 min, m/z = 665 [M + 1] | |
| 21 | 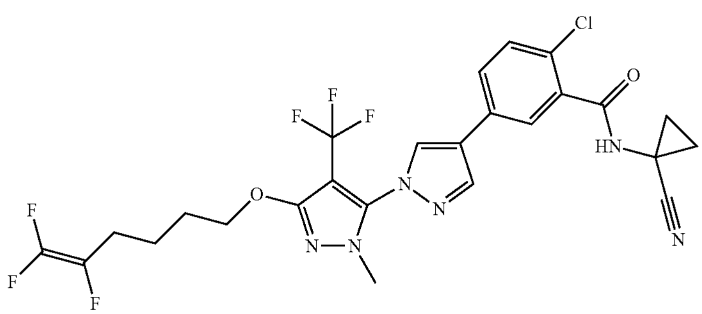 [SMILES: Cn1nc(OCCCCC(F)=C(F)F)c(C(F)(F)F)c1-n1cc(-c2ccc(Cl)c(C(=O)NC3(C#N)CC3)c2)cn1] | LC-MS (D): $t_R$ = 1.86 min, m/z = 587 [M + 1] | |
| 22 | 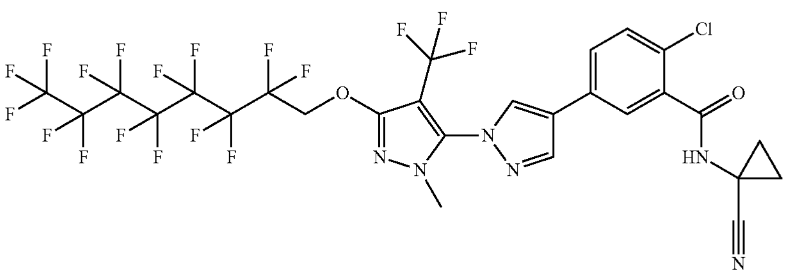 [SMILES: Cn1nc(OCC(F)(F)C(F)(F)C(F)(F)C(F)(F)C(F)(F)C(F)(F)C(F)(F)F)c(C(F)(F)F)c1-n1cc(-c2ccc(Cl)c(C(=O)NC3(C#N)CC3)c2)cn1] | LC-MS (D): $t_R$ = 2.23 min, m/z = 833 [M + 1] | |

TABLE 1-continued

Examples of compounds of formula (I)

| Ex. No. | Structure | (NMR (400 MHz, CDCl₃) δ ppm), LC MS (method) | mp (° C.) |
|---|---|---|---|
| 23 | 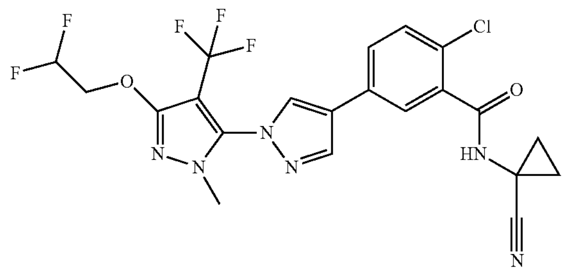 [SMILES: Cn1nc(OCC(F)F)c(C(F)(F)F)c1-n1cc(-c2ccc(Cl)c(C(=O)NC3(C#N)CC3)c2)cn1] | LC-MS (D): $t_R$ = 1.55 min, m/z = 515 [M + 1] | |
| 24 | 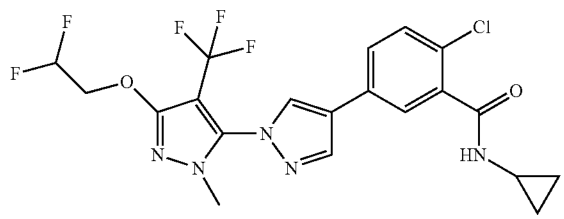 [SMILES: Cn1nc(OCC(F)F)c(C(F)(F)F)c1-n1cc(-c2ccc(Cl)c(C(=O)NC3CC3)c2)cn1] | LC-MS (D): $t_R$ = 1.57 min, m/z = 490 [M + 1] | |
| 25 | 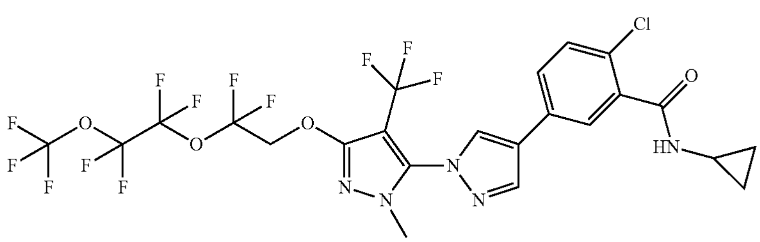 [SMILES: Cn1nc(OCC(F)(F)OC(F)(F)C(F)(F)OC(F)(F)F)c(C(F)(F)F)c1-n1cc(-c2ccc(Cl)c(C(=O)NC3CC3)c2)cn1] | LC-MS (D): $t_R$ = 2.04 min, m/z = 690 [M + 1] | |
| 26 | 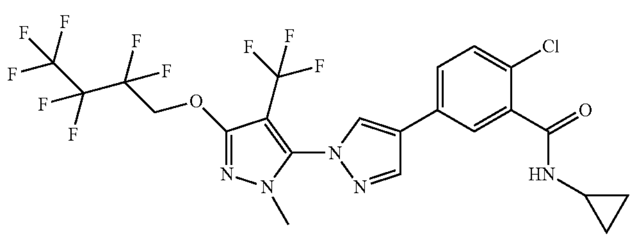 [SMILES: Cn1nc(OCC(F)(F)C(F)(F)C(F)(F)F)c(C(F)(F)F)c1-n1cc(-c2ccc(Cl)c(C(=O)NC3CC3)c2)cn1] | LC-MS (D): $t_R$ = 1.91 min, m/z = 608 [M + 1] | |
| 27 | 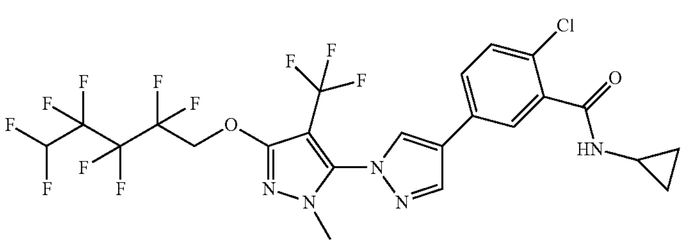 [SMILES: Cn1nc(OCC(F)(F)C(F)(F)C(F)(F)C(F)F)c(C(F)(F)F)c1-n1cc(-c2ccc(Cl)c(C(=O)NC3CC3)c2)cn1] | LC-MS (D): $t_R$ = 1.84 min, m/z = 640 [M + 1] | |
| 28 | 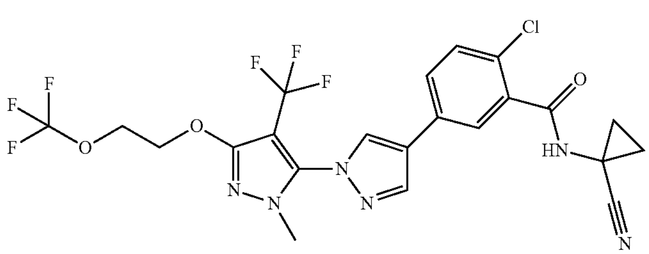 [SMILES: Cn1nc(OCCOC(F)(F)F)c(C(F)(F)F)c1-n1cc(-c2ccc(Cl)c(C(=O)NC3(C#N)CC3)c2)cn1] | LC-MS (D): $t_R$ = 1.68 min, m/z = 563 [M + 1] | |

TABLE 1-continued

Examples of compounds of formula (I)

| Ex. No. | Structure | (NMR (400 MHz, CDCl₃) δ ppm), LC MS (method) | mp (° C.) |
|---|---|---|---|
| 29 | 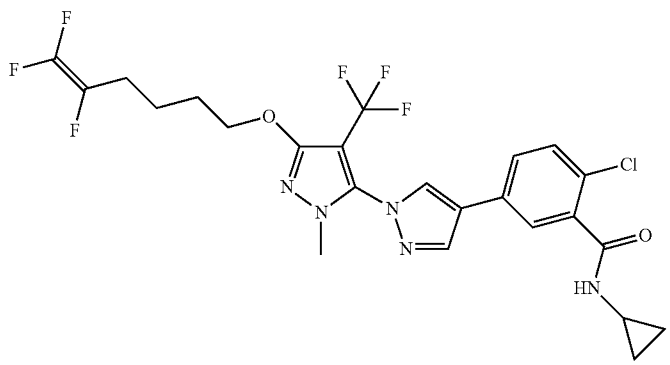 [SMILES: Cn1nc(OCCCCC(F)=C(F)F)c(C(F)(F)F)c1-n1cc(-c2ccc(Cl)c(C(=O)NC3CC3)c2)cn1] | LC-MS (D): $t_R$ = 1.89 min, m/z = 562 [M + 1] | |
| 30 | 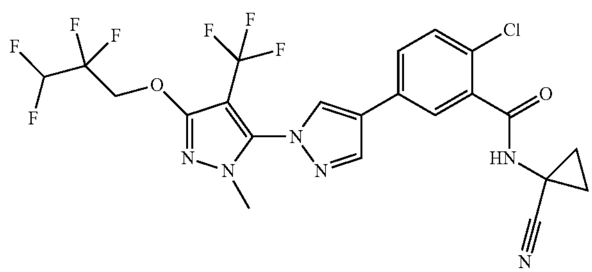 [SMILES: Cn1nc(OCC(F)(F)C(F)F)c(C(F)(F)F)c1-n1cc(-c2ccc(Cl)c(C(=O)NC3(C#N)CC3)c2)cn1] | LC-MS (D): $t_R$ = 1.66 min, m/z = 565 [M + 1] | |
| 31 | 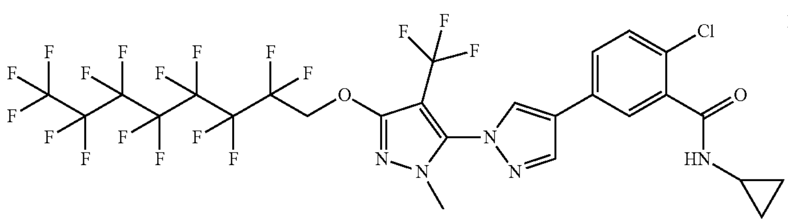 | LC-MS (D): $t_R$ = 2.25 min, m/z = 808 [M + 1] | |
| 32 | 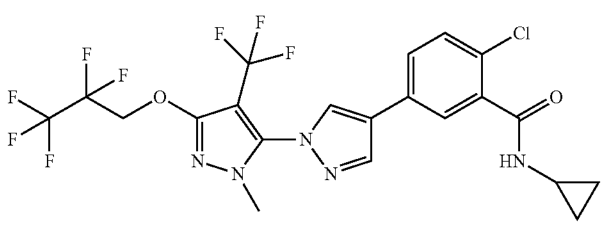 [SMILES: Cn1nc(OCC(F)(F)C(F)(F)F)c(C(F)(F)F)c1-n1cc(-c2ccc(Cl)c(C(=O)NC3CC3)c2)cn1] | LC-MS (D): $t_R$ = 1.81 min, m/z = 558 [M + 1] | |
| 33 | 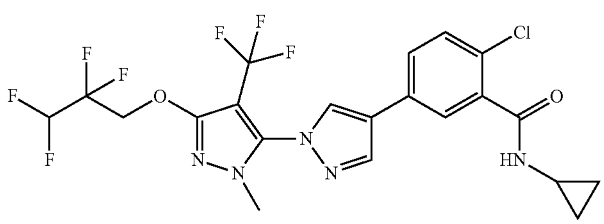 [SMILES: Cn1nc(OCC(F)(F)C(F)F)c(C(F)(F)F)c1-n1cc(-c2ccc(Cl)c(C(=O)NC3CC3)c2)cn1] | LC-MS (D): $t_R$ = 1.68 min, m/z = 540 [M + 1] | |
| 34 | 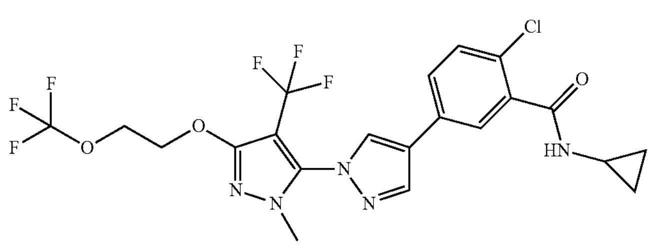 [SMILES: Cn1nc(OCCOC(F)(F)F)c(C(F)(F)F)c1-n1cc(-c2ccc(Cl)c(C(=O)NC3CC3)c2)cn1] | LC-MS (D): $t_R$ = 1.71 min, m/z = 538 [M + 1] | |

TABLE 1-continued

Examples of compounds of formula (I)

| Ex. No. | Structure | (NMR (400 MHz, CDCl$_3$) δ ppm), LC MS (method) | mp (° C.) |
|---|---|---|---|
| 35 | 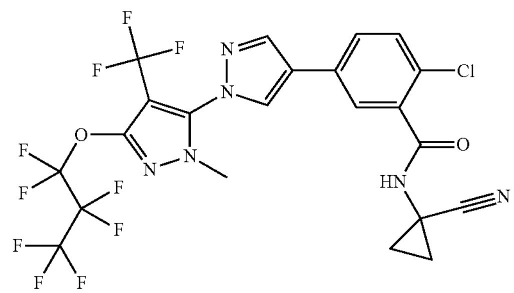 [SMILES: Cn1nc(OC(F)(F)C(F)(F)C(F)(F)F)c(C(F)(F)F)c1-n1cc(-c2ccc(Cl)c(C(=O)NC3(C#N)CC3)c2)cn1] | LC-MS (A): t$_R$ = 1.15 min, m/z = 619 [M + 1] | |
| 36 | 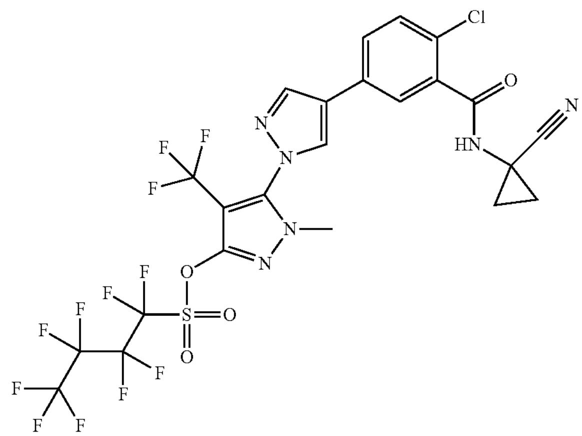 [SMILES: Cn1nc(OS(=O)(=O)C(F)(F)C(F)(F)C(F)(F)C(F)(F)F)c(C(F)(F)F)c1-n1cc(-c2ccc(Cl)c(C(=O)NC3(C#N)CC3)c2)cn1] | LC-MS (A): t$_R$ = 1.25 min, m/z = 733 [M + 1] | |
| 37 | 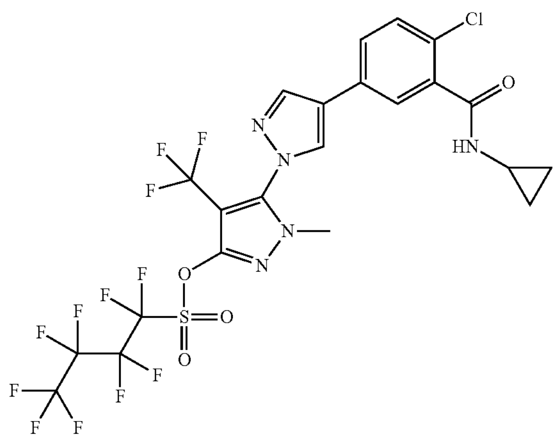 [SMILES: Cn1nc(OS(=O)(=O)C(F)(F)C(F)(F)C(F)(F)C(F)(F)F)c(C(F)(F)F)c1-n1cc(-c2ccc(Cl)c(C(=O)NC3CC3)c2)cn1] | LC-MS (A): t$_R$ = 1.26 min, m/z = 708 [M + 1] | |
| 38 | 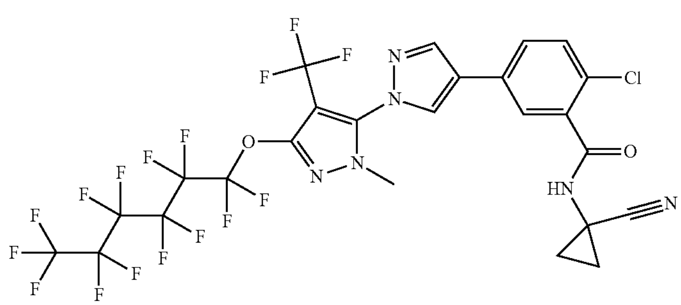 [SMILES: Cn1nc(OC(F)(F)C(F)(F)C(F)(F)C(F)(F)C(F)(F)C(F)(F)F)c(C(F)(F)F)c1-n1cc(-c2ccc(Cl)c(C(=O)NC3(C#N)CC3)c2)cn1] | LC-MS (A): t$_R$ = 1.28 min, m/z = 769 [M + 1] | |

TABLE 1-continued

Examples of compounds of formula (I)

| Ex. No. | Structure | (NMR (400 MHz, CDCl$_3$) δ ppm), LC MS (method) | mp (° C.) |
|---|---|---|---|
| 39 | 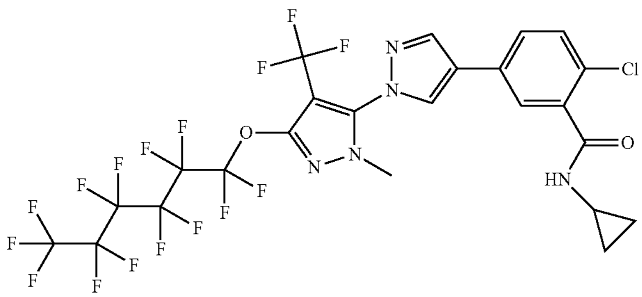 [SMILES: Cn1nc(OC(F)(F)C(F)(F)C(F)(F)C(F)(F)C(F)(F)C(F)(F)F)c(C(F)(F)F)c1-n1cc(-c2ccc(Cl)c(C(=O)NC3CC3)c2)cn1] | LC-MS (A): t$_R$ = 1.30 min, m/z = 744 [M + 1] | |
| 40 | 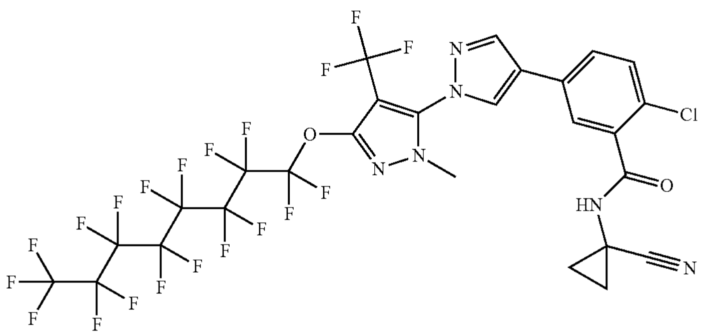 [SMILES: Cn1nc(OC(F)(F)C(F)(F)C(F)(F)C(F)(F)C(F)(F)C(F)(F)C(F)(F)C(F)(F)F)c(C(F)(F)F)c1-n1cc(-c2ccc(Cl)c(C(=O)NC3(C#N)CC3)c2)cn1] | LC-MS (A): t$_R$ = 1.23 min, m/z = 869 [M + 1] | |
| 41 | 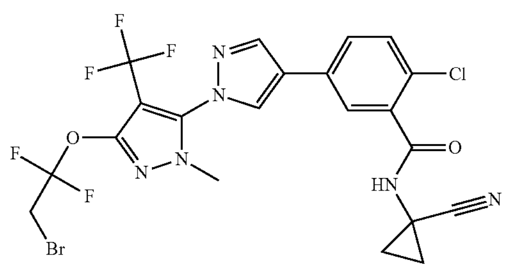 [SMILES: Cn1nc(OC(F)(F)CBr)c(C(F)(F)F)c1-n1cc(-c2ccc(Cl)c(C(=O)NC3(C#N)CC3)c2)cn1] | LC-MS (A): t$_R$ = 1.04 min, m/z = 593, 595 [M + 1] | |
| 42 | 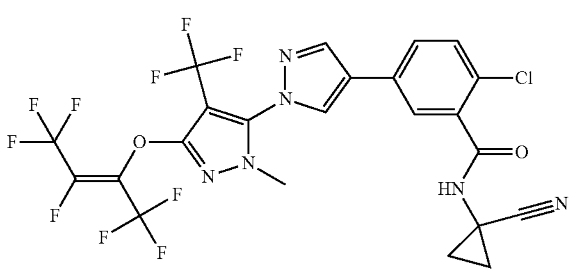 [SMILES: Cn1nc(O/C(=C(/F)C(F)(F)F)C(F)(F)F)c(C(F)(F)F)c1-n1cc(-c2ccc(Cl)c(C(=O)NC3(C#N)CC3)c2)cn1] | LC-MS (A): t$_R$ = 1.17 min, m/z = 631 [M + 1] | |
| 43 | 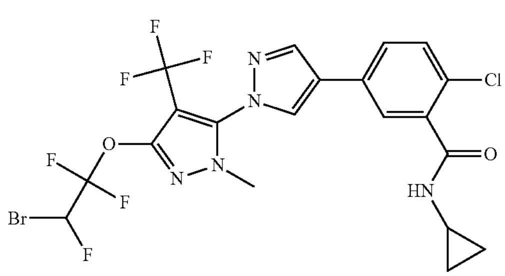 [SMILES: Cn1nc(OC(F)(F)C(F)Br)c(C(F)(F)F)c1-n1cc(-c2ccc(Cl)c(C(=O)NC3CC3)c2)cn1] | LC-MS (A): t$_R$ = 1.07 min, m/z = 586, 588 [M + 1] | |

TABLE 1-continued

Examples of compounds of formula (I)

| Ex. No. | Structure | (NMR (400 MHz, CDCl₃) δ ppm), LC MS (method) | mp (° C.) |
|---|---|---|---|
| 44 | 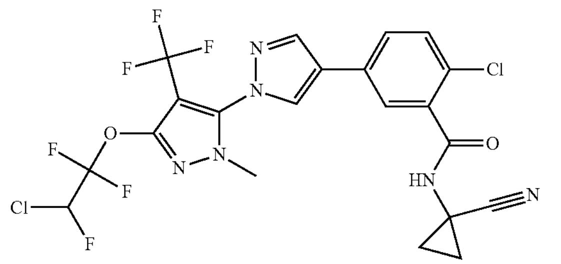 [SMILES: Cn1nc(OC(F)(F)C(F)Cl)c(C(F)(F)F)c1-n1cc(-c2ccc(Cl)c(C(=O)NC3(C#N)CC3)c2)cn1] | LC-MS (A): $t_R$ = 1.06 min, m/z = 567. 569 [M + 1] | |
| 45 | 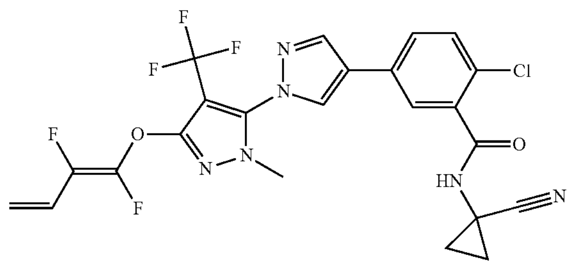 [SMILES: C=C/C(F)=C(\F)Oc1nn(C)c(-n2cc(-c3ccc(Cl)c(C(=O)NC4(C#N)CC4)c3)cn2)c1C(F)(F)F] | LC-MS (A): $t_R$ = 1.10 and 1.11 min, m/z = 539 [M + 1] (E/Z mixture) | |
| 46 | 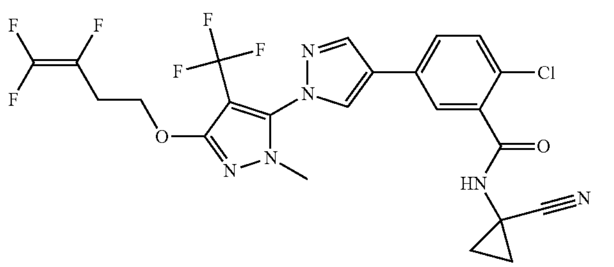 [SMILES: Cn1nc(OCCC(F)=C(F)F)c(C(F)(F)F)c1-n1cc(-c2ccc(Cl)c(C(=O)NC3(C#N)CC3)c2)cn1] | LC-MS (A): $t_R$ = 1.07 min, m/z = 559 [M + 1] | |
| 47 | 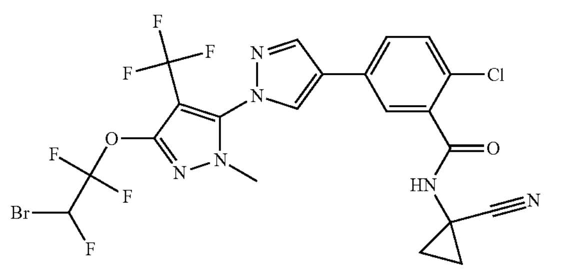 | LC-MS (A): $t_R$ = 1.06 min, m/z = 611, 613 [M + 1] | |
| 48 | 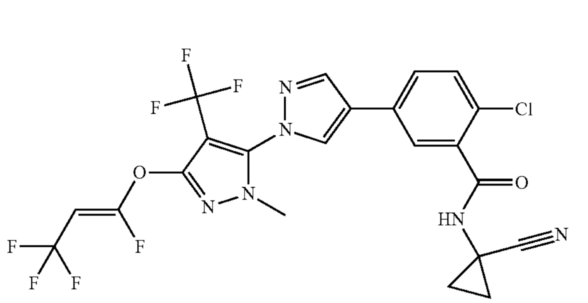 [SMILES: Cn1nc(O/C(F)=C/C(F)(F)F)c(C(F)(F)F)c1-n1cc(-c2ccc(Cl)c(C(=O)NC3(C#N)CC3)c2)cn1] | LC-MS (A): $t_R$ = 1.08 min, m/z = 563 [M + 1] | |

TABLE 1-continued

Examples of compounds of formula (I)

| Ex. No. | Structure | (NMR (400 MHz, CDCl₃) δ ppm), LC MS (method) | mp (° C.) |
|---|---|---|---|
| 49 | 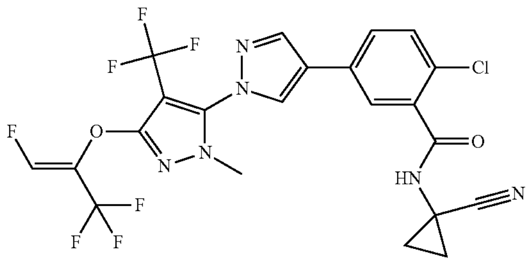 [SMILES: Cn1nc(O/C(=C\F)C(F)(F)F)c(C(F)(F)F)c1-n1cc(-c2ccc(Cl)c(C(=O)NC3(C#N)CC3)c2)cn1] | LC-MS (A): $t_R$ = 1.10 min, m/z = 563 [M + 1] | |
| 50 | 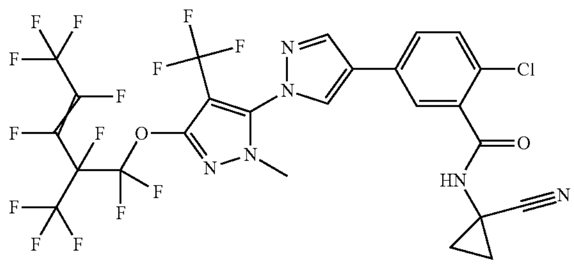 [SMILES: Cn1nc(OC(F)(F)C(F)(C(F)=C(F)C(F)(F)F)C(F)(F)F)c(C(F)(F)F)c1-n1cc(-c2ccc(Cl)c(C(=O)NC3(C#N)CC3)c2)cn1] | LC-MS (A): $t_R$ = 1.24 min, m/z = 731 [M + 1] | |
| 51 | 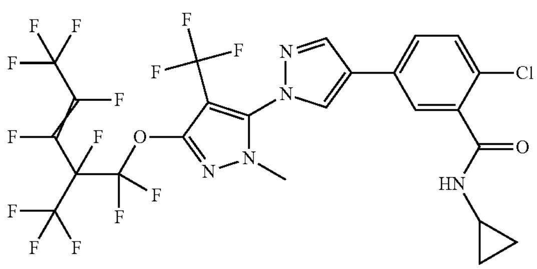 [SMILES: Cn1nc(OC(F)(F)C(F)(C(F)=C(F)C(F)(F)F)C(F)(F)F)c(C(F)(F)F)c1-n1cc(-c2ccc(Cl)c(C(=O)NC3CC3)c2)cn1] | LC-MS (A): $t_R$ = 1.25 min, m/z = 706 [M + 1] | |
| 52 | 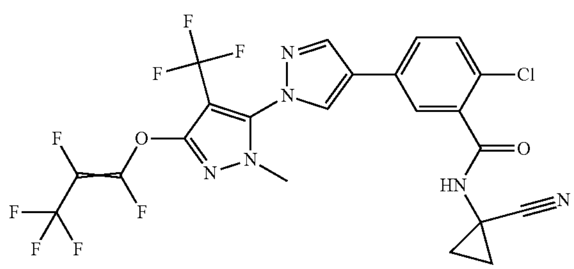 [SMILES: Cn1nc(OC(F)=C(F)C(F)(F)F)c(C(F)(F)F)c1-n1cc(-c2ccc(Cl)c(C(=O)NC3(C#N)CC3)c2)cn1] | LC-MS (A): $t_R$ = 1.15 min, m/z = 581 [M + 1] | |
| 53 | 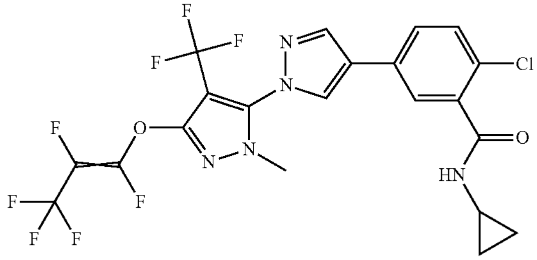 [SMILES: Cn1nc(OC(F)=C(F)C(F)(F)F)c(C(F)(F)F)c1-n1cc(-c2ccc(Cl)c(C(=O)NC3CC3)c2)cn1] | LC-MS (A): $t_R$ = 1.16 min, m/z = 556 [M + 1] | |

TABLE 1-continued

Examples of compounds of formula (I)

| Ex. No. | Structure | (NMR (400 MHz, CDCl₃) δ ppm), LC MS (method) | mp (° C.) |
|---|---|---|---|
| 54 | 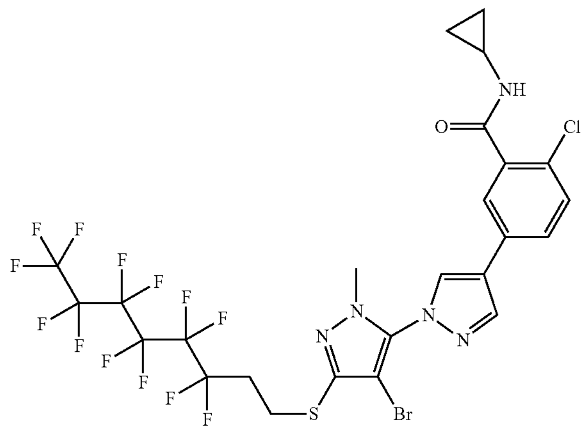 [SMILES: Cn1nc(SCCC(F)(F)C(F)(F)C(F)(F)C(F)(F)C(F)(F)C(F)(F)F)c(Br)c1-n1cc(-c2ccc(Cl)c(C(=O)NC3CC3)c2)cn1] | 0.65-0.72 (m, 2 H) 0.87-0.96 (m, 2 H) 2.51-2.69 (m, 2 H) 2.96 (tq, 1 H) 3.17-3.26 (m, 2 H) 3.88 (s, 3 H) 6.44 (br s, 1 H) 7.40-7.46 (m, 1 H) 7.52 (dd, 1 H) 7.87 (d, 1 H) 8.04 (s, 1 H) 8.09 (s, 1 H) LC-MS (A): $t_R$ = 1.33 min, m/z = 798 [M + 1] | |
| 55 | 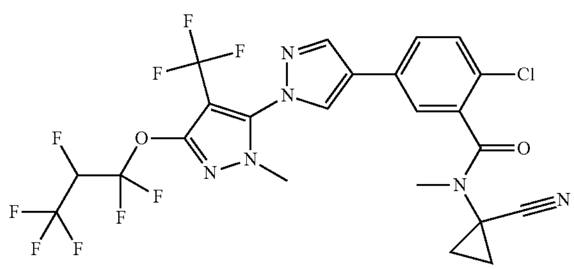 [SMILES: CN(C(=O)c1cc(-c2cnn(-c3c(C(F)(F)F)c(OC(F)(F)C(F)C(F)(F)F)nn3C)c2)ccc1Cl)C1(C#N)CC1] | LC-MS (A): $t_R$ = 1.02 min, m/z = 616 [M + 1] | |
| 56 | 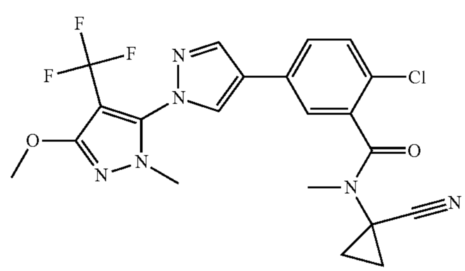 [SMILES: COc1nn(C)c(-n2cc(-c3ccc(Cl)c(C(=O)N(C)C4(C#N)CC4)c3)cn2)c1C(F)(F)F] | LC-MS (A): $t_R$ = 1.02 min, m/z = 479 [M + 1] | |
| 57 | 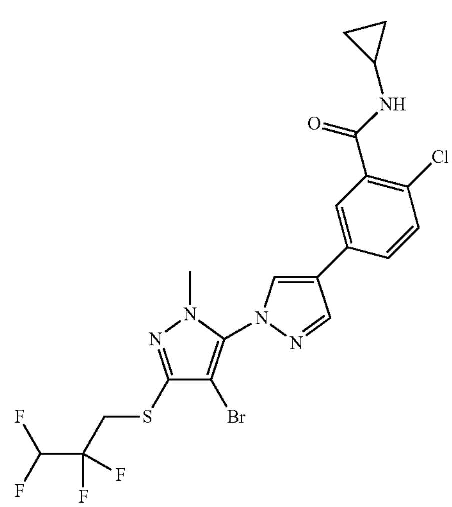 [SMILES: Cn1nc(SCC(F)(F)C(F)F)c(Br)c1-n1cc(-c2ccc(Cl)c(C(=O)NC3CC3)c2)cn1] | 0.62-0.73 (m, 2 H) 0.89-0.98 (m, 2 H) 2.96 (tq, 1 H) 3.59 (t, 2 H) 3.89 (s, 3 H) 6.04 (tt, 1 H) 6.41 (br s, 1 H) 7.43 (d, 1 H) 7.53 (dd, 1 H) 7.88 (d, 1 H) 8.04 (s, 1 H) 8.09 (s, 1 H) LC-MS (A): $t_R$ = 1.05 min, m/z = 566 [M + 1] | |

TABLE 1-continued

Examples of compounds of formula (I)

| Ex. No. | Structure | (NMR (400 MHz, CDCl₃) δ ppm), LC MS (method) | mp (° C.) |
|---|---|---|---|
| 58 | 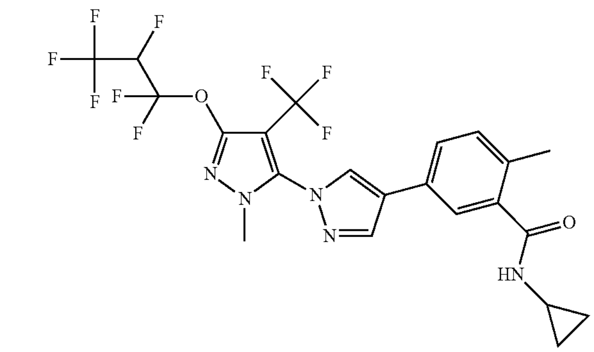 | LC-MS (A): $t_R$ = 1.09 min, m/z = 556 [M + 1] | 140-2 |
| 59 | 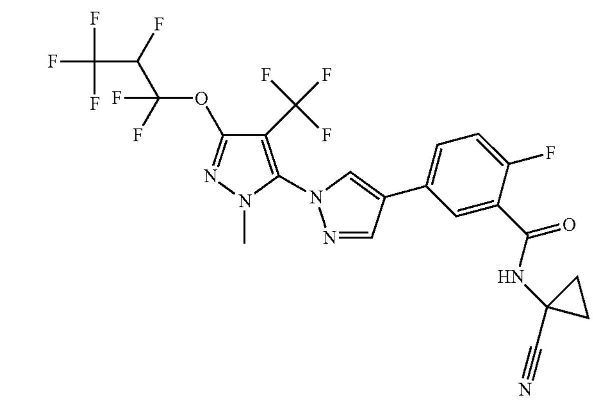 [SMILES: Cn1nc(OC(F)(F)C(F)C(F)(F)F)c(C(F)(F)F)c1-n1cc(-c2ccc(F)c(C(=O)NC3(C#N)CC3)c2)cn1] | LC-MS (A): $t_R$ = 1.08 min, m/z = 585 [M + 1] | 87-90 |
| 60 | 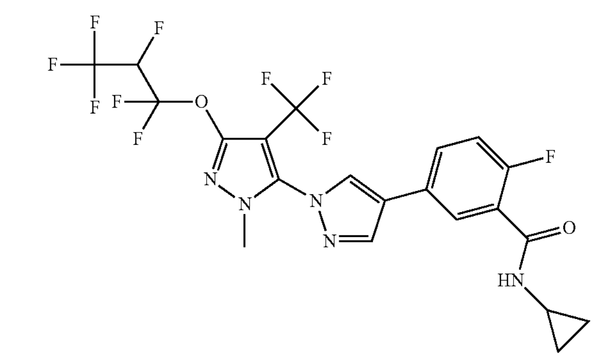 | LC-MS (A): $t_R$ = 1.09 min, m/z = 560 [M + 1] | |
| 61 | 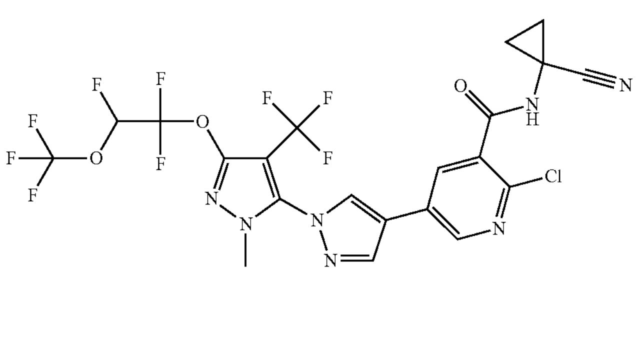 [SMILES: Cn1nc(OC(F)(F)C(F)OC(F)(F)F)c(C(F)(F)F)c1-n1cc(-c2cnc(Cl)c(C(=O)NC3(C#N)CC3)c2)cn1] | LC-MS (A): $t_R$ = 1.08 min, m/z = 618 [M + 1] | |

TABLE 1-continued

Examples of compounds of formula (I)

| Ex. No. | Structure | (NMR (400 MHz, CDCl₃) δ ppm), LC MS (method) | mp (° C.) |
|---|---|---|---|
| 62 | 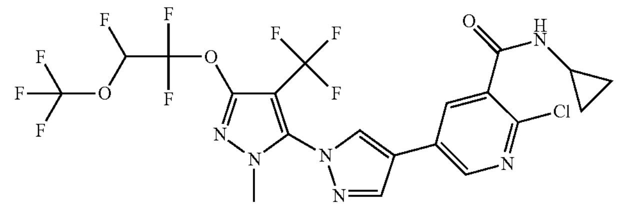 [SMILES: Cn1nc(OC(F)(F)C(F)OC(F)(F)F)c(C(F)(F)F)c1-n1cc(-c2cnc(Cl)c(C(=O)NC3CC3)c2)cn1] | LC-MS (A): t$_R$ = 1.08 min, m/z = 593 [M + 1] | |
| 63 | 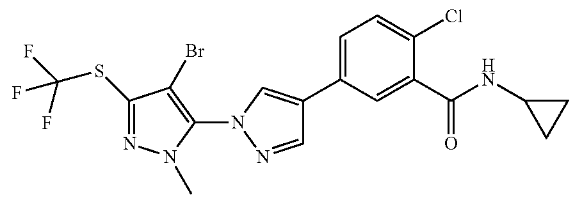 [SMILES: Cn1nc(SC(F)(F)F)c(Br)c1-n1cc(-c2ccc(Cl)c(C(=O)NC3CC3)c2)cn1] | 0.65-0.72 (m, 2 H) 0.91-0.95 (m, 2 H) 2.97 (tq, 1 H) 3.98 (s, 3 H) 6.42 (br s, 1 H) 7.44 (d, 1H) 7.54 (dd, 1 H) 7.89 (d, 1 H) 8.08 (s, 1 H) 8.12 (s, 1 H) LC-MS (A): t$_R$ = 1.09 min, m/z = 520 [M + 1] | |
| 64 | 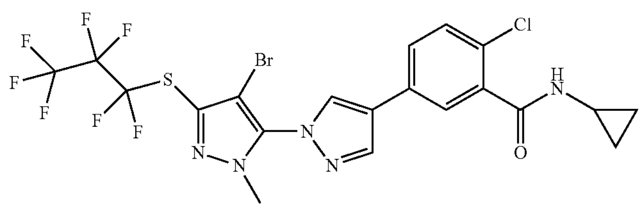 [SMILES: Cn1nc(SC(F)(F)C(F)(F)C(F)(F)F)c(Br)c1-n1cc(-c2ccc(Cl)c(C(=O)NC3CC3)c2)cn1] | 0.60-0.77 (m, 2 H) 0.93 (q, 2 H) 2.97 (tq, 1 H) 3.99 (s, 3 H) 6.41 (br s, 1 H) 7.45 (d, 1 H) 7.54 (dd, 1 H) 7.90 (d, 1 H) 8.08 (s, 1 H) 8.12 (s, 1 H) LC-MS (A): t$_R$ = 1.19 min, m/z = 620 [M + 1] | |
| 65 | 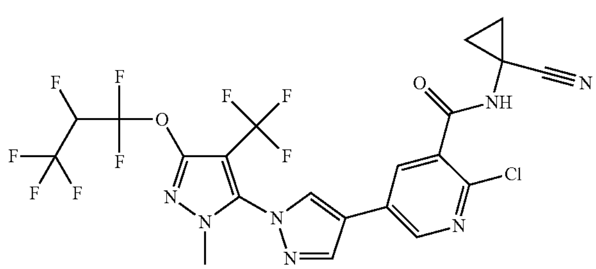 [SMILES: Cn1nc(OC(F)(F)C(F)C(F)(F)F)c(C(F)(F)F)c1-n1cc(-c2cnc(Cl)c(C(=O)NC3(C#N)CC3)c2)cn1] | LC-MS (A): t$_R$ = 1.06 min, m/z = 602 [M + 1] | |
| 66 | 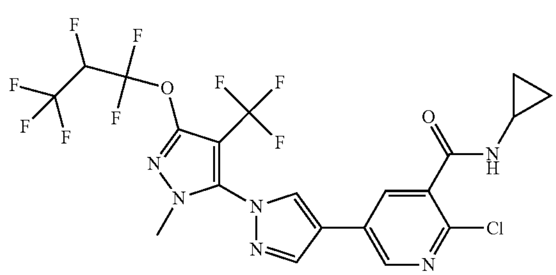 [SMILES: Cn1nc(OC(F)(F)C(F)C(F)(F)F)c(C(F)(F)F)c1-n1cc(-c2cnc(Cl)c(C(=O)NC3CC3)c2)cn1] | LC-MS (A): t$_R$ = 1.06 min, m/z = 577 [M + 1] | |
| 67 | 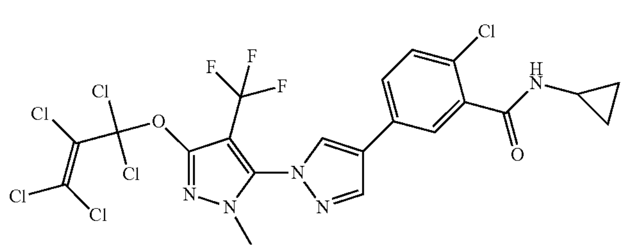 [SMILES: Cn1nc(OC(Cl)(Cl)C(Cl)=C(Cl)Cl)c(C(F)(F)F)c1-n1cc(-c2ccc(Cl)c(C(=O)NC3CC3)c2)cn1] | 0.65-0.71 (m, 2 H) 0.88-0.95 (m, 2 H) 2.96 (tq, 1 H) 3.80 (s, 3 H) 6.43 (br s, 1 H) 7.43 (d, 1 H) 7.51 (dd, 1 H) 7.86 (d, 1 H) 7.94 (s, 1 H) 8.09-8.14 (s, 1 H) LC-MS (A): t$_R$ = 1.25 min, m/z = 636 [M + 1] | |

TABLE 1-continued
Examples of compounds of formula (I)
| Ex. No. | Structure | (NMR (400 MHz, CDCl₃) δ ppm), LC MS (method) | mp (° C.) |
|---|---|---|---|
| 68 | 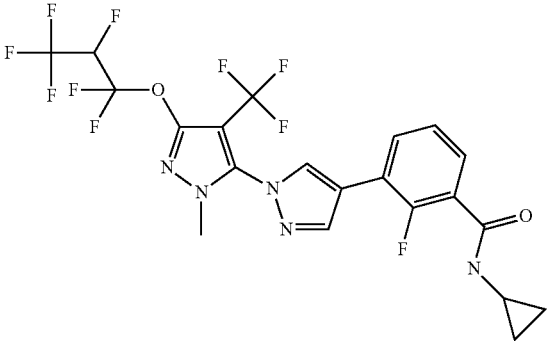 [SMILES: Cn1nc(OC(F)(F)C(F)C(F)(F)F)c(C(F)(F)F)c1-n1cc(-c2cccc(C(=O)NC3CC3)c2F)cn1] | LC-MS (A): $t_R$ = 1.09 min, m/z = 560 [M + 1] | |
| 69 | 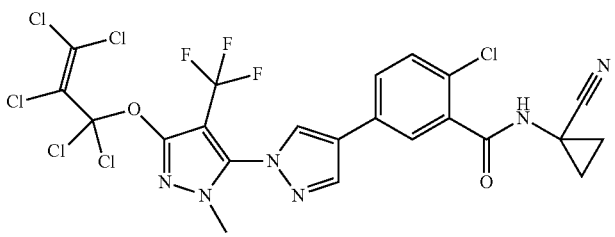 [SMILES: Cn1nc(OC(Cl)(Cl)C(Cl)=C(Cl)Cl)c(C(F)(F)F)c1-n1cc(-c2ccc(Cl)c(C(=O)NC3(C#N)CC3)c2)cn1] | 1.41-1.46 (m, 2 H) 1.68-1.73 (m, 2 H) 3.81 (s, 3 H) 6.93 (s, 1 H) 7.46 (d, 1 H) 7.57 (dd, 1 H) 7.95 (d, 1 H) 7.97 (s, 1 H) 8.14 (s, 1 H) LC-MS (A): $t_R$ = 1.24 min, m/z = 661 [M + 1] | |
| 70 | 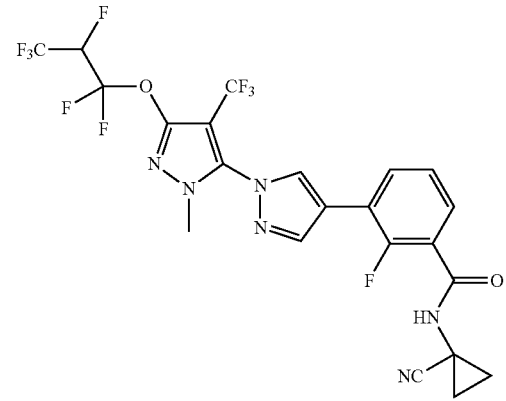 [SMILES: Cn1nc(OC(F)(F)C(F)C(F)(F)F)c(C(F)(F)F)c1-n1cc(-c2cccc(C(=O)NC3(C#N)CC3)c2F)cn1] | ¹H NMR (400 MHz, CDCl₃) δ 8.19 (s, 1H), 8.10-8.03 (m, 2H), 7.80-7.73 (m, 1H), 7.37 (t, J = 7.8 Hz, 1H), 7.19 (d, J = 12.7 Hz, 1H), 5.28-5.05 (m, 1H), 3.80 (s, 3H), 1.73-1.65 (m, 2H), 1.43-1.37 (m, 2H). | 59-61 |
| 71 | 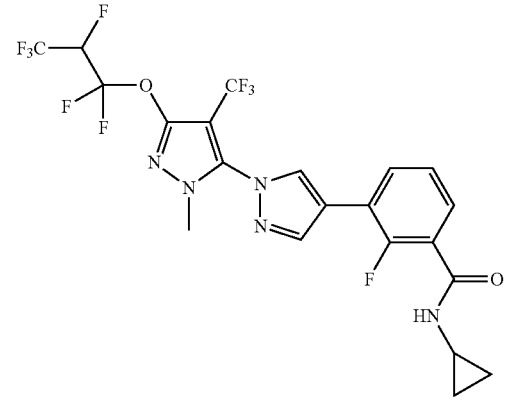 [SMILES: Cn1nc(OC(F)(F)C(F)C(F)(F)F)c(C(F)(F)F)c1-n1cc(-c2cccc(C(=O)NC3CC3)c2F)cn1] | ¹H NMR (400 MHz, CDCl₃) δ 8.17 (s, 1H), 8.04 (s, 1H), 7.99 (t, J = 7.5 Hz, 1H), 7.68 (t, J = 7.3 Hz, 1H), 7.31 (t, J = 7.7 Hz, 1H), 6.76 (d, J = 10.6 Hz, 1H), 5.30-5.02 (m, 1H), 3.78 (s, 3H), 3.00-2.91 (m, 1H), 0.92-0.84 (m, 2H), 0.68-0.61 (m, 2H). | 89-91 |

TABLE 1-continued

Examples of compounds of formula (I)

| Ex. No. | Structure | (NMR (400 MHz, CDCl₃) δ ppm), LC MS (method) | mp (° C.) |
|---|---|---|---|
| 72 | 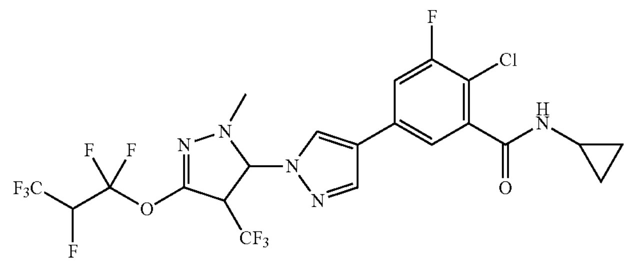 [SMILES: CN1N=C(OC(F)(F)C(F)C(F)(F)F)C(C(F)(F)F)C1n1cc(-c2cc(F)c(Cl)c(C(=O)NC3CC3)c2)cn1] | ¹H NMR (400 MHz, d₆-DMSO) δ 8.90 (s, 1H), 8.67 (d, J = 6.4 Hz, 1H), 8.62 (s, 1H), 7.93 (d, J = 6.4 Hz, 1H), 7.66 (s, 1H), 6.70-6.55 (m, 1H), 3.72 (s, 3H), 2.85-2.82 (m, 1H), 0.73-0.68 (m, 2H), 0.53-0.51 (m, 2H). | 114-116 |
| 73 | 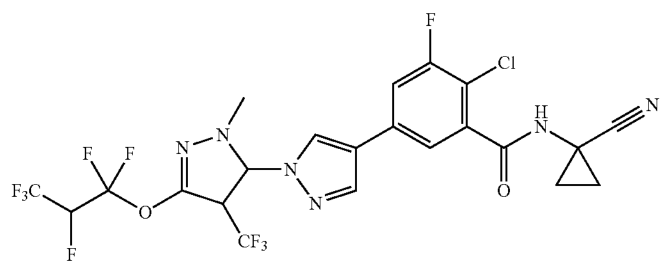 [SMILES: CN1N=C(OC(F)(F)C(F)C(F)(F)F)C(C(F)(F)F)C1n1cc(-c2cc(F)c(Cl)c(C(=O)NC3(C#N)CC3)c2)cn1] | ¹H NMR (400 MHz, d₆-DMSO) δ 9.57 (s, 1H), 8.91 (s, 1H), 8.62 (s, 1H), 7.97 (d, J = 8.0 Hz, 1H), 7.73 (s, 1H), 6.70-6.54 (m, 1H), 3.72 (s, 3H), 1.62-1.58 (m, 2H), 1.29-1.22 (m, 2H). | 82-84 |
| 74 | 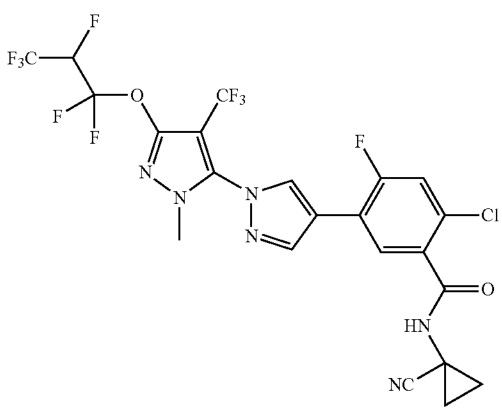 [SMILES: Cn1nc(OC(F)(F)C(F)C(F)(F)F)c(C(F)(F)F)c1-n1cc(-c2cc(C(=O)NC3(C#N)CC3)c(Cl)cc2F)cn1] | ¹H NMR (400 MHz, CDCl₃) δ 8.23 (s, 1H), 8.09-8.11 (m, 2H), 7.28 (s, 1H), 6.98 (s, 1H), 5.37-5.55 (m, 1H), 3.78 (s, 3H), 1.71 (m, 2H), 1.42 (s, 2H). | Gel |
| 75 | 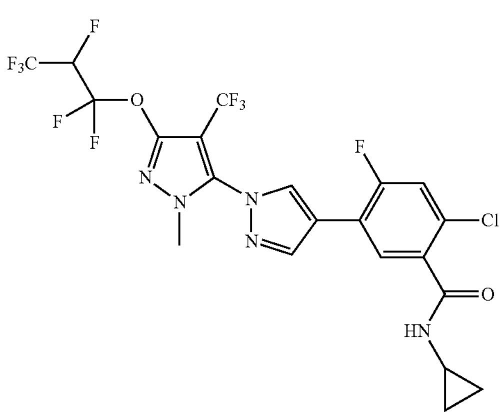 | ¹H NMR (400 MHz, CDCl₃) δ 8.23 (s, 1H), 8.09 (s, 1H), 7.98-8.01 (m, 1H), 7.33-7.15 (m, 1H), 6.55 (s, 1H), 5.78-5.73 (m, 1H), 3.79 (s, 3H), 2.95 (br, 1H), 0.91-0.86 (m, 2H), 0.68 (s, 2H). | 68-70 |

TABLE 1-continued

Examples of compounds of formula (I)

| Ex. No. | Structure | (NMR (400 MHz, CDCl₃) δ ppm), LC MS (method) | mp (° C.) |
|---|---|---|---|
| 76 | 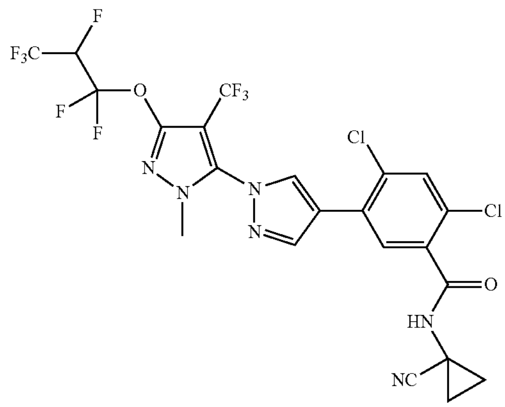 [SMILES: Cn1nc(OC(F)(F)C(F)C(F)(F)F)c(C(F)(F)F)c1-n1cc(-c2cc(C(=O)NC3(C#N)CC3)c(Cl)cc2Cl)cn1] | ¹H NMR (400 MHz, CDCl₃) δ 8.17 (s, 1H), 8.14 (s, 1H), 7.98 (s, 1H), 7.579 (s, 1H), 6.98 (br, 1H), 5.22 (m, 1H), 3.81 (s, 3H), 1.71 (m, 2H), 1.42 (m, 2H). | Gel |
| 77 | 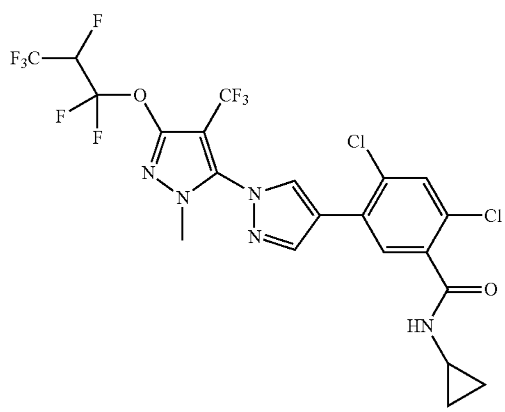 [SMILES: Cn1nc(OC(F)(F)C(F)C(F)(F)F)c(C(F)(F)F)c1-n1cc(-c2cc(C(=O)NC3CC3)c(Cl)cc2Cl)cn1] | ¹H NMR (400 MHz, CDCl₃) δ 8.14 (s, 1H), 8.10 (s, 1H), 7.87 (s, 1H), 7.55 (s, 1H), 6.43 (br, 1H), 5.11 (m, 1H), 3.79 (s, 3H), 2.93 (br, 1H), 0.87 (m, 2H), 0.66 (m, 2H). | Gel |
| 78 | 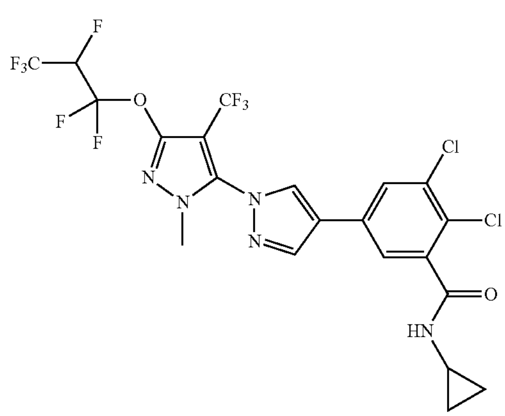 [SMILES: Cn1nc(OC(F)(F)C(F)C(F)(F)F)c(C(F)(F)F)c1-n1cc(-c2cc(Cl)c(Cl)c(C(=O)NC3CC3)c2)cn1] | 1H NMR (301 MHz, CDCl3) δ 8.10 (s, 1H), 7.93 (s, 1H), 7.67 (s, 1H), 7.63 (s, 1H), 6.22 (s, 1H), 5.30-5.01 (m, 1H), 3.78 (s, 3H), 3.03-2.81 (m, 1H), 1.32-1.22 (m, 2H), 0.97-0.89 (m, 2H). | 67-70 |

TABLE 1-continued

Examples of compounds of formula (I)

| Ex. No. | Structure | (NMR (400 MHz, CDCl₃) δ ppm), LC MS (method) | mp (° C.) |
|---|---|---|---|
| 79 | 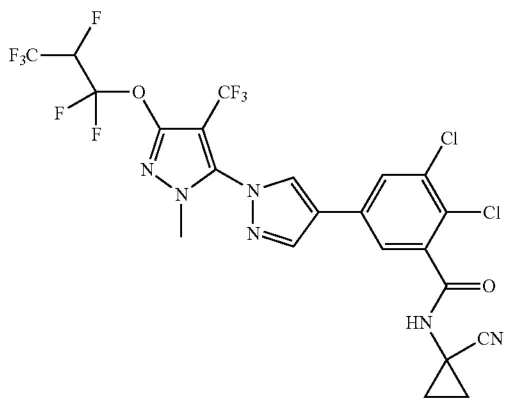 [SMILES: Cn1nc(OC(F)(F)C(F)C(F)(F)F)c(C(F)(F)F)c1-n1cc(-c2cc(Cl)c(Cl)c(C(=O)NC3(C#N)CC3)c2)cn1] | 1H NMR (400 MHz, CDCl3) δ 8.13 (s, 1H), 7.98 (s, 1H), 7.73 (d, J = 1.6 Hz, 1H), 7.70 (d, J = 1.6 Hz, 1H), 6.75 (s, 1H), 5.29-5.03 (m, 1H), 3.79 (s, 3H), 1.71 (dd, J = 8.2, 6.1 Hz, 2H), 1.44 (q, J = 6.0 Hz, 2H). | 162-165 |
| 80 | 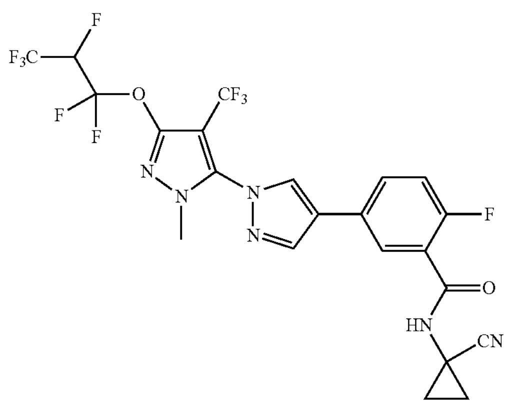 [SMILES: Cn1nc(OC(F)(F)C(F)C(F)(F)F)c(C(F)(F)F)c1-n1cc(-c2ccc(F)c(C(=O)NC3(C#N)CC3)c2)cn1] | $^1$H NMR (301 MHz, CDCl₃) δ 8.32 (d, J = 5.7 Hz, 1H), 8.15 (s, 1H), 7.96 (s, 1H), 7.69 (s, 1H), 7.20 (s, 1H), 5.33-5.07 (m, 2H), 3.81 (s, 3H), 1.73-1.68 (m, 2H), 1.41-1.38 (m, 2H). | Gel |
| 81 | 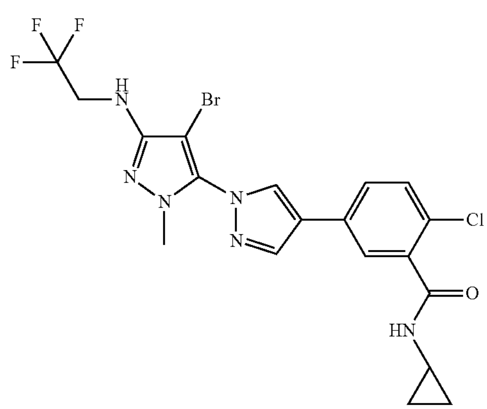 [SMILES: Cn1nc(NCC(F)(F)F)c(Br)c1-n1cc(-c2ccc(Cl)c(C(=O)NC3CC3)c2)cn1] | LC-MS (A): $t_R$ = 0.99 min, m/z = 517 [M + 1] | |

TABLE 1-continued

Examples of compounds of formula (I)

| Ex. No. | Structure | (NMR (400 MHz, CDCl$_3$) δ ppm), LC MS (method) | mp (° C.) |
|---|---|---|---|
| 82 | 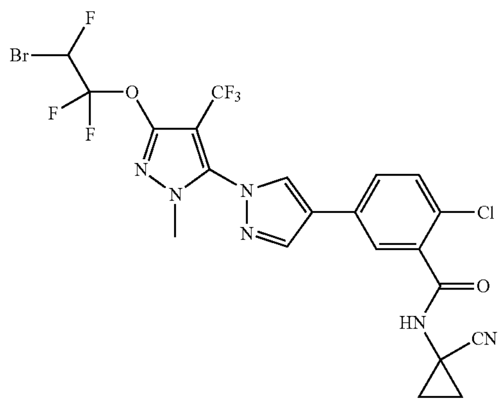 [SMILES: Cn1nc(OC(F)(F)C(F)Br)c(C(F)(F)F)c1-n1cc(-c2ccc(Cl)c(C(=O)NC3(C#N)CC3)c2)cn1] | | |
| 83 | 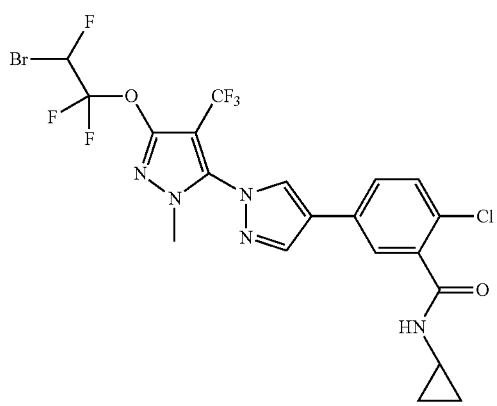 | | |
| 84 | 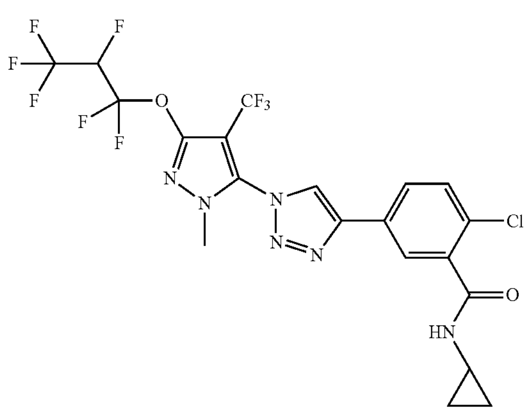 [SMILES: Cn1nc(OC(F)(F)C(F)C(F)(F)F)c(C(F)(F)F)c1-n1cc(-c2ccc(Cl)c(C(=O)NC3CC3)c2)nn1] | | |

TABLE 1-continued

Examples of compounds of formula (I)

| Ex. No. | Structure | (NMR (400 MHz, CDCl₃) δ ppm), LC MS (method) | mp (° C.) |
|---|---|---|---|
| 85 | 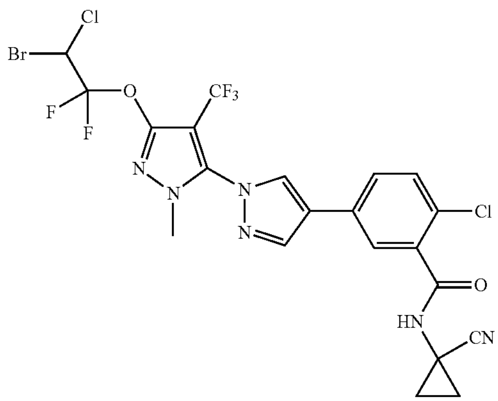 [SMILES: Cn1nc(OC(F)(F)C(Cl)Br)c(C(F)(F)F)c1-n1cc(-c2ccc(Cl)c(C(=O)NC3(C#N)CC3)c2)cn1] | LC-MS (A): $t_R$ = 1.10 min, m/z = 627 [M + 1] | |
| 86 | 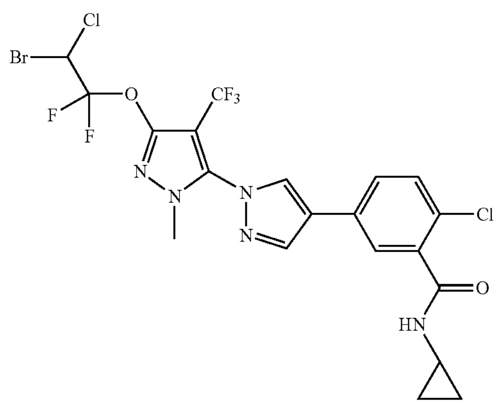 [SMILES: Cn1nc(OC(F)(F)C(Cl)Br)c(C(F)(F)F)c1-n1cc(-c2ccc(Cl)c(C(=O)NC3CC3)c2)cn1] | LC-MS (A): $t_R$ = 1.11 min, m/z = 602 [M + 1] | |
| 87 | 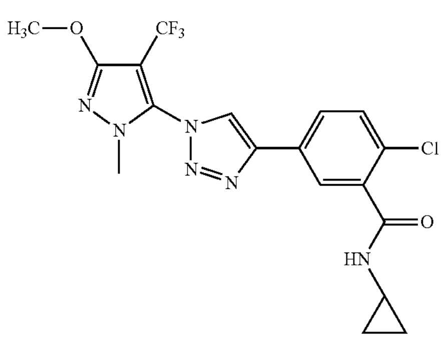 [SMILES: COc1nn(C)c(-n2cc(-c3ccc(Cl)c(C(=O)NC4CC4)c3)nn2)c1C(F)(F)F] | LC-MS (B): $t_R$ = 1.54 min, m/z = 441 [M + 1] | |

Table X: The following compounds of formula (1-1a) may be prepared in analogy to Examples 1 to 87 or according to the methods disclosed herein or according to literature methods, e.g. methods disclosed in WO2012/107434, WO2014/122083 and WO2015/150442. Table X discloses 262 substituent definitions X.001 to X.262 as defined in formula (1-1a):

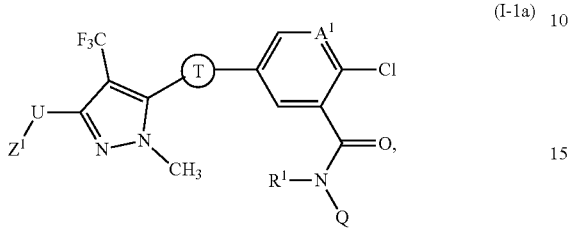

(I-1a)

wherein $Z^1$, U, $A^1$, $R^1$ and Q are as defined below:

TABLE X

| Comp. No | $Z^1$ | U | $A^1$ | $R^1$ | Q |
|---|---|---|---|---|---|
| X.001 | $CF_2H$ | O | C | H | cyclopropyl |
| X.002 | $CF_2CFHCF_3$ | O | C | H | cyclopropyl |
| X.003 | $CF_2CF_2CF_3$ | O | C | H | cyclopropyl |
| X.004 | $CF_2CF_2H$ | O | C | H | cyclopropyl |
| X.005 | $CF_2CF_2OCF_3$ | O | C | H | cyclopropyl |
| X.006 | $CH_2CF_2CF_3$ | O | C | H | cyclopropyl |
| X.007 | $CH(CF_3)CH_2CF_3$ | O | C | H | cyclopropyl |
| X.008 | $CH_2CF_3$ | O | C | H | cyclopropyl |
| X.009 | $CF_2H$ | S | C | H | cyclopropyl |
| X.010 | $CF_2CFHCF_3$ | S | C | H | cyclopropyl |
| X.011 | $CF_2CF_2CF_3$ | S | C | H | cyclopropyl |
| X.012 | $CF_2CF_2H$ | S | C | H | cyclopropyl |
| X.013 | $CF_2CF_2OCF_3$ | S | C | H | cyclopropyl |
| X.014 | $CH_2CF_2CF_3$ | S | C | H | cyclopropyl |
| X.015 | $CH(CF_3)CH_2CF_3$ | S | C | H | cyclopropyl |
| X.016 | $CH_2CF_3$ | S | C | H | cyclopropyl |
| X.017 | $CF_2H$ | SO | C | H | cyclopropyl |
| X.018 | $CF_2CFHCF_3$ | SO | C | H | cyclopropyl |
| X.019 | $CF_2CF_2CF_3$ | SO | C | H | cyclopropyl |
| X.020 | $CF_2CF_2H$ | SO | C | H | cyclopropyl |
| X.021 | $CF_2CF_2OCF_3$ | SO | C | H | cyclopropyl |
| X.022 | $CH_2CF_2CF_3$ | SO | C | H | cyclopropyl |
| X.023 | $CH(CF_3)CH_2CF_3$ | SO | C | H | cyclopropyl |
| X.024 | $CH_2CF_3$ | SO | C | H | cyclopropyl |
| X.025 | $CF_2H$ | $SO_2$ | C | H | cyclopropyl |
| X.026 | $CF_2CFHCF_3$ | $SO_2$ | C | H | cyclopropyl |
| X.027 | $CF_2CF_2CF_3$ | $SO_2$ | C | H | cyclopropyl |
| X.028 | $CF_2CF_2H$ | $SO_2$ | C | H | cyclopropyl |
| X.029 | $CF_2CF_2OCF_3$ | $SO_2$ | C | H | cyclopropyl |
| X.030 | $CH_2CF_2CF_3$ | $SO_2$ | C | H | cyclopropyl |
| X.031 | $CH(CF_3)CH_2CF_3$ | $SO_2$ | C | H | cyclopropyl |
| X.032 | $CH_2CF_3$ | $SO_2$ | C | H | cyclopropyl |
| X.033 | $CF_2H$ | O | N | H | cyclopropyl |
| X.034 | $CF_2CFHCF_3$ | O | N | H | cyclopropyl |
| X.035 | $CF_2CF_2CF_3$ | O | N | H | cyclopropyl |
| X.036 | $CF_2CF_2H$ | O | N | H | cyclopropyl |
| X.037 | $CF_2CF_2OCF_3$ | O | N | H | cyclopropyl |
| X.038 | $CH_2CF_2CF_3$ | O | N | H | cyclopropyl |
| X.039 | $CH(CF_3)CH_2CF_3$ | O | N | H | cyclopropyl |
| X.040 | $CH_2CF_3$ | O | N | H | cyclopropyl |
| X.041 | $CF_2H$ | S | N | H | cyclopropyl |
| X.042 | $CF_2CFHCF_3$ | S | N | H | cyclopropyl |
| X.043 | $CF_2CF_2CF_3$ | S | N | H | cyclopropyl |
| X.044 | $CF_2CF_2H$ | S | N | H | cyclopropyl |
| X.045 | $CF_2CF_2OCF_3$ | S | N | H | cyclopropyl |
| X.046 | $CH_2CF_2CF_3$ | S | N | H | cyclopropyl |
| X.047 | $CH(CF_3)CH_2CF_3$ | S | N | H | cyclopropyl |
| X.048 | $CH_2CF_3$ | S | N | H | cyclopropyl |
| X.049 | $CF_2H$ | SO | N | H | cyclopropyl |
| X.050 | $CF_2CFHCF_3$ | SO | N | H | cyclopropyl |
| X.051 | $CF_2CF_2CF_3$ | SO | N | H | cyclopropyl |
| X.052 | $CF_2CF_2H$ | SO | N | H | cyclopropyl |

TABLE X-continued

| Comp. No | $Z^1$ | U | $A^1$ | $R^1$ | Q |
|---|---|---|---|---|---|
| X.053 | $CF_2CF_2OCF_3$ | SO | N | H | cyclopropyl |
| X.054 | $CH_2CF_2CF_3$ | SO | N | H | cyclopropyl |
| X.055 | $CH(CF_3)CH_2CF_3$ | SO | N | H | cyclopropyl |
| X.056 | $CH_2CF_3$ | SO | N | H | cyclopropyl |
| X.057 | $CF_2H$ | $SO_2$ | N | H | cyclopropyl |
| X.058 | $CF_2CFHCF_3$ | $SO_2$ | N | H | cyclopropyl |
| X.059 | $CF_2CF_2CF_3$ | $SO_2$ | N | H | cyclopropyl |
| X.060 | $CF_2CF_2H$ | $SO_2$ | N | H | cyclopropyl |
| X.061 | $CF_2CF_2OCF_3$ | $SO_2$ | N | H | cyclopropyl |
| X.062 | $CH_2CF_2CF_3$ | $SO_2$ | N | H | cyclopropyl |
| X.063 | $CH(CF_3)CH_2CF_3$ | $SO_2$ | N | H | cyclopropyl |
| X.064 | $CH_2CF_3$ | $SO_2$ | N | H | cyclopropyl |
| X.065 | $CF_2H$ | O | C | $CH_3$ | cyclopropyl |
| X.066 | $CF_2CFHCF_3$ | O | C | $CH_3$ | cyclopropyl |
| X.067 | $CF_2CF_2CF_3$ | O | C | $CH_3$ | cyclopropyl |
| X.068 | $CF_2CF_2H$ | O | C | $CH_3$ | cyclopropyl |
| X.069 | $CF_2CF_2OCF_3$ | O | C | $CH_3$ | cyclopropyl |
| X.070 | $CH_2CF_2CF_3$ | O | C | $CH_3$ | cyclopropyl |
| X.071 | $CH(CF_3)CH_2CF_3$ | O | C | $CH_3$ | cyclopropyl |
| X.072 | $CH_2CF_3$ | O | C | $CH_3$ | cyclopropyl |
| X.073 | $CF_2H$ | S | C | $CH_3$ | cyclopropyl |
| X.074 | $CF_2CFHCF_3$ | S | C | $CH_3$ | cyclopropyl |
| X.075 | $CF_2CF_2CF_3$ | S | C | $CH_3$ | cyclopropyl |
| X.076 | $CF_2CF_2H$ | S | C | $CH_3$ | cyclopropyl |
| X.077 | $CF_2CF_2OCF_3$ | S | C | $CH_3$ | cyclopropyl |
| X.078 | $CH_2CF_2CF_3$ | S | C | $CH_3$ | cyclopropyl |
| X.079 | $CH(CF_3)CH_2CF_3$ | S | C | $CH_3$ | cyclopropyl |
| X.080 | $CH_2CF_3$ | S | C | $CH_3$ | cyclopropyl |
| X.081 | $CF_2H$ | SO | C | $CH_3$ | cyclopropyl |
| X.082 | $CF_2CFHCF_3$ | SO | C | $CH_3$ | cyclopropyl |
| X.083 | $CF_2CF_2CF_3$ | SO | C | $CH_3$ | cyclopropyl |
| X.084 | $CF_2CF_2H$ | SO | C | $CH_3$ | cyclopropyl |
| X.085 | $CF_2CF_2OCF_3$ | SO | C | $CH_3$ | cyclopropyl |
| X.086 | $CH_2CF_2CF_3$ | SO | C | $CH_3$ | cyclopropyl |
| X.087 | $CH(CF_3)CH_2CF_3$ | SO | C | $CH_3$ | cyclopropyl |
| X.088 | $CH_2CF_3$ | SO | C | $CH_3$ | cyclopropyl |
| X.089 | $CF_2H$ | $SO_2$ | C | $CH_3$ | cyclopropyl |
| X.090 | $CF_2CFHCF_3$ | $SO_2$ | C | $CH_3$ | cyclopropyl |
| X.091 | $CF_2CF_2CF_3$ | $SO_2$ | C | $CH_3$ | cyclopropyl |
| X.092 | $CF_2CF_2H$ | $SO_2$ | C | $CH_3$ | cyclopropyl |
| X.093 | $CF_2CF_2OCF_3$ | $SO_2$ | C | $CH_3$ | cyclopropyl |
| X.094 | $CH_2CF_2CF_3$ | $SO_2$ | C | $CH_3$ | cyclopropyl |
| X.095 | $CH(CF_3)CH_2CF_3$ | $SO_2$ | C | $CH_3$ | cyclopropyl |
| X.096 | $CH_2CF_3$ | $SO_2$ | C | $CH_3$ | cyclopropyl |
| X.097 | $CF_2CFHCF_3$ | O | C | $CH_2CH_3$ | cyclopropyl |
| X.098 | $CF_2CF_2CF_3$ | O | C | $CH_2CH_3$ | cyclopropyl |
| X.099 | $CF_2CF_2H$ | O | C | $CH_2CH_3$ | cyclopropyl |
| X.100 | $CF_2CF_2OCF_3$ | O | C | $CH_2CH_3$ | cyclopropyl |
| X.101 | $CH_2CF_2CF_3$ | O | C | $CH_2CH_3$ | cyclopropyl |
| X.102 | $CH(CF_3)CH_2CF_3$ | O | C | $CH_2CH_3$ | cyclopropyl |
| X.103 | $CH_2CF_3$ | O | C | $CH_2CH_3$ | cyclopropyl |
| X.104 | $CF_2H$ | S | C | $CH_2CH_3$ | cyclopropyl |
| X.105 | $CF_2CFHCF_3$ | S | C | $CH_2CH_3$ | cyclopropyl |
| X.106 | $CF_2CF_2CF_3$ | S | C | $CH_2CH_3$ | cyclopropyl |
| X.107 | $CF_2CF_2H$ | S | C | $CH_2CH_3$ | cyclopropyl |
| X.108 | $CF_2CF_2OCF_3$ | S | C | $CH_2CH_3$ | cyclopropyl |
| X.109 | $CH_2CF_2CF_3$ | S | C | $CH_2CH_3$ | cyclopropyl |
| X.110 | $CH(CF_3)CH_2CF_3$ | S | C | $CH_2CH_3$ | cyclopropyl |
| X.111 | $CH_2CF_3$ | S | C | $CH_2CH_3$ | cyclopropyl |
| X.112 | $CF_2H$ | SO | C | $CH_2CH_3$ | cyclopropyl |
| X.113 | $CF_2CFHCF_3$ | SO | C | $CH_2CH_3$ | cyclopropyl |
| X.114 | $CF_2CF_2CF_3$ | SO | C | $CH_2CH_3$ | cyclopropyl |
| X.115 | $CF_2CF_2H$ | SO | C | $CH_2CH_3$ | cyclopropyl |
| X.116 | $CF_2CF_2OCF_3$ | SO | C | $CH_2CH_3$ | cyclopropyl |
| X.117 | $CH_2CF_2CF_3$ | SO | C | $CH_2CH_3$ | cyclopropyl |
| X.118 | $CH(CF_3)CH_2CF_3$ | SO | C | $CH_2CH_3$ | cyclopropyl |
| X.119 | $CH_2CF_3$ | SO | C | $CH_2CH_3$ | cyclopropyl |
| X.120 | $CF_2H$ | $SO_2$ | C | $CH_2CH_3$ | cyclopropyl |
| X.121 | $CF_2CFHCF_3$ | $SO_2$ | C | $CH_2CH_3$ | cyclopropyl |
| X.122 | $CF_2CF_2CF_3$ | $SO_2$ | C | $CH_2CH_3$ | cyclopropyl |
| X.123 | $CF_2CF_2H$ | $SO_2$ | C | $CH_2CH_3$ | cyclopropyl |
| X.124 | $CF_2CF_2OCF_3$ | $SO_2$ | C | $CH_2CH_3$ | cyclopropyl |
| X.125 | $CH_2CF_2CF_3$ | $SO_2$ | C | $CH_2CH_3$ | cyclopropyl |
| X.126 | $CH(CF_3)CH_2CF_3$ | $SO_2$ | C | $CH_2CH_3$ | cyclopropyl |
| X.127 | $CH_2CF_3$ | $SO_2$ | C | $CH_2CH_3$ | cyclopropyl |
| X.128 | $CF_2H$ | O | C | H | $C(CH_2CH_2)CN$ |
| X.129 | $CF_2CFHCF_3$ | O | C | H | $C(CH_2CH_2)CN$ |
| X.130 | $CF_2CF_2CF_3$ | O | C | H | $C(CH_2CH_2)CN$ |

TABLE X-continued

| Comp. No | Z¹ | U | A¹ | R¹ | Q |
|---|---|---|---|---|---|
| X.131 | CF₂CF₂H | O | C | H | C(CH₂CH₂)CN |
| X.132 | CF₂CF₂OCF₃ | O | C | H | C(CH₂CH₂)CN |
| X.133 | CH₂CF₂CF₃ | O | C | H | C(CH₂CH₂)CN |
| X.134 | CH(CF₃)CH₂CF₃ | O | C | H | C(CH₂CH₂)CN |
| X.135 | CH₂CF₃ | O | C | H | C(CH₂CH₂)CN |
| X.136 | CF₂H | S | C | H | C(CH₂CH₂)CN |
| X.137 | CF₂CFHCF₃ | S | C | H | C(CH₂CH₂)CN |
| X.138 | CF₂CF₂CF₃ | S | C | H | C(CH₂CH₂)CN |
| X.139 | CF₂CF₂H | S | C | H | C(CH₂CH₂)CN |
| X.140 | CF₂CF₂OCF₃ | S | C | H | C(CH₂CH₂)CN |
| X.141 | CH₂CF₂CF₃ | S | C | H | C(CH₂CH₂)CN |
| X.142 | CH(CF₃)CH₂CF₃ | S | C | H | C(CH₂CH₂)CN |
| X.143 | CH₂CF₃ | S | C | H | C(CH₂CH₂)CN |
| X.144 | CF₂H | SO | C | H | C(CH₂CH₂)CN |
| X.145 | CF₂CFHCF₃ | SO | C | H | C(CH₂CH₂)CN |
| X.146 | CF₂CF₂CF₃ | SO | C | H | C(CH₂CH₂)CN |
| X.147 | CF₂CF₂H | SO | C | H | C(CH₂CH₂)CN |
| X.148 | CF₂CF₂OCF₃ | SO | C | H | C(CH₂CH₂)CN |
| X.149 | CH₂CF₂CF₃ | SO | C | H | C(CH₂CH₂)CN |
| X.150 | CH(CF₃)CH₂CF₃ | SO | C | H | C(CH₂CH₂)CN |
| X.151 | CH₂CF₃ | SO | C | H | C(CH₂CH₂)CN |
| X.152 | CF₂H | SO₂ | C | H | C(CH₂CH₂)CN |
| X.153 | CF₂CFHCF₃ | SO₂ | C | H | C(CH₂CH₂)CN |
| X.154 | CF₂CF₂CF₃ | SO₂ | C | H | C(CH₂CH₂)CN |
| X.155 | CF₂CF₂H | SO₂ | C | H | C(CH₂CH₂)CN |
| X.156 | CF₂CF₂OCF₃ | SO₂ | C | H | C(CH₂CH₂)CN |
| X.157 | CH₂CF₂CF₃ | SO₂ | C | H | C(CH₂CH₂)CN |
| X.158 | CH(CF₃)CH₂CF₃ | SO₂ | C | H | C(CH₂CH₂)CN |
| X.159 | CH₂CF₃ | SO₂ | C | H | C(CH₂CH₂)CN |
| X.160 | CF₂H | O | N | H | C(CH₂CH₂)CN |
| X.161 | CF₂CFHCF₃ | O | N | H | C(CH₂CH₂)CN |
| X.162 | CF₂CF₂CF₃ | O | N | H | C(CH₂CH₂)CN |
| X.163 | CF₂CF₂H | O | N | H | C(CH₂CH₂)CN |
| X.164 | CF₂CF₂OCF₃ | O | N | H | C(CH₂CH₂)CN |
| X.165 | CH₂CF₂CF₃ | O | N | H | C(CH₂CH₂)CN |
| X.166 | CH(CF₃)CH₂CF₃ | O | N | H | C(CH₂CH₂)CN |
| X.167 | CH₂CF₃ | O | N | H | C(CH₂CH₂)CN |
| X.168 | CF₂H | S | N | H | C(CH₂CH₂)CN |
| X.169 | CF₂CFHCF₃ | S | N | H | C(CH₂CH₂)CN |
| X.170 | CF₂CF₂CF₃ | S | N | H | C(CH₂CH₂)CN |
| X.171 | CF₂CF₂H | S | N | H | C(CH₂CH₂)CN |
| X.172 | CF₂CF₂OCF₃ | S | N | H | C(CH₂CH₂)CN |
| X.173 | CH₂CF₂CF₃ | S | N | H | C(CH₂CH₂)CN |
| X.174 | CH(CF₃)CH₂CF₃ | S | N | H | C(CH₂CH₂)CN |
| X.175 | CH₂CF₃ | S | N | H | C(CH₂CH₂)CN |
| X.176 | CF₂H | SO | N | H | C(CH₂CH₂)CN |
| X.177 | CF₂CFHCF₃ | SO | N | H | C(CH₂CH₂)CN |
| X.178 | CF₂CF₂CF₃ | SO | N | H | C(CH₂CH₂)CN |
| X.179 | CF₂CF₂H | SO | N | H | C(CH₂CH₂)CN |
| X.180 | CF₂CF₂OCF₃ | SO | N | H | C(CH₂CH₂)CN |
| X.181 | CH₂CF₂CF₃ | SO | N | H | C(CH₂CH₂)CN |
| X.182 | CH(CF₃)CH₂CF₃ | SO | N | H | C(CH₂CH₂)CN |
| X.183 | CH₂CF₃ | SO | N | H | C(CH₂CH₂)CN |
| X.184 | CF₂H | SO₂ | N | H | C(CH₂CH₂)CN |
| X.185 | CF₂CFHCF₃ | SO₂ | N | H | C(CH₂CH₂)CN |
| X.186 | CF₂CF₂CF₃ | SO₂ | N | H | C(CH₂CH₂)CN |
| X.187 | CF₂CF₂H | SO₂ | N | H | C(CH₂CH₂)CN |
| X.188 | CF₂CF₂OCF₃ | SO₂ | N | H | C(CH₂CH₂)CN |
| X.189 | CH₂CF₂CF₃ | SO₂ | N | H | C(CH₂CH₂)CN |
| X.190 | CH(CF₃)CH₂CF₃ | SO₂ | N | H | C(CH₂CH₂)CN |
| X.191 | CH₂CF₃ | SO₂ | N | H | C(CH₂CH₂)CN |
| X.192 | CF₂H | O | C | CH₃ | C(CH₂CH₂)CN |
| X.193 | CF₂CFHCF₃ | O | C | CH₃ | C(CH₂CH₂)CN |
| X.194 | CF₂CF₂CF₃ | O | C | CH₃ | C(CH₂CH₂)CN |
| X.195 | CF₂CF₂H | O | C | CH₃ | C(CH₂CH₂)CN |
| X.196 | CF₂CF₂OCF₃ | O | C | CH₃ | C(CH₂CH₂)CN |
| X.197 | CH₂CF₂CF₃ | O | C | CH₃ | C(CH₂CH₂)CN |
| X.198 | CH(CF₃)CH₂CF₃ | O | C | CH₃ | C(CH₂CH₂)CN |
| X.199 | CH₂CF₃ | O | C | CH₃ | C(CH₂CH₂)CN |
| X.200 | CF₂H | S | C | CH₃ | C(CH₂CH₂)CN |
| X.201 | CF₂CFHCF₃ | S | C | CH₃ | C(CH₂CH₂)CN |
| X.202 | CF₂CF₂CF₃ | S | C | CH₃ | C(CH₂CH₂)CN |
| X.203 | CF₂CF₂H | S | C | CH₃ | C(CH₂CH₂)CN |
| X.204 | CF₂CF₂OCF₃ | S | C | CH₃ | C(CH₂CH₂)CN |
| X.205 | CH₂CF₂CF₃ | S | C | CH₃ | C(CH₂CH₂)CN |
| X.206 | CH(CF₃)CH₂CF₃ | S | C | CH₃ | C(CH₂CH₂)CN |
| X.207 | CH₂CF₃ | S | C | CH₃ | C(CH₂CH₂)CN |
| X.208 | CF₂H | SO | C | CH₃ | C(CH₂CH₂)CN |
| X.209 | CF₂CFHCF₃ | SO | C | CH₃ | C(CH₂CH₂)CN |
| X.210 | CF₂CF₂CF₃ | SO | C | CH₃ | C(CH₂CH₂)CN |
| X.211 | CF₂CF₂H | SO | C | CH₃ | C(CH₂CH₂)CN |
| X.212 | CF₂CF₂OCF₃ | SO | C | CH₃ | C(CH₂CH₂)CN |
| X.213 | CH₂CF₂CF₃ | SO | C | CH₃ | C(CH₂CH₂)CN |
| X.214 | CH(CF₃)CH₂CF₃ | SO | C | CH₃ | C(CH₂CH₂)CN |
| X.215 | CH₂CF₃ | SO | C | CH₃ | C(CH₂CH₂)CN |
| X.216 | CF₂H | SO₂ | C | CH₃ | C(CH₂CH₂)CN |
| X.217 | CF₂CFHCF₃ | SO₂ | C | CH₃ | C(CH₂CH₂)CN |
| X.218 | CF₂CF₂CF₃ | SO₂ | C | CH₃ | C(CH₂CH₂)CN |
| X.219 | CF₂CF₂H | SO₂ | C | CH₃ | C(CH₂CH₂)CN |
| X.220 | CF₂CF₂OCF₃ | SO₂ | C | CH₃ | C(CH₂CH₂)CN |
| X.221 | CH₂CF₂CF₃ | SO₂ | C | CH₃ | C(CH₂CH₂)CN |
| X.222 | CH(CF₃)CH₂CF₃ | SO₂ | C | CH₃ | C(CH₂CH₂)CN |
| X.223 | CH₂CF₃ | SO₂ | C | CH₃ | C(CH₂CH₂)CN |
| X.224 | CF₂CFHCF₃ | O | C | CH₂CH₃ | C(CH₂CH₂)CN |
| X.225 | CF₂CF₂CF₃ | O | C | CH₂CH₃ | C(CH₂CH₂)CN |
| X.226 | CF₂CF₂H | O | C | CH₂CH₃ | C(CH₂CH₂)CN |
| X.227 | CF₂CF₂OCF₃ | O | C | CH₂CH₃ | C(CH₂CH₂)CN |
| X.228 | CH₂CF₂CF₃ | O | C | CH₂CH₃ | C(CH₂CH₂)CN |
| X.229 | CH(CF₃)CH₂CF₃ | O | C | CH₂CH₃ | C(CH₂CH₂)CN |
| X.230 | CH₂CF₃ | O | C | CH₂CH₃ | C(CH₂CH₂)CN |
| X.231 | CF₂H | S | C | CH₂CH₃ | C(CH₂CH₂)CN |
| X.232 | CF₂CFHCF₃ | S | C | CH₂CH₃ | C(CH₂CH₂)CN |
| X.233 | CF₂CF₂CF₃ | S | C | CH₂CH₃ | C(CH₂CH₂)CN |
| X.234 | CF₂CF₂H | S | C | CH₂CH₃ | C(CH₂CH₂)CN |
| X.235 | CF₂CF₂OCF₃ | S | C | CH₂CH₃ | C(CH₂CH₂)CN |
| X.236 | CH₂CF₂CF₃ | S | C | CH₂CH₃ | C(CH₂CH₂)CN |
| X.237 | CH(CF₃)CH₂CF₃ | S | C | CH₂CH₃ | C(CH₂CH₂)CN |
| X.238 | CH₂CF₃ | S | C | CH₂CH₃ | C(CH₂CH₂)CN |
| X.239 | CF₂H | SO | C | CH₂CH₃ | C(CH₂CH₂)CN |
| X.240 | CF₂CFHCF₃ | SO | C | CH₂CH₃ | C(CH₂CH₂)CN |
| X.241 | CF₂CF₂CF₃ | SO | C | CH₂CH₃ | C(CH₂CH₂)CN |
| X.242 | CF₂CF₂H | SO | C | CH₂CH₃ | C(CH₂CH₂)CN |
| X.243 | CF₂CF₂OCF₃ | SO | C | CH₂CH₃ | C(CH₂CH₂)CN |
| X.244 | CH₂CF₂CF₃ | SO | C | CH₂CH₃ | C(CH₂CH₂)CN |
| X.245 | CH(CF₃)CH₂CF₃ | SO | C | CH₂CH₃ | C(CH₂CH₂)CN |
| X.246 | CH₂CF₃ | SO | C | CH₂CH₃ | C(CH₂CH₂)CN |
| X.247 | CF₂H | SO₂ | C | CH₂CH₃ | C(CH₂CH₂)CN |
| X.248 | CF₂CFHCF₃ | SO₂ | C | CH₂CH₃ | C(CH₂CH₂)CN |
| X.249 | CF₂CF₂CF₃ | SO₂ | C | CH₂CH₃ | C(CH₂CH₂)CN |
| X.250 | CF₂CF₂H | SO₂ | C | CH₂CH₃ | C(CH₂CH₂)CN |
| X.251 | CF₂CF₂OCF₃ | SO₂ | C | CH₂CH₃ | C(CH₂CH₂)CN |
| X.252 | CH₂CF₂CF₃ | SO₂ | C | CH₂CH₃ | C(CH₂CH₂)CN |
| X.253 | CH(CF₃)CH₂CF₃ | SO₂ | C | CH₂CH₃ | C(CH₂CH₂)CN |
| X.254 | CH₂CF₃ | SO₂ | C | CH₂CH₃ | C(CH₂CH₂)CN |
| X.255 | CF₂H | NMe | C | CH₂CH₃ | cyclopropyl |
| X.256 | CF₂CFHCF₃ | NMe | C | CH₂CH₃ | cyclopropyl |
| X.257 | CF₂CF₂CF₃ | NMe | C | CH₂CH₃ | cyclopropyl |
| X.258 | CF₂CF₂H | NMe | C | CH₂CH₃ | cyclopropyl |
| X.259 | CF₂CF₂OCF₃ | NMe | C | CH₂CH₃ | cyclopropyl |
| X.260 | CH₂CF₂CF₃ | NMe | C | CH₂CH₃ | cyclopropyl |
| X.261 | CH(CF₃)CH₂CF₃ | NMe | C | CH₂CH₃ | cyclopropyl |
| X.262 | CH₂CF₃ | NMe | C | CH₂CH₃ | cyclopropyl |

Table 1: This table discloses the 262 compounds 1.001 to 1.262 of formula (1-1), wherein $Z^1$, U, $A^1$, $R^1$ and Q are as defined in Table X.

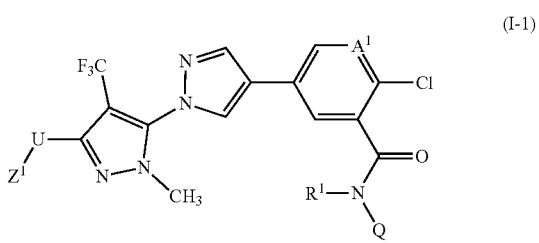

(I-1)

For example, compound No. 1.001 has the following structure:

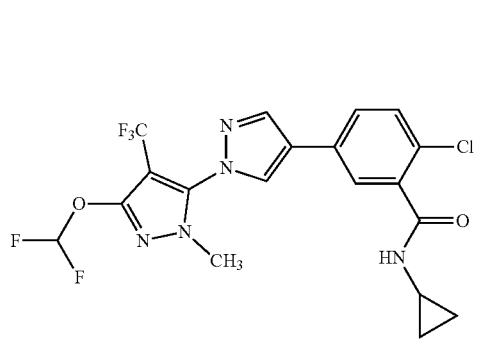
(1.001)

Table 2: This table discloses the 262 compounds 2.001 to 2.262 of the formula (1-2), wherein $Z^1$, U, $A^1$, $R^1$ and Q are as defined in Table X.

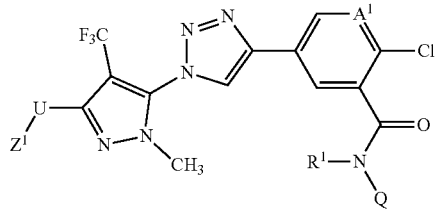
(I-2)

Table 3: This table discloses the 262 compounds 3.001 to 3.262 of the formula (1-3), wherein $Z^1$, U, $A^1$, $R^1$ and Q are as defined in Table X.

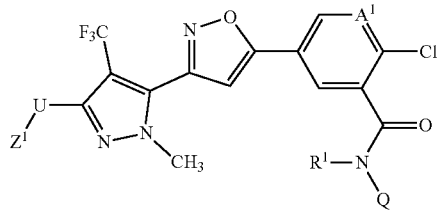
(I-3)

Table 4: This table discloses the 262 compounds 4.001 to 4.262 of the formula (1-4), wherein $Z^1$, U, $A^1$, $R^1$ and Q are as defined in Table X.

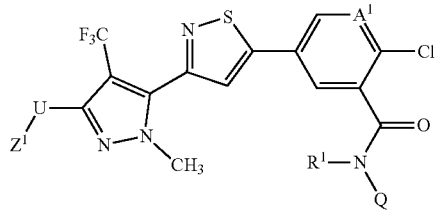
(I-4)

Table 5: This table discloses the 262 compounds 5.001 to 5.262 of the formula (1-5), wherein $Z^1$, U, $A^1$, $R^1$ and Q are as defined in Table X.

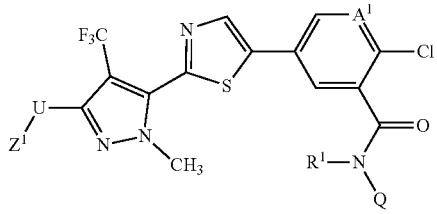
(I-5)

Table 6: This table discloses the 262 compounds 6.001 to 6.262 of the formula (1-6), wherein $Z^1$, U, $A^1$, $R^1$ and Q are as defined in Table X.

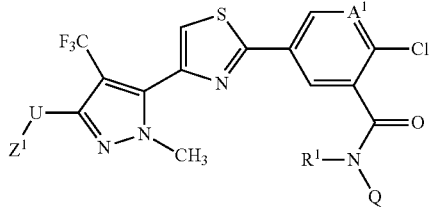
(I-6)

Table 7: This table discloses the 262 compounds 7.001 to 7.262 of the formula (1-7), wherein $Z^1$, U, $A^1$, $R^1$ and Q are as defined in Table X.

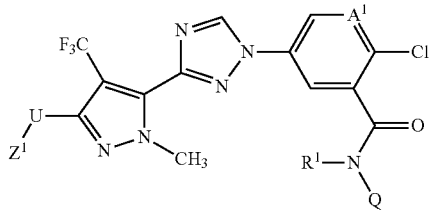
(I-7)

Table 8: This table discloses the 262 compounds 8.001 to 8.262 of the formula (1-8), wherein $Z^1$, U, $A^1$, $R^1$ and Q are as defined in Table X.

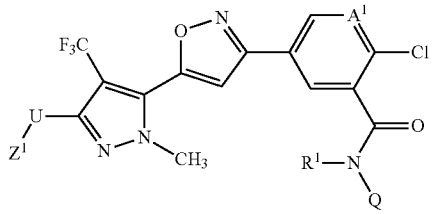
(I-8)

Table 9: This table discloses the 262 compounds 9.001 to 9.262 of the formula (1-9), wherein $Z^1$, U, $A^1$, $R^1$ and Q are as defined in Table X.

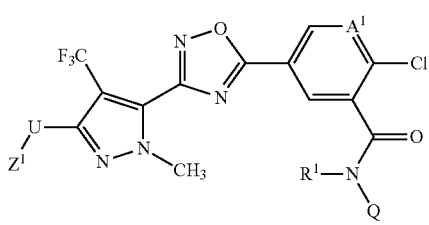
(I-9)

Table 10: This table discloses the 262 compounds 10.001 to 10.262 of the formula (1-10), wherein $Z^1$, U, $A^1$, $R^1$ and Q are as defined in Table X.

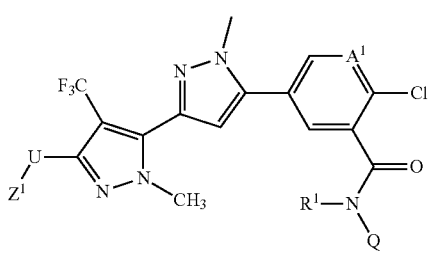
(I-10)

Table 11: This table discloses the 262 compounds 11.001 to 11.262 of the formula (1-11), wherein $Z^1$, U, $A^1$, $R^1$ and Q are as defined in Table X.

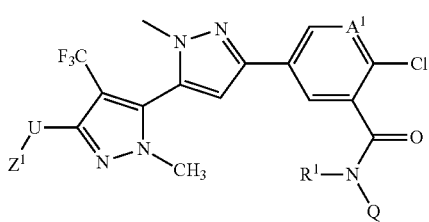
(I-11)

Table 12: This table discloses the 262 compounds 12.001 to 12.262 of the formula (1-12), wherein $Z^1$, U, $A^1$, $R^1$ and Q are as defined in Table X.

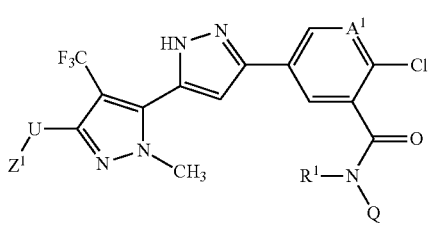
(I-12)

Formulation Examples (%=Percent by Weight)

| Example F1: Emulsion concentrates | a) | b) | c) |
|---|---|---|---|
| Active ingredient | 25% | 40% | 50% |
| Calcium dodecylbenzenesulfonate | 5% | 8% | 6% |
| Castor oil polyethylene glycol ether (36 mol of EO) | 5% | — | — |
| Tributylphenoxypolyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

| Example F2: Solutions | a) | b) | c) | d) |
|---|---|---|---|---|
| Active ingredient | 80% | 10% | 5% | 95% |
| Ethylene glycol monomethyl ether | 20% | — | — | — |
| Polyethylene glycol MW 400 | — | 70% | — | — |
| N-Methylpyrrolid-2-one | — | 20% | — | — |
| Epoxidized coconut oil | — | — | 1% | 5% |
| Petroleum ether (boiling range: 160-190°) | — | — | 94% | — |

The solutions are suitable for use in the form of microdrops.

| Example F3: Granules | a) | b) | c) | d) |
|---|---|---|---|---|
| Active ingredient | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredient is dissolved in dichloromethane, the solution is sprayed onto the carrier(s), and the solvent is subsequently evaporated in vacuo.

| Example F4: Dusts | a) | b) |
|---|---|---|
| Active ingredient | 2% | 5% |
| Highly disperse silica | 1% | 5% |
| Talc | 97% | — |
| Kaolin | — | 90% |

Ready-to-use dusts are obtained by intimately mixing the carriers and the active ingredient.

| Example F5: Wettable powders | a) | b) | c) |
|---|---|---|---|
| Active ingredient | 25% | 50% | 75% |
| Sodium lignosulfonate | 5% | 5% | — |
| Sodium lauryl sulfate | 3% | — | 5% |
| Sodium diisobutyl-naphthalenesulfonate | — | 6% | 10% |
| Octylphenoxypolyethylene glycol ether (7-8 mol of EO) | — | 2% | — |
| Highly disperse silica | 5% | 10% | 10% |
| Kaolin | 62% | 27% | — |

The active ingredient is mixed with the additives and the mixture is ground thoroughly in a suitable mill. This gives wettable powders, which can be diluted with water to give suspensions of any desired concentration.

| Example F6: Extruder granules | |
|---|---|
| Active ingredient | 10% |
| Sodium lignosulfonate | 2% |
| Carboxymethylcellulose | 1% |
| Kaolin | 87% |

The active ingredient is mixed with the additives, and the mixture is ground, moistened with water, extruded, granulated and dried in a stream of air.

| Example F7: Coated granules | |
|---|---|
| Active ingredient | 3% |
| Polyethylene glycol (MW 200) | 3% |
| Kaolin | 94% |

In a mixer, the finely ground active ingredient is applied uniformly to the kaolin, which has been moistened with the polyethylene glycol. This gives dust-free coated granules.

| Example F8: Suspension concentrate | |
|---|---|
| Active ingredient | 40% |
| Ethylene glycol | 10% |
| Nonylphenoxypolyethylene glycol ether (15 mol of EO) | 6% |
| Sodium lignosulfonate | 10% |
| Carboxymethylcellulose | 1% |
| 37% aqueous formaldehyde solution | 0.2% |
| Silicone oil (75% aqueous emulsion) | 0.8% |
| Water | 32% |

The finely ground active ingredient is mixed intimately with the additives. Suspensions of any desired concentration can be prepared from the thus resulting suspension concentrate by dilution with water.

| Example F9: Powders for dry seed treatment | a) | b) | c) |
|---|---|---|---|
| active ingredient | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The combination is thoroughly mixed with the adjuvants and the mixture is thoroughly ground in a suitable mill, affording powders that can be used directly for seed treatment.

| Example F10: Emulsifiable concentrate | |
|---|---|
| active ingredient | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Example F11: Flowable concentrate for seed treatment | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

The activity of the compositions according to the invention can be broadened considerably, and adapted to prevailing circumstances, by adding other insecticidally, acaricidally and/or fungicidally active ingredients. The mixtures of the compounds according to any one of embodiments 1 to 78 with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds according to any one of embodiments 1 to 78 with active ingredients are preferred (the abbreviation "TX" means "one compound selected from the compounds according to any one of embodiments 1 to 78, preferably embodiment 78):

an adjuvant selected from the group of substances consisting of petroleum oils (alternative name) (628)+TX,
an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, bromfenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+

TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure B₁ (alternative name) (839)+TX, trimedlure B2 (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, El 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, etafenprox (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxy-aminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebucon-azole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3][112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, copppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimetho-morph [110488-70-5]+TX, SYP-L190 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (dislosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H,11Hnaphtho[2,1-b]pyrano[3,4-e]pyran-4-yl] methyl-cyclopropanecarboxylate [915972-17-7]+TX and 1,3,5-trimethyl-N-(2-methyl-1-oxopropyl)-N-[3-(2-methylpropyl)-4-[2,2,2-trifluoro-1-methoxy-1-(trifluoromethyl) ethyl]phenyl]-1H-pyrazole-4-carboxamide [926914-55-8]+ TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood: *Compendium of Pesticide Common Names*, Copyright © 1995-2004].

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "develoment code" is used or, if neither one of those designations nor a "common name" is used, an "alternative name" is employed. "CAS Reg. No" means the Chemical Abstracts Registry Number.

The active ingredient mixture of the compounds according to any one of embodiments 1 to 78 with active ingredients described above comprises a compound according to any one of embodiments 1 to 78 and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of according to any one of embodiments 1 to 78 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds according to any one of embodiments 1 to 78 and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound according to any one of embodiments 1 to 78. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with according to any one of embodiments 1 to 78. Further, it is hereby made available, a composition comprising a plant propagation material treated with a compound according to any one of embodiments 1 to 78.

Seed treatment comprises all suitable seed treatment techniques known in the art, such as seed dressing, seed coating, seed dusting, seed soaking and seed pelleting. The seed treatment application of the compound according to any one of embodiments 1 to 78 can be carried out by any known methods, such as spraying or by dusting the seeds before sowing or during the sowing/planting of the seeds.

The pesticidal/insecticidal properties of the compounds according to any one of embodiments 1 to 78 can be illustrated via the following tests:

*Spodoptera littoralis* (Egyptian Cotton Leaf Worm)

Cotton leaf discs were placed on agar in 24-well microtiter plates and sprayed with aqueous test solutions prepared from 10'000 ppm DMSO stock solutions. After drying the leaf discs were infested with five L1 larvae. The samples were assessed for mortality, anti-feedant effect, and growth inhibition in comparison to untreated samples 3 days after infestation. Control of *Spodoptera littoralis* by a test sample is when at least one of mortality, anti-feedant effect, and growth inhibition is higher than the untreated sample. The following compounds resulted in at least 80% control at an application rate of 200 ppm: compounds 1,2, 3, 4, 6, 7, 9, 10, 11, 12, 15, 16, 17, 18, 19, 20, 22, 23, 24, 25, 26, 27, 30, 32, 33, 34, 35, 38, 39, 41, 42, 43, 45, 46, 47, 48, 49, 50, 51, 53, 54, 55, 57, 58, 59, 60, 61, 62, 63, 64 and 68.

*Plutella xylostella* (Diamond Back Moth):

24-well microtiter plates with artificial diet were treated with aqueous test solutions prepared from 10'000 ppm DMSO stock solutions by pipetting. After drying, the plates were infested with L2 larvae (10 to 15 per well). The samples were assessed for mortality and growth inhibition in comparison to untreated samples 5 days after infestation. The following compounds resulted in at least 80% control at an application rate of 200 ppm: compounds 1,2, 3, 4, 6, 7, 9, 10, 11, 12, 15, 16, 17, 18, 19, 20, 22, 23, 24, 25, 26, 27, 30, 31, 32, 33, 34, 35, 36, 37, 38, 39, 41, 42, 43, 45, 46, 47, 48, 50, 51, 53, 54, 55, 56, 58, 59, 60, 61, 62, 63, 64, 65 and 66.

*Diabrotica balteata*, (Corn Root Worm)

Maize sprouts, placed on an agar layer in 24-well microtiter plates were treated with aqueous test solutions prepared from 10'000 ppm DMSO stock solutions by spraying. After drying, the plates were infested with L2 larvae (6 to 10 per well). The samples were assessed for mortality and growth inhibition in comparison to untreated samples 4 days after infestation. The following compounds resulted in at least 80% control at an application rate of 200 ppm: compounds 1,2, 3, 4, 6, 7, 9, 10, 11, 12, 15, 16, 17, 18, 19, 20, 22, 23, 24, 25, 26, 27, 29, 30, 32, 33, 34, 35, 36, 37, 38, 39, 41, 42, 43, 44, 47, 48, 50, 51, 53, 53, 55, 56, 58, 58, 59, 60, 61, 62, 63, 64, 65, 67 and 68.

*Thrips tabaci* (Onion Thrips):

Sunflower leaf discs were placed on agar in 24-well microtiter plates and sprayed with aqueous test solutions prepared from 10'000 ppm DMSO stock solutions. After drying the leaf discs were infested with a thrips population of mixed ages. The samples were assessed for mortality 6 days after infestation. The following compounds resulted in at least 80% control at an application rate of 200 ppm: compounds 2, 3, 4, 6, 7, 9, 10, 11, 12, 15, 16, 17, 18, 19, 20, 23, 25, 26, 27, 30, 32, 33, 35, 36 37, 38, 39, 41,43,44,45, 46,47,48,50,51,52,53,55,58,59,60,61,62,63,64,65,66, 67 and 68.

*Tetranychus urticae* (Two-Spotted Spider Mite):

Bean leaf discs on agar in 24-well microtiter plates were sprayed with aqueous test solutions prepared from 10'000 ppm DMSO stock solutions. After drying the leaf discs were infested with a mite population of mixed ages. The samples were assessed for mortality on mixed population (mobile stages) 8 days after infestation. The following compounds resulted in at least 80% control at an application rate of 200 ppm: compounds 2, 3, 4, 6, 7, 9, 10, 11, 12, 14, 15, 16, 17, 18, 19, 20, 21, 23, 24, 25, 26, 27, 30, 32, 33, 34, 35, 39, 41, 43, 44, 45, 47, 48, 49, 50, 51, 52, 53, 55, 58, 59, 60, 61, 62, 63, 64, 65, 66 and 68.

*Euschistus heros* (Neotropical Brown Stink Bug):

Soybean leaves on agar in 24-well microtiter plates were sprayed with aqueous test solutions prepared from 10'000 ppm DMSO stock solutions. After drying the leaves were infested with N2 nymphs. The samples were assessed for mortality and growth inhibition in comparison to untreated samples 5 days after infestation.

The following compounds gave an effect of at least 80% in at least one of the two categories (mortality or growth inhibition) at an application rate of 200 ppm: compounds 1,2, 3, 4, 6, 9, 11, 12, 15, 16, 17, 18, 19, 20, 21, 23, 24, 25, 26, 27, 28, 30, 32, 33, 34, 35, 36, 37, 38, 39, 41, 42, 43, 44, 45, 47, 48, 49, 50, 51, 52, 53, 55, 59, 60, 61, 62, 63, 64, 65 and 66.

*Myzus persicae* (Green Peach Aphid):

Sunflower leaf discs were placed on agar in a 24-well microtiter plate and sprayed with test solutions at an application rate of 200 ppm. After drying, the leaf discs were infested with an aphid population of mixed ages. After an incubation period of 6 DAT, samples were checked for mortality. The following compounds gave at least 80% mortality of *Myzus persicae*: compounds 1,2, 3, 4, 5, 6, 11, 12, 15, 17, 18, 19, 20, 23, 24, 25, 26, 27, 30, 32, 33, 34 35, 41, 43, 44, 47, 50, 55, 58, 59, 60, 61, 62, 63, 64, 65 and 66.

*Myzus persicae* (Green Peach Aphid):

Test compounds were applied by pipette into 24 well plates and mixed with Sucrose solution. Application rate: 12.5 ppm. The plates were closed with a stretched parafilm. A plastic stencil with 24 holes is placed onto the plate and infested pea seedlings were placed directly on the Parafilm. The infested plate is closed with a gel blotting paper and another plastic stencil and then turned upside down. 5 days after infestation the samples were checked on mortality.

The following compounds gave at least 80% mortality of *Myzus persicae* at a test rate of 12 ppm: compounds 1,2, 3, 4, 5, 6, 9, 10, 11, 12, 15, 17, 18, 19, 20, 23, 24, 25, 26, 27, 28, 30, 32, 33, 34, 35, 36, 37, 44, 45, 47, 48, 49, 50, 51, 52, 53, 55, 56, 58, 59 and 60.

The compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, 6 ppm, 3 ppm, 1.5 ppm, 0.8 ppm or 0.2 ppm.

Biological Comparison Data:

Compound A and B are disclosed in WO2014/122083 as example (Ic-1) (p. 76) and (Ic-2) (p. 82, Table 3). The activities of compounds A and B to treat different pests are compared with the activities of compound 4, 6, 15 and 35 according to the present invention. The tests are carried out at different concentrations (ppm). It can be seen that compounds 4, 6, 15 and 35 of the present invention have surprisingly improved activity in comparison with compounds A and B.

a) Insecticidal Activity Against *Spodoptera littoralis* (Egyptian Cotton Leaf Worm, Larvicide L-3, Feeding/Contact)

Soybean plants were sprayed with diluted test solutions in an application chamber. The plants (2 replicates) were infested with 10 $L_3$ larvae 1 day after treatment. Samples were checked 5 days after infestation for mortality, feeding behavior, and growth regulation.

| Compound | Compound structure | Concentration (ppm) | Mortality (%) |
|---|---|---|---|
| A | 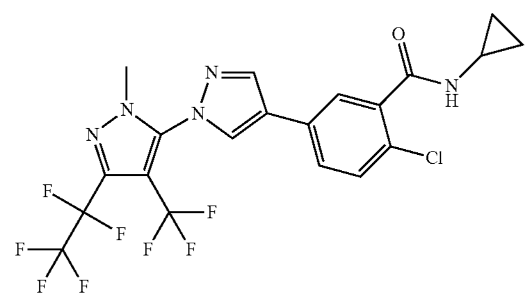 [SMILES: Cn1nc(C(F)(F)C(F)(F)F)c(C(F)(F)F)c1-n1cc(-c2ccc(Cl)c(C(=O)NC3CC3)c2)cn1] | 12.5<br>3.0<br>0.8<br>0.2 | 85<br>55<br>15<br>0 |
| Cpd 6 | 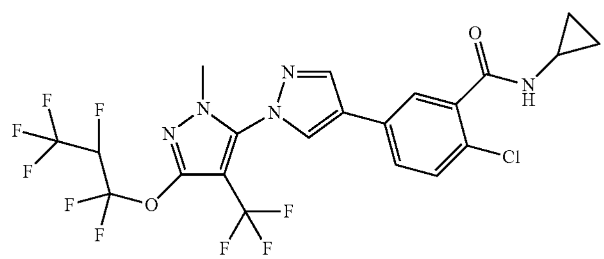 [SMILES: Cn1nc(OC(F)(F)C(F)C(F)(F)F)c(C(F)(F)F)c1-n1cc(-c2ccc(Cl)c(C(=O)NC3CC3)c2)cn1] | 12.5<br>3.0<br>0.8<br>0.2 | 100<br>100<br>0<br>0 |
| B | 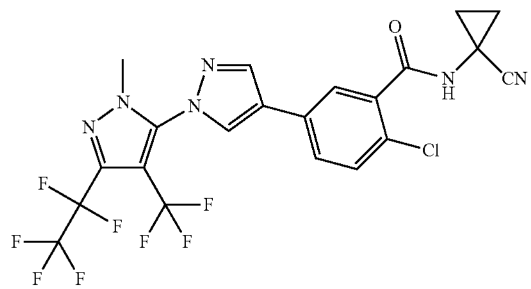 [SMILES: Cn1nc(C(F)(F)C(F)(F)F)c(C(F)(F)F)c1-n1cc(-c2ccc(Cl)c(C(=O)NC3(C#N)CC3)c2)cn1] | 12.5<br>3.0<br>0.8<br>0.2 | 100<br>100<br>75<br>20 |
| Cpd 35 | | 12.5<br>3.0<br>0.8<br>0.2 | 100<br>100<br>100<br>0 | b) Insecticidal Activity Against *Thrips tabaci* (Onion Thrips):

Sunflower leaf discs were placed on agar in 24-well microtiter plates and sprayed with aqueous test solutions prepared from 10'000 ppm DMSO stock solutions. After drying the leaf discs were infested with a thrips population of mixed ages. The samples were assessed for mortality 6 days after infestation.

| Compound | Compound structure | Concentration (ppm) | Mortality (%) |
|---|---|---|---|
| B |  | 200<br>50<br>12.5<br>3.12<br>0.781 | 100<br>100<br>90<br>25<br>0 |
| Cpd 15 | 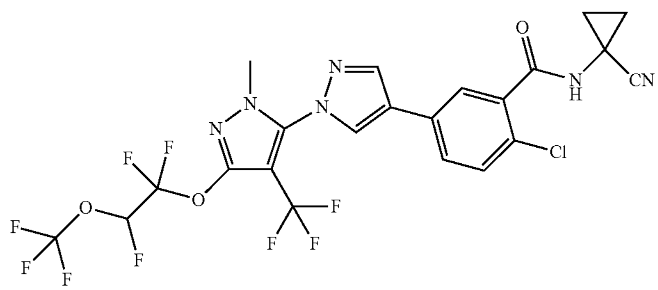 [SMILES: Cn1nc(OC(F)(F)C(F)OC(F)(F)F)c(C(F)(F)F)c1-n1cc(-c2ccc(Cl)c(C(=O)NC3(C#N)CC3)c2)cn1] | 200<br>50<br>12.5<br>3.12<br>0.781 | 100<br>100<br>90<br>90<br>0 |
| B |  | 12.5<br>3<br>0.8<br>0.2<br>0.05 | 100<br>100'<br>90<br>25<br>0 |
| Cpd 4 | 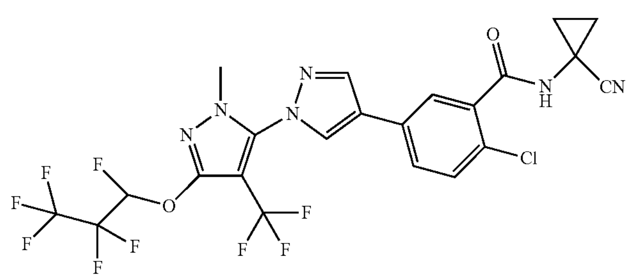 [SMILES: Cn1nc(OC(F)C(F)(F)C(F)(F)F)c(C(F)(F)F)c1-n1cc(-c2ccc(Cl)c(C(=O)NC3(C#N)CC3)c2)cn1] | 12.5<br>3<br>0.8<br>0.2<br>0.05 | 100<br>100<br>100<br>90<br>65 |

Furthermore, besides of the insecticidal properties, the compounds according to any one of embodiments 1 to 78 have surprisingly shown to have improved degradation properties compared with prior art compounds. Additionally, the compounds according to any one of embodiments 1 to 78 have surprisingly shown to be less toxic to bees compared with prior art compounds.

The invention claimed is:
1. A compound of formula (I),

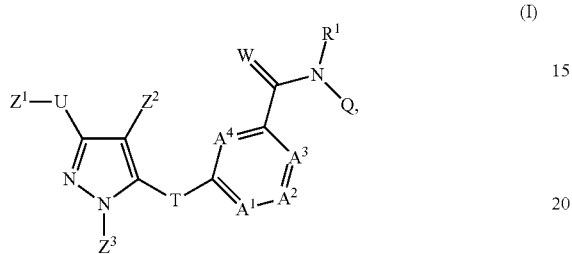

wherein
$R^1$ is selected from H, $C_1$-$C_6$-alkyl, $C_2$-$C_6$ alkenyl, $C_2$-$C_6$ alkynyl, $C_3$-$C_7$ cycloalkyl, $C_3$-$C_7$ cycloalkyl-$C_1$-$C_3$-alkyl, $C_1$-$C_6$-alkylcarbonyl, $C_1$-$C_6$-alkoxycarbonyl, aryl($C_0$-$C_3$)-alkyl and heteroaryl($C_0$-$C_3$)-alkyl, wherein each of $C_1$-$C_6$-alkyl, $C_2$-$C_6$ alkenyl, $C_2$-$C_6$ alkynyl, $C_3$-$C_7$ cycloalkyl, $C_3$-$C_7$ cycloalkyl-$C_1$-$C_3$-alkyl, $C_1$-$C_6$-alkylcarbonyl, $C_1$-$C_6$-alkoxycarbonyl, aryl($C_0$-$C_3$)-alkyl and heteroaryl($C_0$-$C_3$)-alkyl is unsubstituted or substituted with 1 to 10 substituents independently selected from halogen, cyano, $C_1$-$C_6$-alkoxy and $C_1$-$C_6$-alkoxycarbonyl;
Q is selected from H, hydroxy, HC(=O)—, methylsulfonyl, carbamothioylcyclopropyl, 1-carbamoylcyclopropyl, $C_1$-$C_6$-alkyl, $C_1$-$C_6$-alkoxy, $C_3$-$C_6$ alkenyl, $C_3$-$C_6$ alkynyl, $C_3$-$C_7$ cycloalkyl, $C_3$-$C_7$ heterocycloalkyl, $C_3$-$C_7$ cycloalkyl-$C_1$-$C_3$-alkyl, $C_1$-$C_3$-alkyl-$C_3$-$C_7$ cycloalkyl, aryl($C_0$-$C_3$)-alkyl, heteroaryl($C_0$-$C_3$)-alkyl, N—$C_1$-$C_6$-alkylamino, N—$C_1$-$C_6$-alkylcarbonylamino and N,N-di ($C_1$-$C_6$-alkyl)amino, wherein each of $C_1$-$C_6$-alkyl, $C_1$-$C_6$-alkoxy, $C_3$-$C_6$ alkenyl, $C_3$-$C_6$ alkynyl, $C_3$-$C_7$ cycloalkyl, $C_3$-$C_7$ heterocycloalkyl, $C_3$-$C_7$ cycloalkyl-$C_1$-$C_3$-alkyl, $C_1$-$C_3$-alkyl-$C_3$-$C_7$ cycloalkyl, aryl($C_0$-$C_3$)-alkyl, heteroaryl($C_0$-$C_3$)-alkyl, N—$C_1$-$C_6$-alkylamino, N—$C_1$-$C_6$-alkylcarbonylamino and N,N-di ($C_1$-$C_6$-alkyl)amino is unsubstituted or substituted with 1 to 10 substituents independently selected from halogen, hydroxyl, nitro, amino, cyano, $C_1$-$C_6$-alkoxy, $C_1$-$C_6$-alkoxycarbonyl, hydroxycarbonyl, $C_1$-$C_6$-alkylcarbamoyl, $C_3$-$C_6$-cycloalkylcarbamoyl and phenyl;
W is O or S;
$A^1$ is $CR^2$ or N;
$A^2$ is $CR^3$ or N;
$A^3$ is $CR^4$ or N;
$A^4$ is $CR^5$ or N;
with the proviso that no more than 3 of $A^1$, $A^2$, $A^3$ and $A^4$ are N;
$R^2$, $R^3$, $R^4$ and $R^5$ are independently selected from H, halogen, cyano, nitro, $C_1$-$C_6$-alkyl, $C_1$-$C_6$-alkoxy, N—$C_1$-$C_6$-alkoxy-imino-$C_1$-$C_3$-alkyl, $C_1$-$C_6$-alkylsulfanyl, $C_1$-$C_6$-alkylsulfinyl, $C_1$-$C_6$-alkylsulfonyl, N—$C_1$-$C_6$-alkylamino and N,N-di-$C_1$-$C_6$-alkylamino, wherein each of $C_1$-$C_6$-alkyl, $C_1$-$C_6$-alkoxy, N—$C_1$-$C_6$-alkoxy-imino-$C_1$-$C_3$-alkyl, $C_1$-$C_6$-alkylsulfanyl, $C_1$-$C_6$-alkylsulfinyl, $C_1$-$C_6$-alkylsulfonyl, N—$C_1$-$C_6$-alkylamino and N,N-di-$C_1$-$C_6$-alkylamino is unsubstituted or substituted with 1 to 5 substituents independently selected from halogen, hydroxy, nitro, amino, cyano, $C_1$-$C_6$-alkoxy, $C_1$-$C_6$-alkoxycarbonyl, hydroxycarbonyl, $C_1$-$C_6$-alkylcarbamoyl, $C_3$-$C_6$-cycloalkylcarbamoyl and phenyl;
T is a 5-membered heteroaryl of formula

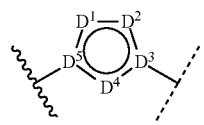

wherein

indicates the bond to the pyrazole group;
$D^1$ is selected from $CR^{6a}$, N, $NR^{6b}$, O and S;
$D^2$ is selected from $CR^{7a}$, N, $NR^{7b}$, O and S;
$D^3$ is C or N;
$D^4$ is selected from $CR^{8a}$, N, $NR^{8b}$, S and O;
$D^5$ is C or N;
with the proviso that at least one of $D^1$, $D^2$, $D^3$, $D^4$ and $D^5$ is selected from N, O and S, and that no more than one of $D^1$, $D^2$ and $D^4$ is O or S, and that at least one of $D^3$ and $D^5$ is C;
$R^{6a}$, $R^{7a}$ and $R^{8a}$ are independently selected from H, halogen, cyano, nitro, amino, $C_1$-$C_6$-alkyl, $C_1$-$C_6$-alkoxy, $C_1$-$C_6$-alkylcarbonyl, $C_1$-$C_6$-alkylsulfanyl, $C_1$-$C_6$-alkylsulfinyl and $C_1$-$C_6$-alkylsulfonyl, wherein each of $C_1$-$C_6$-alkyl, $C_1$-$C_6$-alkoxy, $C_1$-$C_6$-alkylcarbonyl, $C_1$-$C_6$-alkylsulfanyl, $C_1$-$C_6$-alkylsulfinyl, $C_1$-$C_6$-alkylsulfonyl is unsubstituted or substituted with 1 to 5 halogen;
$R^{6b}$, $R^{7b}$ and $R^{8b}$ are independently selected from H and $C_1$-$C_6$-alkyl, wherein each of $C_1$-$C_6$-alkyl is unsubstituted or substituted with 1 to 5 halogen;
U is selected from —O— and —$NR^{100}$—;
$R^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 13 substituents independently selected from halogen;
$Z^1$ is selected from $C_1$-$C_{10}$-alkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_2$-$C_{10}$-alkenyl, $C_2$-$C_{10}$-alkynyl, —($C_0$-$C_6$-alkyl)-$C_3$-$C_7$ heterocycloalkyl, —($C_0$-$C_6$-alkyl)-$C_3$-$C_6$-cycloalkyl and $C_1$-$C_{10}$-alkylsulfonyl, wherein each of $C_1$-$C_{10}$-alkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_2$-$C_{10}$-alkenyl, $C_2$-$C_{10}$-alkynyl, —($C_0$-$C_6$-alkyl)-$C_3$-$C_7$ heterocycloalkyl, —($C_0$-$C_6$-alkyl)-$C_3$-$C_6$-cycloalkyl and $C_1$-$C_{10}$-alkylsulfonyl is unsubstituted or substituted with 1 to 20 substituents independently selected from halogen, hydroxy, nitro, amino, cyano, $C_1$-$C_6$- alkoxy, $C_1$-$C_6$-alkoxycarbonyl, hydroxycarbonyl, $C_1$-$C_6$-alkylcarbamoyl, $C_3$-$C_6$-cycloalkylcarbamoyl and phenyl;

$Z^2$ is selected from H, halogen, cyano, nitro, amino, $C_1$-$C_6$-alkyl, $C_1$-$C_6$-alkylcarbonyl, $C_1$-$C_6$-alkylsulfanyl, $C_1$-$C_6$-alkylsulfinyl and $C_1$-$C_6$-alkylsulfonyl, wherein each of $C_1$-$C_6$-alkyl, $C_1$-$C_6$-alkylcarbonyl, $C_1$-$C_6$-alkylsulfanyl, $C_1$-$C_6$-alkylsulfinyl and $C_1$-$C_6$-alkylsulfonyl is unsubstituted or substituted with 1 to 5 substituents independently selected from halogen, hydroxy, nitro, amino, cyano, $C_1$-$C_6$-alkoxy, $C_1$-$C_6$-alkoxycarbonyl, hydroxycarbonyl, $C_1$-$C_6$-alkylcarbamoyl, $C_3$-$C_6$-cycloalkylcarbamoyl and phenyl; and $Z^3$ is selected from H, $C_1$-$C_6$-alkyl, $C_1$-$C_6$-cycloalkyl, $C_1$-$C_6$-alkenyl, $C_1$-$C_6$-alkynyl, aryl and heteroaryl, wherein each of $C_1$-$C_6$-alkyl, $C_1$-$C_6$-cycloalkyl, $C_1$-$C_6$-alkenyl, $C_1$-$C_6$-alkynyl, aryl and heteroaryl is unsubstituted or substituted with 1 to 5 substituents independently selected from halogen, hydroxy, nitro, amino, cyano, $C_1$-$C_6$-alkoxy, $C_1$-$C_6$-alkoxycarbonyl, hydroxycarbonyl, $C_1$-$C_6$-alkylcarbamoyl, $C_3$-$C_6$-cycloalkylcarbamoyl and phenyl;

or an agrochemically acceptable salt or N-oxide thereof.

2. The compound or salt according to claim 1, wherein T is selected from

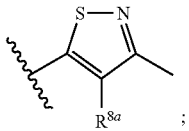
T7

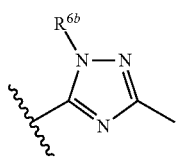
T10

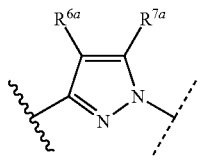
T11

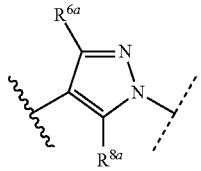
T13

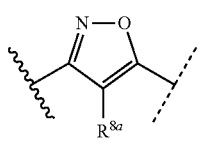
T14

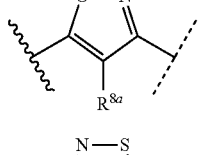
T15

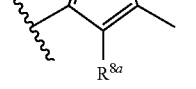 and

-continued

T16 wherein

indicates the bond to the pyrazole group.

3. The compound or salt according to claim 1, wherein T is selected from

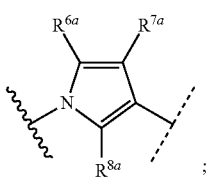
T45

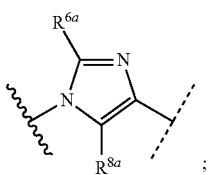
T46

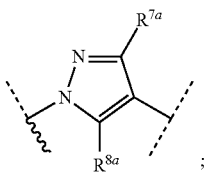
T47

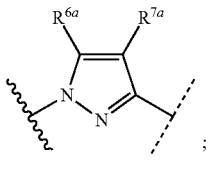
T48

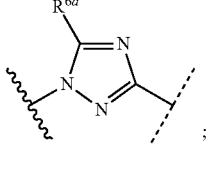
T49

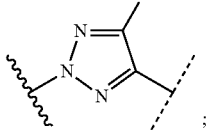
T50

; and

-continued

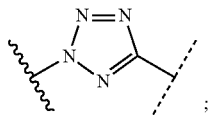
T51 wherein

indicates the bond to the pyrazole group.

4. The compound or salt according to claim 1, wherein U is —O—.

5. The compound or salt according to claim 1, wherein U is —NR$^{100}$—, and R$^{100}$ is selected from H, $C_1$-$C_6$-alkyl, $C_2$-$C_6$-alkenyl, $C_2$-$C_6$-alkynyl, $C_1$-$C_6$-alkoxy, $C_1$-$C_6$-alkylcarbonyl, $C_1$-$C_6$-alkoxycarbonyl and $C_3$-$C_6$-cycloalkyl, wherein each of $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl is unsubstituted or substituted with 1 to 13 substituents independently selected from halogen.

6. The compound or salt according to claim 1, wherein R$^1$ is H;
Q is selected from 1-cyano-cyclopropyl, (E)-1,2,3,3,3-pentafluoroprop-1-enyl, cyanomethyl, benzyl, cyclopropyl, methyl, ethyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
A$^1$ is CR$^2$ or N;
A$^2$ is CR$^3$ or N;
A$^3$ is CR$^4$ or N;
A$^4$ is CR$^5$ or N;
with the proviso that no more than 3 of A$^1$, A$^2$, A$^3$ and A$^4$ are N;
R$^2$ and R$^5$ are independently selected from H, methyl, fluoro and chloro;
R$^3$ and R$^4$ are independently selected from H, fluoro, chloro, bromo, iodo, cyano, nitro, methyl, ethyl, fluoromethyl, difluoromethyl, chlorodifluoromethyl, trifluoromethyl, 2,2,2-trifluoroethyl, methoxy, ethoxy, n-propoxy, 1-methylethoxy, fluoromethoxy, difluoromethoxy, chloro-difluoromethoxy, dichloro-fluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)-ethyl, methylsulfanyl, trifluoromethylsulfanyl, methylsulfonyl, methylsulfinyl, trifluoromethylsulfonyl and trifluoromethylsulfinyl;
U—Z$^1$ is selected from
difluoromethoxy;
2,2,2-trifluoroethoxy;
1,1,2,3,3,3-hexafluoropropoxy;
methoxy;
1,1,2,2-tetrafluoroethoxy;
2-bromo-1,1,2,2-tetrafluoroethoxy;
1,1,2,3,4,4,4-heptafluoro-3-(trifluoromethyl)butoxy;
1,1,2,4,4,4-hexafluoro-3-(trifluoromethyl)but-2-enoxy;
1,1,2-trifluoro-2-(trifluoromethoxy)ethoxy;
1,1,2-trifluoro-2-(1,1,2,2,3,3,3-heptafluoropropoxy)ethoxy;
2,2-difluoro-2-[1,1,2,2-tetrafluoro-2-(trifluoromethoxy)ethoxy]ethoxy;
2,2,3,3,4,4,4-heptafluorobutoxy;
5,6,6-trifluorohex-5-enoxy;
2,2,3,3,4,4,5,5,6,6,7,7,8,8,8-pentadecafluorooctoxy;
2,2-difluoroethoxy;
2,2,3,3,4,4,5,5-octafluoropentoxy;
2-(trifluoromethoxy)ethoxy;
2,2,3,3-tetrafluoropropoxy;
1,1,2,2,3,3,3-heptafluoropropoxy;
1,1,2,2,3,3,4,4,5,5,6,6,6-tridecafluorohexoxy;
1,1,2,2,3,3,4,4,5,5,6,6,7,7,8,8,8-heptadeccafluorooctoxy;
2-bromo-1,1-difluoro-ethoxy;
(E)-2,3,3,3-tetrafluoro-1-(trifluoromethyl)prop-1-enoxy;
2-bromo-1,1,2-trifluoro-ethoxy;
2-chloro-1,1,2-trifluoro-ethoxy;
(1E)-1,2-difluorobuta-1,3-dienoxy;
3,4,4-trifluorobut-3-enoxy;
(Z)-1,3,3,3-tetrafluoroprop-1-enoxy;
(Z)-2-fluoro-1-(trifluoromethyl)vinyloxy;
2,2,3,3,4,4,5,5-octafluoropentoxy;
1,1,2,3,4,5,5,5-octafluoro-2-(trifluoromethyl)pent-3-enoxy;
1,2,3,3,3-pentafluoroprop-1-enoxy;
1,1,2,3,3,3-hexafluoropropoxy;
1,1,2-trifluoro-2-(trifluoromethoxy)ethoxy;
1,1,2,3,3,3-hexafluoropropoxy;
1,1,2,3,3-pentachloroallyloxy;
1,1,2,3,3,3-hexafluoropropoxy;
1,1,2,3,3-pentachloroallyloxy;
1,1,2-trifluoropropoxy;
2,2,2-trifluoroethylamino;
2-bromo-1,1,2-trifluoro-ethoxy; and
2-bromo-2-chloro-1,1-difluoro-ethoxy;

Z$^2$ is selected from H, halogen, cyano, nitro, amino, methyl, ethyl, 1,1-dimethylethyl, difluoromethyl, trichloromethyl, chlorodifluoromethyl, dichlorofluoromethyl, trifluoromethyl, bromodichloromethyl, 1-fluoroethyl, 1-fluoro-1 methylethyl, 2-fluoroethyl, 2,2-difluoroethyl, 2,2,2-trifluoroethyl, 1,2,2,2-tetrafluoroethyl, 1-chlor-1,2,2,2-tetrafluoroethyl, 2,2,2-trichloroethyl, 2-chloro-2,2-difluoroethyl, 1,1-difluoroethyl, pentafluoroethyl heptafluoro-n-propyl, heptafluoro-isopropyl, nonafluoro-n-butyl, methylsulfanyl, methylsulfinyl, methylsulfonyl, ethylthio, ethylsulfinyl, ethylsulfonyl, trifluoromethylsulfanyl, trifluoromethylsulfinyl, trifluoromethylsulfonyl, chloro-difluoromethylsulfanyl, chloro-difluoromethylsulfinyl, chloro-difluoromethylsulfonyl, dichloro-fluoromethylsulfanyl, dichloro-fluoromethylsulfinyl, dichloro-fluoromethylsulfonyl;

Z$^3$ is selected from H, methyl, ethyl, n-propyl, isopropyl, n-butyl, isobutyl, s-butyl, t-butyl, ethenyl, 1-propenyl, 1-propynyl, 1-butynyl, difluoromethyl, trichloromethyl, chlorodifluoromethyl, dichlorofluoromethyl, trifluoromethyl, 1-fluoroethyl, 1 fluoro-1-methylethyl, 2-fluoroethyl, 2,2-difluoroethyl, 2,2,2-trifluoroethyl, phenyl, 2-chlorophenyl, 3-chlorophenyl, 4-chlorophenyl, 2,5-dichlorophenyl, 3,4-dichlorophenyl, 2,6-dichlorophenyl 2,6-dichloro-4-trifluoromethylphenyl, 3-chlor-5-trifluoromethylpyridin-2-yl, 4-NO$_2$-phenyl and 3-chloro-pyridin-2-yl.

7. The compound or salt according to claim 1, wherein T is

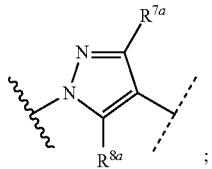

R¹ is H;
R$^{7a}$ and R$^{8a}$ are independently selected from H, methyl and trifluoromethoxy;
Q is selected from 1-cyano-cyclopropyl, (E)-1,2,3,3,3-pentafluoroprop-1-enyl, cyanomethyl, benzyl, cyclopropyl, methyl, ethyl, 2-thienylmethyl, carbamothioylcyclopropyl, pyrid-4-yl, 2,2,2-trifluorethyl, methylsulfonyl, thietan-3-yl and 1-carbamoylcyclopropyl;
W is O;
A¹ and A⁴ are CH;
A² is CH or CF;
A³ is CH or CCl;
U—Z¹ is selected from
difluoromethoxy;
2,2,2-trifluoroethoxy;
1,1,2,3,3,3-hexafluoropropoxy;
methoxy;
1,1,2,2-tetrafluoroethoxy;
2-bromo-1,1,2,2-tetrafluoroethoxy;
1,1,2,3,4,4,4-heptafluoro-3-(trifluoromethyl)butoxy;
1,1,2,4,4,4-hexafluoro-3-(trifluoromethyl)but-2-enoxy;
1,1,2-trifluoro-2-(trifluoromethoxy)ethoxy;
1,1,2-trifluoro-2-(1,1,2,2,3,3,3-heptafluoropropoxy)ethoxy;
2,2-difluoro-2-[1,1,2,2-tetrafluoro-2-(trifluoromethoxy)ethoxy]ethoxy;
2,2,3,3,4,4,4-heptafluorobutoxy;
5,6,6-trifluorohex-5-enoxy;
2,2,3,3,4,4,5,5,6,6,7,7,8,8,8-pentadecafluorooctoxy;
2,2-difluoroethoxy;
2,2,3,3,4,4,5,5-octafluoropentoxy;
2-(trifluoromethoxy)ethoxy;
2,2,3,3-tetrafluoropropoxy;
1,1,2,2,3,3,3-heptafluoropropoxy;
1,1,2,2,3,3,4,4,5,5,6,6,6-tridecafluorohexoxy;
1,1,2,2,3,3,4,4,5,5,6,6,7,7,8,8,8-heptadeccafluorooctoxy;
2-bromo-1,1-difluoro-ethoxy;
(E)-2,3,3,3-tetrafluoro-1-(trifluoromethyl)prop-1-enoxy;
2-bromo-1,1,2-trifluoro-ethoxy;
2-chloro-1,1,2-trifluoro-ethoxy;
(1E)-1,2-difluorobuta-1,3-dienoxy;
3,4,4-trifluorobut-3-enoxy;
(Z)-1,3,3,3-tetrafluoroprop-1-enoxy;
(Z)-2-fluoro-1-(trifluoromethyl)vinyloxy;
2,2,3,3,4,4,5,5-octafluoropentoxy;
1,1,2,3,4,5,5,5-octafluoro-2-(trifluoromethyl)pent-3-enoxy;
1,2,3,3,3-pentafluoroprop-1-enoxy;
1,1,2,3,3,3-hexafluoropropoxy;
1,1,2-trifluoro-2-(trifluoromethoxy)ethoxy;
1,1,2,3,3,3-hexafluoropropoxy;
1,1,2,3,3-pentachloroallyloxy;
1,1,2,3,3,3-hexafluoropropoxy;
1,1,2,3,3-pentachloroallyloxy;
1,1,2-trifluoropropoxy;
2,2,2-trifluoroethylamino;
2-bromo-1,1,2-trifluoro-ethoxy; and
2-bromo-2-chloro-1,1-difluoro-ethoxy;
Z² is CF₃;
Z³ is selected from methyl and ethyl.

8. A pesticidal composition, which comprises at least one compound according to claim 1, or an agrochemically acceptable salt or N-oxide thereof, as active ingredient and at least one auxiliary.

9. The composition according to claim 8, further comprising one or more active agents selected from insecticidally, acaricidally, nematicidally and fungicidally.

10. A method for controlling pests, which comprises applying the composition according to claim 8 to the pests or their environment with the exception of a method for treatment of the human or animal body by surgery or therapy.

11. A method for the protection of plant propagation material from the attack by pests, which comprises treating the propagation material or the site, where the propagation material is planted, with the compound of claim 1.

12. A coated plant propagation material, wherein a coating of the plant propagation material comprises in the compound of claim 1.

13. A compound of formula (I),

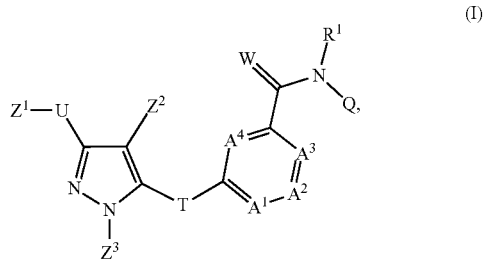

wherein
R¹ is selected from H, C₁-C₆-alkyl, C₂-C₆ alkenyl, C₂-C₆ alkynyl, C₃-C₇ cycloalkyl, C₃-C₇ cycloalkyl-C₁-C₃-alkyl, C₁-C₆-alkylcarbonyl, C₁-C₆-alkoxycarbonyl, aryl(C₀-C₃)-alkyl and heteroaryl(C₀-C₃)-alkyl, wherein each of C₁-C₆-alkyl, C₂-C₆ alkenyl, C₂-C₆ alkynyl, C₃-C₇ cycloalkyl, C₃-C₇ cycloalkyl-C₁-C₃-alkyl, C₁-C₆-alkylcarbonyl, C₁-C₆-alkoxycarbonyl, aryl(C₀-C₃)-alkyl and heteroaryl(C₀-C₃)-alkyl is unsubstituted or substituted with 1 to 10 substituents independently selected from halogen, cyano, C₁-C₆-alkoxy and C₁-C₆-alkoxycarbonyl;
Q is selected from H, hydroxy, HC(=O)—, methylsulfonyl, carbamothioylcyclopropyl, 1-carbamoylcyclopropyl, C₁-C₆-alkyl, C₁-C₆-alkoxy, C₃-C₆alkenyl, C₃-C₆ alkynyl, C₃-C₇ cycloalkyl, C₃-C₇ heterocycloalkyl, C₃-C₇ cycloalkyl-C₁-C₃-alkyl, C₁-C₃-alkyl-C₃-C₇ cycloalkyl, aryl(C₀-C₃)-alkyl, heteroaryl(C₀-C₃)-alkyl, N—C₁-C₆-alkylamino, N—C₁-C₆-alkylcarbonylamino and N,N-di (C₁-C₆-alkyl)amino, wherein each of C₁-C₆-alkyl, C₁-C₆-alkoxy, C₃-C₆ alkenyl, C₃-C₆ alkynyl, C₃-C₇ cycloalkyl, C₃-C₇ heterocycloalkyl, C₃-C₇ cycloalkyl-C₁-C₃-alkyl, C₁-C₃-alkyl-C₃-C₇ cycloalkyl, aryl(C₀-C₃)-alkyl, heteroaryl(C₀-C₃)-alkyl, N—C₁-C₆-alkylamino, N—C₁-C₆-alkylcarbonylamino and N,N-di (C₁-C₆-alkyl)amino is unsubstituted or substituted with 1 to 10 substituents independently selected from halogen, hydroxyl, nitro, amino, cyano, $C_1$-$C_6$-alkoxy, $C_1$-$C_6$-alkoxycarbonyl, hydroxycarbonyl, $C_1$-$C_6$-alkylcarbamoyl, $C_3$-$C_6$-cycloalkylcarbamoyl and phenyl;

W is O or S;
$A^1$ is $CR^2$ or N;
$A^2$ is $CR^3$ or N;
$A^3$ is $CR^4$ or N;
$A^4$ is $CR^5$ or N;
with the proviso that no more than 3 of $A^1$, $A^2$, $A^3$ and $A^4$ are N;
$R^2$, $R^3$, $R^4$ and $R^5$ are independently selected from H, halogen, cyano, nitro, $C_1$-$C_6$-alkyl, $C_1$-$C_6$-alkoxy, N—$C_1$-$C_6$-alkoxy-imino-$C_1$-$C_3$-alkyl, $C_1$-$C_6$-alkylsulfanyl, $C_1$-$C_6$-alkylsulfinyl, $C_1$-$C_6$-alkylsulfonyl, N—$C_1$-$C_6$-alkylamino and N,N-di-$C_1$-$C_6$-alkylamino, wherein each of $C_1$-$C_6$-alkyl, $C_1$-$C_6$-alkoxy, N—$C_1$-$C_6$-alkoxy-imino-$C_1$-$C_3$-alkyl, $C_1$-$C_6$-alkylsulfanyl, $C_1$-$C_6$-alkylsulfinyl, $C_1$-$C_6$-alkylsulfonyl, N—$C_1$-$C_6$-alkylamino and N,N-di-$C_1$-$C_6$-alkylamino is unsubstituted or substituted with 1 to 5 substituents independently selected from halogen, hydroxy, nitro, amino, cyano, $C_1$-$C_6$-alkoxy, $C_1$-$C_6$-alkoxycarbonyl, hydroxycarbonyl, $C_1$-$C_6$-alkylcarbamoyl, $C_3$-$C_6$-cycloalkylcarbamoyl and phenyl;

T is a 5-membered heteroaryl of formula:

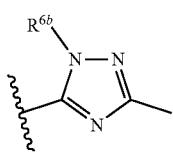
T7

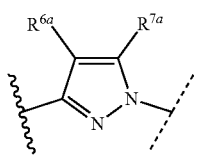
T10

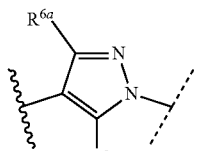
T11

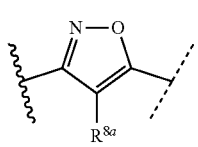
T13

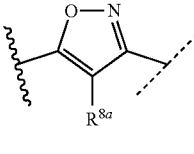
T14

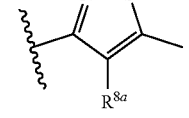
T15

-continued
and

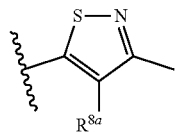
T16 or
T is a 5-membered heteroaryl of formula

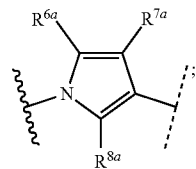
T45

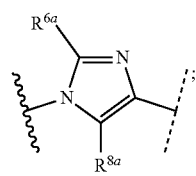
T46

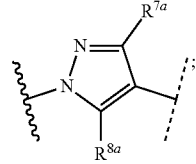
T47

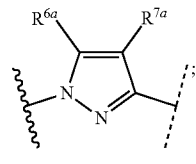
T48

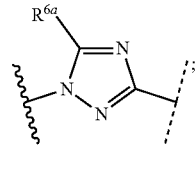
T49

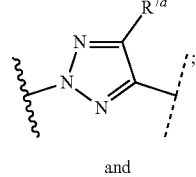
T50 and

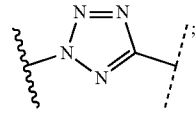
T51 wherein

indicates the bond to the pyrazole group;
$R^{6a}$, $R^{7a}$ and $R^{8a}$ are independently selected from H, halogen, cyano, nitro, amino, $C_1$-$C_6$-alkyl, $C_1$-$C_6$-alkoxy, $C_1$-$C_6$-alkylcarbonyl, $C_1$-$C_6$-alkylsulfanyl, $C_1$-$C_6$-alkylsulfinyl and $C_1$-$C_6$-alkylsulfonyl, wherein each of $C_1$-$C_6$-alkyl, $C_1$-$C_6$-alkoxy, $C_1$-$C_6$-alkylcarbonyl, $C_1$-$C_6$-alkylsulfanyl, $C_1$-$C_6$-alkylsulfinyl, $C_1$-$C_6$-alkylsulfonyl is unsubstituted or substituted with 1 to 5 halogen;
$R^{6b}$, $R^{7b}$ and $R^{8b}$ are independently selected from H and $C_1$-$C_6$-alkyl, wherein each of $C_1$-$C_6$-alkyl is unsubstituted or substituted with 1 to 5 halogen;
U is selected from —S—, —SO— and —$SO_2$—;
$Z^1$ is selected from $C_1$-$C_{10}$-alkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_2$-$C_{10}$-alkenyl, $C_2$-$C_{10}$-alkynyl, —($C_0$-$C_6$-alkyl)-$C_3$-$C_7$ heterocycloalkyl, —($C_0$-$C_6$-alkyl)-$C_3$-$C_6$-cycloalkyl and $C_1$-$C_{10}$-alkylsulfonyl, wherein each of $C_1$-$C_{10}$-alkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_2$-$C_{10}$-alkenyl, $C_2$-$C_{10}$-alkynyl, —($C_0$-$C_6$-alkyl)-$C_3$-$C_7$ heterocycloalkyl, —($C_0$-$C_6$-alkyl)-$C_3$-$C_6$-cycloalkyl and $C_1$-$C_{10}$-alkylsulfonyl is unsubstituted or substituted with 1 to 20 substituents independently selected from halogen, hydroxy, nitro, amino, cyano, $C_1$-$C_6$-alkoxy, $C_1$-$C_6$-alkoxycarbonyl, hydroxycarbonyl, $C_1$-$C_6$-alkylcarbamoyl, $C_3$-$C_6$-cycloalkylcarbamoyl and phenyl;
$Z^2$ is selected from H, halogen, cyano, nitro, amino, $C_1$-$C_6$-alkyl, $C_1$-$C_6$-alkylcarbonyl, $C_1$-$C_6$-alkylsulfanyl, $C_1$-$C_6$-alkylsulfinyl and $C_1$-$C_6$-alkylsulfonyl, wherein each of $C_1$-$C_6$-alkyl, $C_1$-$C_6$-alkylcarbonyl, $C_1$-$C_6$-alkylsulfanyl, $C_1$-$C_6$-alkylsulfinyl and $C_1$-$C_6$-alkylsulfonyl is unsubstituted or substituted with 1 to 5 substituents independently selected from halogen, hydroxy, nitro, amino, cyano, $C_1$-$C_6$-alkoxy, $C_1$-$C_6$-alkoxycarbonyl, hydroxycarbonyl, $C_1$-$C_6$-alkylcarbamoyl, $C_3$-$C_6$-cycloalkylcarbamoyl and phenyl; and
$Z^3$ is selected from H, $C_1$-$C_6$-alkyl, $C_1$-$C_6$-cycloalkyl, $C_1$-$C_6$-alkenyl, $C_1$-$C_6$-alkynyl, aryl and heteroaryl, wherein each of $C_1$-$C_6$-alkyl, $C_1$-$C_6$-cycloalkyl, $C_1$-$C_6$-alkenyl, $C_1$-$C_6$-alkynyl, aryl and heteroaryl is unsubstituted or substituted with 1 to 5 substituents independently selected from halogen, hydroxy, nitro, amino, cyano, $C_1$-$C_6$-alkoxy, $C_1$-$C_6$-alkoxycarbonyl, hydroxycarbonyl, $C_1$-$C_6$-alkylcarbamoyl, $C_3$-$C_6$-cycloalkylcarbamoyl and phenyl;
or an agrochemically acceptable salt or N-oxide thereof.

14. The compound or salt according to claim 13, wherein $R^1$ is H;
Q is selected from 1-cyano-cyclopropyl, (E)-1,2,3,3,3-pentafluoroprop-1-enyl, cyanomethyl, benzyl, cyclopropyl, methyl, ethyl, 2-thienylmethyl, carbamothioyl-cyclopropyl, pyrid-4-yl, 2,2,2-trifluoroethyl, methylsulfonyl, thietan-3-yl and 1-carbamoylcyclopropyl;
W is O;
$A^1$ is $CR^2$ or N;
$A^2$ is $CR^3$ or N;
$A^3$ is $CR^4$ or N;
$A^4$ is $CR^5$ or N;
with the proviso that no more than 3 of $A^1$, $A^2$, $A^3$ and $A^4$ are N;
$R^2$ and $R^5$ are independently selected from H, methyl, fluoro and chloro;
$R^3$ and $R^4$ are independently selected from H, fluoro, chloro, bromo, iodo, cyano, nitro, methyl, ethyl, fluoromethyl, difluoromethyl, chlorodifluoromethyl, trifluoromethyl, 2,2,2-trifluoroethyl, methoxy, ethoxy, n-propoxy, 1-methylethoxy, fluoromethoxy, difluoromethoxy, chloro-difluoromethoxy, dichloro-fluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)-ethyl, methylsulfanyl, trifluoromethylsulfanyl, methylsulfonyl, methylsulfinyl, trifluoromethylsulfonyl and trifluoromethylsulfinyl;
U—$Z^1$ is selected from trifluoromethylsulfonate;
1,1,2,2,3,3,4,4,4-nonafluorobutane-1-sulfonate;
3,3,4,4,5,5,6,6,7,7,8,8,8-tridecafluorooctylsulfanyl;
2,2,3,3-tetrafluoropropylsulfanyl;
trifluoromethylsulfanyl;
1,1,2,2,3,3,3-heptafluoropropylsulfanyl;
$Z^2$ is selected from H, halogen, cyano, nitro, amino, methyl, ethyl, 1,1-dimethylethyl, difluoromethyl, trichloromethyl, chlorodifluoromethyl, dichlorofluoromethyl, trifluoromethyl, bromodichloromethyl, 1-fluoroethyl, 1-fluoro-1 methylethyl, 2-fluoroethyl, 2,2-difluoroethyl, 2,2,2-trifluoroethyl, 1,2,2,2-tetrafluoroethyl, 1-chlor-1,2,2,2-tetrafluoroethyl, 2,2,2-trichloroethyl, 2-chloro-2,2-difluoroethyl, 1,1-difluoroethyl, pentafluoroethyl heptafluoro-n-propyl, heptafluoro-isopropyl, nonafluoro-n-butyl, methylsulfanyl, methylsulfinyl, methylsulfonyl, ethylthio, ethylsulfinyl, ethylsulfonyl, trifluoromethylsulfanyl, trifluoromethylsulfinyl, trifluoromethylsulfonyl, chloro-difluoromethylsulfanyl, chloro-difluoromethylsulfinyl, chloro-difluoromethylsulfonyl, dichloro-fluoromethylsulfanyl, dichloro-fluoromethylsulfinyl, dichloro-fluoromethylsulfonyl; and
$Z^3$ is selected from H, methyl, ethyl, n-propyl, isopropyl, n-butyl, isobutyl, s-butyl, t-butyl, ethenyl, 1-propenyl, 1-propynyl, 1-butynyl, difluoromethyl, trichloromethyl, chlorodifluoromethyl, dichlorofluoromethyl, trifluoromethyl, 1-fluoroethyl, 1 fluoro-1-methylethyl, 2-fluoroethyl, 2,2-difluoroethyl, 2,2,2-trifluoroethyl, phenyl, 2-chlorophenyl, 3-chlorophenyl, 4-chlorophenyl, 2,5-dichlorophenyl, 3,4-dichlorophenyl, 2,6-dichlorophenyl 2,6-dichloro-4-trifluoromethylphenyl, 3-chlor-5-trifluoromethylpyridin-2-yl, 4-$NO_2$-phenyl and 3-chloro-pyridin-2-yl.

15. The compound or salt according to claim 13, wherein T is

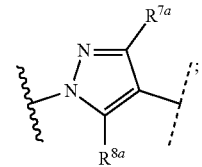

R¹ is H;

R⁷ᵃ and R⁸ᵃ are independently selected from H, methyl and trifluoromethoxy;

Q is selected from 1-cyano-cyclopropyl, (E)-1,2,3,3,3-pentafluoroprop-1-enyl, cyanomethyl, benzyl, cyclopropyl, methyl, ethyl, 2-thienylmethyl, carbamothioylcyclopropyl, pyrid-4-yl, 2,2,2-trifluorethyl, methylsulfonyl, thietan-3-yl and 1-carbamoylcyclopropyl;

W is O;

A¹ and A⁴ are CH;

A² is CH or CF;

A³ is CH or CCl;

U—Z¹ is selected from trifluoromethylsulfonate;

1,1,2,2,3,3,4,4,4-nonafluorobutane-1-sulfonate;

3,3,4,4,5,5,6,6,7,7,8,8,8-tridecafluorooctylsulfanyl;

2,2,3,3-tetrafluoropropylsulfanyl;

trifluoromethylsulfanyl;

1,1,2,2,3,3,3-heptafluoropropylsulfanyl;

Z² is CF₃; and

Z³ is selected from methyl and ethyl.

16. The compound or salt according to claim 13, wherein T is selected from

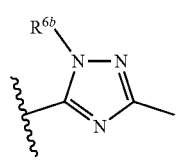
T7

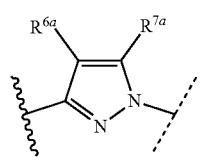
T10

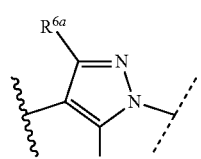
T11

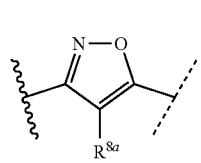
T13

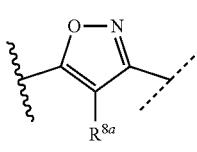
T14

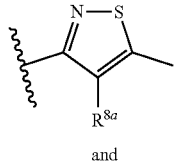
T15 and

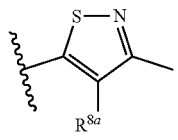
T16 wherein

indicates the bond to the pyrazole group.

17. The compound or salt according to claim 13, wherein T is selected from

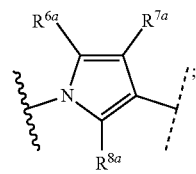
T45

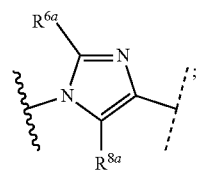
T46

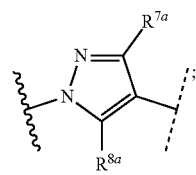
T47

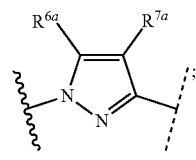
T48

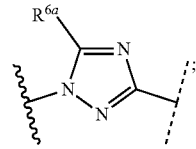
T49

-continued

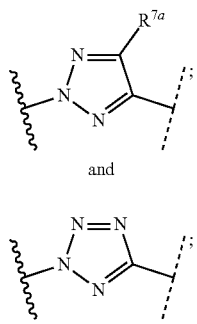

and wherein

indicates the bond to the pyrazole group.

18. A compound selected from:

2-chloro-N-(1-cyanocyclopropyl)-5-[1-[5-[(Z)-2-fluoro-1-(trifluoromethyl)vinyloxy]-2-methyl-4-(trifluoromethyl)pyrazol-3-yl]pyrazol-4-yl]benzamide;

2-chloro-N-cyclopropyl-5-[1-[2-methyl-5-(2,2,2-trifluoroethoxy)-4-(trifluoromethyl)pyrazol-3-yl]pyrazol-4-yl]benzamide;

2-chloro-N-(1-cyanocyclopropyl)-5-[1-[2-methyl-5-(2,2,2-trifluoroethoxy)-4-(trifluoromethyl)pyrazol-3-yl]pyrazol-4-yl]benzamide;

2-chloro-N-(1-cyanocyclopropyl)-5-[1-[5-(1,1,2,3,3,3-hexafluoropropoxy)-2-methyl-4-(trifluoromethyl)pyrazol-3-yl]pyrazol-4-yl]benzamide;

2-chloro-N-(1-cyanocyclopropyl)-5-[1-[5-methoxy-2-methyl-4-(trifluoromethyl)pyrazol-3-yl]pyrazol-4-yl]benzamide;

2-chloro-N-cyclopropyl-5-[1-[5-(1,1,2,3,3,3-hexafluoropropoxy)-2-methyl-4-(trifluoromethyl)pyrazol-3-yl]pyrazol-4-yl]benzamide;

2-chloro-N-(1-cyanocyclopropyl)-5-[1-[5-(1,1,2,3,3,3-hexafluoropropoxy)-2-methyl-4-(trifluoromethyl)pyrazol-3-yl]pyrazol-4-yl]-N-[(E)-1,2,3,3,3-pentafluoroprop-1-enyl]benzamide;

2-chloro-N-cyclopropyl-5-[1-[5-(difluoromethoxy)-2-methyl-4-(trifluoromethyl)pyrazol-3-yl]pyrazol-4-yl]benzamide;

2-chloro-N-ethyl-5-[1-[5-(1,1,2,3,3,3-hexafluoropropoxy)-2-methyl-4-(trifluoromethyl)pyrazol-3-yl]pyrazol-4-yl]benzamide;

2-chloro-N-(cyanomethyl)-5-[1-[5-(1,1,2,3,3,3-hexafluoropropoxy)-2-methyl-4-(trifluoromethyl)pyrazol-3-yl]pyrazol-4-yl]benzamide;

2-chloro-N-(1-cyanocyclopropyl)-5-[1-[2-methyl-5-(1,1,2,2-tetrafluoroethoxy)-4-(trifluoromethyl)pyrazol-3-yl]pyrazol-4-yl]benzamide;

5-[1-[5-(2-bromo-1,1,2,2-tetrafluoro-ethoxy)-2-methyl-4-(trifluoromethyl)pyrazol-3-yl]pyrazol-4-yl]-2-chloro-N-(1-cyanocyclopropyl)benzamide;

2-chloro-N-(1-cyanocyclopropyl)-5-[1-[5-[1,1,2,3,4,4,4-heptafluoro-3-(trifluoromethyl)butoxy]-2-methyl-4-(trifluoromethyl)pyrazol-3-yl]pyrazol-4-yl]benzamide;

2-chloro-N-(1-cyanocyclopropyl)-5-[1-[5-[1,1,2,4,4,4-hexafluoro-3-(trifluoromethyl)but-2-enoxy]-2-methyl-4-(trifluoromethyl)pyrazol-3-yl]pyrazol-4-yl]benzamide;

2-chloro-N-(1-cyanocyclopropyl)-5-[1-[2-methyl-4-(trifluoromethyl)-5-[1,1,2-trifluoro-2-(trifluoromethoxy)ethoxy]pyrazol-3-yl]pyrazol-4-yl]benzamide;

[5-[4-[4-chloro-3-[(1-cyanocyclopropyl)carbamoyl]phenyl]pyrazol-1-yl]-1-methyl-4-(trifluoromethyl)pyrazol-3-yl]trifluoromethanesulfonate;

2-chloro-N-(1-cyanocyclopropyl)-5-[1-[2-methyl-5-[1,1,2-trifluoro-2-(1,1,2,2,3,3,3-heptafluoropropoxy)ethoxy]-4-(trifluoromethyl)pyrazol-3-yl]pyrazol-4-yl]benzamide;

2-chloro-N-(1-cyanocyclopropyl)-5-[1-[5-[2,2-difluoro-2-[1,1,2,2-tetrafluoro-2-(trifluoromethoxy)ethoxy]ethoxy]-2-methyl-4-(trifluoromethyl)pyrazol-3-yl]pyrazol-4-yl]benzamide;

2-chloro-N-(1-cyanocyclopropyl)-5-[1-[5-(2,2,3,3,4,4,4-heptafluorobutoxy)-2-methyl-4-(trifluoromethyl)pyrazol-3-yl]pyrazol-4-yl]benzamide;

2-chloro-N-(1-cyanocyclopropyl)-5-[1-[2-methyl-5-(2,2,3,3,4,4,5,5-octafluoropentoxy)-4-(trifluoromethyl)pyrazol-3-yl]pyrazol-4-yl]benzamide;

2-chloro-N-(1-cyanocyclopropyl)-5-[1-[2-methyl-5-(5,6,6-trifluorohex-5-enoxy)-4-(trifluoromethyl)pyrazol-3-yl]pyrazol-4-yl]benzamide;

2-chloro-N-(1-cyanocyclopropyl)-5-[1-[2-methyl-5-(2,2,3,3,4,4,5,5,6,6,7,7,8,8,8-pentadecafluorooctoxy)-4-(trifluoromethyl)pyrazol-3-yl]pyrazol-4-yl]benzamide;

2-chloro-N-(1-cyanocyclopropyl)-5-[1-[5-(2,2-difluoroethoxy)-2-methyl-4-(trifluoromethyl)pyrazol-3-yl]pyrazol-4-yl]benzamide;

2-chloro-N-cyclopropyl-5-[1-[5-(2,2-difluoroethoxy)-2-methyl-4-(trifluoromethyl)pyrazol-3-yl]pyrazol-4-yl]benzamide;

2-chloro-N-cyclopropyl-5-[1-[5-[2,2-difluoro-2-[1,1,2,2-tetrafluoro-2-(trifluoromethoxy)ethoxy]ethoxy]-2-methyl-4-(trifluoromethyl)pyrazol-3-yl]pyrazol-4-yl]benzamide;

2-chloro-N-cyclopropyl-5-[1-[5-(2,2,3,3,4,4,4-heptafluorobutoxy)-2-methyl-4-(trifluoromethyl)pyrazol-3-yl]pyrazol-4-yl]benzamide;

2-chloro-N-cyclopropyl-5-[1-[2-methyl-5-(2,2,3,3,4,4,5,5-octafluoropentoxy)-4-(trifluoromethyl)pyrazol-3-yl]pyrazol-4-yl]benzamide;

2-chloro-N-(1-cyanocyclopropyl)-5-[1-[2-methyl-5-[2-(trifluoromethoxy)ethoxy]-4-(trifluoromethyl)pyrazol-3-yl]pyrazol-4-yl]benzamide;

2-chloro-N-cyclopropyl-5-[1-[2-methyl-5-(5,6,6-trifluorohex-5-enoxy)-4-(trifluoromethyl)pyrazol-3-yl]pyrazol-4-yl]benzamide;

2-chloro-N-(1-cyanocyclopropyl)-5-[1-[2-methyl-5-(2,2,3,3-tetrafluoropropoxy)-4-(trifluoromethyl)pyrazol-3-yl]pyrazol-4-yl]benzamide;

2-chloro-N-cyclopropyl-5-[1-[2-methyl-5-(2,2,3,3,4,4,5,5,6,6,7,7,8,8,8-pentadecafluorooctoxy)-4-(trifluoromethyl)pyrazol-3-yl]pyrazol-4-yl]benzamide;

2-chloro-N-cyclopropyl-5-[1-[2-methyl-5-(2,2,3,3,3-pentafluoropropoxy)-4-(trifluoromethyl)pyrazol-3-yl]pyrazol-4-yl]benzamide;

2-chloro-N-cyclopropyl-5-[1-[2-methyl-5-(2,2,3,3-tetrafluoropropoxy)-4-(trifluoromethyl)pyrazol-3-yl]pyrazol-4-yl]benzamide;

2-chloro-N-cyclopropyl-5-[1-[2-methyl-5-[2-(trifluoromethoxy)ethoxy]-4-(trifluoromethyl)pyrazol-3-yl]pyrazol-4-yl]benzamide;

2-chloro-N-(1-cyanocyclopropyl)-5-[1-[5-(1,1,2,2,3,3,3-heptafluoropropoxy)-2-methyl-4-(trifluoromethyl)pyrazol-3-yl]pyrazol-4-yl]benzamide;
[5-[4-[4-chloro-3-(cyclopropylcarbamoyl)phenyl]pyrazol-1-yl]-1-methyl-4-(trifluoromethyl)pyrazol-3-yl]1,1,2,2,3,3,4,4,4-nonafluorobutane-1-sulfonate;
[5-[4-[4-chloro-3-(cyclopropylcarbamoyl)phenyl]pyrazol-1-yl]-1-methyl-4-(trifluoromethyl)pyrazol-3-yl]1,1,2,2,3,3,4,4,4-nonafluorobutane-1-sulfonate;
2-chloro-N-(1-cyanocyclopropyl)-5-[1-[2-methyl-5-(1,1,2,2,3,3,4,4,5,5,6,6,6-tridecafluorohexoxy)-4-(trifluoromethyl)pyrazol-3-yl]pyrazol-4-yl]benzamide;
2-chloro-N-cyclopropyl-5-[1-[2-methyl-5-(1,1,2,2,3,3,4,4,5,5,6,6,6-tridecafluorohexoxy)-4-(trifluoromethyl)pyrazol-3-yl]pyrazol-4-yl]benzamide;
2-chloro-N-(1-cyanocyclopropyl)-5-[1-[5-(1,1,2,2,3,3,4,4,5,5,6,6,7,7,8,8,8-heptadecafluorooctoxy)-2-methyl-4-(trifluoromethyl)pyrazol-3-yl]pyrazol-4-yl]benzamide;
5-[1-[5-(2-bromo-1,1-difluoro-ethoxy)-2-methyl-4-(trifluoromethyl)pyrazol-3-yl]pyrazol-4-yl]-2-chloro-N-(1-cyanocyclopropyl)benzamide;
2-chloro-N-(1-cyanocyclopropyl)-5-[1-[2-methyl-5-(E)-2,3,3,3-tetrafluoro-1-(trifluoromethyl)prop-1-enoxy]-4-(trifluoromethyl)pyrazol-3-yl]pyrazol-4-yl]benzamide
5-[1-[5-(2-bromo-1,1,2-trifluoro-ethoxy)-2-methyl-4-(trifluoromethyl)pyrazol-3-yl]pyrazol-4-yl]-2-chloro-N-cyclopropyl-benzamide;
2-chloro-5-[1-[5-(2-chloro-1,1,2-trifluoro-ethoxy)-2-methyl-4-(trifluoromethyl)pyrazol-3-yl]pyrazol-4-yl]-N-(1-cyanocyclopropyl)benzamide;
2-chloro-N-(1-cyanocyclopropyl)-5-[1-[5-[(1E)-1,2-difluorobuta-1,3-dienoxy]-2-methyl-4-(trifluoromethyl)pyrazol-3-yl]pyrazol-4-yl]benzamide;
2-chloro-N-(1-cyanocyclopropyl)-5-[1-[2-methyl-5-(3,4,4-trifluorobut-3-enoxy)-4-(trifluoromethyl)pyrazol-3-yl]pyrazol-4-yl]benzamide;
5-[1-[5-(2-bromo-1,1,2-trifluoro-ethoxy)-2-methyl-4-(trifluoromethyl)pyrazol-3-yl]pyrazol-4-yl]-2-chloro-N-(1-cyanocyclopropyl)benzamide;
2-chloro-N-(1-cyanocyclopropyl)-5-1-[2-methyl-5-[(Z)-1,3,3,3-tetrafluoroprop-1-enoxy]-4-(trifluoromethyl)pyrazol-3-yl]pyrazol-4-yl]benzamide; 2-chloro-N-(1-cyanocyclopropyl)-5-[1-[5-[(Z)-2-fluoro-1-(trifluoromethyl)vinyloxy]-2-methyl-4-(trifluoromethyl)pyrazol-3-yl]pyrazol-4-yl]benzamide;
2-chloro-N-(1-cyanocyclopropyl)-5-[1-[2-methyl-5-[(E or Z)-1,1,2,3,4,5,5,5-octafluoro-2-(trifluoromethyl)pent-3-enoxy]-4-(trifluoromethyl)pyrazol-3-yl]pyrazol-4-yl]benzamide;
2-chloro-N-cyclopropyl-5-[1-[2-methyl-5-[(E or Z)-1,1,2,3,4,5,5,5-octafluoro-2-(trifluoromethyl)pent-3-enoxy]-4-(trifluoromethyl)pyrazol-3-yl]pyrazol-4-yl]benzamide;
2-chloro-N-(1-cyanocyclopropyl)-5-[1-[2-methyl-5-[(E or Z)-1,2,3,3,3-pentafluoroprop-1-enoxy]-4-(trifluoromethyl)pyrazol-3-yl]pyrazol-4-yl]benzamide;
2-chloro-N-cyclopropyl-5-[1-[2-methyl-5-[(E or Z)-1,2,3,3,3-pentafluoroprop-1-enoxy]-4-(trifluoromethyl)pyrazol-3-yl]pyrazol-4-yl]benzamide;
5-[1-[4-bromo-2-methyl-5-(3,3,4,4,5,5,6,6,7,7,8,8,8-tridecafluorooctylsulfanyl)pyrazol-3-yl]pyrazol-4-yl]-2-chloro-N-cyclopropyl-benzamide;
2-chloro-N-(1-cyanocyclopropyl)-5-1-[5-(1,1,2,3,3,3-hexafluoropropoxy)-2-methyl-4-(trifluoromethyl)pyrazol-3-yl]pyrazol-4-yl]-N-methyl-benzamide;
2-chloro-N-(1-cyanocyclopropyl)-5-[1-[5-methoxy-2-methyl-4-(trifluoromethyl)pyrazol-3-yl]pyrazol-4-yl]-N-methyl-benzamide;
5-[1-[4-bromo-2-methyl-5-(2,2,3,3-tetrafluoropropylsulfanyl)pyrazol-3-yl]pyrazol-4-yl]-2-chloro-N-cyclopropyl-benzamide;
N-cyclopropyl-5-[1-[5-(1,1,2,3,3,3-hexafluoropropoxy)-2-methyl-4-(trifluoromethyl)pyrazol-3-yl]pyrazol-4-yl]-2-methyl-benzamide;
N-(1-cyanocyclopropyl)-2-fluoro-5-[1-[5-(1,1,2,3,3,3-hexafluoropropoxy)-2-methyl-4-(trifluoromethyl)pyrazol-3-yl]pyrazol-4-yl]benzamide;
N-cyclopropyl-2-fluoro-5-[1-[5-(1,1,2,3,3,3-hexafluoropropoxy)-2-methyl-4-(trifluoromethyl)pyrazol-3-yl]pyrazol-4-yl]benzamide;
2-chloro-N-(1-cyanocyclopropyl)-5-[1-[2-methyl-4-(trifluoromethyl)-5-[1,1,2-trifluoro-2-(trifluoromethoxy)ethoxy]pyrazol-3-yl]pyrazol-4-yl]pyridine-3-carboxamide;
2-chloro-N-cyclopropyl-5-[1-[2-methyl-4-(trifluoromethyl)-5-[1,1,2-trifluoro-2-(trifluoromethoxy)ethoxy]pyrazol-3-yl]pyrazol-4-yl]pyridine-3-carboxamide;
5-[1-[4-bromo-2-methyl-5-(trifluoromethylsulfanyl)pyrazol-3-yl]pyrazol-4-yl]-2-chloro-N-cyclopropyl-benzamide;
5-[1-[4-bromo-5-(1,1,2,2,3,3,3-heptafluoropropylsulfanyl)-2-methyl-pyrazol-3-yl]pyrazol-4-yl]-2-chloro-N-cyclopropyl-benzamide;
2-chloro-N-(1-cyanocyclopropyl)-5-[1-[5-(1,1,2,3,3,3-hexafluoropropoxy)-2-methyl-4-(trifluoromethyl)pyrazol-3-yl]pyrazol-4-yl]pyridine-3-carboxamide;
2-chloro-N-cyclopropyl-5-[1-[5-(1,1,2,3,3,3-hexafluoropropoxy)-2-methyl-4-(trifluoromethyl)pyrazol-3-yl]pyrazol-4-yl]pyridine-3-carboxamide;
2-chloro-N-cyclopropyl-5-[1-[2-methyl-5-(1,1,2,3,3-pentachloroallyloxy)-4-(trifluoromethyl)pyrazol-3-yl]pyrazol-4-yl]benzamide;
N-cyclopropyl-2-fluoro-3-[1-[5-(1,1,2,3,3,3-hexafluoropropoxy)-2-methyl-4-(trifluoromethyl)pyrazol-3-yl]pyrazol-4-yl]benzamide;
2-chloro-N-(1-cyanocyclopropyl)-5-[1-[2-methyl-5-(1,1,2,3,3-pentachloroallyloxy)-4-(trifluoromethyl)pyrazol-3-yl]pyrazol-4-yl]benzamide;
3-[1-[2,4-dimethyl-5-(1,1,2-trifluoropropoxy)pyrazol-3-yl]pyrazol-4-yl]-2-fluoro-N-(1-cyanocyclopropyl)benzamide;
N-cyclopropyl-3-[1-[2,4-dimethyl-5-(1,1,2-trifluoropropoxy)pyrazol-3-yl]pyrazol-4-yl]-2-fluoro-benzamide;
2-chloro-N-cyclopropyl-5-[1-[2,4-dimethyl-5-(1,1,2-trifluoropropoxy)pyrazol-3-yl]pyrazol-4-yl]-3-fluoro-benzamide;
2-chloro-N-(1-cyanocyclopropyl)-5-[1-[2,4-dimethyl-5-(1,1,2-trifluoropropoxy)pyrazol-3-yl]pyrazol-4-yl]-3-fluoro-benzamide;
2-chloro-5-[1-[2,4-dimethyl-5-(1,1,2-trifluoropropoxy)pyrazol-3-yl]pyrazol-4-yl]-4-fluoro-N-(1-cyanocyclopropyl)benzamide;
2-chloro-N-cyclopropyl-5-[1-[2,4-dimethyl-5-(1,1,2-trifluoropropoxy)pyrazol-3-yl]pyrazol-4-yl]-4-fluoro-benzamide;
2,4-dichloro-5-[1-[2,4-dimethyl-5-(1,1,2-trifluoropropoxy)pyrazol-3-yl]pyrazol-4-yl]-N-(1-cyanocyclopropyl)benzamide;
2,4-dichloro-N-cyclopropyl-5-[1-[2,4-dimethyl-5-(1,1,2-trifluoropropoxy)pyrazol-3-yl]pyrazol-4-yl]benzamide;

2,3-dichloro-N-cyclopropyl-5-[1-[2,4-dimethyl-5-(1,1,2-trifluoropropoxy)pyrazol-3-yl]pyrazol-4-yl]benzamide;
2,3-dichloro-5-[1-[2,4-dimethyl-5-(1,1,2-trifluoropropoxy)pyrazol-3-yl]pyrazol-4-yl]-N-(1-cyanocyclopropyl)benzamide;
5-[1-[2,4-dimethyl-5-(1,1,2-trifluoropropoxy)pyrazol-3-yl]pyrazol-4-yl]-2-fluoro-N-(1-cyanocyclopropyl)benzamide;
5-[1-[4-bromo-2-methyl-5-(2,2,2-trifluoroethylamino)pyrazol-3-yl]pyrazol-4-yl]-2-chloro-N-cyclopropylbenzamide;
5-[1-[5-(2-bromo-1,1,2-trifluoro-ethoxy)-2,4-dimethylpyrazol-3-yl]pyrazol-4-yl]-2-chloro-N-(1-cyanocyclopropyl)benzamide;
5-[1-[5-(2-bromo-1,1,2-trifluoro-ethoxy)-2,4-dimethylpyrazol-3-yl]pyrazol-4-yl]-2-chloro-N-cyclopropylbenzamide;
2-chloro-N-cyclopropyl-5-[1-[5-(1,1,2,3,3,3-hexafluoropropoxy)-2,4-dimethyl-pyrazol-3-yl]triazol-4-yl]benzamide;
5-[1-[5-(2-bromo-2-chloro-1,1-difluoro-ethoxy)-2,4-dimethyl-pyrazol-3-yl]pyrazol-4-yl]-2-chloro-N-(1-cyanocyclopropyl)benzamide;
5-[1-[5-(2-bromo-2-chloro-1,1-difluoro-ethoxy)-2,4-dimethyl-pyrazol-3-yl]pyrazol-4-yl]-2-chloro-N-cyclopropyl-benzamide; and
2-chloro-N-cyclopropyl-5-[1-(5-methoxy-2,4-dimethyl-pyrazol-3-yl)triazol-4-yl]benzamide;
or an agrochemically acceptable salt or N-oxide thereof.

* * * * *